United States Patent [19]
Wong et al.

[11] Patent Number: 6,120,997
[45] Date of Patent: Sep. 19, 2000

[54] NUCLEIC ACID BINDERS HAVING AN HYDROXYAMINE MOTIF

[75] Inventors: Chi-Huey Wong, Rancho Santa Fe, Calif.; Martin Hendrix, Cologne, Germany; Phil Alper, San Diego, Calif.; E. Scott Priestley, Greenville, Del.

[73] Assignee: The Scripps Research Institute, La Jolla, Calif.

[21] Appl. No.: 09/006,597

[22] Filed: Jan. 13, 1998

Related U.S. Application Data

[60] Provisional application No. 60/035,483, Jan. 13, 1997.
[51] Int. Cl.[7] ........................................................ C12Q 1/68
[52] U.S. Cl. ........................ 435/6; 435/7.1; 435/DIG. 38; 436/501; 536/1.11; 536/16.6; 536/17.9; 536/29.1; 530/322
[58] Field of Search ............................ 435/7.1, 85, 287.1; 436/501; 424/1.73; 514/42; 536/1.11, 17.9, 16.6, 29.1; 530/322

*Primary Examiner*—Bennett Celsa
*Assistant Examiner*—Maurie E. Garcia
*Attorney, Agent, or Firm*—Donald G. Lewis

[57] ABSTRACT

The invention relates to the combination of hydroxyamines with nucleic acid binding motifs to generate molecules and libraries of molecules targeting specific nucleic acid sequences. In particular, a series of libraries are constructed which contain hydroxyamine functionalities that are attached to various template backbones which display varying degrees of molecular recognition to phosphodiesters and varying degrees of sequence specific recognition to nucleic acids.

1 Claim, 70 Drawing Sheets

| Receptor | Anion | $K_a$, $M^{-1}$ [a] | $\Delta\delta_{max}$(OH) |
|---|---|---|---|
| 2·H⁺ | Cl⁻ | 49 ± 3 | + 0.11 |
| | (MeO)₂PO₂⁻ | 490 ± 12 | + 0.84 |
| 3·H⁺ | Cl⁻ | 36 ± 6 | + 0.09 |
| | (MeO)₂PO₂⁻ | 254 ± 27 | + 0.66 |
| 4·H⁺ | Cl⁻ | 51 ± 1 | − 0.01 |
| | (MeO)₂PO₂⁻ | 132 ± 19 | + 0.38 |
| 5·H⁺ | Cl⁻ | 53 ± 4 | + 0.08 |
| | (MeO)₂PO₂⁻ | 230 ± 25 | + 0.56 |
| 6·H⁺ | Cl⁻ | 27 ± 1 | N/A |
| | (MeO)₂PO₂⁻ | 342 ± 51 | N/A |

FIG. 3

□ RBE3
◇ wt-RRE-II
─○─ RBE3-neg
─△─ Neo16-bd

Rev 27:
Suc-CAAAATRQARRNRRRRWRERQRAAAAR-am

□ RBE3
◇ wt-RRE-II
─○─ RBE3-neg
─△─ Neo16-bd

Rev 27:
Suc-CAAAATRQARRNRRRRWRERQRAAAAR-am wt-RRE-II

RBE3

RBE3-neg

Neo16-bd

| | |
|---|---|
| $R^1$ | Cbz-Ala, Cbz-Arg(di-Cbz), Cbz-Asn, Cbz-Gln, Cbz-Gly, Cbz-Ile, Cbz-Leu Cbz-Lys(Cbz), Cbz-Phe, Cbz-Pro, Cbz-Thr, Cbz-Val, Cbz |
| $R^2$ | Bn, propyl, isopropyl, $(CH_2)_2NH_2$, $(CH_2)_3NH_2$, $CH_2CH(NH_2)CH_3$, $(CH_2)_4NH_2$, $(CH_2)_6NH_2$, $(CH_2)_2NHEt$, $(CH_2)_2NH(CH_2)_2NH_2$, $(CH_2)_3NH(CH_2)_3NH_2$, $(CH_2)_3NH(CH_2)_4NH(CH_2)_3NH_2$, $(CH_2)_4NH(CH_2)_3NH_2$, $(CH_2)_2NH(CH_2)_2NH_2$, $(CH_2)_2N(CH_2CH_2NH_2)_2$, $(CH_2)_2OH$, $(CH_2)_3OH$, $CH(CH_2OH)_2$ |
| $R^{1'}$ | Ala, Arg, Asn, Gln, Gly, Ile, Leu, Lys, Phe, Pro, Thr, Val, H |
| $R^{2'}$ | H, propyl, isopropyl, $(CH_2)_2NH_2$, $(CH_2)_3NH_2$, $CH_2CH(NH_2)CH_3$, $(CH_2)_4NH_2$, $(CH_2)_6NH_2$, $(CH_2)_2NHEt$, $(CH_2)_2NH(CH_2)_2NH_2$, $(CH_2)_3NH(CH_2)_3NH_2$, $(CH_2)_3NH(CH_2)_4NH(CH_2)_3NH_2$, $(CH_2)_4NH(CH_2)_3NH_2$, $(CH_2)_2NH(CH_2)_2NH_2$, $(CH_2)_2N(CH_2CH_2NH_2)_2$, $(CH_2)_2OH$, $(CH_2)_3OH$, $CH(CH_2OH)_2$ |

FIG. 20B

100: Neamine; R=H
200: Ribostamycin; R=β-D-ribose
300: Neomycin B : R= NH₂
400: Paromomycin : R=OH

| Compound | $K_d$ AS wt[a] ($\mu M$) | $K_d$ AS U1495A[a] ($\mu M$) | Specificity Factor[b] |
|---|---|---|---|
| 100 | 7.8 | 31 | 4 |
| 200 | 25 | 90 | 4 |
| 300 | 0.019 | 0.38 | 20 |
| 400 | 0.20 | 2.7 | 14 |
| 500 | 1.7 | 10 | 6 |
| 600 | 0.26 | 1.6 | 6 |
| 700 | 28 | 123 | 4 |
| 800 | 0.70 | 14 | 19 |
| Streptomycin | 95 | 74 | 1 |

FIG. 38

| Diameters of zones of inhibition (DZI), mm[a] | | | | |
|---|---|---|---|---|
| Antibiotic | Amount | E. coli | S. aureus | Ps.aeruginosa |
| 100 | 200nmol | 18.5 | 18.5 | N.I. |
| 200 | 33nmol | 16.5 | 14.5 | N.I. |
| 300 | 33nmol | 20.5 | 21.5 | 9.5 |
| 400 | 33nmol | 18 | 19.5 | N.I. |
| 500 | 33nmol | 18.5 | 18.5 | N.I. |
| 600 | 33nmol | 19 | 21 | N.I. |
| 700 | 33nmol | 16.5 | 11.5 | N.I. |
| 800 | 33nmol | 19 | 19.5 | N.I. |

FIG. 39A

| Minimum inhibitory concentrations (MICs) against E. coli ATCC 25922.[b] | | |
|---|---|---|
| Antibiotic | MIC ($\mu$M) | MIC ($\mu$g/mL) |
| 100 | 50 | 26 |
| 200 | 12.5 | 8 |
| 300 | 1.6 | 1.5 |
| 400 | 6.25 | 5.5 |
| 500 | 3.1 | 2.3 |
| 600 | 1.6 | 1.4 |
| 700 | 12.5 | 10 |
| 800 | 3.1 | 2.6 |

FIG. 39B

| | C1 | C2 | C3 | C4 | C5 | C6 | C1' | C2' | C3' | C4' | C5' | C6' |
|---|---|---|---|---|---|---|---|---|---|---|---|---|
| Neo B | 51.4 | 29.9 | 49.9 | 77.3 | 86.3 | 74.0 | 97.0 | 55.0 | 69.6 | 72.1 | 70.8 | 41.6 |
| 500 | 51.3 | 29.5 | 49.9 | 76.8 | 86.2 | 74.0 | 97.1 | 55.0 | 69.5 | 72.0 | 70.9 | 41.5 |
| 600 | 51.3 | 29.5 | 49.9 | 76.9 | 86.2 | 74.0 | 97.1 | 55.0 | 69.5 | 72.0 | 70.9 | 41.5 |
| 700 | 51.3 | 29.5 | 49.9 | 76.9 | 86.3 | 73.9 | 97.0 | 54.9 | 69.5 | 72.0 | 70.9 | 41.6 |
| 800 | 51.3 | 29.5 | 49.9 | 76.7 | 86.3 | 73.9 | 97.0 | 54.9 | 69.5 | 72.0 | 70.9 | 41.6 |

| | J (H2ax, H1) | J (H2eq, H1) | J (H2ax, H3) | J (H2eq, H3) |
|---|---|---|---|---|
| neo B | 12.6 Hz | 4.1 Hz | 12.6 Hz | 4.1 Hz |
| 500 | 12.6 Hz | 4.1 Hz | 12.6 Hz | 4.1 Hz |
| 600 | 12.6 Hz | 4.1 Hz | 12.6 Hz | 4.1 Hz |
| 700 | 12.6 Hz | 4.1 Hz | 12.6 Hz | 4.1 Hz |
| 800 | 12.6 Hz | 4.1 Hz | 12.6 Hz | 4.1 Hz |

| | J (H2ax, H2eq) | J (H3, H4) | J (H4, H5) | J (H5, H6) |
|---|---|---|---|---|
| neo B | 12.6 Hz | broad | broad | 9.4 Hz |
| 500 | 12.6 Hz | 10.5 Hz | 10.1 Hz | |
| 600 | 12.6 Hz | 10.4 Hz | 9.9 Hz | |
| 700 | 12.6 Hz | 10.3 Hz | 10.3 Hz | 9.2 Hz |
| 800 | 12.6 Hz | 10.2 Hz | 10.2 Hz | 9.3 Hz |

| | J (H1, H6) | J (H1', H2') | J (H2', H3') | J (H3', H4') |
|---|---|---|---|---|
| neo B | 10.4 Hz | 4.0 Hz | 10.8 Hz | 9.2 Hz |
| 500 | 10.7 Hz | 4.0 Hz | 10.8 Hz | 9.3 Hz |
| 600 | 10.6 Hz | 3.9 Hz | 10.9 Hz | 9.5 Hz |
| 700 | 10.6 Hz | 4.0 Hz | | 9.4 Hz |
| 800 | 10.4 Hz | 4.0 Hz | 10.9 Hz | 9.3 Hz |

| | J (H4', H5') | J (H5', H6'a) | J (H6'a, H6'b) |
|---|---|---|---|
| neo B | | 6.7 Hz | 13.6 Hz |
| 500 | 9.3 Hz | 6.4 Hz | 13.6 Hz |
| 600 | 9.5 Hz | 6.4 Hz | 13.2 Hz |
| 700 | 9.4 Hz | 6.3 Hz | 13.7 Hz |
| 800 | 9.3 Hz | 6.4 Hz | 13.7 Hz |

FIG. 40

| Compound | Footprints [a] | Resistance | Organism |
|---|---|---|---|
| Hygromycin B | G1494 (s)<br>A1408 (e) | U1495C | Tetrahymena |
| Neomycin B | G1494 (s) | G1491C [c] | E. coli |
| Paromomycin | A1408 (s) | G1491A [d] | Tetrahymena |
| Kanamycins | G1491 (w) | C1409G [d] | Yeast mitochondria |
| Gentamycins | C525 (e) | 7mG1405 [e] | Microm.purp. |
|  |  | 1mA1408 [f] | Strept. tenjim. |
| Neamine | G1494 (s) | 1mA1408 [f] | Strept. tenjim. |
| Apramycin | A1408 (s)<br>G1491 (w) |  |  |
| Ribostamycin |  | 1mA1408 [f] | Strept. tenjim. |

FIG. 42

| Sequence | $K_d$ (μM) |
|---|---|
| AS-wt | 0.15 |
| AS-U1495A | 2.83 |
| RBE3-neg | 3.19 |

| Compound | AS-wt | U1406A | U1495A | AS-res | ΔA1492 |
|---|---|---|---|---|---|
| Neomycin B | 0.019 | <0.01 | 0.38 | 0.48 | 0.32 |
| Ribostamycin-3″-R¹ | 0.26 | 0.075 | 1.6 | 0.89 | 0.58 |
| Paromomycin | 0.20 | 0.027 | 2.7 | 5.7 | 5.7 |
| 2″-OH-Neomycin B | 0.70 | 0.090 | 14 | 7.3 | 6.2 |
| Ribostamycin-3″-R² | 1.7 | 0.17 | 10 | 6.7 | 5.1 |
| Kanamycin B | 1.4 | 4.4 | 4.0 | 3.5 | 2.7 |
| Tobramycin | 1.5 | 2.1 | 4.1 | 7.9 | 4.5 |
| Gentamycin | 1.7 | 9.9 | 12 | 18 | 16 |
| Apramycin | 6.3 | 9.3 | 13 | | |
| 2‴,6‴-di-(OH)-Neo. B | 28 | 4.9 | >100 | >100 | >100 |
| Ribostamycin | 25 | 11 | 90 | 52 | 38 |
| Kanamycin A | 18 | 28 | 33 | 37 | 32 |
| Neamine | 7.8 | 5.5 | 31 | | |
| Butirosin | 27 | 1.8 | 99 | | |
| Paromamine | >100 | >100 | >100 | >100 | >100 |
| Hygromycin B | >100 | >100 | >100 | >100 | >100 |
| Streptomycin | 94 | 66 | 74 | | |

$R^1 = (CH_2)_2NH(CH_2)_3NH_2 \quad R^2 = (CH_2)_2NH_2$

FIG. 46

(structures of other aminoglycosides in Figure 1)

| Compound | AS-wt | U1495A | Specificity vs. U1495A |
|---|---|---|---|
| Paromomycin | | | |
| HBS-buffer alone | 0.20 | 2.7 | 14 |
| + 50 mM NH4Cl | 0.29 | 6.5 | 23 |
| + 150 mM NH4Cl | 1.1 | 32 | 28 |
| pH 7.8 | 0.53 | 7.7 | 15 |
| Neomycin B | | | |
| HBS-buffer alone | 0.019 | 0.38 | 20 |
| + 50 mM NH4Cl | 0.025 | 1.1 | 43 |
| + 150 mM NH4Cl | 0.15 | 6.7 | 43 |
| pH 7.8 | 0.044 | 0.91 | 21 |

FIG. 49

| Compound | Average $K_d$(nonspec.) (μM) | Specificity vs. AS-wt | Specificity vs. U1406A |
|---|---|---|---|
| 4,5-linked | | | |
| Neomycin B | 0.39 | 20 | >40 |
| Paromomycin | 4.7 | 20 | 200 |
| 2'''-OH-Neomycin B | 9.0 | 10 | 100 |
| 2''',6'''-di-(OH)-Neo. B | 150 | 5 | 30 |
| Ribostamycin-3''-$R^2$ | 7.4 | 4 | 40 |
| Ribostamycin-3''-$R^1$ | 1.0 | 4 | 10 |
| Butirosin | 99 | 4 | 60 |
| Neamine | 31 | 4 | 6 |
| Ribostamycin | 60 | 2 | 5 |
| 4,6-linked | | | |
| Gentamycin | 16 | 9 | 2 |
| Tobramycin | 5.5 | 4 | 3 |
| Kanamycin B | 3.4 | 2 | <1 |
| Apramycin | 13 | 2 | 1 |
| Kanamycin A | 34 | 2 | 1 |
| Control | | | |
| Streptomycin | 74 | <1 | 1 |

| Compound | Neo16-bd | AS-wt | RBE3 | RBE3-neg | wt-RRE-II |
|---|---|---|---|---|---|
| Neomycin B | <0.01 | 0.019 | 0.24 | 0.16 | 0.25 |
| Ribostamycin-3'''-R$^1$ | <0.01 | 0.26 | 0.38 | 0.56 | 0.31 |
| Paromomycin | 0.19 | 0.20 | 2.3 | 2.8 | 2.8 |
| 2'''-OH-Neomycin B | <0.01 | 0.70 | 3.1 | 3.5 | 7.8 |
| Ribostamycin-3'''-R$^2$ | <0.01 | 1.7 | 1.7 | 5.2 | 2.7 |
| Kanamycin B | 0.09 | 1.4 | 1.2 | 0.80 | 0.51 |
| Tobramycin | 0.39 | 1.5 | 0.38 | 0.16 | 0.41 |
| 2''',6'''-di-(OH)-Neo. B | 0.08 | 28 | 36 | 150 | 57 |
| Ribostamycin | 0.09 | 25 | 15 | 26 | 25 |
| Kanamycin A | 2.1 | 18 | 8.3 | 14 | 5.9 |
| Streptomycin | >100 | 94 | 100 | nd | 80 |

| Compound / temperature (°C) | AS-wt | Neo16bd | RBE3 |
| --- | --- | --- | --- |
| Paromomycin | | | |
| 500 | 0.058 | 0.059 | 1.4 |
| 1500 | 0.10 | 0.11 | 1.7 |
| 2500 | 0.18 | 0.19 | 2.4 |
| 3500 | 0.45 | 0.32 | 3.0 |
| Neomycin B [a] | | | |
| 500 | 0.11 | <0.01 | 2.2 |
| 1500 | 0.17 | <0.01 | 2.9 |
| 2500 | 0.22 | <0.01 | 3.2 | a conditions: HBS-buffer + 150 mM NH4Cl.

FIG. 52

| Sequence | $K_d$ (µM) |
|---|---|
| Neo16bd | <0.01 |
| AS-wt | 0.22 |
| RBE3 | 3.22 |

Phosphates

GC Base Pair

Hydroxyamines 1,3-

1,2-

|  | R¹CO | R²NH | AS-wt | U1406A | U1495A | AS-res | ΔA1492 |
|---|---|---|---|---|---|---|---|
| 15000a | Gly | GlyNH₂ | 110 | 81 | 95 | 140 | 120 |
| 15000b |  | AlaNH₂ | 140 | 110 | 120 | 430 | 270 |
| 15000c |  | ValNH₂ | 310 | 250 | 270 | >500 | >500 |
| 15000d |  | PheNH₂ | 60 | 43 | 71 | 120 | 100 |
| 15000g |  | NH₂ | 79 | 86 | 110 | 96 | 81 |
| 15000h |  | NH(CH₂)₂NH₂ | 38 | 38 | 39 | 64 | 46 |
| 16000a | Ala | GlyNH₂ | 34 | 25 | 27 | 54 | 37 |
| 16000b |  | AlaNH₂ | 480 | 320 | 350 | >500 | >500 |
| 16000c |  | ValNH₂ | >500 | >500 | >500 | >500 | >500 |
| 16000d |  | PheNH₂ | 170 | 150 | 150 | 180 | 130 |
| 16000g |  | NH₂ | 120 | 100 | 100 | 130 | 130 |
| 16000f |  | NH(CH₂)₂NH₂ | 59 | 57 | 57 | 83 | 56 |
| 17000a | Lys | GlyNH₂ | 26 | 31 | 34 | 43 | 62 |
| 17000b |  | AlaNH₂ | 66 | 48 | 55 | 150 | 92 |
| 17000c |  | ValNH₂ | 180 | 150 | 140 | 370 | 300 |
| 17000d |  | PheNH₂ | 290 | 260 | 240 | 350 | 360 |
| 17000g |  | NH₂ | 16 | 13 | 14 | 34 | 19 |
| 17000f |  | NH(CH₂)₂NH₂ | 19 | 18 | 17 | 51 | 30 |

6,120,997

SEQUENCE LISTING

<160> NUMBER OF SEQ ID NOS: 27

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: DNA
      template

<400> SEQUENCE: 1
taatacgact cactatag                                                       18

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence: DNA
      template

<400> SEQUENCE: 2
ggtgtaccgt cagccgaagc tgcgcccacc tatagtgagt cgtatta                       47

<210> SEQ ID NO 3
<211> LENGTH: 30
<212> TYPE: RNA
<213> ORGANISM: Artificial Sequence
<220> FEATURE:
<223> OTHER INFORMATION: Description of Artificial Sequence:
      5'-phosphorothioate-RNA nucleotide
<220> FEATURE:
<221> NAME/KEY: precursor_RNA
<222> LOCATION: (1)
<223> OTHER INFORMATION: 5'-phosphorothioate modified site

<400> SEQUENCE: 3 gguggcgca gcuucggcug acgguacacc                                           30

<210> SEQ ID NO 4
<211> LENGTH: 30
<212> TYPE: RNA
<213> ORGANISM: Artificial Sequence
<220> FEATURE:
<223> OTHER INFORMATION: Description of Artificial Sequence:
      5'-biotinylated-RNA
<220> FEATURE:
<221> NAME/KEY: stem_loop
<222> LOCATION: (1)
<223> OTHER INFORMATION: 5'-biotinylated modified site

<400> SEQUENCE: 4 gguggcgca gcuucggcug acgguacacc                                           30

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: synthetic
      peptide Rev27

<400> SEQUENCE: 5

Cys Ala Ala Ala Ala Thr Arg Gln Ala Arg Arg Asn Arg Arg Arg
 1               5                  10                  15

Trp Arg Glu Arg Gln Arg Ala Ala Ala Ala Arg

-continued

<210> SEQ ID NO 6
<211> LENGTH: 67
<212> TYPE: RNA
<213> ORGANISM: Human immunodeficiency virus type 1

<400> SEQUENCE: 6
ggcacuaugg gcgcagcguc aaugacgcug acgguacagg ccagacaauu auugucuggu     60
auagugc                                                               67

<210> SEQ ID NO 7
<211> LENGTH: 30
<212> TYPE: RNA
<213> ORGANISM: Artificial Sequence
<220> FEATURE:
<223> OTHER INFORMATION: Description of Artificial Sequence: REB3
      oligonucleotide

<400> SEQUENCE: 7
ggugggcgca gcuucggcug acgguacacc                                      30

<210> SEQ ID NO 8
<211> LENGTH: 28
<212> TYPE: RNA
<213> ORGANISM: Artificial Sequence
<220> FEATURE:
<223> OTHER INFORMATION: Description of Artificial Sequence: RBE3-neg
      oligonucleotide

<400> SEQUENCE: 8
gguguccgca gcuucggcug cggacacc                                        28

<210> SEQ ID NO 9
<211> LENGTH: 29
<212> TYPE: RNA
<213> ORGANISM: Artificial Sequence
<220> FEATURE:
<223> OTHER INFORMATION: Description of Artificial Sequence: Neo16-bd
      oligonucleotide

<400> SEQUENCE: 9
ggcguccugg gcgagaaguu uaggacgcc                                       29

<210> SEQ ID NO 10
<211> LENGTH: 13
<212> TYPE: RNA
<213> ORGANISM: Escherichia coli

<400> SEQUENCE: 10
cgcccgucac acc                                                        13

<210> SEQ ID NO 11
<211> LENGTH: 15
<212> TYPE: RNA
<213> ORGANISM: Escherichia coli

<400> SEQUENCE: 11
ggugaagucg uaaca                                                      15

<210> SEQ ID NO 12
<211> LENGTH: 27
<212> TYPE: RNA
<213> ORGANISM: Artificial Sequence
<220> FEATURE:

<223> OTHER INFORMATION: Description of Artificial Sequence: AS-wt

<400> SEQUENCE: 12
ggcgucacac cuucggguga agucgcc                                              27

<210> SEQ ID NO 13
<211> LENGTH: 27
<212> TYPE: RNA
<213> ORGANISM: Artificial Sequence
<220> FEATURE:
<223> OTHER INFORMATION: Description of Artificial Sequence: AS-U1495A

<400> SEQUENCE: 13
ggcgucacac cuucggguga agacgcc                                              27

<210> SEQ ID NO 14
<211> LENGTH: 27
<212> TYPE: RNA
<213> ORGANISM: Artificial Sequence
<220> FEATURE:
<223> OTHER INFORMATION: Description of Artificial Sequence: AS-U1406A

<400> SEQUENCE: 14
ggcgacacac cuucggguga agucgcc                                              27

<210> SEQ ID NO 15
<211> LENGTH: 26
<212> TYPE: RNA
<213> ORGANISM: Artificial Sequence
<220> FEATURE:
<223> OTHER INFORMATION: Description of Artificial Sequence: AS-A1492

<400> SEQUENCE: 15
ggcgucacac cuucggguga gucgcc                                               26

<210> SEQ ID NO 16
<211> LENGTH: 27
<212> TYPE: RNA
<213> ORGANISM: Artificial Sequence
<220> FEATURE:
<223> OTHER INFORMATION: Description of Artificial Sequence: AS-res

<400> SEQUENCE: 16
ggcgucauac cuucggguca agucgcc                                              27

<210> SEQ ID NO 17
<211> LENGTH: 27
<212> TYPE: RNA
<213> ORGANISM: Artificial Sequence
<220> FEATURE:
<223> OTHER INFORMATION: Description of Artificial Sequence: AS-U1495A

<400> SEQUENCE: 17
ggcgucacac cuucggguga agacgcc                                              27

<210> SEQ ID NO 18
<211> LENGTH: 13
<212> TYPE: RNA
<213> ORGANISM: Saccharomyces cerevisiae

<400> SEQUENCE: 18
gcccgucgcu agu                                                             13

<210> SEQ ID NO 19
<211> LENGTH: 15

```
<212> TYPE: RNA
<213> ORGANISM: Saccharomyces cerevisiae

<400> SEQUENCE: 19
acuaaaaguc guaac                                                    15

<210> SEQ ID NO 20
<211> LENGTH: 12
<212> TYPE: RNA
<213> ORGANISM: Saccharomyces cerevisiae

<400> SEQUENCE: 20
gcccgucacg cg                                                       12

<210> SEQ ID NO 21
<211> LENGTH: 14
<212> TYPE: RNA
<213> ORGANISM: Saccharomyces cerevisiae

<400> SEQUENCE: 21
ugcgaagucg uaac                                                     14

<210> SEQ ID NO 22
<211> LENGTH: 12
<212> TYPE: RNA
<213> ORGANISM: Nicotiana tabacum

<400> SEQUENCE: 22
gcccgucaca cu                                                       12

<210> SEQ ID NO 23
<211> LENGTH: 14
<212> TYPE: RNA
<213> ORGANISM: Nicotiana tabacum

<400> SEQUENCE: 23
agugaagucg uaac                                                     14

<210> SEQ ID NO 24
<211> LENGTH: 13
<212> TYPE: RNA
<213> ORGANISM: Homo sapiens

<400> SEQUENCE: 24
gcccgucccu acu                                                      13

<210> SEQ ID NO 25
<211> LENGTH: 15
<212> TYPE: RNA
<213> ORGANISM: Homo sapiens

<400> SEQUENCE: 25
aguaaaaguc guaac                                                    15

<210> SEQ ID NO 26
<211> LENGTH: 14
<212> TYPE: RNA
<213> ORGANISM: Homo sapiens

<400> SEQUENCE: 26
gcccgucacc cucu                                                     14

<210> SEQ ID NO 27
```

```
<211> LENGTH: 16
<212> TYPE: RNA
<213> ORGANISM: Homo sapiens

<400> SEQUENCE: 27
agagacaagu cguaac                                         16
```

NUCLEIC ACID BINDERS HAVING AN HYDROXYAMINE MOTIF

This Application claims benefit of provisional application 60/035,483 Jan. 13, 1997.

SPECIFICATION

1. Field of the Invention

The present invention relates to a class of compounds and libraries thereof which inhibit protein synthesis by binding to nucleic acids by means of an hydroxyamine motif. The present invention also relates to methods for synthesizing such compounds and for assaying the nucleic acid binding activity of such compounds. More particularly, the present invention relates to compounds having hydroxyamine motifs attached to template backbones which mediate binding to phosphodiesters and to specific nucleotide sequences.

2. Background

A number of compounds with known therapeutic utility contain hydroxyamine substructures. Neomycin B belongs to the class of naturally occuring aminoglycoside antibiotics possessing antibacterial activity (Moellering, R. C. in *Reviews of Infectious Diseases* Vol. 5, Suppl. 2, S212–232). It contains several 1,2 and 1,3-hydroxyamine substructures. Neamine, a pseudodisaccharide, belongs to the same class and it too has hydroxyamine substructures. Both compounds have been shown to interact directly with RNA (Moazed, D.; Noeller, H. F. *Nature* 1987, 327, 389–394; Woodcock, J.; Moazed, D.; Cannon, M.; Davies, J.; Noeller, H. F. *EMBO J.* 1991, 10, 3099–3103). Amikacin is a semisynthetic aminoglycoside antibiotic active against bacteria which carries an acyl side chain containing a 1,3-hydroxyamines.

There are also examples of naturally occuring peptide antibiotics containing nonstandard aminoacids which have hydroxyamines. For example, tuberactinomycin A inhibits both initiation and elongation steps of bacterial protein synthesis (Liou, Y. F.; Tanaka, N. *Biochem. Biophys. Res. Commun.* 1976, 71, 477–483). Another example is negamycin, which also posseses antibacterial potency (Hamada, M.; Takeuchi, T.; Kondo, S.; Ikeda, Y.; Naganawa, H. *J. Anibiot.* 1970, 23, 170–171; Japan. pat. 71 28,835, 1971). Like neomycin B or neamine, this antibiotic also induces miscoding during translation (Uehara, Y.; Kondo, S.; Umezawa, H.; Suzukake, K.; Hori, M. *J. Antibiot.* 1972, 25, 685–688).

The molecular recognition of phosphodiesters has received much attention due to its biological importance. In protein-nucleic acid complexes, binding of the phosphodiester backbone is often achieved through a dense network of hydrogen bonding frequently involving a bidentate interaction with the guanidinium group of arginine (Sanger et al. *Principles of Nucleic Acid Structure* Springer:New York, Berlin, 1983; X-Ray structures of RNA-protein complexes: Rould et al. *Science* 1989, 246, 1135; Ruff et al *Science* 1991, 252, 1682; Biou et al. *Science* 1994, 263, 1404; Valegard et al. *Nature* 1994, 371, 623). In order to identify the underlying principles of phosphodiester recognition in biological systems, various phosphate receptor models have been developed, including synthetic receptors incorporating guanidinium moieties (Hamilton et al. *Bioorganic Chemistry Frontiers*, Vol. 3 (Eds.:H. Dugas, F. P. Schmidtchen), Springer, Heidelberg 1993, p193–255; Dietrich et al. *J. Chem. Soc. Chem. Comm.* 1978, 934; Dietrich et al. *Helv. Chim. Acta* 1979, 62, 2763; Müller et al. *Angew. Chem.* 1988, 100, 1574; *Angew. Chem. Int. Ed. Engl.* 1988, 27, 1516; Schmidtchen et al. *Tetrahedron Lett.* 1989, 30, 4493; Kurzmeier et al. *J. Org. Chem.* 1990, 55, 3749; Galán et al. *Tetrahedron Lett.* 1991, 32, 1827; Galáan et al. *J. Am. Chem. Soc.* 1991, 113, 9424 Ariga et al. *J. Org. Chem.* 1992, 57, 417; Deslongchamps et al. *Angew. Chem.* 1992, 104, 58; *Angew. Chem. Int. Ed. Engl.* 1992, 31, 61; Kneeland et al. *J. Am. Chem. Soc.* 1993, 115, 10042; Schiessl et al. *J. Org. Chem.* 1994, 59, 509; Kato et al. *Angew. Chem.* 1995, 107, 1343; *Angew. Chem. Int. Ed. Engl.* 1995, 34, 1237), linear and macrocyclic polyamines (Dietrich et al. *J. Am. Chem. Soc.* 1981, 103, 1282; *Helv. Chim. Acta* 1983, 66, 1262; Kodama et al. *J. Chem. Soc. Dalton Trans.* 1980, 2536; Kimura et al. *J. Am. Chem. Soc.* 1982, 104, 3182; Marecek et al. *Tetrahedron Lett.* 1988, 29, 6231), ureas (Kelly et al. *J. Am. Chem. Soc.* 1994, 116, 7072), amidines (Göbel et al. *Angew. Chem.* 1992, 104, 217; *Angew. Chem. Int. Ed. Engl.* 1992, 31, 207; Müller et al. *Liebigs, Ann. Chem.* 1994, 1075 ), aminopyridines (Flatt et al. *Tetrahedron Lett.* 1992, 33, 2785; Chu et al. *J. Am. Chem. Soc.* 1994, 116, 4194), porphyrins (Iverson et al. *J. Am. Chem. Soc.* 1993, 115, 11022; Aoyama et al. *Chem. Lett.* 1991, 1241) and uranyl complexes (Rudkevitch et al. *J. Am. Chem. Soc.* 1992, 114, 9671; Rudkevitch et al. *J. Am. Chem. Soc* 1994, 116, 4341).

Aminoglycoside antibiotics (Aminoglycoside Antibiotics (Eds.: H. Umezawa, I. R. Hooper) Springer Verlag, New York, Heidelberg, 1982) have been shown to directly interact with a number of RNA sequences (Moazed et al. *Nature* 1987, 327, 389; von Ahsen et al. *Nature* 1991, 353, 368; von Ahsen et al. *J. Mol. Biol.* 1992, 226, 935; Stage et al. RNA 1995, 1, 95; Clouet-d'Orval et al. *Biochemistry* 1995, 34, 11186) including two important HIV regulatory domains, RRE (Zapp et al. *Cell* 1993, 74, 969; Werstuck et al. *Chem. & Biol.* 1996, 3, 129) and TAR (Mei et al. *Bioorganic & Med. Chem. Lett.* 1995, 5, 2755).

Although it has long been known that aminoglycosides have a general affinity for RNA, much remains uncertain about their mechanism of action (Tanaka, N. "Mechanism of Action of Aminoglycosides Antibiotics" in *Handbook of Experimental Pharmacology* 1982, 62, 221; Cundliffe, E. "Recognition Sites for Antibiotics within rRNA" in *The Ribosome*; Hill, W. E. et al. (Eds.) 1990, 479; Noller, H. F. *Annu. Rev. Biochem.* 1991, 60, 191). Their bactericidal effects are thought to be due to interference with the proper functioning of the prokaryotic ribosome. Several antibiotic binding sites have been identified by footprinting on the *E. coli* 16S ribosomal RNA (Moazed et al. *Nature* 1987, 327, 389; Puhroit et al. *Nature*, 1994, 370, 659; Recht et al. *J. Mol. Biol.* 1996, 262, 421; Miyaguchi et al. *Nucl. Acids Res.* 1996, 24, 3700). Aminoglycosides of the neomycin family bind to the A-site of the ribosomal decoding region and induce translational misreading (Davies et al. *J. Biol. Chem.* 1968, 243, 3312) Very recently an NMR structure of the complex of paromomycin with an A-site analog RNA hairpin has been reported (Fourmy et al. *Science* 1996, 274, 1367). Paromomycin sits in a pocket created by a bulged residue and a non-canonical A:A base pair stacking against the underside of another base pair. Specific contacts are formed to hydrogen bond acceptors in the RNA major groove and certain phosphates, including the apparent tridentate interaction of one amine and two hydroxyl groups with a particular phosphodiester oxygen. A few other naturally occurring aminoglycoside binding sites have also been discovered. In addition to the HIV regulatory sequences RRE and TAR, these include the group I intron (von Ahsen et al. *Nature* 1991, 353, 368; von Ahsen et al. *J. Mol.Biol.* 1992, 226, 935; von Ahsen et al. *Science* 1993, 260, 1500 and hammerhead ribozyme (Stage et al. *RNA*, 1995, 1, 95; Clouet-d'Orval et al. *Biochemistry* 1995, 34, 11186) both of which interact most strongly with neomycin B. Other aminoglycoside-binding RNA sequences have been derived by in vitro selection, stimulated in part by the hypothesis that antibiotics may have played a role in the evolution of an RNA world as so-called low-molecular-weight effectors (Davies et al. *J. Molec. Microbiol.* 1990, 4, 1227; Davies et al. in "The RNA World", Gesteland, R. F.; Atkins, J. F. (Eds.) Cold Spring Harbor Laboratory Press, New York 1993, 185; Schroeder et al. *Science* 1993, 260, 1443; Hirao et al. *Curr. Biol.* 1995, 5, 1017.

Targeting specific RNA sequences with small molecule drugs is a potentially attractive approach to the therapy of many diseases. Aminoglycosides belong to the small group of low molecular weight compounds known to date that bind selectively to specific RNA sequences. Neomycin B and related structures, for example, have been shown to bind two important regulatory domains in HIV-1 mRNA, the Rev responsive element (RRE) and the trans-activation response element (TAR), and inhibit binding of their cognate proteins Rev and Tat, respectively. By facilitating the nuclear export and subsequent expression of unspliced or partially spliced mRNAs, Rev acts as a crucial switch between viral latency and active viral replication.

What is needed is a class of compounds or library of compounds with a common functionality which displays strong molecular recognition for phosphodiesters and sequence specific recognition for nucleic acids for inhibition of translation or transciption related processes.

SUMMARY OF THE INVENTION

One aspect of the invention is directed generally to a class of compounds which include an hydroxyamine motif capable of inhibiting protein synthesis by binding with nucleic acids.

Another preferred embodiment of these hydroxyamine containing compounds is represented by the following structure:

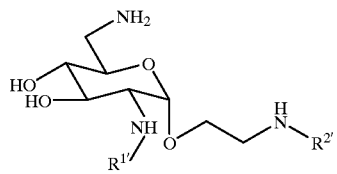

In the preferred species of this embodiment, $R^{1'}$ is selected from a group consisting of a hydrogen radical and amide linked radicals of the following amino acids: Ala, Arg, Asn, Gln, Gly, Ile, Leu, Lys, Phe, Pro, Thr, and Val, and $R^{2'}$ is selected from a group consisting of the following radicals —H, propyl, isopropyl, —$(CH_2)_2NH_2$, —$(CH_2)_3NH_2$, —$CH_2CH(NH_2)CH_3$, —$(CH_2)_4NH_2$, —$(CH_2)_6NH_2$, —$(—H_2)_2NHEt$, —$(CH_2)_2NH(CH_2)_2NH_2$, —$(CH_2)_3NH(CH_2)_3NH_2$, —$(CH_2)_3NH(CH_2)_4NH(CH_2)_3NH_2$, —$(CH_2)_4NH(CH_2)_3NH_2$, —$(CH_2)_2NH(CH_2)_2NH(CH_2)_2NH_2$, —$(CH_2)_2N(CH_2CH_2NH_2)_2$, —$(CH_2)_2OH$, —$(CH_2)_3OH$, and —$CH(CH_2OH)_2$.

Another preferred embodiment of these hydroxyamine containing compounds is represented by the following structure:

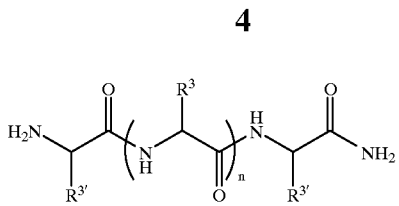

In this embodiment, $0 \leq n \leq 18$ and each $R^{3'}$ is independently selected from the group consisting of side chains of naturally occuring amino acids and radicals represented by the following structures:

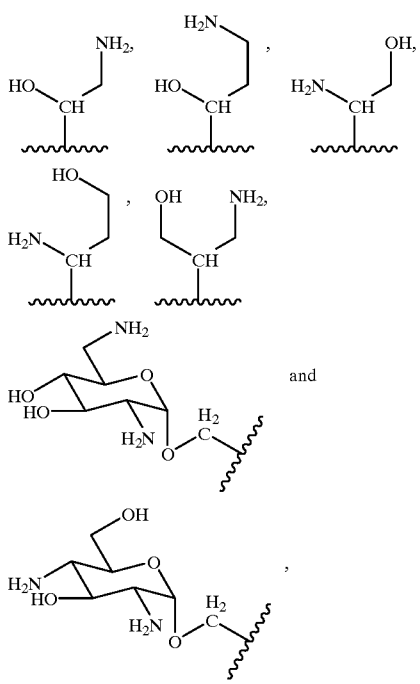

However, there is a proviso that for $0 \leq n \leq 1$, all of the $R^{3'}$ are selected from said radicals only, and for $2 \leq n \leq 18$, at least 3 of $R^{3'}$ are selected from said radicals.

Another preferred embodiment of these hydroxyamine containing compounds is represented by the following structure:

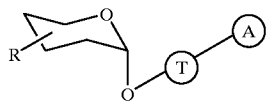

wherein

is selected from a group consisting of diradicals represented by the following structures:

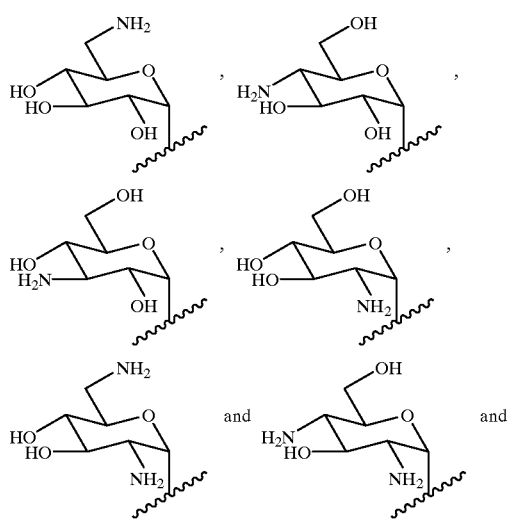

wherein ⓣ is selected from a group consisting of radicals represented by the following structures:

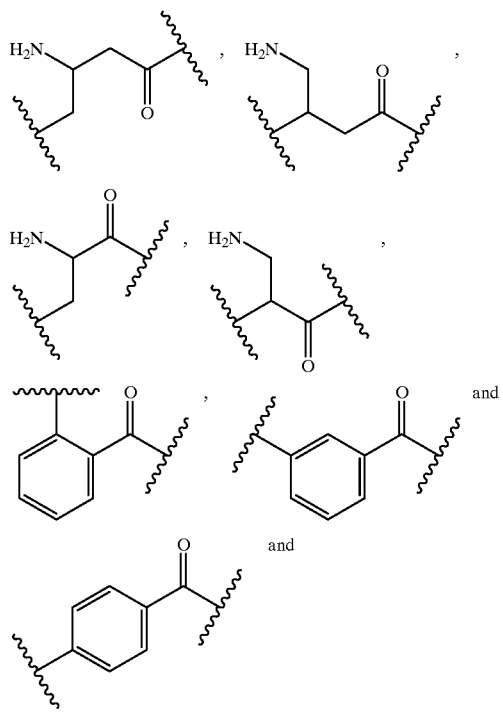

wherein Ⓐ is selected from a group consisting of radicals represented by the following structures:

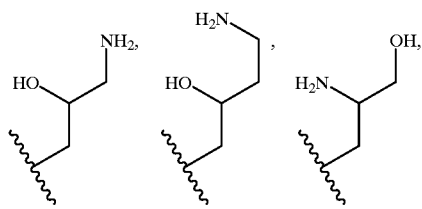

-continued

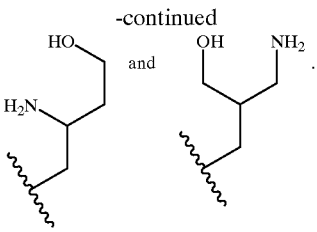

wherein the carbonyl of ⓣ is linked to Ⓐ.

Another preferred embodiment of these hydroxyamine containing compounds is represented by the following structure:

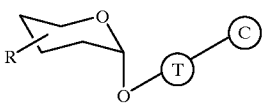

wherein

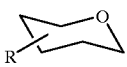

is selected from a group consistinig of radicals represented by the following structures:

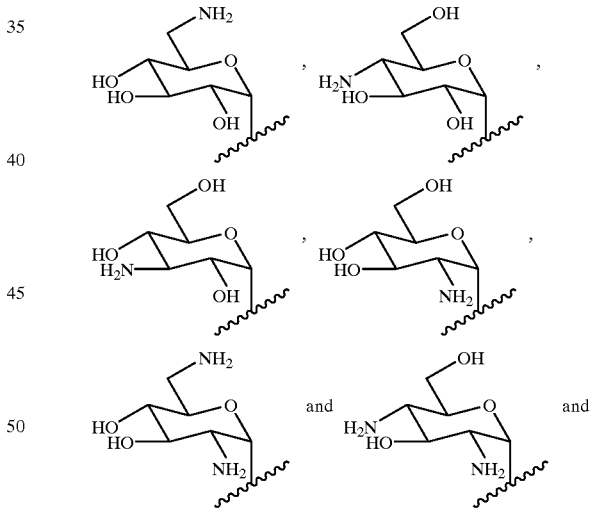

wherein ⓣ is selected from a group consistinig of diradicals represented by the following structures:

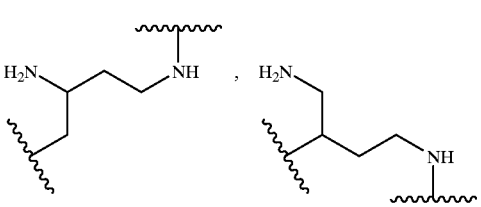

-continued

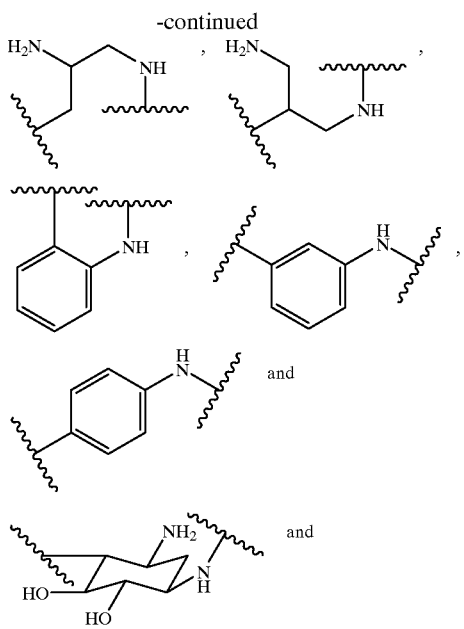

wherein Ⓒ is selected from a group consisting of radicals represented by the following structures:

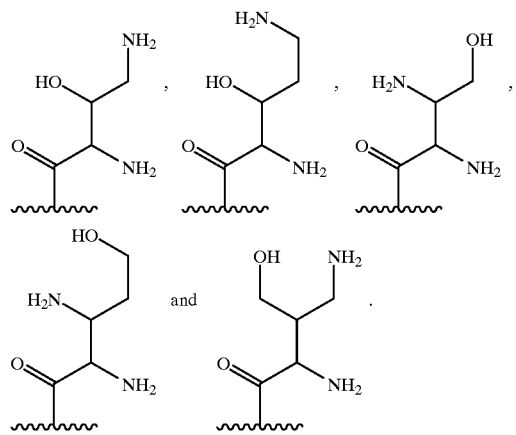

wherein the carbonyl of Ⓣ is linked to Ⓒ.

Another embodiment of these hydroxyamine containing compounds is represented by the following structure:

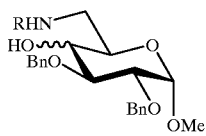

wherein R is selected from the group of radicals consisting of H and benzyl. Preferred species within this embodiment include compounds represented by the following structures:

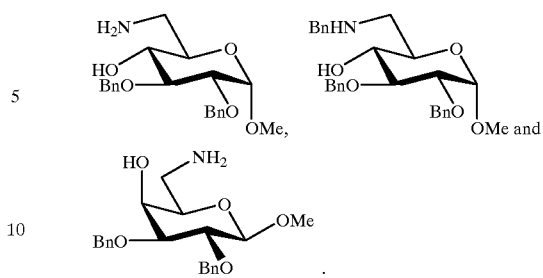

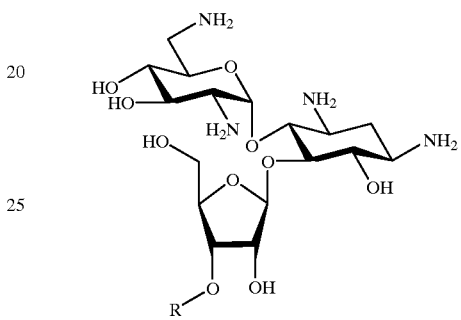

Another preferred embodiment of these hydroxyamine containing compounds is represented by the following structure:

$$\text{(structure)}$$

wherein R is selected from a group consisting of a radical represented by one of the following structures:

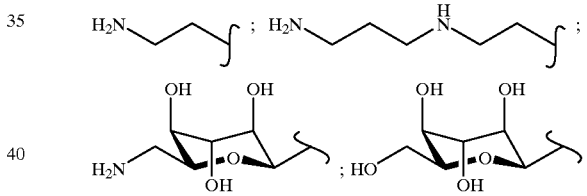

Another aspect of the invention is directed to a library of the above compounds having nucleic acid binding hydroxyamine substructures. Each library includes a plurality of the compounds described above.

Another aspect of the invention is directed to methods for synthesizing the compounds described above.

Another aspect of the invention is directed to a sensorchip employable for surface plasmon resonance having a surface with immobilized RNA attached thereto. In a preferred sensorchip, the surface is coated with streptavidin, the RNA is biotinylated, and the RNA is immobilized onto the surface of the sensochip by streptavidin/biotin binding. In another preferred embodiment, a compound with a nucleic acid binding hydroxyamine substructure is bound to the surface of the sensorchip. In this embodiment, the preferred compounds are as described above. Another aspect of the invention is directed to a method for detecting binding of a compound to RNA. The method includes a first step wherein the compound is contacted with sensorchip employable for surface plasmon resonance. Then the surface plasmon resonance of the sensorchip is compared with and without contact with compound.

BRIEF DESCRIPTION OF FIGURES

FIG. 3 shows binding constants for hydroxyamines vs. guanidine. [a] NMR dilution experiments with the preformed 1:1 salt complexes were performed in DMSO-$d_6$ at 293Å1 K; [b] calculated maximum shift at full complexation in ppm.

FIGS. 20A and 20B illustrate the synthesis of library 23 wherein $R^{1'}$ and $R^{2'}$ represent various combinations of the indicated functionalities. Compound 18 is selected from the group consisting of Cbz-Ala-OSu, Cbz-Arg(di-Cbz)-OSu, Cbz-Asn-ONp, Cbz-Gln-ONp, Cbz-Gly-OSu, Cbz-Ile-OSu, Cbz-Leu-OSu, Cbz-Lys(Cbz)-OSu, Cbz-Phe-OSu, Cbz-Pro-OSu, Cbz-Thr-OSu, Z-Val-OSu, Cbz-OSu wherein Su=succinimide; Np=p-nitrophenyl. Compound 20 is selected from the group consisting of benzylamine, propylamine, isopropylamine, ethylenediamine, 1,3-diaminopropane, 1,2-diaminopropane, 1,4-diaminobutane, 1,6-hexanediamine, N-ethylethylenediamine, diethylenetriamine, 3,3'-iminobispropylamine, spermine, spermidine, triethylenetetramine, tris(2-aminoethyl)amine, ethanolamine, 3-aminopropanol, serinol or their hydrochloride salts available from Aldrich.

FIG. 38 shows a table displaying in vitro binding data for the natural antibiotics and synthetic analogs used in this study (a) All Kd values were determined in duplicate except for Kd (AS wt) of 400 and 800 which were determined in triplicate. The deviation from the mean was <100% in all cases. The standard deviation for Kd (AS wt) of 400 and 800 was 29% and 49%, respectively. Solution conditions: 150 mM NaCl, 10 mM HEPES (pH 7.4), 3.4 mM EDTA. (b) Kd (AS U1495A)/Ki (AS wt).

FIG. 39 shows a table displaying antibacterial activities of aminoglycosides: (a) The zones of inhibition as determined by the Kirby-Bauer disc method are given. In the case of neomycin, 30 mg (33 nmol) of neomycin sulfate was used per disc. For all other compounds, the molar amount was kept constant at 33 nmol, except for the neamine standard, which was increased 6-fold due to its low activity; (b) The minimum inhibitory concentrations are given in both mM and mg/mL. (Weight/mL was calculated based on the predicted molecular weights of the compounds' sulfate salts.) N.I=no inhibition.

FIG. 40 shows a table displaying 13C-NMR shifts and coupling constants of neomycin B and the synthetic analogs.

FIG. 42 illustrates biochemical evidence for the interaction of some aminoglycoside antibiotics with ribosomal decoding region A-site RNA. (Data taken from (a) Cundliffe, E. in "The Ribosome: Structure, Function and Evolution", Hill, W. E. et al. (Eds.), American Society for Microbiology, Washington DC 1990, p. 479ff (b) Moazed, D.; Noller, H.; F. Nature 1987, 327, 389 (c) Woodcock, J.; Moazed, D.; Cannon, M.; Davies, J.; Noller, H.; F. EMBO J. 1989, 8, 607). The following footnotes: (a) on E. coli 70S ribosome (b) suppresion of dependence (c) broad spectrum (d) paromomycin (e) gentamycin, kanamycin (f) kanamycin, ribostamycin, neamine, apramycin.

FIG. 46 shows a table of the binding of aminoglycosides to variants of the decoding region A-site. (All values are dissociation constants in units of mM).

FIG. 49 shows a table which indicates the influence of pH and ionic strength on the specificity of RNA recognition. (Values of dissociation constants in units of mM).

FIG. 50 shows specificity of recognition of AS-wt and AS-U1406A. (compound Average Kd(nonspec.)).

FIGS. 51A and 51B show a table which indicates binding of aminoglycosides to an RNA aptamer and variants of the HIV Rev Responsive Element (RRE). (Values of dissociation constants in units of mM) (SEQ ID NOS 6–9).

FIG. 52 shows a table which indicates influence of temperature on the specificity of RNA recognition (Values of dissociation constants in units of mM).

DETAILED DESCRIPTION OF THE INVENTION

Figure 1:
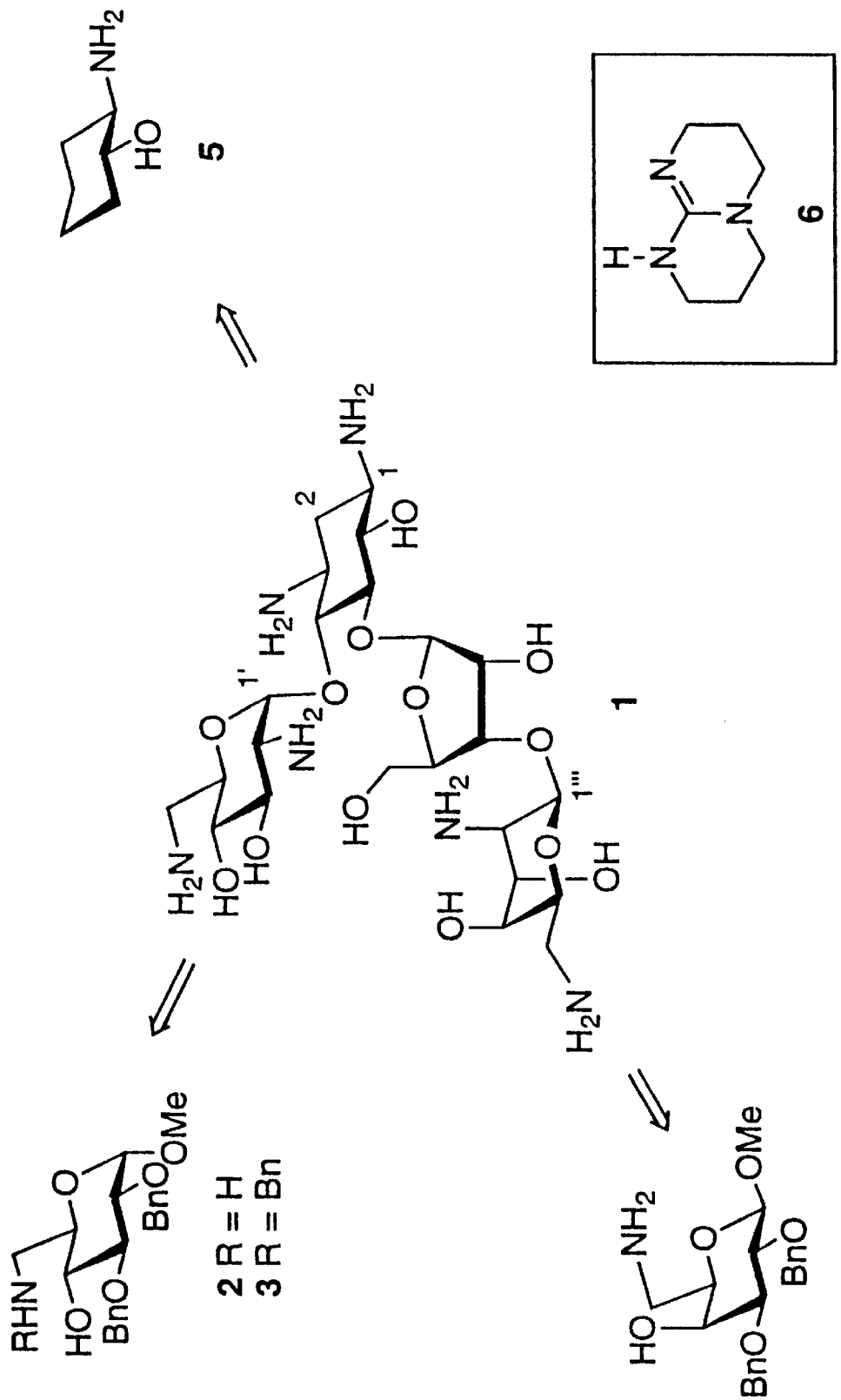
FIG. 1 illustrates the structure of neomycin B (1) and model compounds 2–5 designed to isolate 1,3- and 1,2-trans-hydroxyamine substructures and study their phosphodiester recognition capabilities. Bicyclic guanidine 6 is a known phosphate binder included as a reference.

The invention is directed to hydroxyamine core structures commonly found in aminoglycoside antibiotics as a new recognition motif for the complexation of phosphodiesters and the Hoogsten face of guanosine. This core structure should find useful applications in many molecular recognition systems where the complexation of phosphodiesters is desired. A further embodiment of the invention relates to the combination of hydroxyamines with other nucleic acid binding motifs to generate molecules and libraries of molecules targeting specific nucleic acid sequences.

General Description of the Library Design

Libraries containing hydroxyamine binding motifs are being constructed in three different ways: (1) Using a carbohydrate as the scaffold by sequential acylation and reductive amination. These libraries are related to neamine and neomycin B, sharing the 2,6-diaminoglucose ring, the alpha-glycosidic linkage and one aminogroup of the 2-deoxystreptamine ring. (2) Using a peptide scaffold by condensing amino acid type building blocks. These libraries are related to peptide antibiotics such as tuberactnomycin A. (3) Using a template for sequential glycosidation and acylation. These libraries are related to aminoglycosides neomycin B, neamine and also amikacin, which has an acyl side chain attached to its 2-deoxystreptamine ring.

EXAMPLE 1

Synthesis and Exemplary Use of Hydroxylamine Containing Libraries as Inhibitors of Protein Synthesis The construction of libraries having a sugar scaffold (FIGS. 19–20) starts with N-acetylglucosamine (13) which is transformed to common precursor 17. This can then be acylated using succinimide esters 18 or any other suitably activated acyldonor. A free aldehyde is subsequently revealed by ozonolysis. Other protected precursors of the aldehyde function may be used instead of the terminal alkene (e.g., a dialkylacetal cleaved by mild acid). The aldehyde is then reacted with any primary amine 21 to give 13 which is deprotected to 23.

Construction of hydroxyamine containing libraries having a peptide scaffold (FIG. 21) relies on the unnatural aminoacids 24–30. The hydroxy and amino functions of these building blocks are suitably blocked as benzyl and carboxybenzyl (Cbz) derivatives, respectively, but other protecting groups may be used as applicable. These are ondensed using standard peptide coupling methods to dipeptides 31 and tripeptides 32. These are deprotected to 33.

Figure 22:
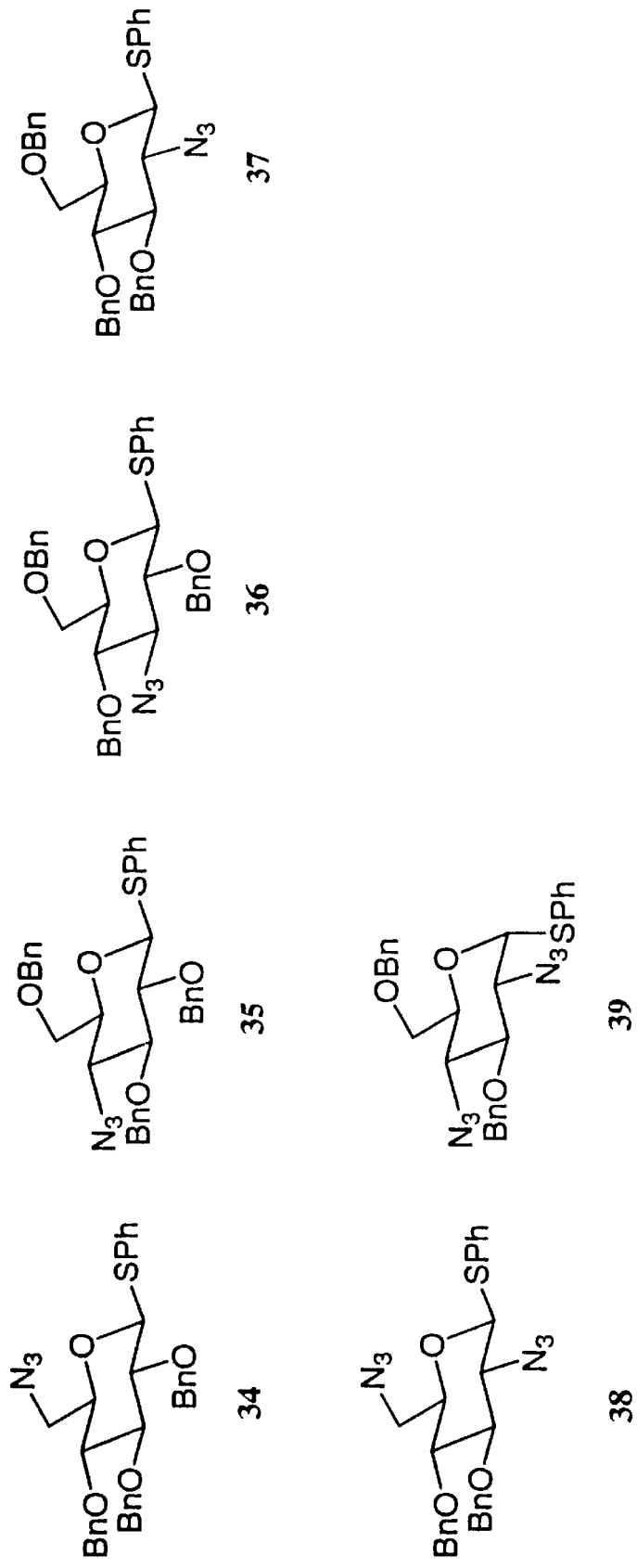
FIG. 22 illustrates the template molecules for the libarary formed in FIGS. 24 and 25.
Figure 23A:
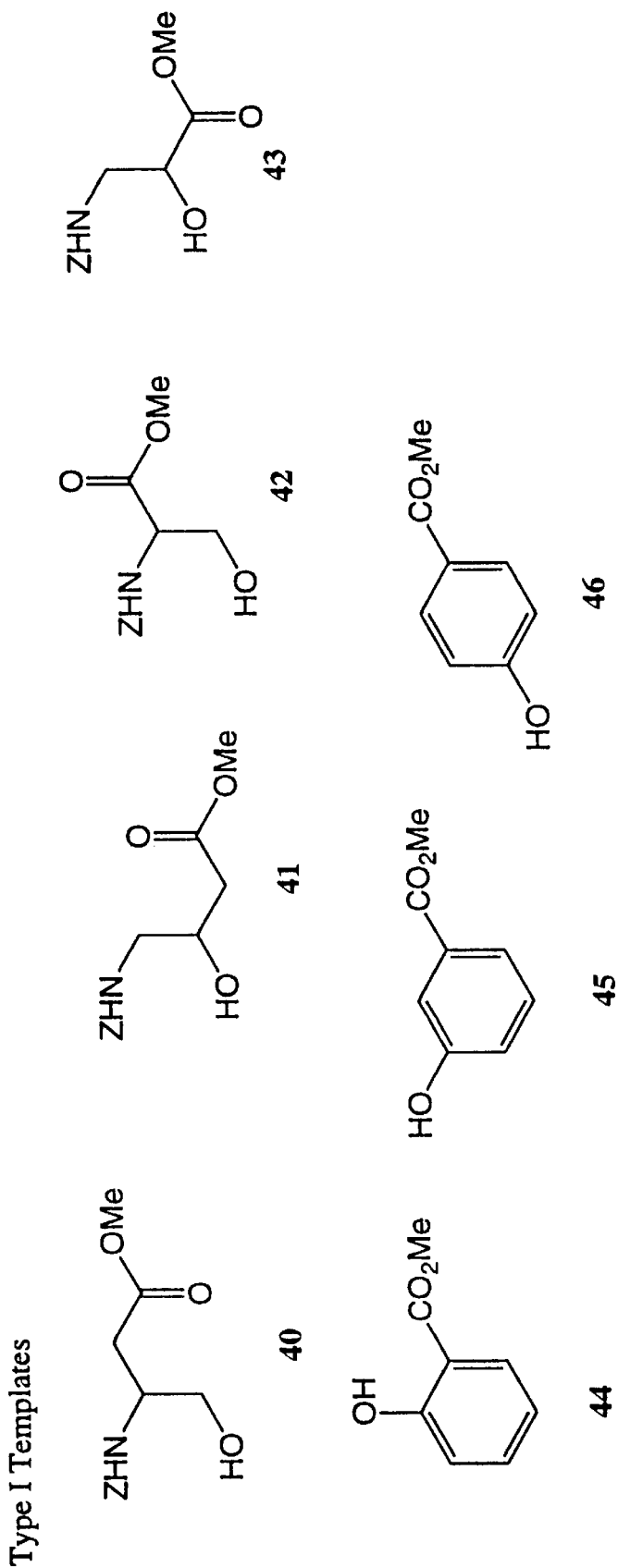
FIGS. 23A and 23B illustrate the template molecules for the libarary formed in FIGS. 24 and 25.
Figure 23B:
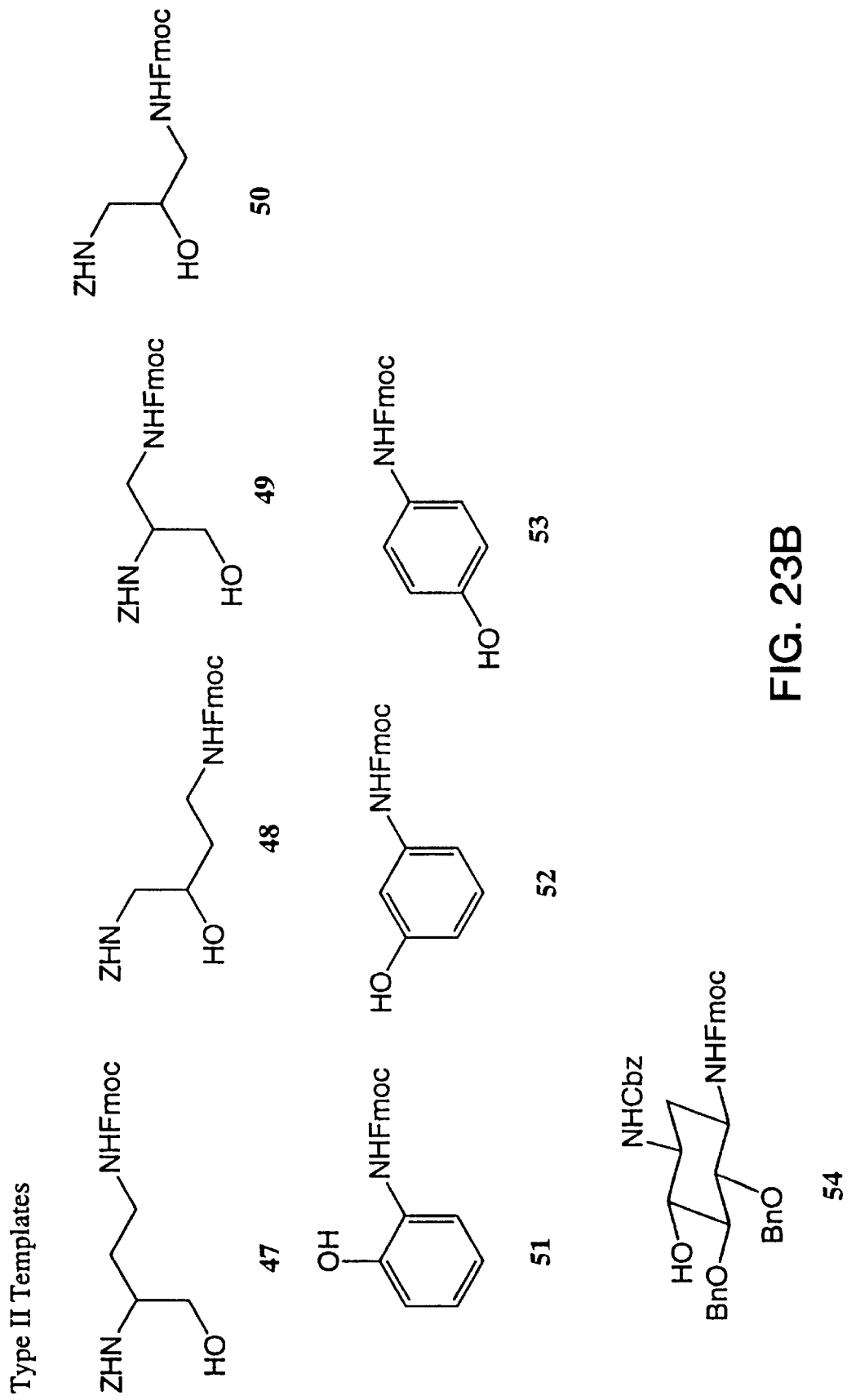

For the construction of building libraries using sequential glycosidation and acylation the glycosyl donors 34–39 containing protected hydroxyamine structures are used (FIG. 22). To types of templates are used as shown in FIG. 23. Type I templates contain a free hydroxyl group and a masked carboxylic acid (40–46). Type II templates contain a free hydroxyl group and a masked amino group (47–59).

Figure 24A:
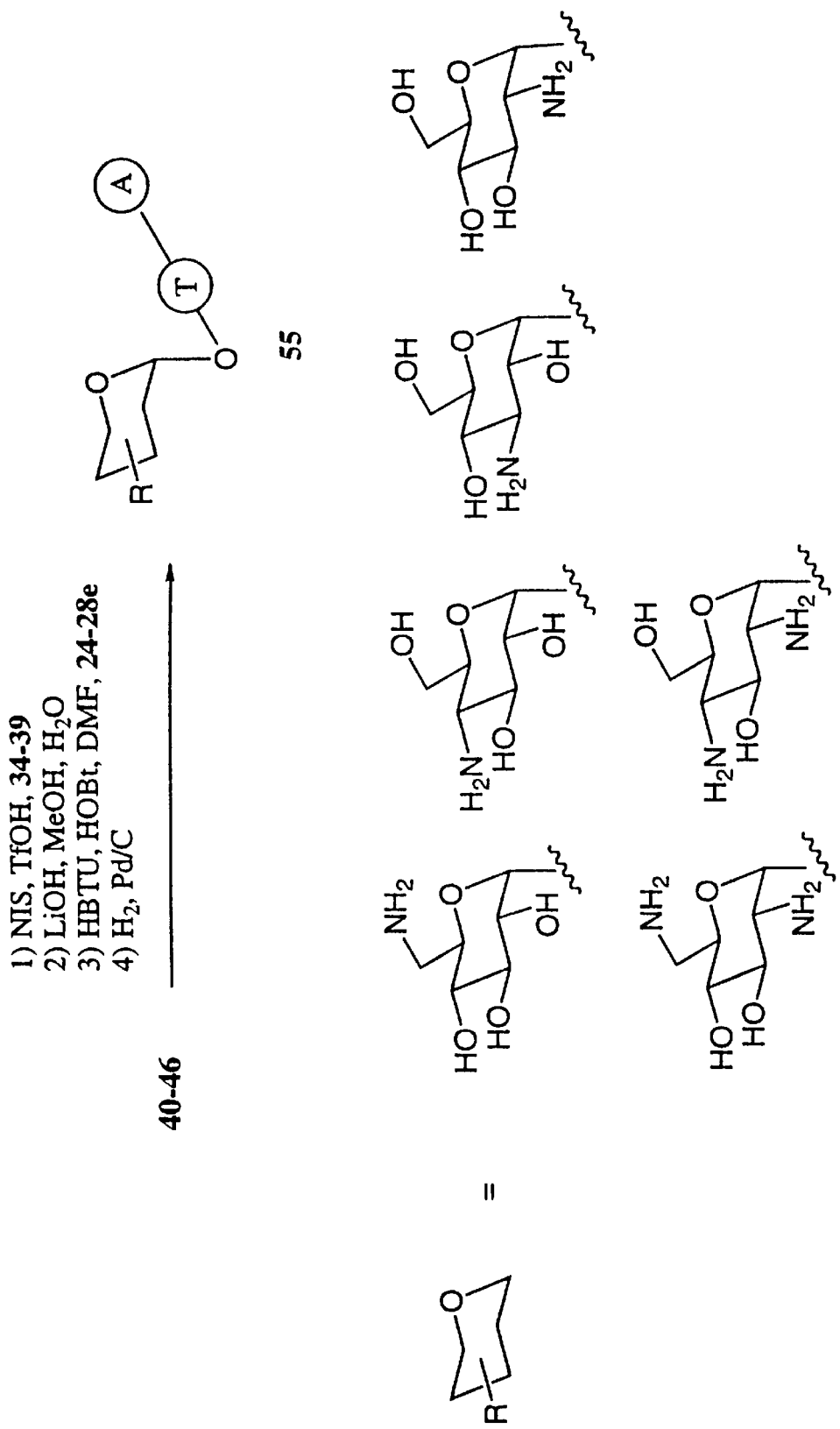
FIGS. 24A and 24B illustrate the synthesis of library 55 starting from the protected scaffolds 40–46, wherein T and A represent the various combinations of the indicated templates with hydroxyl amine containing functionalities.
Figure 24B:
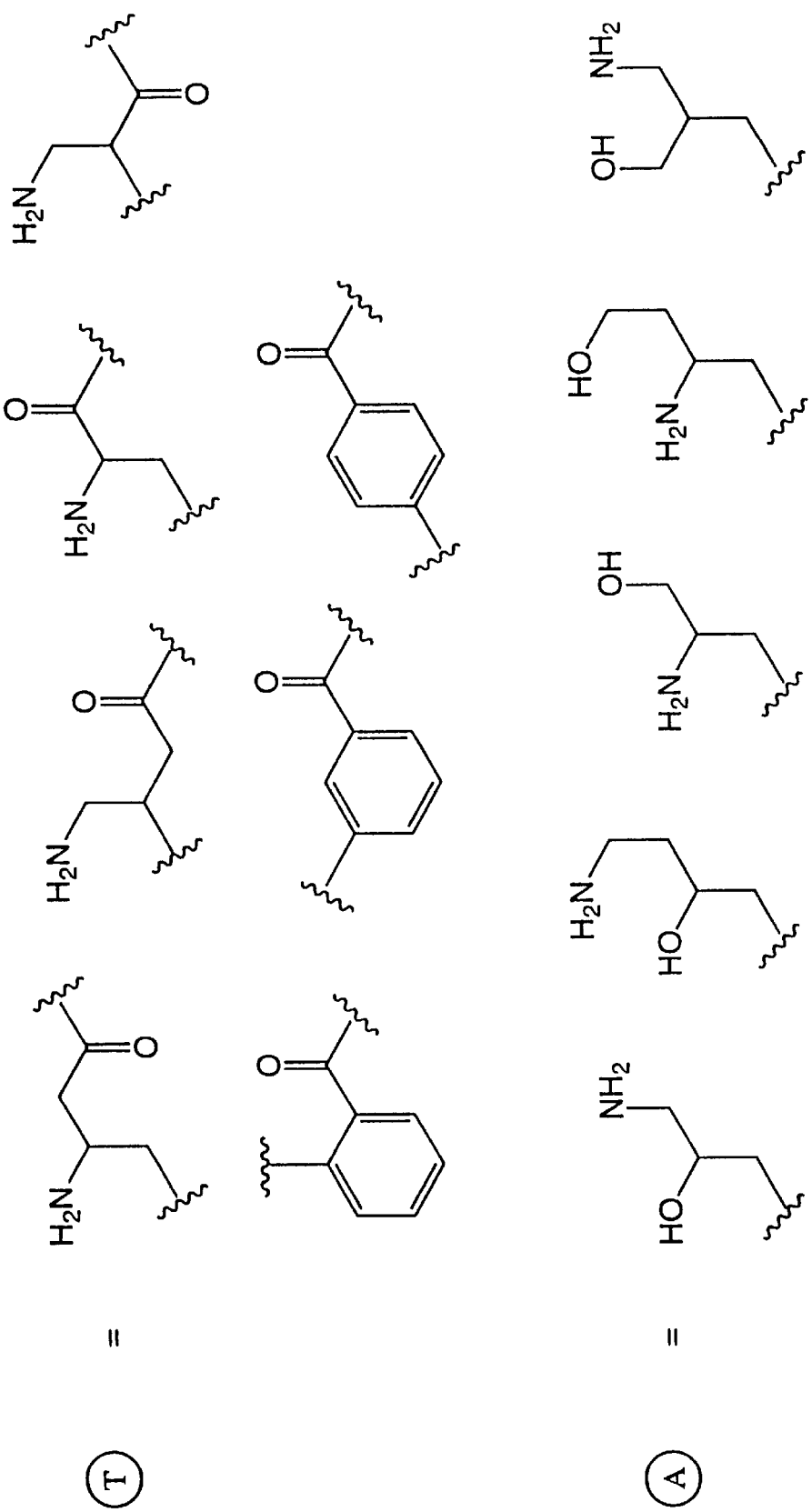
Figure 25A:
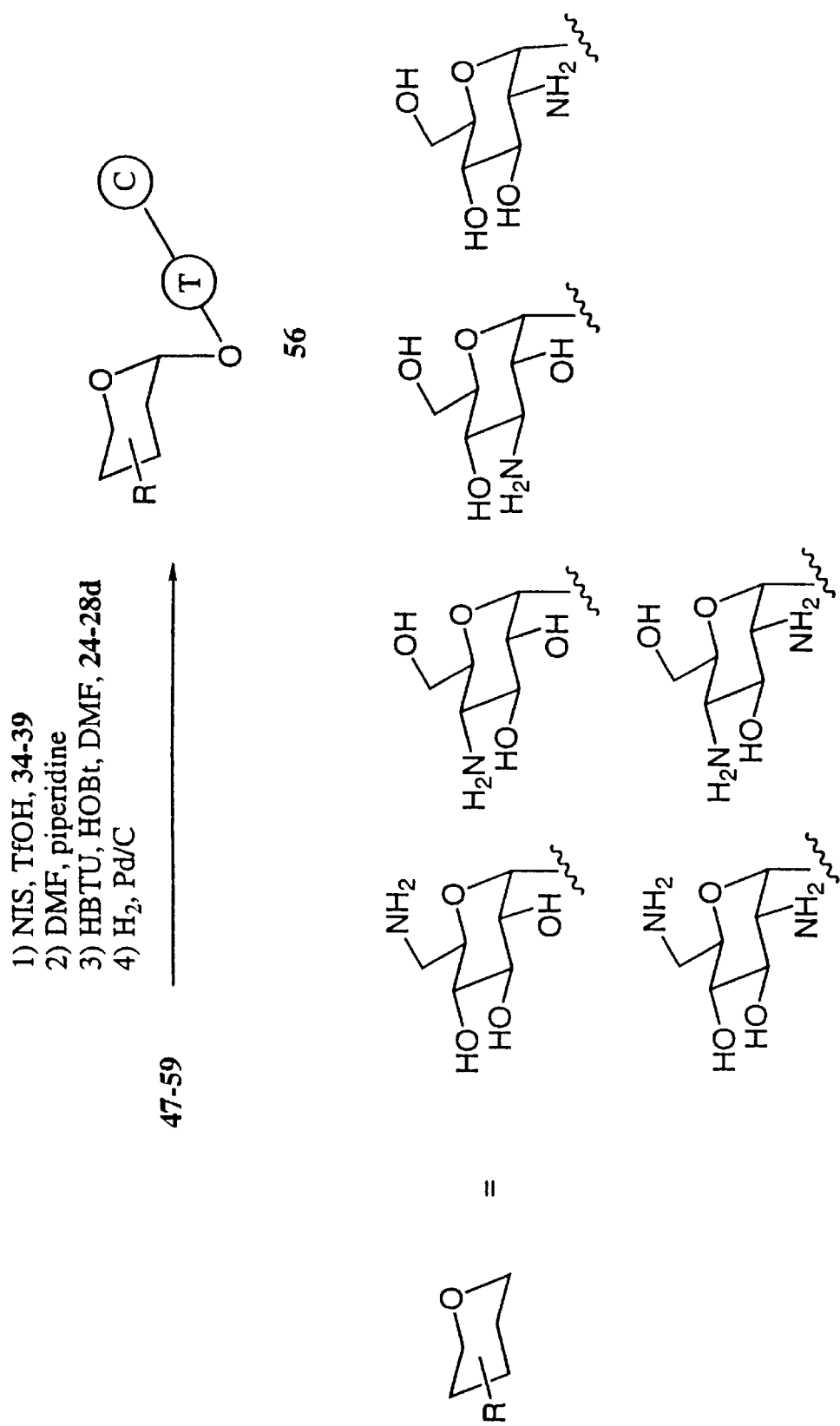
FIGS. 25A and 25B illustrate the synthesis of library 56 starting from the protected scaffolds 47–59, wherein T and A represent the various combinations of the indicated templates with hydroxyl amine containing functionalities.
Figure 25B:
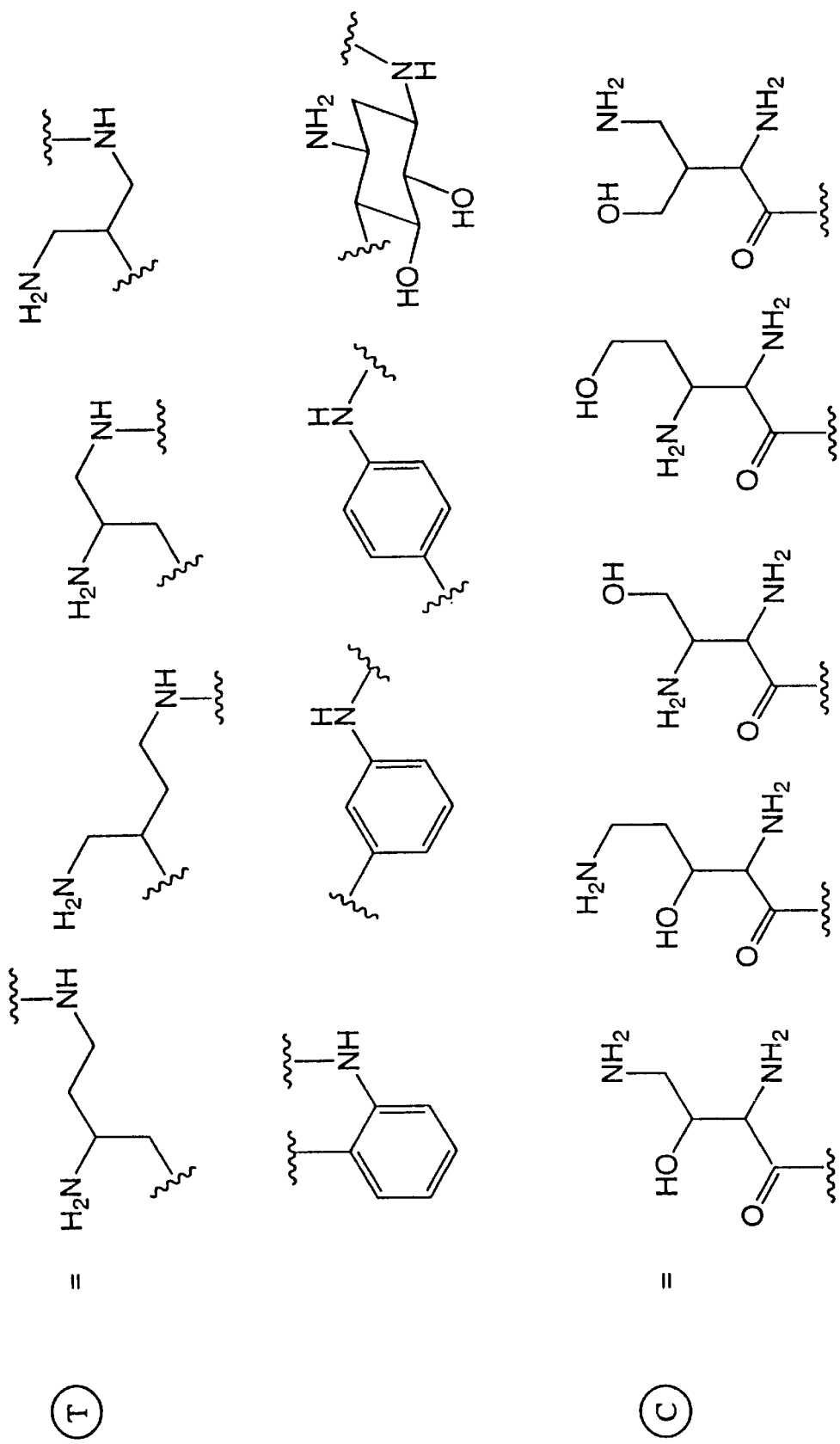

As outlined in FIGS. 24–25, these templates are first glycosylated and then deprotected and coupled with 24–38 using standard amide bond formation methods. For type I templates the deprotected, glycosylated intermediate is the acyl donor which is activated and coupled with 24–38$e$ which contain a free amine. For type II templates the deprotected, glycosylated intermediate is the acyl acceptor and is coupled with 24–30$d$ containing a free carbocylic acid. After deprotection of this coupling product the final products 55 and 56 for type I and type II templates, respectively, are obtained.

EXAMPLE 2

Synthesis and Exemplary Use of Hydroxylamines as a New Motif for the Molecular Recognition of Phosphodiesters: Implications for Aminoglycoside-RNA Interactions We speculated that the hydroxyamine substructures often found in these molecules may play an important role in recognition. A typical member of the class, neomycin B (1, FIG. 1), has a number of different 1,2- and 1,3-hydroxyamine substructures. We therefore prepared the model compounds 2–5 to first evaluate their individual binding capacities to dimethyl phosphate as a model phosphodiester. To compare our results for phosphodiester binding by hydroxyamines we chose the well characterized bicyclic guanidine 6, since it has been used as a standard model for phosphate recognition (Hamilton et al. *Bioorganic Chemistry Frontiers*, Vol. 3 (Eds.:H. Dugas, F. P. Schmidtchen), Springer, Heidelberg 1993, p193–255; Dietrich et al. *J. Chem. Soc. Chem. Comm.* 1978, 934). Compound 6 is symmetrical and presents only one hydrogen bond donor face, unlike arginine, which has two, allowing straightforward interpretation of spectroscopically derived binding data.

Figure 2:
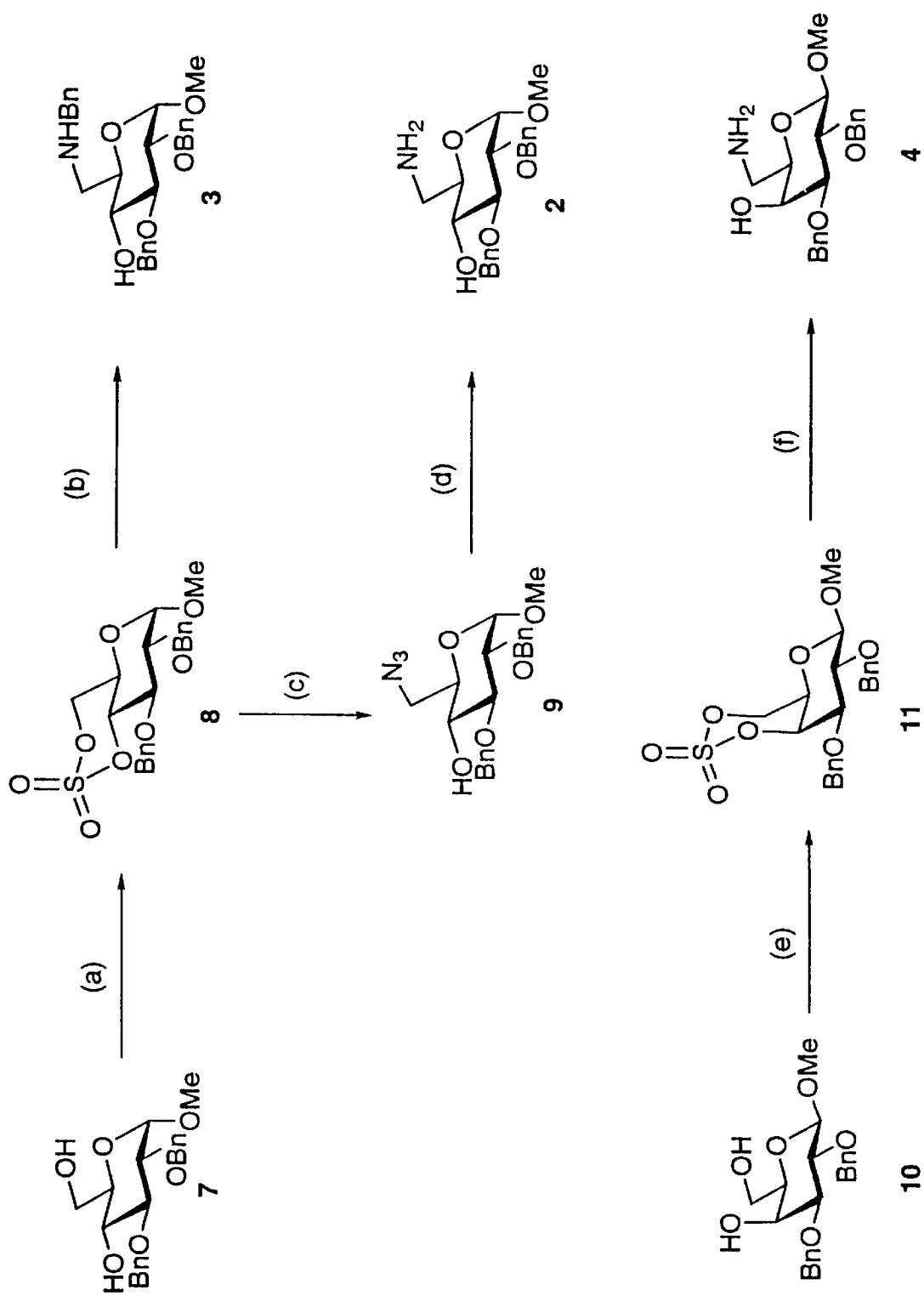
FIG. 2 illustrates the synthesis of hydroxyamine model compounds. (a) i. NMM, $SOCl_2$, $CH_2Cl_2$, RT, 2h; ii. $NaIO4$, cat. $RuCl_3$, $CH_2Cl_2$, $CH_3CN$, $H_2O$, 0% C to RT (76%); (b) i. $BnNH_2$, DMF, RT, 10h; ii. 60% $HClO_4$, THF (70%); (c) i. $NaN_3$, DMF, RT, 10h; ii. 60% $HClO_4$, THF (97%); (d) i. $PMe_3$, THF, 0.1N NaOH ii. HCl, $Et_2O$ (84%); (e) i. NMM, $SOCl_2$, $CH_2Cl_2$, RT, 2h; ii. $NaIO_4$, cat. $RuCl_3$, $CH_2Cl_2$, $CH_3CN$, $H_2O$, 0% C to RT (52%); (f) i. $NaN_3$, DMF, RT, 10h; ii. 60% $HClO_4$, THF (87%); iii. $PMe_3$, THF, 0.1N NaOH iv. HCl, $Et_2O$ (84%)
Figure 4A:
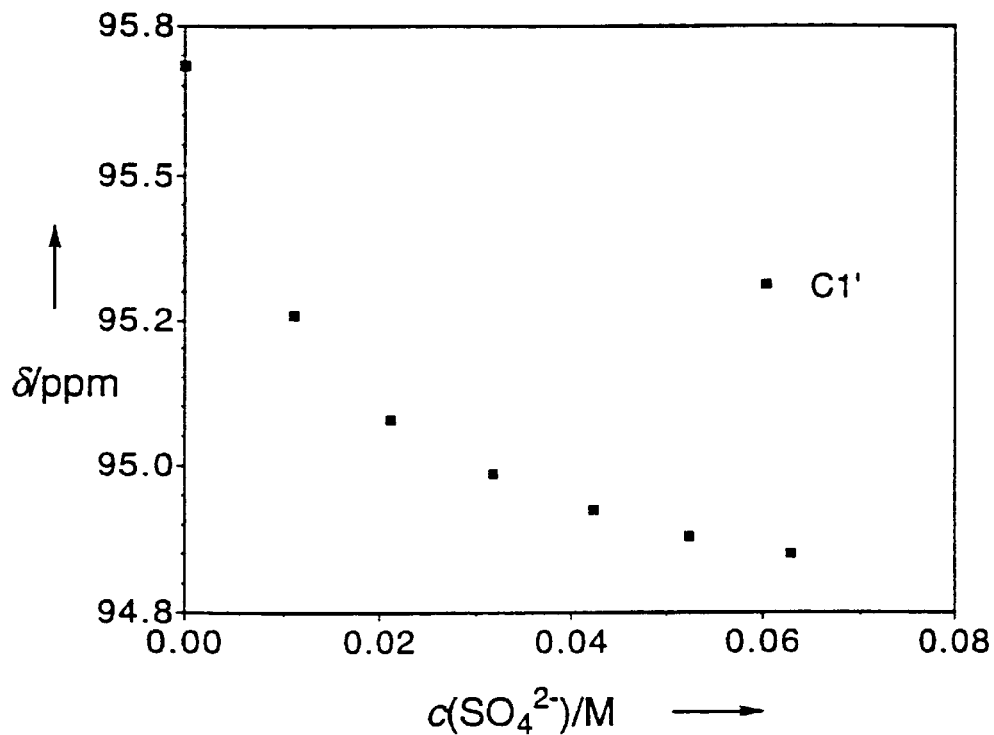
FIGS. 4A–4D illustrate the titration of neamine (12) with sodium sulfate at pH 3.5: (A) Titration curve for C1'. (B) Job plot; x=% complex formation. (C) Structure of neamine indicating the sites of maximum observed shift. (D) Maximum observed shift.
Figure 4B:
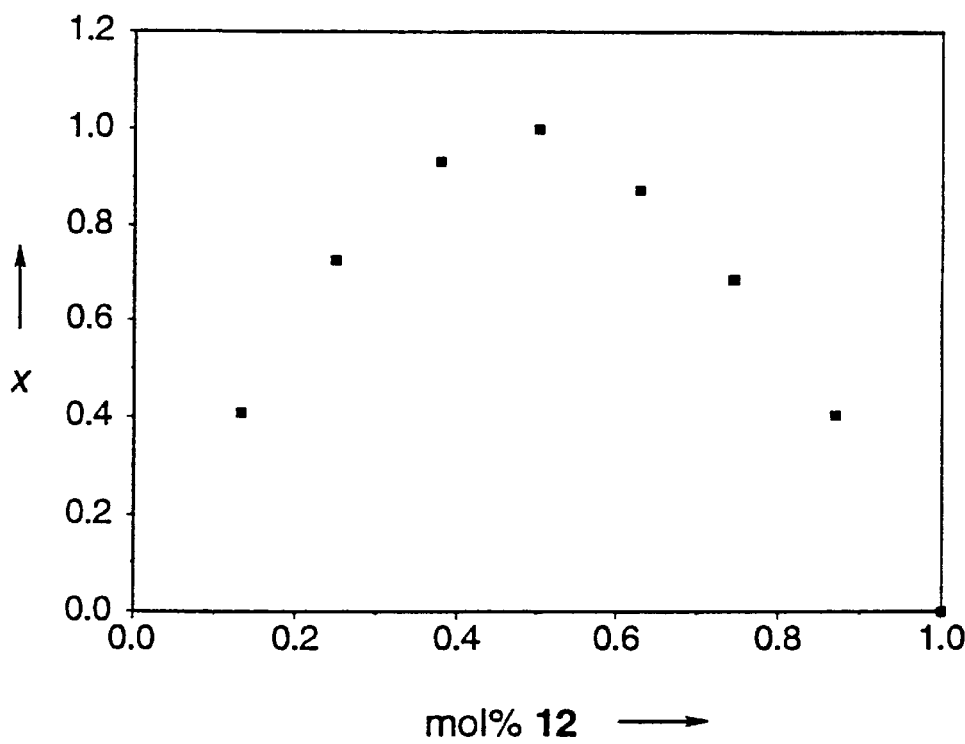
Figure 4C:
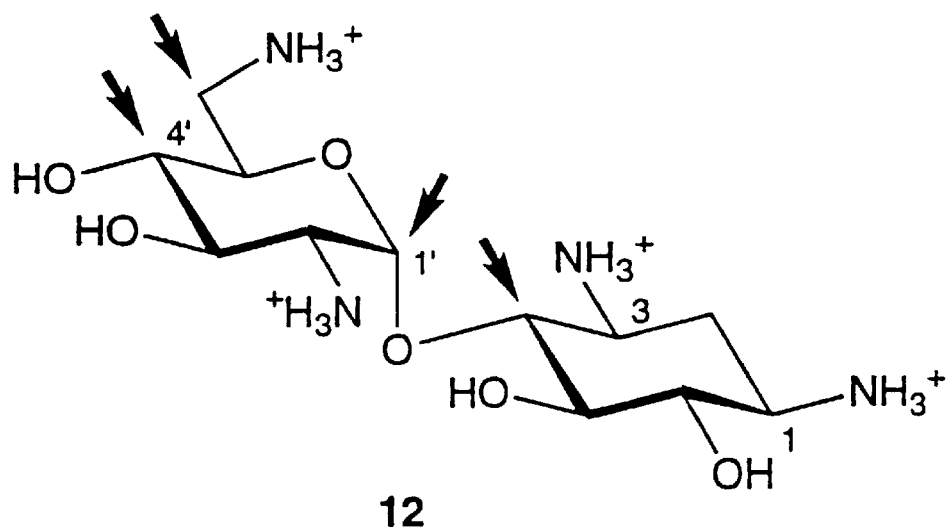
Figure 4D:
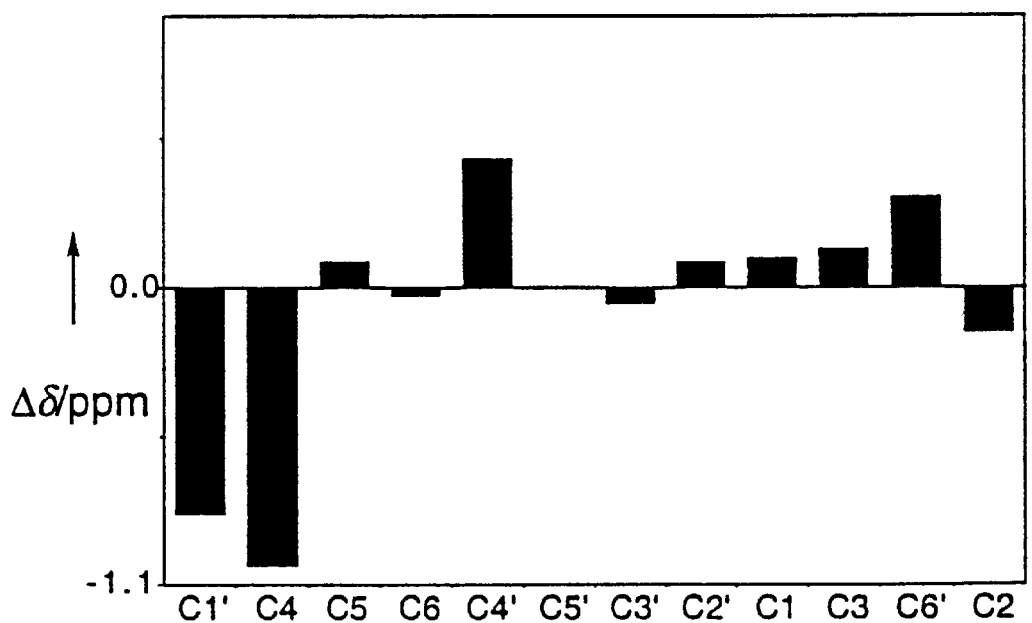

The synthesis of 1,3-hydroxyamines 2–4 was conveniently achieved from the respective diol precursors via a cyclic sulfate (for a review of the chemistry of cyclic sulfates see: B. B. Lohray, *Synthesis* 1992, 1035) intermediate as shown in FIG. 2. The galacto-configured hydroxyamine 4 was designed to mimic the 4′′′, 6′′′-hydroxyamine substructure found in the L-ido-ring of neomycin B. The latter exists in a triaxial $^4C_1$-chair conformation as shown in FIG. 1 (Botto et al. *J. Am. Chem. Soc.* 1983, 105, 1021; Botto et al. *J. Carbohydr. Chem.* 1984, 3, 545; Reid et al. *J. Biol. Chem.* 1987, 262, 7967). While the absolute stereochemistry of the hydroxyamine substructure in 4 is enantiomeric to that of L-idose the relative orientation of the equatorial aminomethyl and the axial hydroxyl group is the same and therefore their interactions with achiral compounds will be equivalent.

In order to determine binding constants we prepared defined 1:1 salt complexes and measured their dissociation upon stepwise dilution in [D$_6$]DMSO by following the shifts of NH and OH resonances. The chemical shift values of the totally uncomplexed state ($_o$) and the fully complexed state ($_n$) and the stability constant $K_a$ were subsequently determined by curve fitting. This procedure has the advantage that it does not rely on experimentally determined values of $_o$ which require separate measurements with a non-complexing counterion that may nonetheless have some residual binding affinity (Horman et al. *Anal. Chem.* 1983, 55, 1219). FIG. 3 shows the results of dilution experiments with chloride and phosphodiester counterions for compounds 2–6 (Dimethyl-phosphate salts were prepared from the respective chlorides by reaction with sodium dimethylphosphate; for the preparation of $Na_2OP(O)(OMe)_2$ see: Bunton et al. *J. Chem. Soc.* 30 1960, 3293). In all cases, data could be fitted to a 1:1 binding isotherm. Importantly, the gluco-configured 1,3-hydroxyamine 2 binds dimethylphosphate with higher affinity than bicyclic guanidine 6. In contrast, the galacto-epimer 4 shows reduced binding. The 1,2-trans-hydroxyamine 5 binds dimethylphosphate with lower affinity than either 2 or 6, but is still superior to 4. All three hydroxyamines show substantial selectivity for dimethylphosphate over chloride (FIG. 3), suggesting the involvement of hydrogen bonds in addition to ionic contributions, which are typically somewhat larger for the more localized charge of protonated amines (Dietrich et al. *Helv. Chim. Acta* 1979, 62, 2763). Evidence for the involvement of a bidentate (Bidentate interactions have recently been suggested for the much weaker interaction of phosphates with carbohydrate polyols although no differential selectivity was found compared to chloride: Coterón et al. *J. Org. Chem.* 1996, 61, 1429; for binding of phosphonates to alkylglucosides see G. Das, A. D. Hamilton, *J. Am. Chem. Soc.* 1994, 116, 11139) recognition for 2 was provided by the large downfield shift of its OH resonance upon complexation ($_{max}$=0.84 ppm). A smaller shift of the OH signal was seen in 5 ($_{max}$=0.56 ppm) and in 4 ($_{max}$=0.38 ppm). This order mirrors the order of binding affinities and is consistent with the interpretation that differential involvement of the hydroxyl group in hydrogen bonding provides for the energetic differences in complexation.

A structural model for the interaction of 1,3-hydroxyamines with phosphodiesters could involve either two (I) or three (II) hydrogen bonds. The latter arrangement simultaneously donates H-bonds from above and below the OPO-plane which is common for coordination of phosphates in biological systems (Alexander et al. *J. Am. Chem. Soc.* 1990, 112, 933). Results obtained with compound 3 which

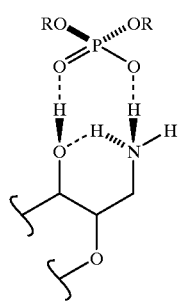

I

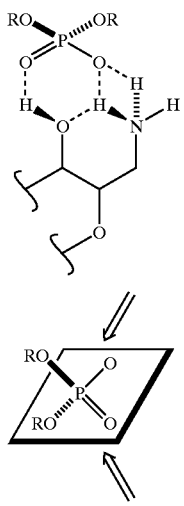

II features an additional benzyl substituent compared to 2 are consistent with this model. The intrinsic ion binding capability of 3 is reduced by this substitution as seen from lower chloride binding compared to 2, 4 and 5. This may be due to added steric bulk and higher basicity of the secondary amine, decreasing its hydrogen bonding donor strength. However, the selectivity for dimethylphosphate over chloride is only slightly diminished (7-fold vs. 10-fold for 2) suggesting that the principal hydrogen bonding network involved in recognition is still intact. The clear difference in the phosphate recognition abilities of 2 and 4 is interesting. Careful analysis of the coupling constants between H5 and H6a/H6b in 2 reveals the presence of largely a single rotamer around the C5–C6 bond in the uncomplexed state ($J_{5,6a}$ ≈ 2 Hz, $J_{5,6b}$ =8–9 Hz) which does not rearrange significantly upon binding of the phosphodiester. This contrasts with galacto-epimer 4 which in the uncomplexed state ($J_{5,6a}$=4.5 Hz, $J_{5,6b}$=8.5 Hz at 17% complexation) probably exists in an equilibrium between two rotamers. Upon complexation of dimethylphosphate the molecule rearranges resulting in a changed torsional angle for the C5–C6 bond ($J_{5,6a}$ ë $J_{5,6b}$=6.5 Hz at 65% complexation). Thus it is likely that 2 is perfectly preorganized for binding of phosphodiesters while 4 must undergo rearrangement, accounting for its reduced binding affinity.

The results from the phosphodiester binding studies suggest that hydroxyamines share some of the molecular recognition properties of guanidines, and it is known that in protein-nucleic acid complexes the guanidinium group of arginine frequently makes contact to the Hoogsten face of guanosine (Pabo et al. *Annu. Rev. Biochem.* 1992, 61, 1053). When 9-ethylguanine was titrated with 4 a downfield shift of H8 due to hydroxyamine binding was indeed observed. Possible complex structures as shown in III and IV are therefore proposed.

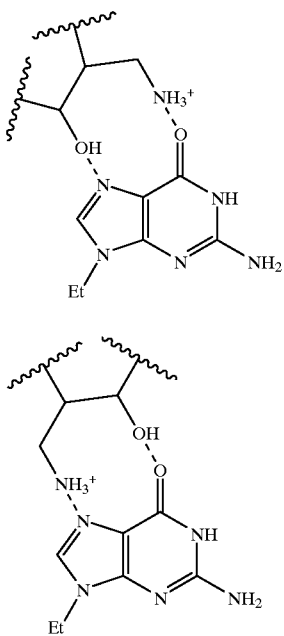

To investigate whether 1,3-hydroxyamine substructures may be involved in binding in aqueous solution, we turned our attention to neamine (12; FIG. 4), a pseudodisaccharide substructure commonly found in a wide range of aminoglycoside antibiotics. However, initial studies with dimethylphosphate in water showed no detectable binding in the concentration ranges accessible by NMR. This may not be surprising since ionic and hydrogen bonding interactions are severely reduced in water. These weak forces may, however, be enhanced by increasing the charge of the interacting species. In fact, many recognition events involving nucleic acids—including those by aminoglycosides—are likely to have a strong contribution from their polyionic character. We therefore turned our attention to sulfate, as it is a tetrahedral oxyanion similar to phosphate and its double negative charge mimics the effect of a polyanion. Furthermore, it has a defined ionization state. Since the spectra of aminoglycosides are highly dependent on pH, and even minor pH changes can outweigh any small complexation induced shifts, we performed binding studies at low pH, where neamine is fully protonated. Upon addition of sodium sulfate to a solution of neamine.4HCl at pH 3.5, only small changes were observed in the 1H-NMR spectrum and their interpretation was complicated by severe overlap of signals. Analysis of $^{13}$C-NMR spectra provided a clearer picture (FIG. 4). Signals for all carbons were assigned unambigously through 2D COSY and NOESY spectra and were in full agreement with the assignments made earlier (Koch et al. *J. Am. Chem. Soc.* 1974, 96, 3300), based on comparison of chemical shift values with model compounds. Following the shift of C1' allowed the calculation of an apparent binding constant $K_{app}=294 \text{ Å } 26 \text{ M}^{-1}$ for the competitive binding of sulfate over chloride through curve fitting procedures (Binding constants determined from following either C4' or C6' were in close agreement with this value) Investigation of the binding stoichiometry by the method of Job (Job et al. *Ann. Chim.* (10th series) 1928, 9, 113) revealed the predominant existence of a 1:1 complex with only minor contributions from two sulfates binding simultaneously. Tabulation of the maximum observed shifts provides an interesting picture: significant changes are seen for C4, C1', C4' and C6'. The changes for C4 and C1' are opposite in sign to all other shifts and can be interpreted as resulting from a change in glycosidic torsion angles (Daniels et al. *J. Chem. Soc. Perkin Trans.* 1 1981, 2209) due to altered electrostatic repulsion after complexation of sulfate. The changes for C4' and C6' are indicative of binding at the respective sites. In particular, C4' is the only hydroxyl substituted carbon showing a large shift. These observations provide clear evidence for anion recognition by a 1,3-hydroxyamine substructure in water (Preliminary results obtained with derivatives of neomycin B suggest that both the 6' and 6''' aminogroups are involved in binding of RRE. Acylating these groups sharply reduces their affinity ($K_i>0.1$ mM) in a filter binding assay: Daly et al. *Biochemistry* 1993, 32, 10497). Thus, the selectivity found in aqueous solution is in full agreement with the order of binding affinities determined in the model compounds.

EXAMPLE 3

A Novel Direct Observation of Hydroxyamine Containing Aminoalycosides—RNA Interactions By Surface Plasmon Resonance We have developed inhibitors of the interaction between RRE and its cognate protein Rev as potential therapeutics against HIV. Additionally, in this example we disclose a novel assay based on surface plasmon resonance (SPR) that allows the direct observation of aminoglycoside-RNA interactions and is able to test for specificity and elucidate the recognition motif of hydroxyamine interactions with both phosphodiester and guanosine moieties.

The specificity of neomycin B and related aminoglycoside antibiotics in their interaction with the Rev Responsive Element (RRE) of HIV-1 mRNA has been studied by directly observing the aminoglycoside-RNA complexes using surface plasmon resonance. Several different RNA sequences, each with a biotin tag, have been prepared using T7 RNA polymerase-catalyzed transcription of synthetic DNA templates and have been immobilized on a streptavidin-coated surface for the binding study. The results indicate that neomycin B is not specific for the G-rich bubble region in RRE. Rather, it appears to interact with three different sites, each with a submicromolar dissociation constant, within the 67-nucleotide domain II of RRE. Further analysis of neomycin B binding with three short synthetic RNA hairpins showed binding with submicromolar affinity and 1:1 stoichiometry in each case. This suggests that neomycin B may generally bind with this affinity to regular A-form RNA or hairpin loops.

The plasmon resonance approach described here is generally useful for understanding the fundamental interactions involved in the specific recognition of nucleic acids by small molecules which is the basis of rational drug design.

A crucial element in understanding aminoglygcoside-RNA recognition is the development of detailed structure-activity relationships and the analysis of sequence specificity. Frequently, protein binding to nucleic acids is evaluated by gel mobility shift or filter binding assays. For smaller molecules, however, complexes with RNA are often difficult to observe directly. Instead, they are usually screened in a competition assay in the presence of an RNA binding protein. In this type of competition assay, however, it is impossible to test for specificity, i.e. the ability to discriminate between different RNA sequences.

We have developed a novel assay based on surface plasmon resonance (SPR) that allows the direct observation of aminoglycoside-RNA interactions and is able to test for specificity.

SPR can be used to detect binding to ligands that are immobilized on special SPR-sensorchip surfaces. Depending on the experimental design, both thermodynamic and kinetic information can be derived. SPR has been applied to the direct monitoring of a wide range of macromolecular interactions (Malmquist, M. *Nature* 1993, 361, 186) but only recently have technical improvements in the accuracy of detection put the analysis of small molecule binding within reach. We have developed a general SPR-based method for monitoring small molecule-RNA interactions. Specifically, we have synthesized several 5'-biotinylated RNA transcripts and immobilized them on the surface of streptavidin-coated sensorchips. Using this system we were able to study in detail the binding of aminoglycoside antibiotics to these sequences. Analysis of the binding data has allowed us to gain new insights into aminoglycoside-RNA interactions.

We have examined three different sequences related to RRE. The first sequence is the wild type domain II of RRE (wt-RRE-II, see drawing) which contains the high affinity Rev-protein binding site of RRE. The second sequence is the abbreviated 30 nt stem-loop RBE3, which still contains the essential elements for Rev recognition and which has been shown to bind Rev-derived peptides with high specificity. Its structure, both in solution and in the peptide-complexed form, has been determined by NMR. The G-rich bubble which is partially closed by the formation of purine-purine base pairs widens the major groove enough to accommodate the -helical RNA-binding domain of Rev. Based on footprinting experiments, it has been suggested that the G-rich bubble in this sequence is also the binding site for neomycin B. The third RRE-related sequence is a designed hairpin, RBE3-neg, where the Rev-binding site has been disrupted by mutating the bubble region. This was accomplished by deleting two looped out nucleotides, A68 and U72 (wt-numbering), and changing the two purine-purine base pairs, G47:A73 and G48:G71, to standard Watson-Crick pairs. Finally, we have included Neo16bd, a neomycin B binding sequence that is not related to RRE and consequently is not expected to bind Rev. This sequence is derived from an RNA-aptamer that was selected to bind neomycin B.

Synthesis and Immobilization of RNAS.

Figure 5:
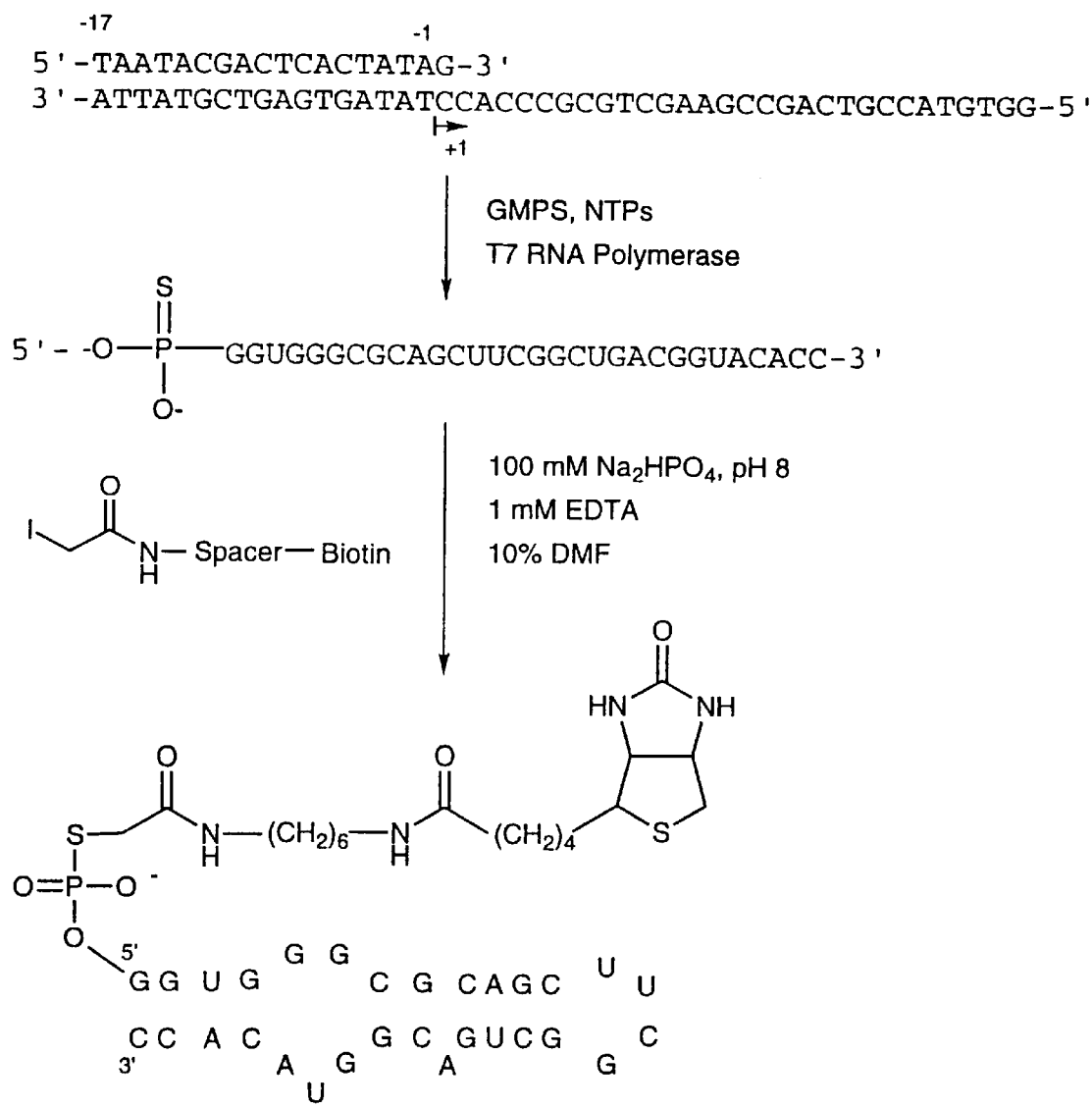
FIG. 5 illustrates the synthesis of RNA-5'-phosphorothioates by in vitro transcription with T7 RNA polymerase in the presence of GMPS, followed by biotinylation with a biotin iodoacetamide derivative that allows specific immobilization (SEQ ID NOS. 1–4).

Biotin-RNA conjugates were prepared as shown in FIG. 5. In vitro transcription of a DNA template in the presence of guanosine-5'-monophosphorothioate (GMPS), catalyzed by T7 RNA polymerase, produced a 5'-phosphorothioate-RNA oligonucleotide. Subsequent modification with an extended biotin-iodoacetamide reagent gave the desired 5'-biotinylated RNA.

Figure 6A:
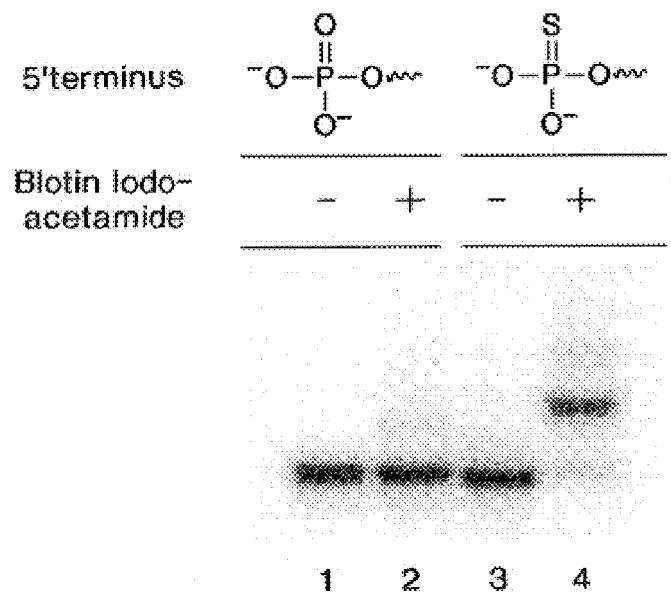
FIGS. 6A and 6B illustrate the biotinylation and immobilization of RBE3 RNA. (A) Storage phosphor autoradiogram of a 20% denaturing polyacrylamide gel used to separate products of biotinylation reactions on $^{32}$P-labeled RBE3-5'-phosphate and RBE3-5'-phosphorothioate (RBE3-5'-ps). Only the 5'-phosphorothioate containing RNA (lane 3, 4) is biotinylated. (B) Superposition of the injection traces for RBE3-5'-ps and RBE3-5'-biotin. Only the biotinylated RNA is successfully immobilized on the streptavidin coated sensorchip surface.

As shown in FIG. 6a for the case of RBE3, 5'-phosphorothioate oligonucleotides are quantitatively modified with biotin, while 5'-phosphates are unreactive, demonstrating selective reaction at the single sulfur atom. Using this approach should be generally useful for the preparation of a wide range of specifically modified RNA sequences.

Figure 6B:
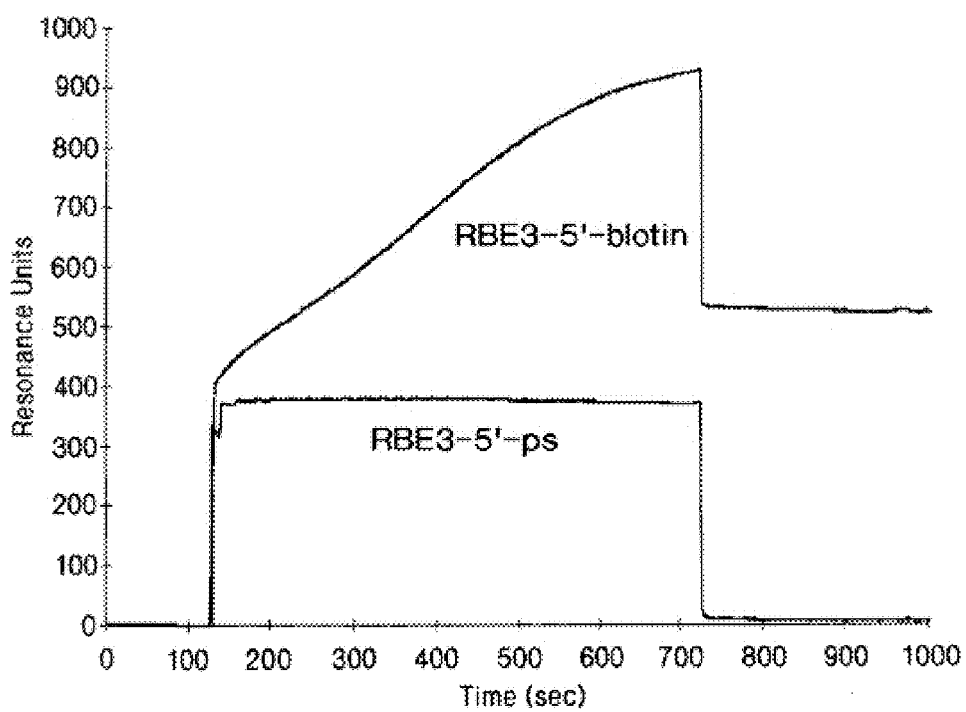

When streptavidin-coated sensorchips were exposed to solutions of gel-purified, biotinylated RNA oligomers, time-dependent stable immobilization was observed (FIG. 6b). Rigorous purification of the 5'-biotinylated RNAs by gel electrophoresis to remove free biotin was critical for successful immobilization. Simple ethanol precipitation was not sufficient for this purpose and resulted in low levels of captured RNA. During the optimization of the immobilization parameters to reduce consumption of the RNA conjugates, we found that lowering the pH from 7.4 to 6.8 resulted in substantially higher levels of immobilization. This is presumably due to improved preconcentration of the negatively charged biotin-RNA conjugates at the streptavidin coated surface (pI 5–6). The immobilization was specific for biotinylated sequences, as unbiotinylated RBE3-5'-phosphorothioate did not lead to any appreciable capture of RNA-ligand (<5 RU, lower trace in FIG. 6b). Immediately following exposure to the unbiotinylated RNA, biotinylated RBE3 was injected in the same flowcell, resulting in the usual level of functionalization (ca. 580 RU, upper trace in FIG. 2b). Furthermore, immobilization is dependent on the level of streptavidin loading. In a gradient sensorchip having four different levels of streptavidin loading, the amount of captured biotin-RNA was proportional to the streptavidin loading levels. Taken together, these observations clearly demonstrate that biotin-RNA conjugates are specifically immobilized on the surface through the streptavidin linker.

Binding of RNAs to Rev peptide.

Figure 7A:
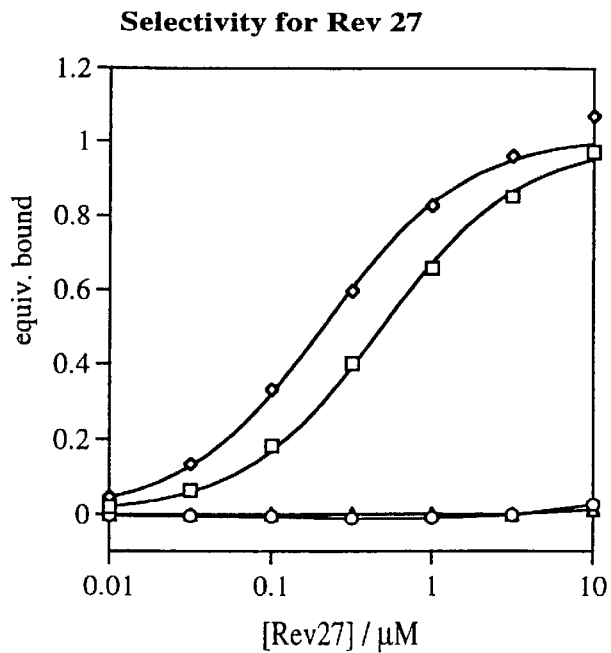
FIGS. 7A–7C illustrate the binding selectivity for Rev27. (A) Titration curve under stringent conditions; pH 7.4, 10 mM HEPES, 3.4 mM EDTA, 5 mM DTT, 150 mM NaCl, 150 mM $Na_2SO_4$; $K_d$ (wt-RRE-II)=200 nM, $K_d$ (RBE3)= 430 nM. (B) Scatchard plot of data in A. (C) Titration under lower stringency conditions at 10% C (solid lines) and 25% C (dashed lines), pH 7.4, 10 mM HEPES, 3.4 mM EDTA, 5 mM DTT, 300 mM NaCl (SEQ ID NO 5).
Figure 7B:
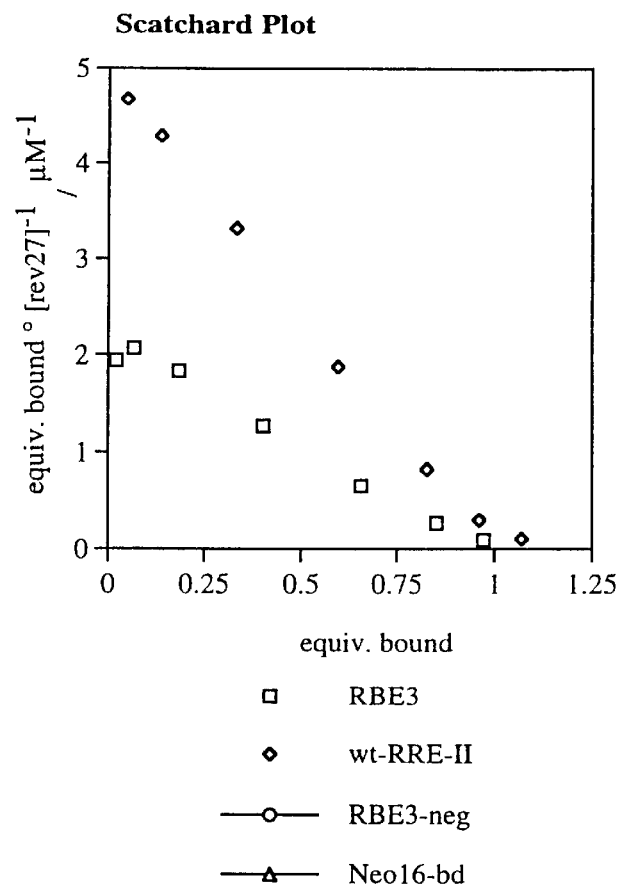
Figure 7C:
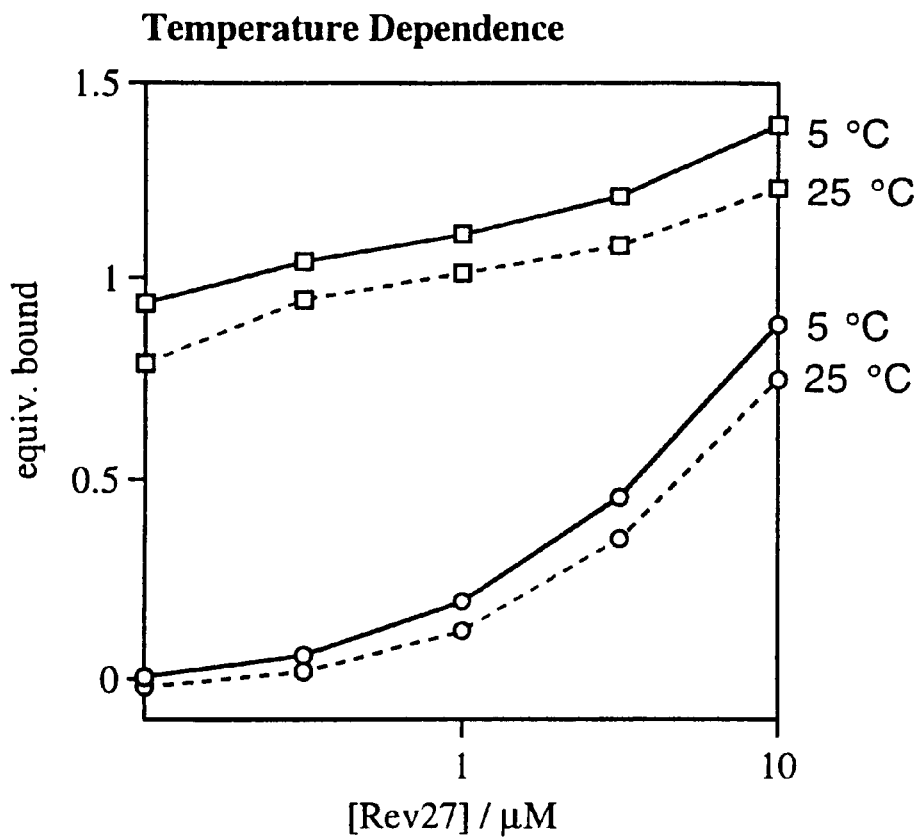
Figure 8A:
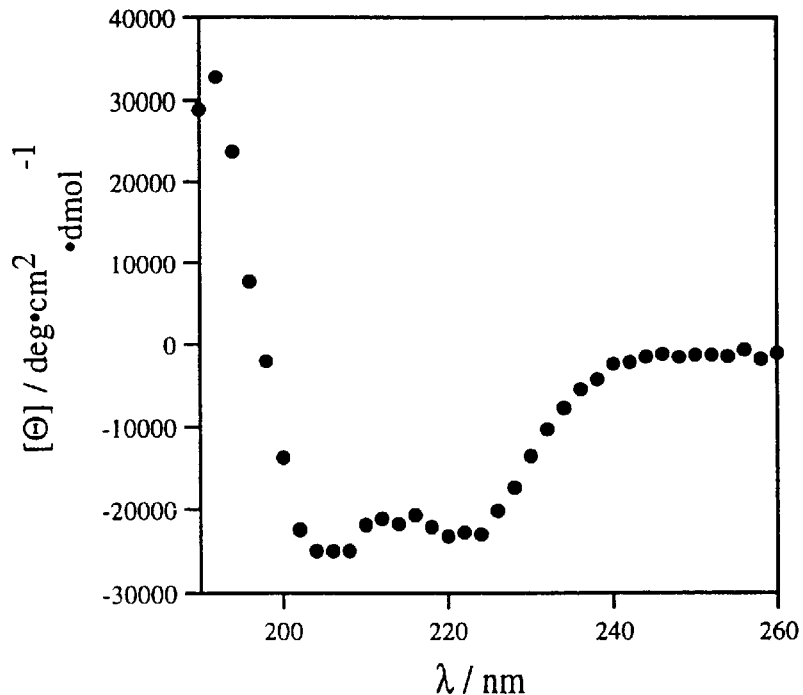
FIGS. 8A and 8B illustrate the following: (A) CD-Spectrum of Rev27 at 5% C showing double minima at 208 and 222 which are indicative of the -helical structure. (B) Temperature dependence of—helical content. Each data point represents a 0.5% C step.
Figure 8B:
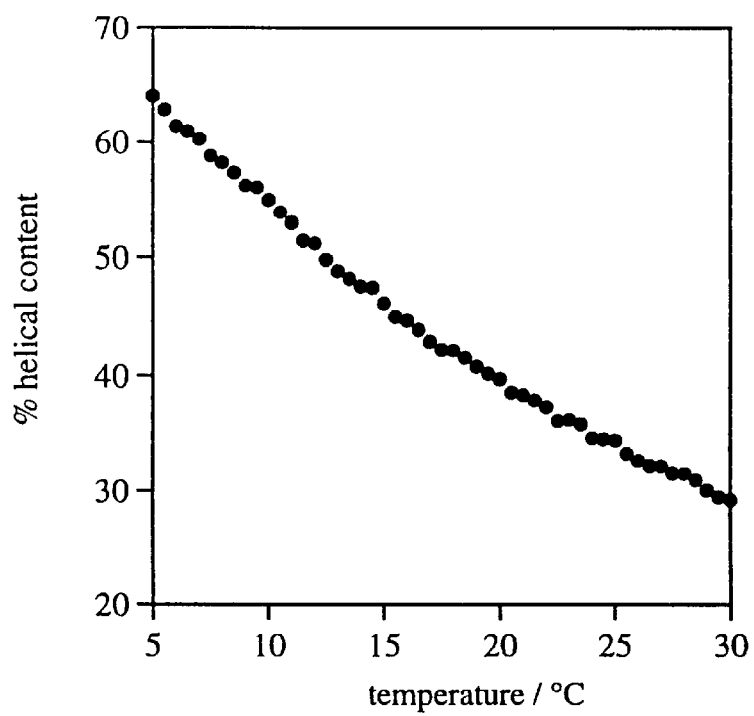

To establish that the immobilized RNA was properly folded, we investigated the binding of the four RNA sequences to Rev27 (FIG. 7). This synthetic peptide contains the -helical RNA-binding domain of Rev protein ($Rev_{34-50}$) which contacts the major groove of the bubble region. The flanking alanine residues were designed to increase -helical content and the N-terminal cysteine was included to allow future modifications. When solutions of Rev27 were injected under conditions of high stringency (10 % C, pH 7.4, 150 mM NaCl, 150 mM $Na_2SO_4$), selective formation of a 1:1 complex was observed for wt-RRE-II ($K_d$=215Å10 nM) and RBE3 ($K_d$=490Å30 nM), but not for RBE3-neg or Neo16-bd (FIG. 7a/b). Under less stringent buffer conditions (10 % C, pH 7.4, 300 mM NaCl) the binding strength is significantly increased while the selectivity remains high. However, under these conditions only an upper limit can be derived for the dissociation constant ($K_d$<10 nM at 5% C) due to surface transport limitations. At higher concentration nonspecific binding is observed to all three sequences. The binding strength and selectivity are somewhat higher at lower temperature (FIG. 7c). This trend is consistent with previous observations by gel-shift experiments and can be explained by higher -helical content of the peptide at lower temperature. As shown in FIG. 8, the CD-spectrum of Rev27 at 5% C has two minima at 222 and 210 nm characteristic of an -helical structure. From the molar ellipticity at 222 nm an -helical content of 64% was determined. Raising the temperature gradually unfolds the helix and at 30% C the -helical content is reduced to 29%.

Binding of Aminoglycosides.

Figure 9A:
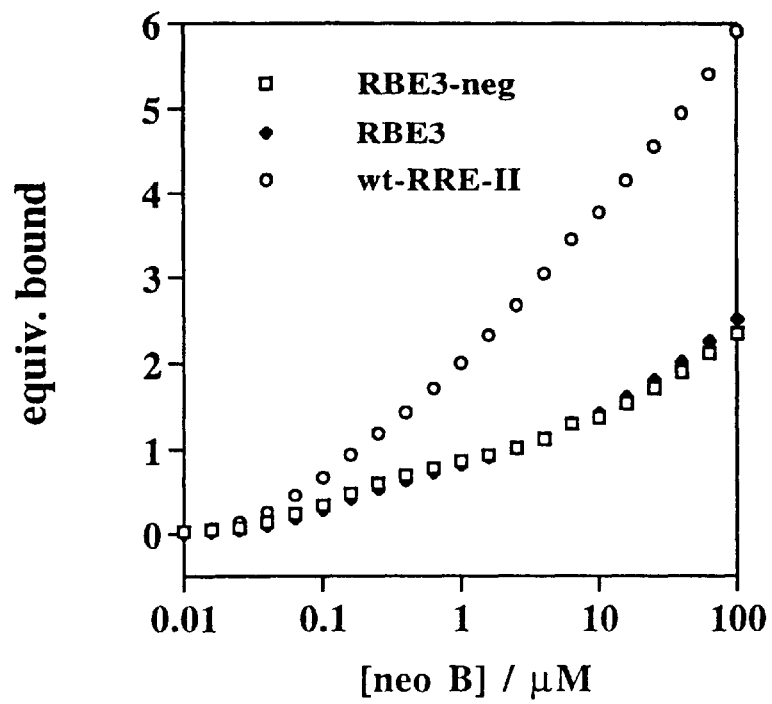
FIGS. 9A and 9B illustrate neomycin B binding to RBE3, RBE3-neg and wt-RRE-II. (A) Semilogarithmic plot. (B) Scatchard plot; x-axis intercepts: 0.98 (RBE3-neg), 1.01 (RBE3); $K_d$ values calculated from slope: 160 nM (RBE3-neg), 210 nM (RBE3). Conditions: pH 7.0, 10 mM HEPES, 150 mM NaCl, 0.1 mM EDTA, 25% C.
Figure 9B:
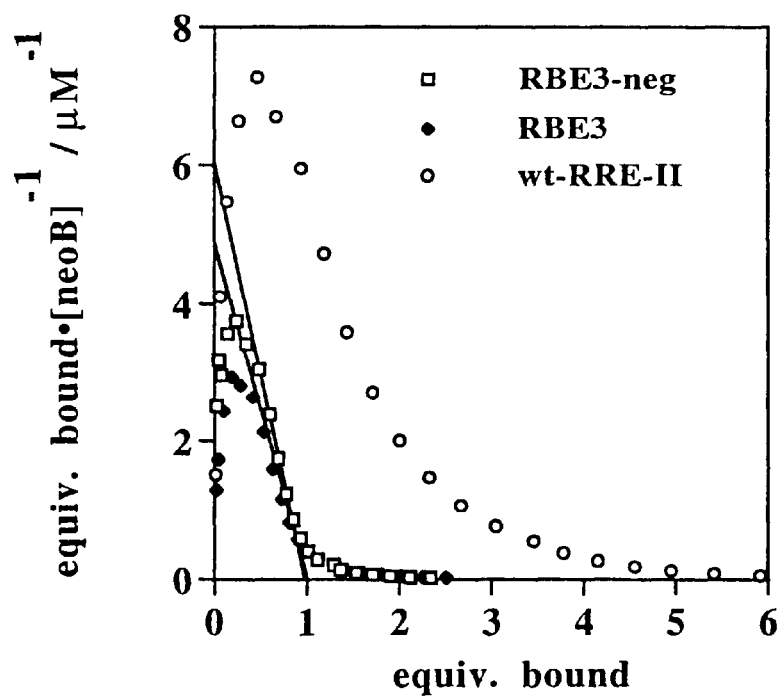

FIG. 9a shows the titration curve of neomycin B with wt-RRE-II, RBE3 and RBE3-neg. Binding of the aminoglycoside to all three RNA oligonucleotides is observed starting in the low nanomolar concentration range and is non-saturable over the concentration range investigated. No significant changes to the binding isotherm were observed in the presence of 2 mM $Mg^2$+suggesting that the binding and the structure of the RNA hairpin is not influenced by divalent metals. The high degree of non-specific binding is not surprising considering that aminoglycosides are highly charged polycations that tend to associate nonspecifically with the polyanionic phosphate backbone of RNA. A Scatchard plot of the data is shown in FIG. 9b. The initial part of the plot reveals the presence of surface transport limitations at very low concentrations of neomycin B, which prevent reaching the equilibrium. This results in data points that lie systematically to the lower left of the true equilibrium curve. Data points corresponding to 0.5 or more equivalents of neomycin B represent equilibrium values and can be analyzed with respect to stoichiometry and affinity of aminoglycoside binding. Interestingly, there is no signficant difference in the binding of neomycin B to RBE3 vs. RBE3-neg. Both sequences bind one molecule of neomycin B with submicromolar affinity followed by weaker association with several additional equivalents of the antibiotic. This clearly shows that, while the G-rich bubble region is essential for Rev-binding, it is not a determining factor for binding of neomycin B. Either neomycin B binds to a set of nucleotides within regular A-form RNA that is conserved between RBE3 and RBE3-neg or binds to the UUCG tetraloop that is not part of the wt-RRE sequence. In support of the latter possibility, selection experiments with RNA aptamers have established that aminoglycosides have a general affinity for stem loops, and these selection experiments have failed to identify any aminoglycoside binding motif within regular double stranded A-form RNA. (Wang, Y., et al., Chem. & Biol. 1995, 2, 281; Lato, S. M., et al., Chem. & Biol. 1995, 2, 291; and Wang, Y., et al., Biochemistry 1996, 35, 12338.) However, recent footprinting experiments on comparable RNA hairpins have yielded no evidence of direct association to the UUCG tetraloop.

For wt-RRE-II three molecules of neomycin B are bound with submicromolar affinity. Following the reasoning outlined above, it is possible that two of these molecules bind at the two hairpin loops present. The third equivalent might bind at the three-helix junction, overlapping with the binding site for the intact protein. This would be consistent with both the inhibitory effect of neomycin B on Rev-RRE binding and the reported footprinting data for binding of neomycin B in that region.

Paromomycin binding.

Figure 10A:
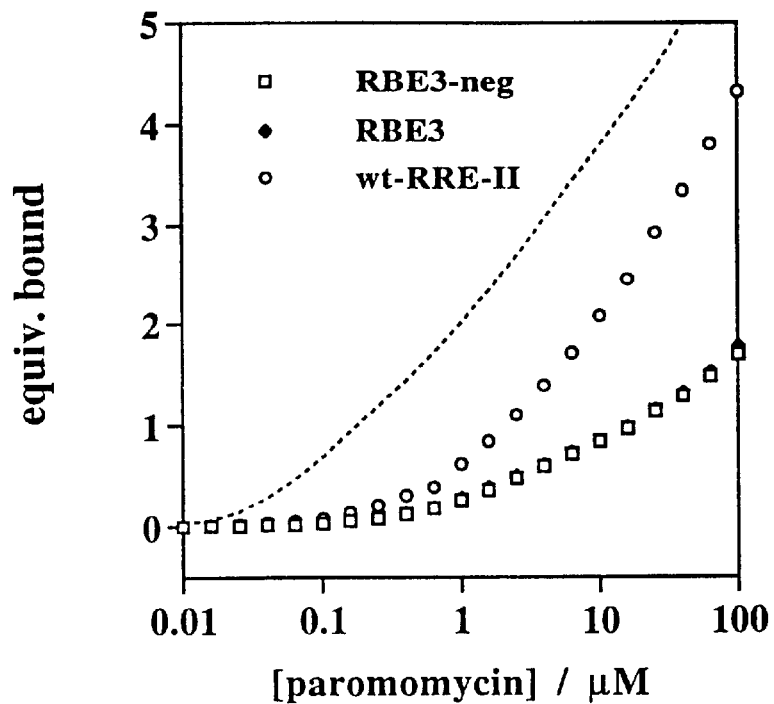
FIGS. 10A and 10B illustrate paromomycin binding to RBE3, RBE3-neg and wt-RRE-II. (A) Semilogarithmic plot; the dashed line indicates the binding of neomycin B to wt-RRE-II for comparison (B) Scatchard plot. The dotted line represents the binding of neomycin B to RBE3; x-axis intercepts: 1.05 (RBE3-neg), 1.04 (RBE3); $K_d$ calculated from slope: 3.1 mM (RBE3-neg), 2.8 mM (RBE3). Conditions: pH 7.0, 10 mM HEPES, 150 mM NaCl, 0.1 mM EDTA, 25% C.
Figure 10B:
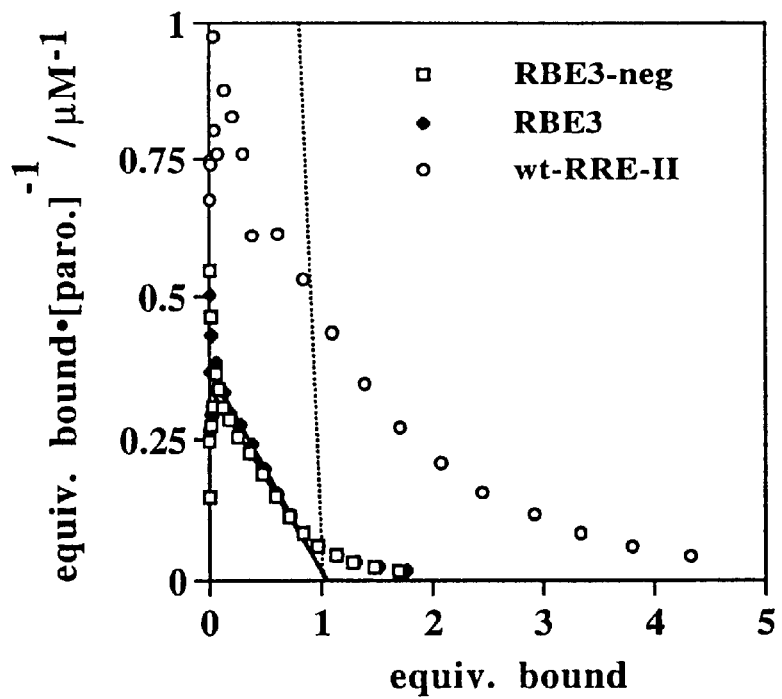
Figure 12:
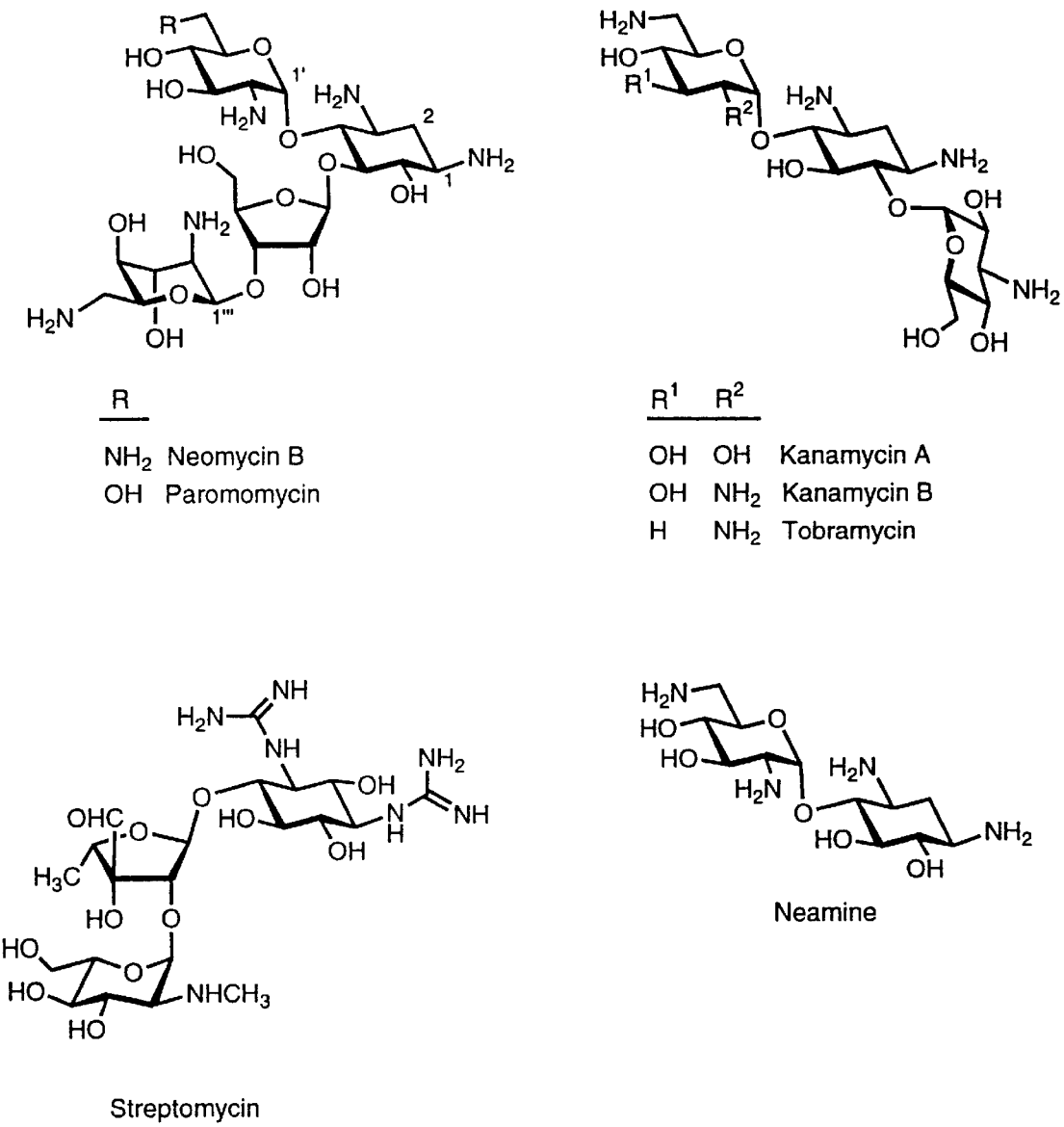
FIG. 12 illustrates the structures of aminoglycosides. The neomycin family is characterized by a 2-deoxy streptamine cyclitol core. Streptomycin belongs to a different family of aminoglyosides and is characterized by its guanidinium groups.

Another aminoglycoside that is closely related to neomycin B in structure but which has been reported to have virtually no inhibitory effect on the Rev-RRE binding is paromomycin (FIG. 12). The only difference between the two molecules lies in the replacement of neomycin's 6'-amino function with a hydroxyl group in paromomycin. As shown in FIG. 10, equilibrium binding measurements did indeed show that paromomycin has approximately 15-fold lower affinity for wt-RRE-II, RBE3 and RBE3-neg compared to neomycin B. However, the relative affinity for the three sequences is unchanged and the curves of the respective semilogarithmic plots are superimposable when shifted horizontally. This indicates that the specificity of binding is unchanged.

Figure 11:
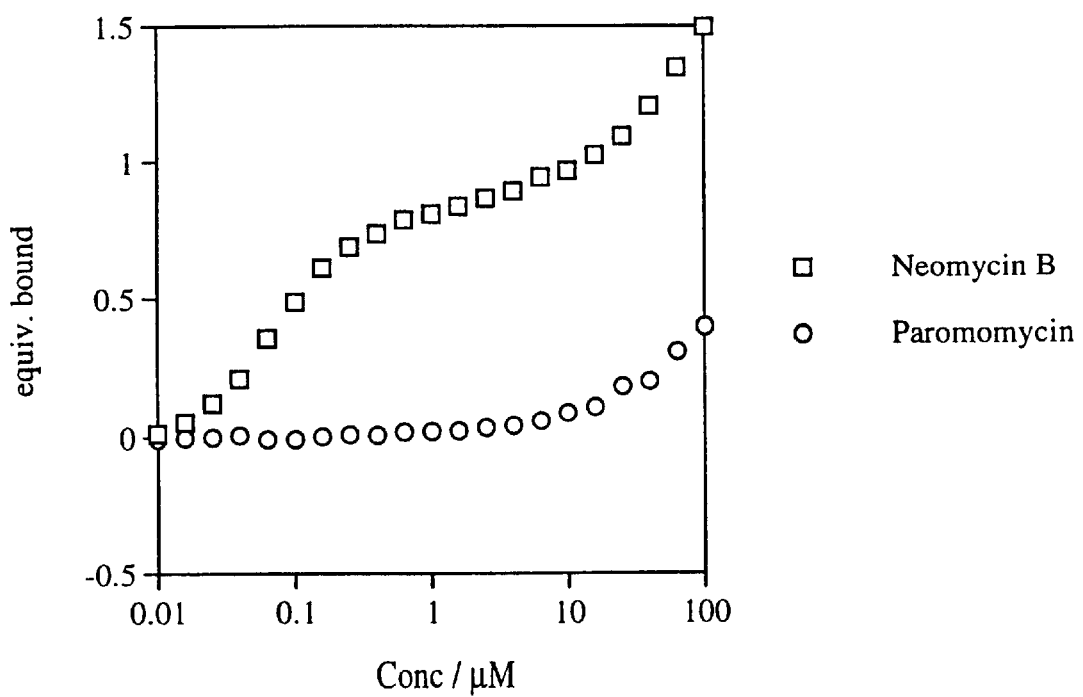
FIG. 11 illustrates the kinetic stability of wt-RRE-II complexes with neomycin B vs. paromomycin. Equilibrium was reached at the indicated concentrations of aminoglycoside and then dissociation was affected by injecting aminoglycoside-free buffer (10 mM HEPES, pH 7.4, 150 mM NaCl, 3.4 mM EDTA). Data points were taken after 1 min of dissociation.

The difference in equilibrium binding affinity between neomycin B and paromomycin is too small to account for the extremely large reported inhibition differences observed in gel-shift assays (>100-fold). However, careful examination of the dissociation phase revealed profoundly different dissociation kinetics for the two compounds. Data taken at different time points after switching from injecting aminoglycoside-containing buffer to aminoglycoside-free buffer represent time slices through the dissociation phase. FIG. 11 shows the results obtained for wt-RRE-II after 1 min. The curve for neomycin B has the shape of an apparent 1:1 binding isotherm, contrasting with the shape of the equilibrium curve. This is due to the different dissociation rates for specific and non-specific binding, with non-specifically bound molecules dissociating much faster. Even more interesting is the difference between the two aminoglycosides: No apparent 1:1 binding isotherm is discernible for paromomycin, implying that the high-affinity binding sites for paromomycin within RRE are characterized by off-rates that are at least as fast as those of non-specifically bound molecules. The same trend shown here for wt-RRE-II was also observed for RBE3 and RBE3-neg. Thus it is apparent that while the equilibrium binding values do not reflect a large difference between these two closely related aminoglycosides, their dissociation kinetics are very different and may account for the large difference in inhibitory potency that has been observed by gel shift. Interestingly, these observations are also consistent with our previous finding in model systems that the 1,3-hydroxyamine substructure of the gluco-ring is an effective recognition element for phosphodiesters. Altering this substructure may therefore change binding.

Other aminoglycosides.

Figure 13:
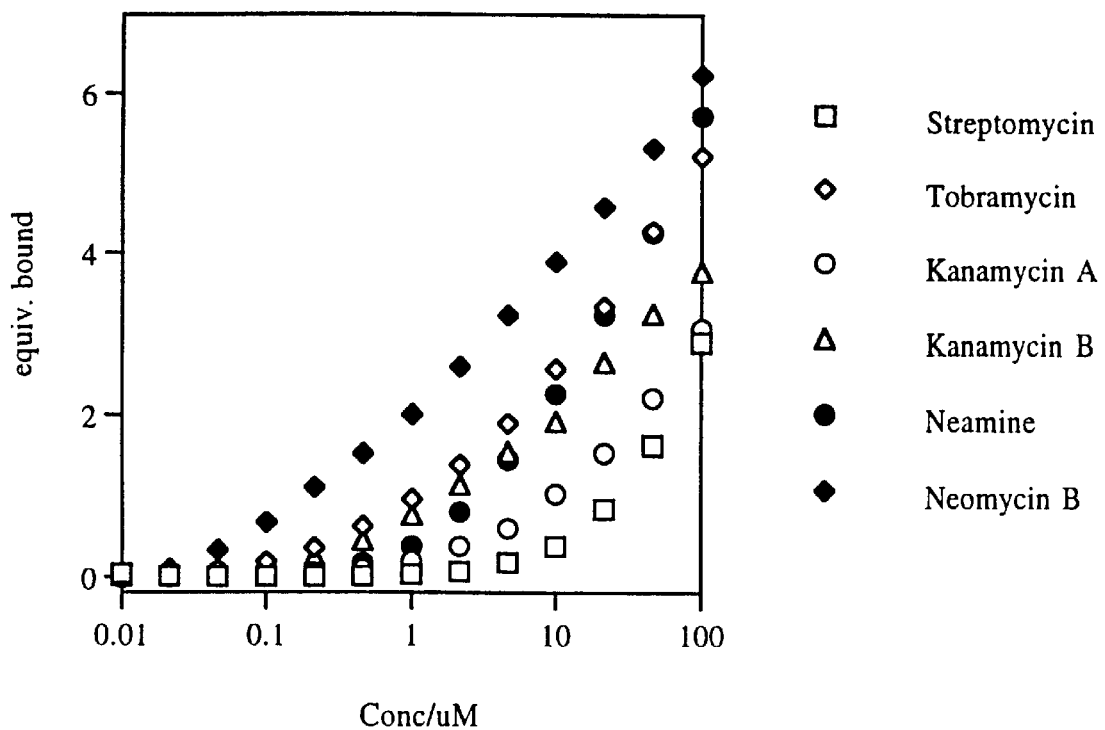
FIG. 13 illustrates the comparison of equilibrium binding to wt-RRE-II for various aminoglycosides.

We have examined a number of other aminoglycosides belonging to the neomycin family, as well as streptomycin, an unrelated aminoglycoside antibiotic (FIG. 12). Substantial differences exist with respect to their binding affinity for wt-RRE-II, spanning from neomycin B, which has the highest affinity, to streptomycin, which is weakest (FIG. 13). All show non-saturable binding in the micromolar concentration range. The same trend that was observed for wt-RRE-II was seen with RBE3 and RBE3-neg. The observed affinities for different aminoglycosides largely correlate with the total number of amines on the molecule and therefore with the overall charge.

Influence of competing ions.

Figure 14:
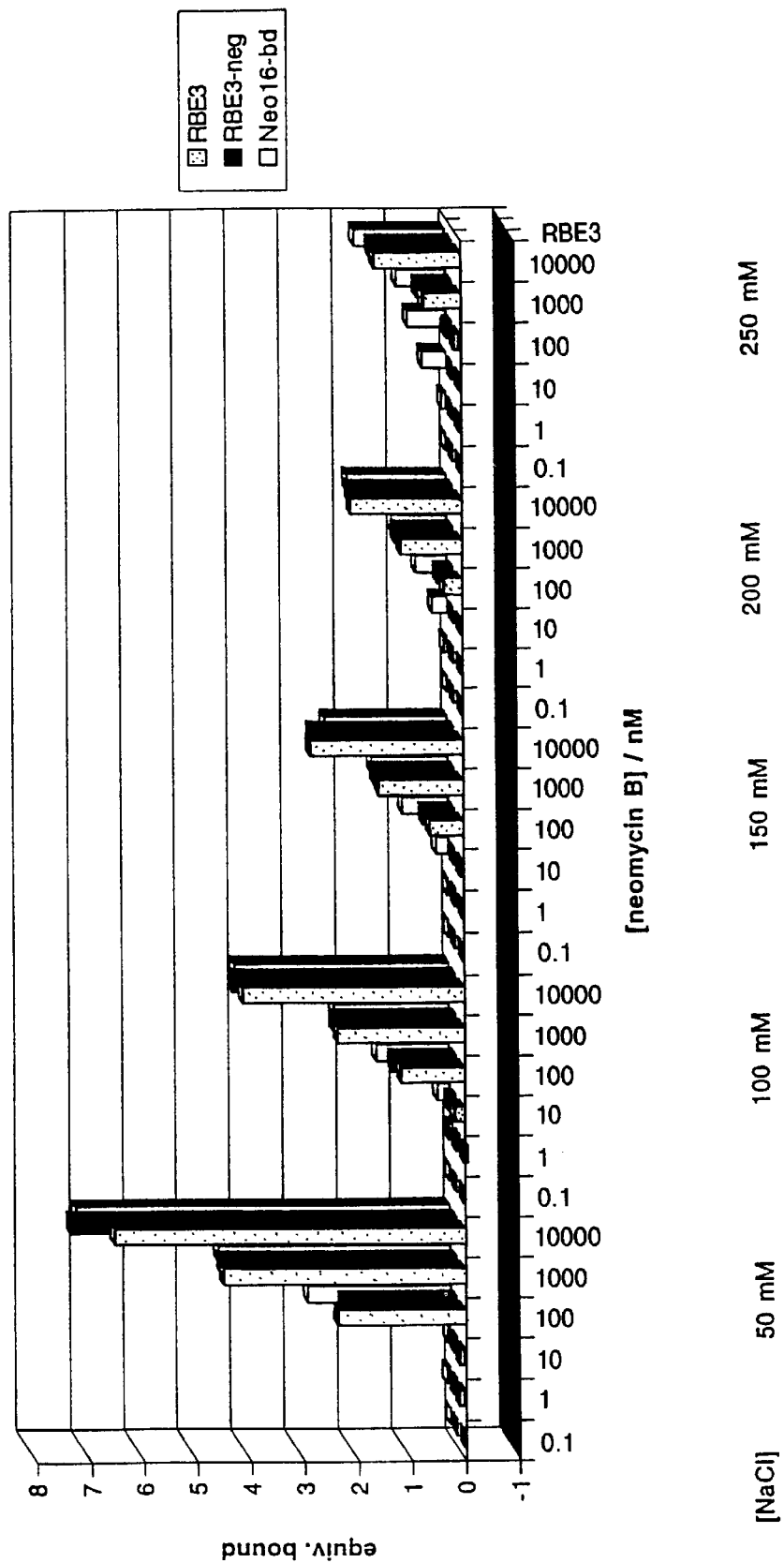
FIG. 14 illustrates the influence of ionic strength on binding of neomycin B to RBE3, RBE3-neg and Neo16-bd. Conditions: 10 mM HEPES (pH 7.4), 0.1 mM EDTA and NaCl as indicated.
Figure 15:
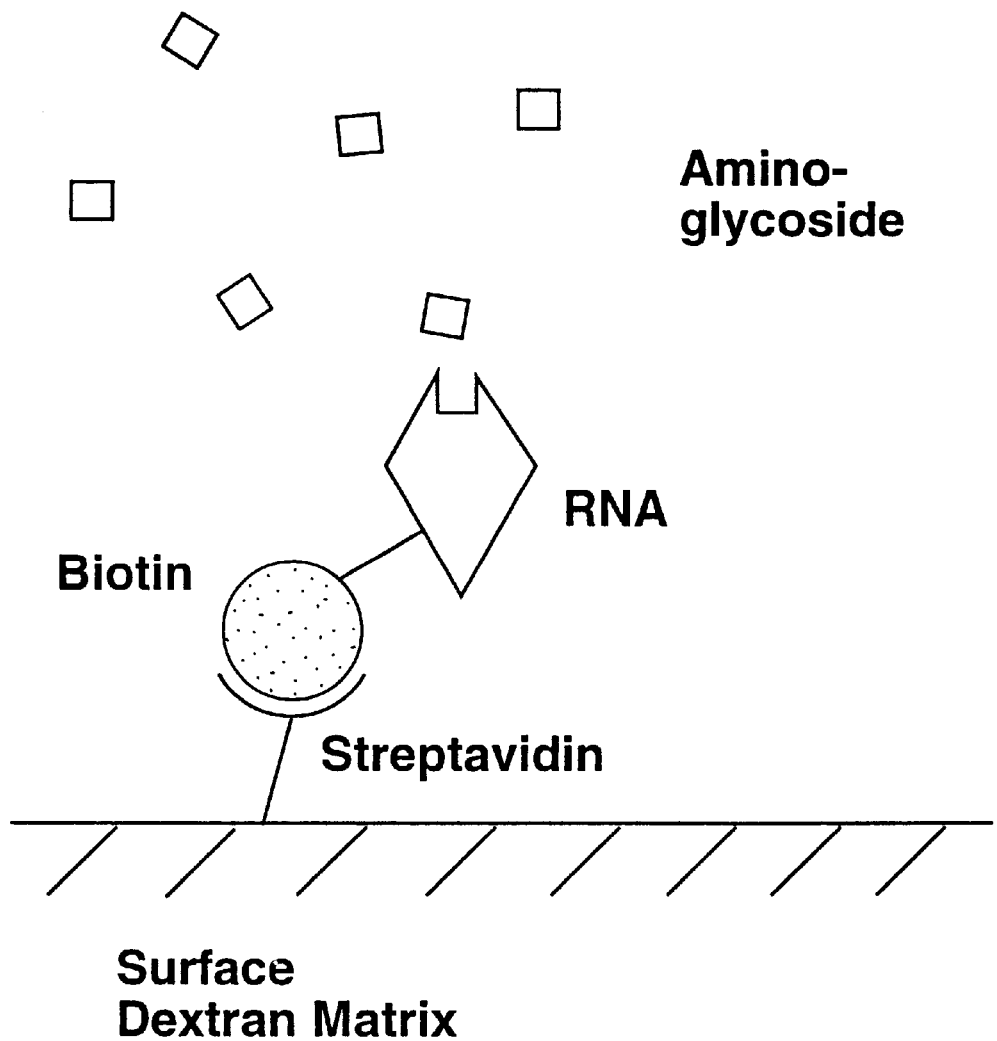
FIG. 15 illustrates the Surface Plasmon Resonance (SPR)-based method for monitoring small molecule RNA interactions. Specifically, we have synthesized several 5'-biotinylated RNA transcripts and immobilized them on the surface of streptavidin-coated sensorchips. Using this system we were able to study in detail the binding of aminoglycoside antibiotics to these sequences. Analysis of the binding data has allowed us to gain new insights into aminoglycoside-RNA interactions.
Figure 16:
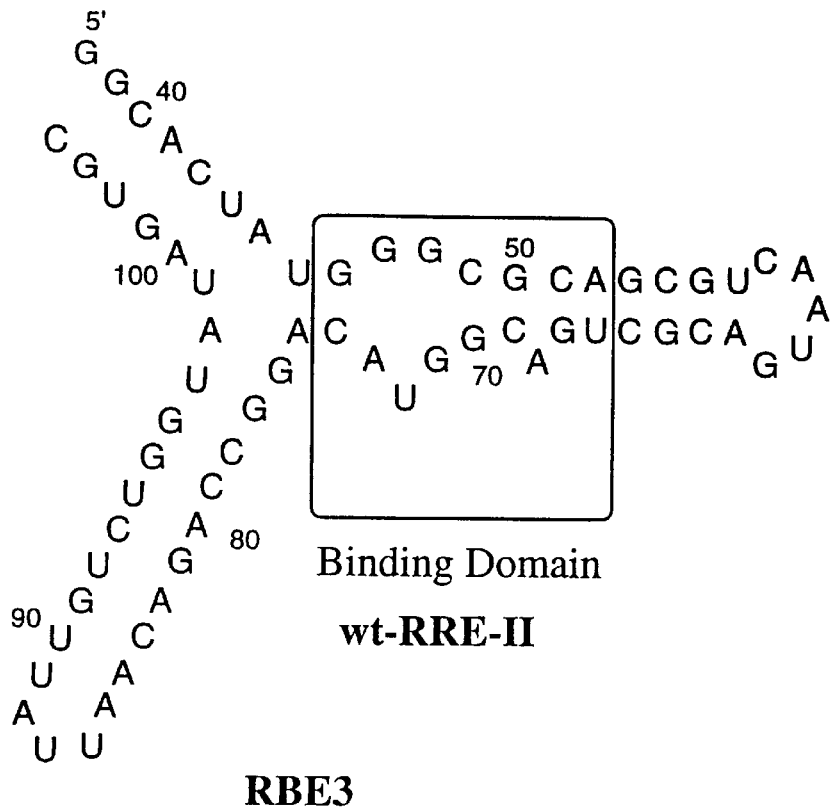
FIG. 16 illustrates the oligonucleotides used which were quantitatively modified with biotin for the Surface Plasmon Resonance (SPR) binding study (SEQ ID NOS 6–9).
Figure 16:
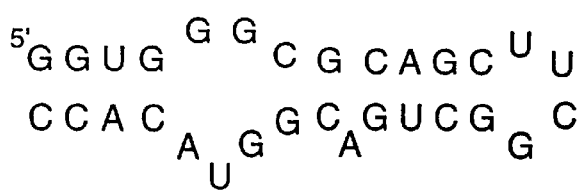
Figure 16:
Figure 16:
Figure 17:
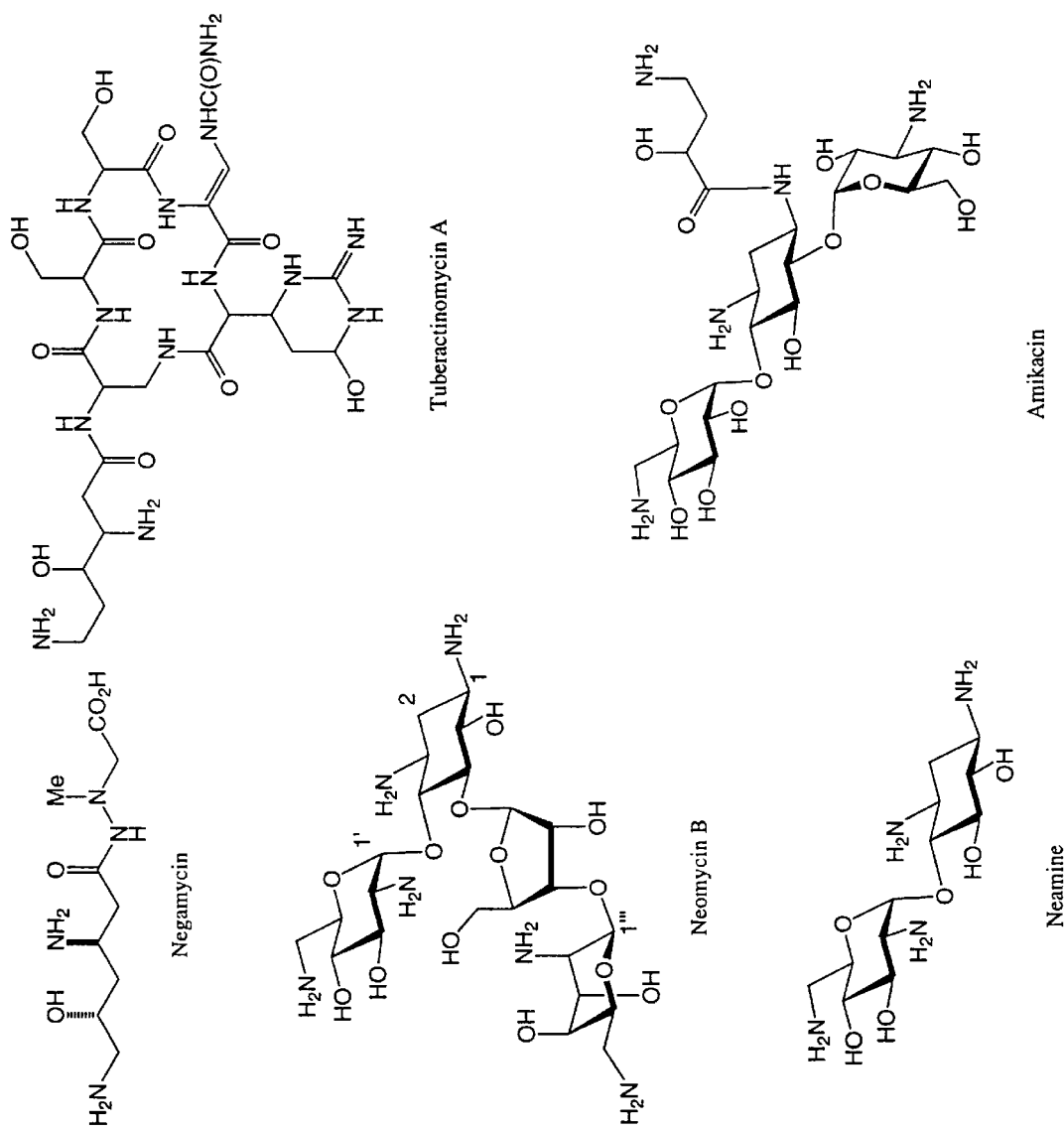
FIG. 17 illustrates examples of naturally occuring aminoglycoside and peptide antibiotics which inhibit protein synthesis.
Figure 18A:
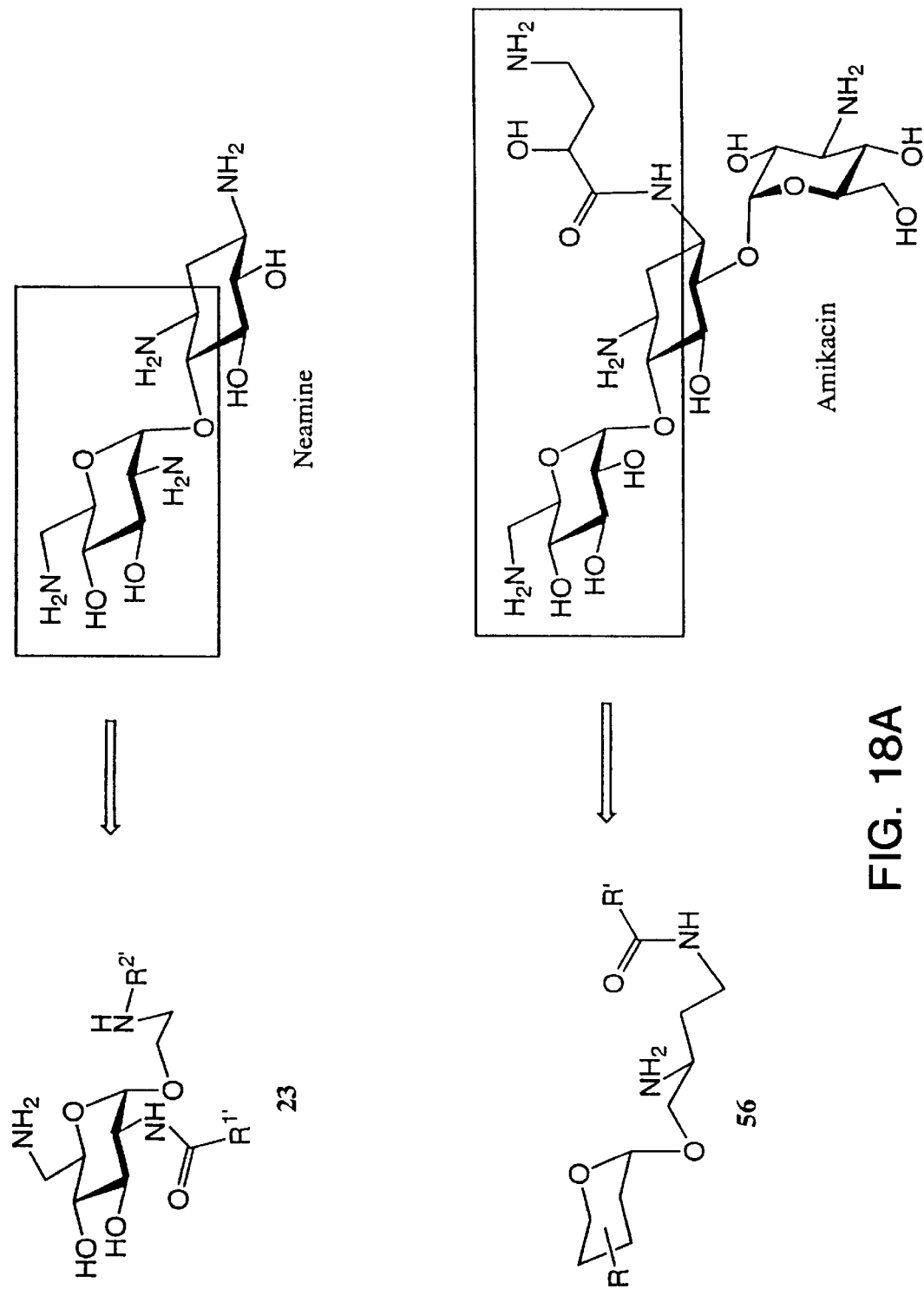
FIGS. 18A and 18B illustrate various nucleotide and phosphodiester binding motif scaffolds taken from naturally occuring aminoglycoside and peptide building blocks. The boxed areas around the naturally occuring products represent the active functionalities responsible for recognition and dissemble to the simplified inhibitors.
Figure 18B:
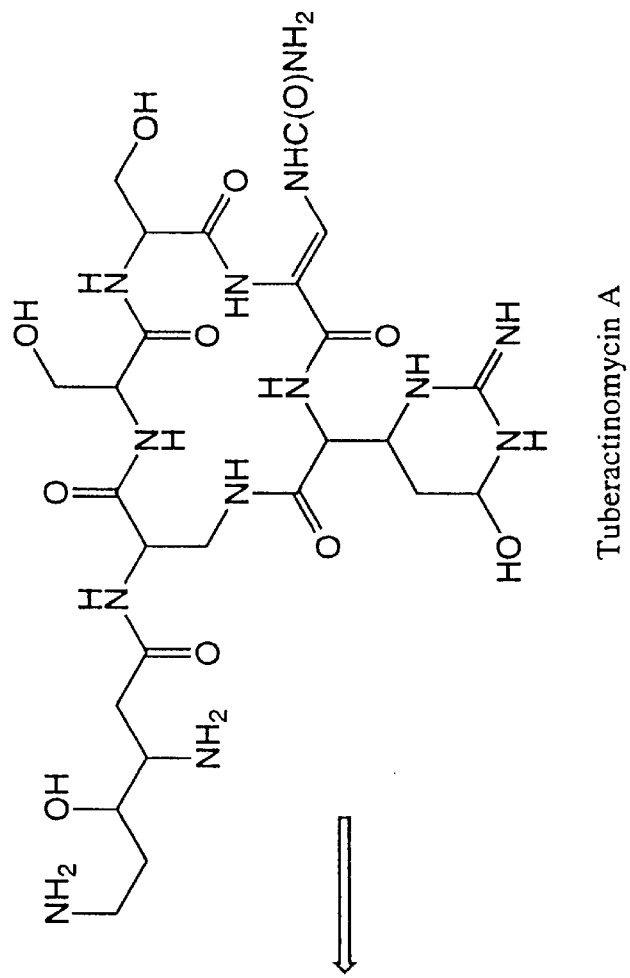
Figure 18B:
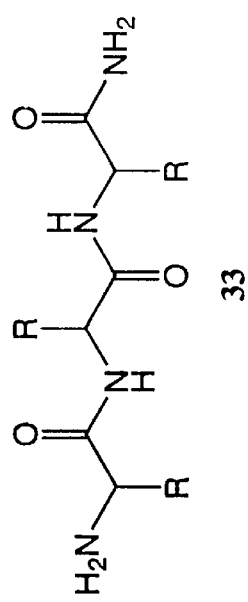

The binding of aminoglycosides to RNA is likely to involve substantial ionic contributions and therefore should be strongly influenced by competing buffer ions. In agreement with this notion, the inhibitory effects of aminoglycosides on ribosomal protein synthesis in vitro decrease with higher ionic strength of the medium. Likewise, a strong salt dependence has been found for the inhibitory activity of neomycin B on hammerhead ribozyme activity. We studied the salt dependence of neomycin B binding to RBE3, RBE3-neg and Neo16-bd (FIG. 14) by varying the concentration of NaCl included in the injection buffer (10 mM HEPES, pH 7.4, 0.1 mM EDTA). At low concentrations of NaCl (100 or 50 mM) an increase in the amount of non-specific binding was observed. However, at low ionic strength mass transport to the surface became an association rate limiting factor and at low concentrations of neomycin B equilibrium could not be reached during the usual length of the association phase (10–20 min). At higher salt concentrations (200 and 250 mM) binding was sharply reduced for both RBE3 and RBE3-neg. The behavior of Neo16-bd under these conditions is especially interesting. This neomycin binding motif was obtained by in vitro selection under conditions of high ionic strength. At 250 mM NaCl Neo16-bd still shows strong binding to neomycin B. Under these conditions the selectivity for binding Neo16-bd vs. RBE3 or RBE3-neg is approximately 100-fold. Interestingly, this advantage of Neo16-bd does not exist under less stringent salt conditions. Rather, it seems that specific binding to Neo16-bd is insensitive to ionic competition, whereas the binding to RBE3 and RBE3-neg is competed off by buffer salts. The non-specific binding is sensitive to increasing ionic strength in both cases.

The SPR assay is operationally simple and can easily be automated to ensure good reproducibility. It yields direct information on the stoichiometry of ligand binding and it is generally applicable to any kind of ligand without the need for labeling or modification. A wide variety of solution conditions can be employed. However, a number of limitations exist. Specific immobilization of the RNA via modification of the 5'-phosphothioate requires an additional synthetic step in the preparation of the RNA. In principle, the immobilization matrix including the streptavidin-biotin complex may interfere with ligand binding, although no such difficulties were encountered in this study.

Furthermore, kinetic limitations at low ligand concentrations, either through interaction kinetics or surface transport kinetics, may prevent the attainment of equilibrium in a reasonable time frame. Fortunately, the interaction kinetics of aminoglycosides are generally quite fast in the concentration range of interest (>100 nM), and if equilibrium is not reached it can be detected and taken into account. Analysis of the equilibrium response data through Scatchard plots seems particularly useful for both the simple detection of non-equilibrium data points and the determination of binding constants and stoichiometry.

Analysis of binding curves obtained with aminoglycosides reveals the presence of non-saturable binding in the micromolar range for all RNA sequences studied. These results make intuitive sense given the polyionic character of these molecules. Similarly, a large number of non-specific aminoglycoside binding sites has been found by equilibrium dialysis measurements on intact ribosomes. High affinity binding with defined stoichiometry was found in the nanomolar range for all sequences. No significant difference exists in the binding of neomycin B to RBE3 and RBE3-neg. This contrasts sharply with the high selectivity of Rev-peptide binding to the same sequences, ruling out a specific recognition of the G-rich bubble region of RRE by neomycin. Taken together with the fact that up to three molecules neomycin B are bound to the longer wt-RRE-II at submicromolar aminoglycoside concentrations, the results suggests that neomycin B may generally bind with this affinity to regular A-form duplex RNA or hairpin loops.

The relative lack of specificitiy for the interaction between neomycin B and wt-RRE-II, RBE3 or RBE3-neg is not surprising considering that neomycin B has not been produced in nature for the purpose of binding to RNA sequences in HIV. Any inhibitory effect is therefore likely to be accidental and not a specific, optimized recognition event. In this regard, the comparison of the RRE-related sequences and Neo16-bd is instructive. The latter RNA hairpin has been evolved in the laboratory to bind neomycin B under conditions of high salt. In accordance with this selection pressure, Neo16-bd has an evolved binding site that is largely insensitive to competing ions. This is in contrast to the RRE-related sequences, for which binding decreases strongly with increasing ionic strength.

An interesting aspect of aminoglycoside binding to RNA which can be readily studied by our method is the substantial difference in dissociation kinetics between neomycin B and paromomycin.

Inhibition of Protein Synthesis:

Inhibition of protein synthesis by RNA binding compounds having hydroxyamine substructures may be assayed by conventional methodologies disclosed by U.S. Pat. No. 5,556,829, No. 5,496,831, No. 5,336,664, No. 4,625,014, and No. 4,569,789, incorporated herein by reference.

EXAMPLE 4

Probing the Specificity of Aminoalycoside-Ribosomal RNA Interactions With Designed Synthetic Analogs In this example, the binding of neomycin B and related aminoglycoside antibiotics to the prokaryotic ribosomal RNA decoding region has been investigated using the surface plasmon resonance assay. A number of naturally occurring aminoglycosides containing a neamine or neamine-like substructure bind specifically to a model of the wt-A-site of the ribosomal decoding region RNA. This recognition event is the basis of the antibacterial activity of this class of compounds. A series of analogs was designed and synthesized to probe the role of neomycin ring IV (2,6-dideoxy-2,6-diamino-$\beta$-idopyranose). The binding results indicate that the positive charge presented on the idose ring is necessary for specific binding in vitro and cannot be replaced by amines attached via flexible linkers. However, the antibiotic activity (minimum inhibitory concentration) of the analog where ring IV is replaced with a diamine tail is the same as neomycin B in a liquid culture assay against *Escherichia coli.*

Figure 32:
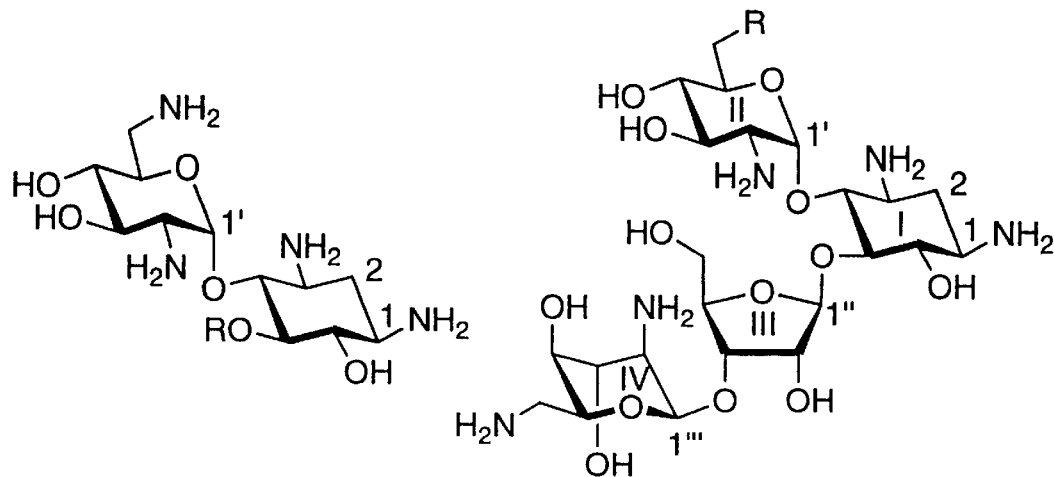
FIG. 32 illustrates structures of representative aminoglycoside antibiotics.
Figure 33:
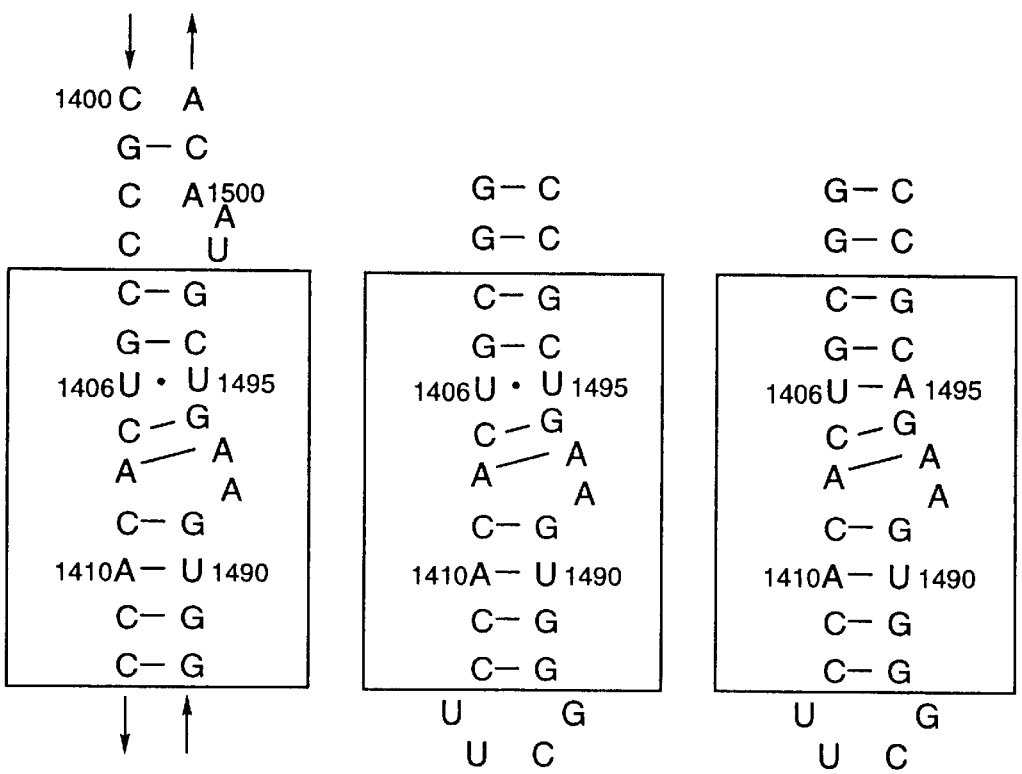
FIG. 33 illustrates sequences of the RNA molecules used in this study (SEQ ID NOS 10–13).
Figure 35:
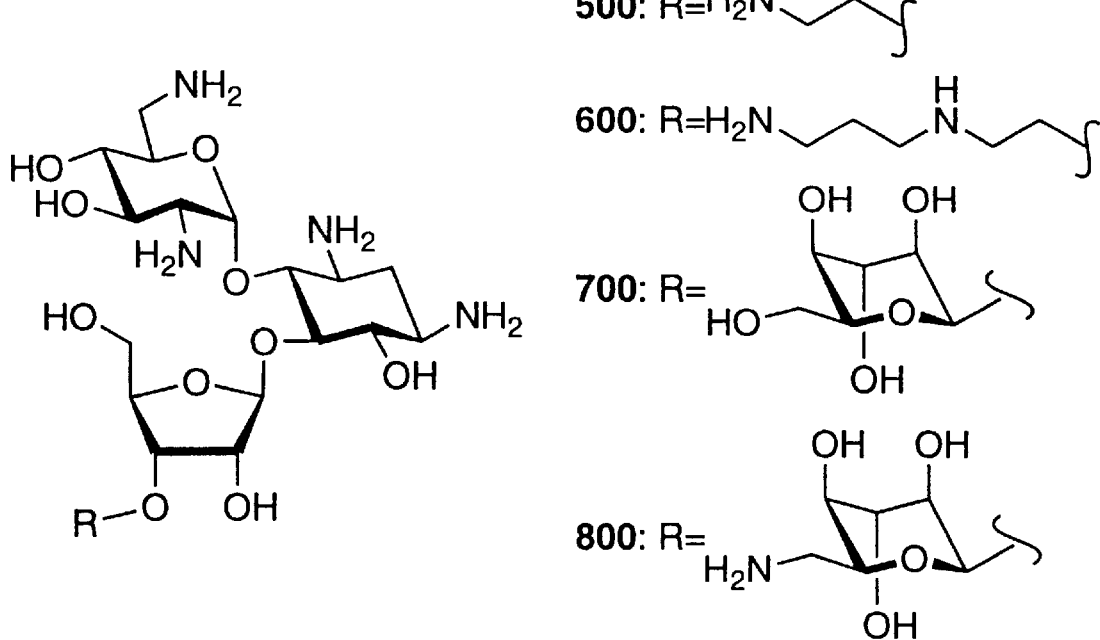
FIG. 35 illustrates target molecules to study the role of ring IV of neomycin B.

We have investigated the specificity of aminoglycoside binding to the A-site RNA with a series of naturally occurring aminoglycosides (100–400; FIG. 32) using our developed surface plasmon resonance based assay and compared RNA binding affinities for AS-wt and AS-U1495A. To address the contribution of ring IV, we synthesized a series of neomycin B derivatives modified in the idose ring. To examine whether the amino groups of ring IV need to be displayed on a rigid platform, the L-idose ring was replaced with an acyclic side chain presenting either one (500) or two (600) amines (FIG. 35). To dissect the role of specific charges while maintaining the native idose ring, either both (700) or one (800) of the amines was replaced with a hydroxyl group (FIG. 35).

We reasoned that this modification would provide the cleanest test for probing the ionic contribution, since hydrogen bond donor abilities, electronegativity and steric demand are similar for both functional groups. In order to learn how well the model system correlates with in vivo activity, we checked the new compounds for antibacterial activity against three bacterial strains using the disc method (Kirby-Bauer technique). The minimum inhibitory concentrations (MICs) of the compounds were then determined using the broth dilution technique. For antibiotic testing protocols, see: (a) Disk testing protocols: Phillips, I.; Williams, D., in Laboratory Methods in Antimicrobial Chemotherapy, Garrod, L. (ed.) Churchill Livingstone Press: Edinburgh, 1978, pp. 3–30. (b) MIC determination: Waterworth, P. M., in Laboratory Methods in Antimicrobial Chemotherapy, Garrod, L. (ed.) Churchill Livingstone Press: Edinburgh, 1978, pp. 31–40; Barry, A. L. The Antimicrobic Susceptibility Test: Principles and Practice, Lea and Febiger: Philadelphia (1976). (c) Standards: Lorian, V., Antibiotics in Laboratory Medicine (2nd. ed.), Williams and Wilkins: Baltimore, 1986.

Figure 26:
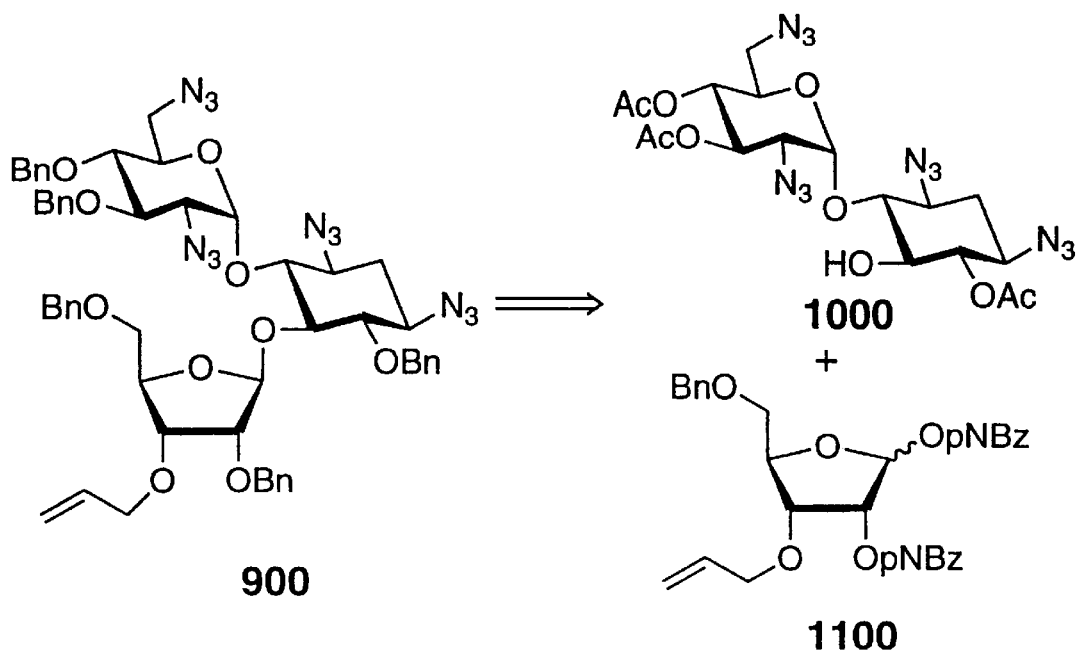
FIG. 26 illustrates a retrosynthetic analysis of compound 900.

Our retrosynthetic analysis (FIG. 26) led us to fragments 1000 and 1100 as suitable precursors for the key pseudotrisaccharide unit 900 from which all desired compounds can be constructed. Compound 1000 can be easily prepared from 100 which in turn is available by acidic hydrolysis of neomycin B (300) (FIG. 26).

The choice of a suitable nitrogen protecting group was crucial to our effort. Past synthetic work on the aminoglycosides has relied on the use of alkyl carbamates, (including benzyloxycarbonyl groups, cyclic carbamates and tert-butyloxycarbonyl groups) and trifluoroacetamides for the protection of the various primary amines. In our experience, the presence of multiple Cbz groups makes NMR spectra of the intermediates difficult to interpret, presumably due to the slow inter conversion of rotamers. The stability of the ethyl and cyclic carbamates can cause severe problems during deprotection and the solubility characteristics of polycarbamoylated aminoglycosides are not always compatible with the requirements for glycosidation. The lability associated with the trifluoroacetamide and Boc groups made strategies utilizing these groups unattractive. Finally, none of the acyl-type protecting groups address the issue of protecting the acidic NH that is formed upon acylation of a primary amine. These problems can be overcome by the use of azides as nitrogen protecting groups. To this end, we have introduced a metal catalyzed version of the original diazo transfer protocol which allows the convenient conversion of amines to azides with retention of stereochemistry. Using this protocol, neamine (100) was converted into tetraazido neamine, which was regioselectively acetylated to afford 1000.

Figure 27:
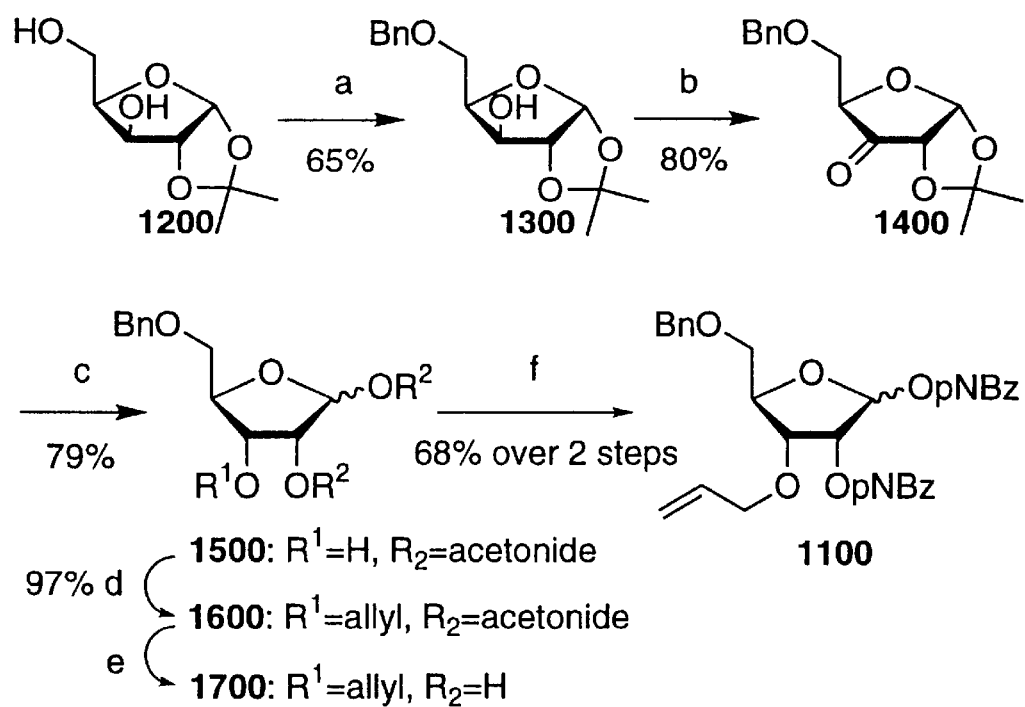
FIG. 27 illustrates the synthesis of compounds 1100 and 1700 with the following conditions: (a) i. Bu2SnO, toluene, azeotropic H2O removal, ii. BnBr, TBAI, 110° C.; (b) Swern oxidation; (c) NaBH4, MeOH; (d) NaH, allyl bromide, DMF; (e) DMF, 1 N HCl, D; (f) PNBzCl, Pyridine.

The next building block, ribose donor 1100 was constructed in a seven step sequence starting with the 1,2-O-isopropylidene xylose (1200)(FIG. 27). Stannyl ester activation and subsequent benzylation provided 1300. A two step oxidation/reduction sequence served to invert the stereochemistry at the 3 position and provide 1500. Alkylation with allyl bromide served to install the allyl group to afford 1600. Finally, the acetonide was removed to afford 1700 (FIG. 27).

Figure 28:
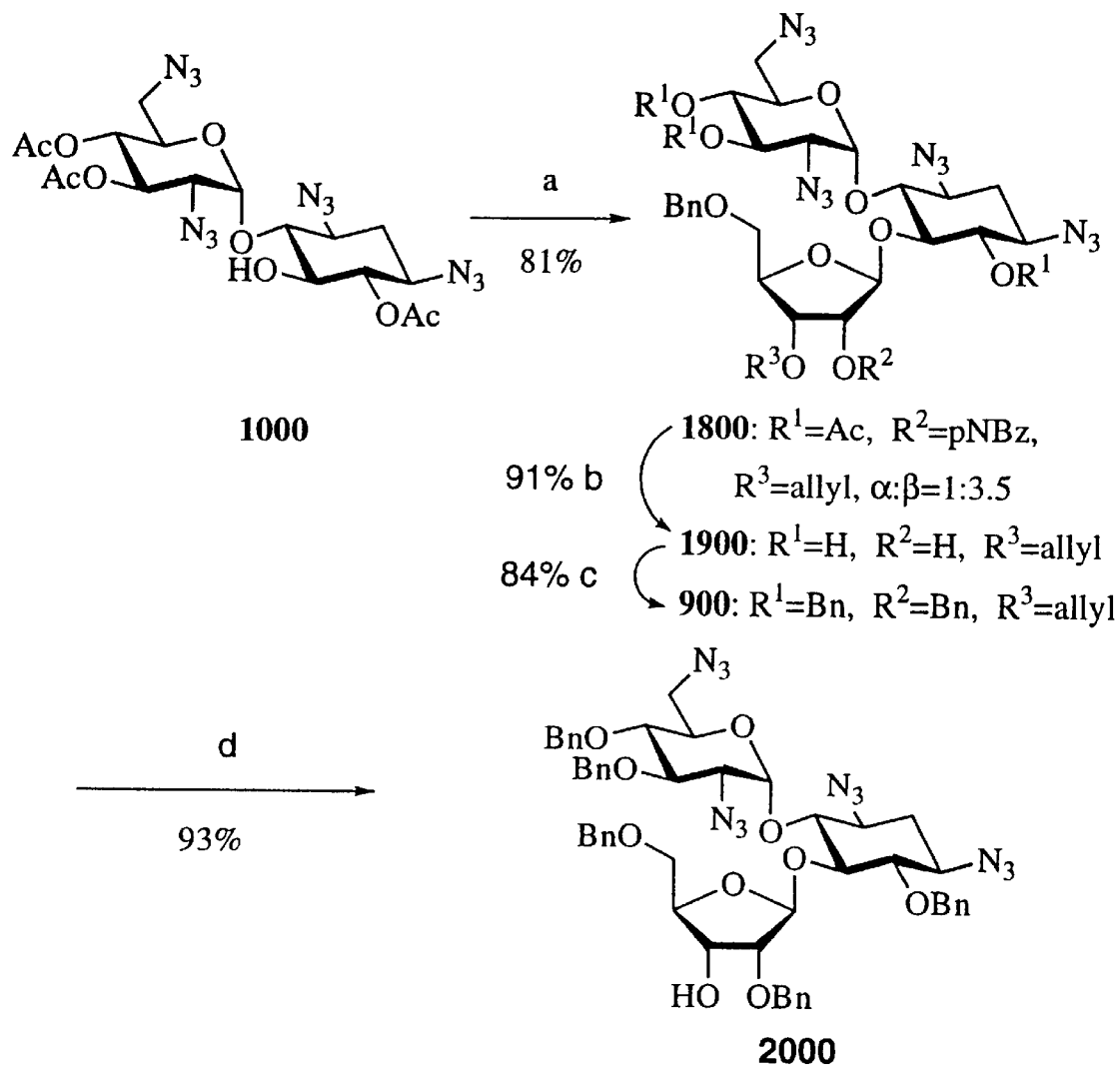
FIG. 28 illustrates the synthesis of compounds 900 and 2000 with the following conditions: (a) 1100, BF3.OEt2, CH2Cl2; (b) LiOH, H2O, MeOH; (c) BnBr, NaH, DMF; (d) i. bis(methyl diphenylphosphino)COD Ir(I) PF6 activated by hydrogen, THF, ii. OsO4, Me4NO.2H2O, CH2Cl2.

The para-nitrobenzoyl ester was installed in the anomeric position to give 1100 rather than the acetate which was employed by Umezawa and coworkers. The reason for this was that the attempted condensation of acceptor 1000 with the anomeric acetate led to poor conversions, presumably due to the reversible nature of this glycosidation. However, the para-nitrobenzoyl group solved this problem since para-nitrobenzoic acid precipitates from the reaction mixture and thus shifts the equilibrium in favor of the condensation (FIG. 28).

Reaction of 1000 and 1100 provided the desired β-linked pseudotrisaccharide 1800 in 63% yield along with an additional 18% of the α anomer which could be equilibrated to the desired product by resubjecting it to the glycosidation conditions. The anomeric configuration of 1800 was assigned based on the observed coupling constants of the H1" proton. The protecting groups were subsequently normalized to benzyl ethers to obtain the key pseudotrisaccharide 900. The allyl group was then used in a dual role. For access to the alkyl amino derivatives (FIG. 29), the allyl group of 900 could be converted to an aldehyde to set up the introduction of nitrogen by reductive amination (vide infra). In order to construct glycosylated derivatives, a mild two step deallylation of 900 yielded a suitable acceptor for subsequent glycosidation reactions.

For the preparation of 500 and 600, compound 900 was cleaved to the key aldehyde 2100 by ozonolysis. Compound 2100, in turn, was reductively aminated with the mono-Cbz adduct of propylene diamine to give 2200. By contrast, use of unprotected propylene diamine resulted in the formation of an aminal, which was not reduced. The deprotection proceeded via a two step sequence to yield the desired 600. First, the azides were reduced via Staudinger reaction, and the 6 remaining protecting groups were reductively cleaved using sodium in ammonia. The attempted direct treatment of azido protected aminoglycosides with Na/NH$_3$ led to mixtures of products containing deaminated derivatives which presumably arose from the homolysis of the C—N bond following the one electron reduction of an azide.

Synthesis of 500 proved to be somewhat more challenging. Attempts to use benzylamine as the nitrogen source in order to avoid extra steps led to a very unexpected deprotection problem. During attempted dissolving metal reduction, the N-benzyl group was reduced to the corresponding inert Birch product. To circumvent this problem, compound 2100 was converted to 2300 by reductive amination with para-methoxy benzylamine followed by carbamoylation with ZOSu. The PMB group was then oxidatively cleaved using CAN to afford 2400 and the standard two step deprotection protocol was used to obtain the desired analog 500.

Figure 30:
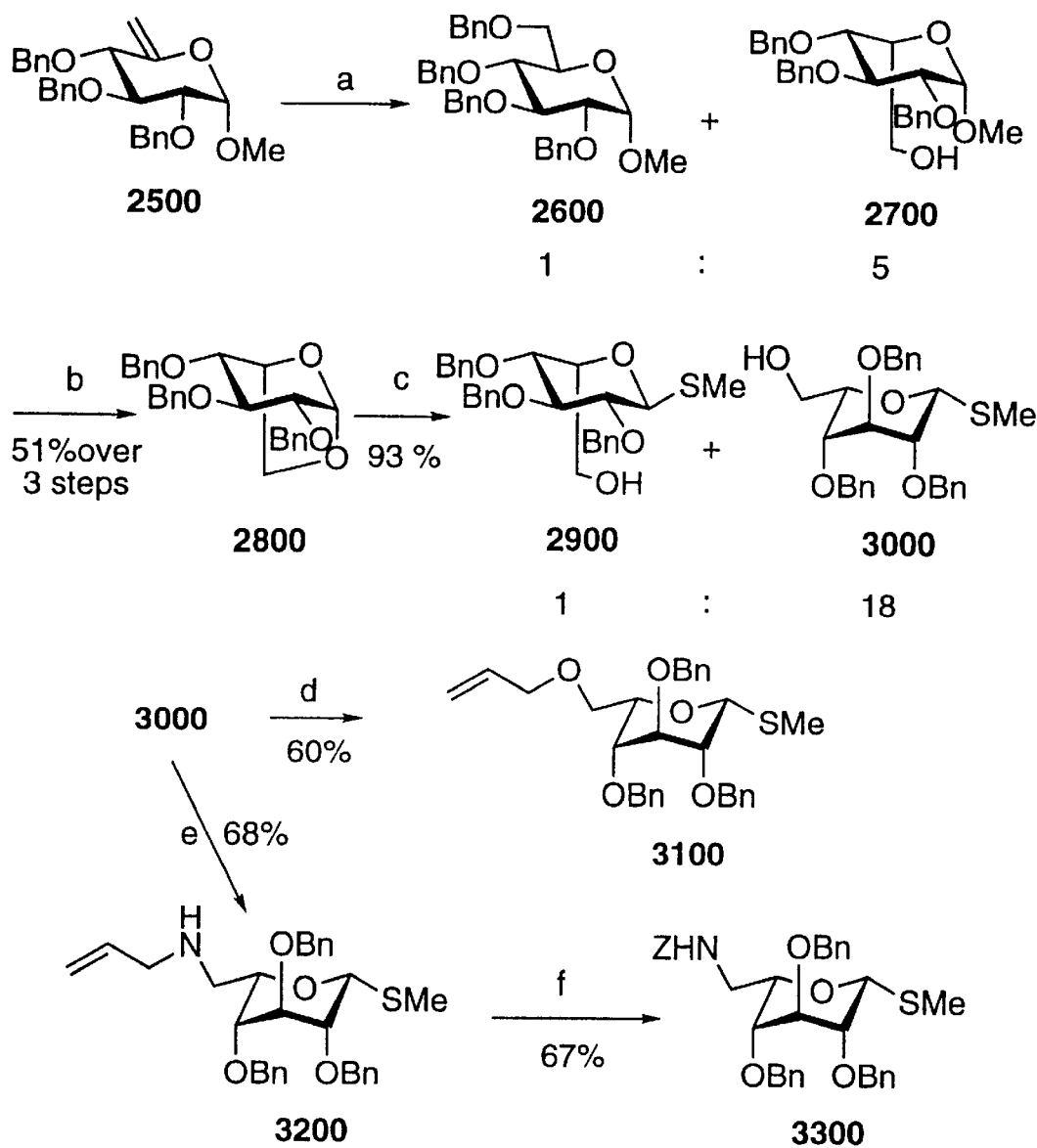
FIG. 30 illustrates the synthesis of compound 3300 with the following conditions a) i. BH3.THF, THF, 0° C., ii. HOOH, NaOH; (b) AcOH, conc. HCl, 70° C.; (c) i. MeSTMS, TMSOTf, CH2Cl2, ii. TBAF; (d) DMF, NaH, allyl bromide; (e) allylamine, AcOH, pH 6, NaBH3CN; (f) i. Wilkinson's catalyst, acetonitrile:H2O (84:16), distillation, ii. Z-OSu, CH2Cl2.

Attention was then focused on the idose synthesis. A number of approaches to L-ido and L-gulo configured systems have been described in the literature. However, none of the known methods was concise, with the possible exception of Paulsen's elegant rearrangement of per-acetylated D-glucose to D-idose but to prepare the L-derivative would require the expensive L-glucose pentaacetate (FIG. 30).

A low temperature hydroboration of 2500 with excess borane followed by oxidation of the carbon boron bond yielded a mixture of 2600 and 2700 which could be separated by chromatography, but separation was achieved much more readily after closure to the anhydrosugar 2800. Compound 2800 was remarkably stable, but proved to be labile to a sulfur nucleophile under TMSOTf promotion. The equilibrium was shifted towards the otherwise disfavored open form due to the strength of the resulting O—Si bond. Removal of the TMS group led to a 1:18 mixture of the anomers 2900 and 3000. The C6 oxygenated donor was constructed by allylation of 3000 at C6 to afford 3100. Attempts to introduce nitrogen at C6 of 3000 by activating the 6-position as the mesylate followed by displacement with azide proved to be fruitless due to intramolecular participation of the anomeric methyl sulfide which was followed by attack at the anomeric center to yield a product with sulfur at the 6 position. However, introduction of an amino substituent at C6 was eventually achieved through a chemoselective Swern oxidation followed by reductive amination with allylamine to afford 3200. Subsequent deallylation and Cbz protection led to the desired donor 3300 (FIG. 31).

Figure 31:
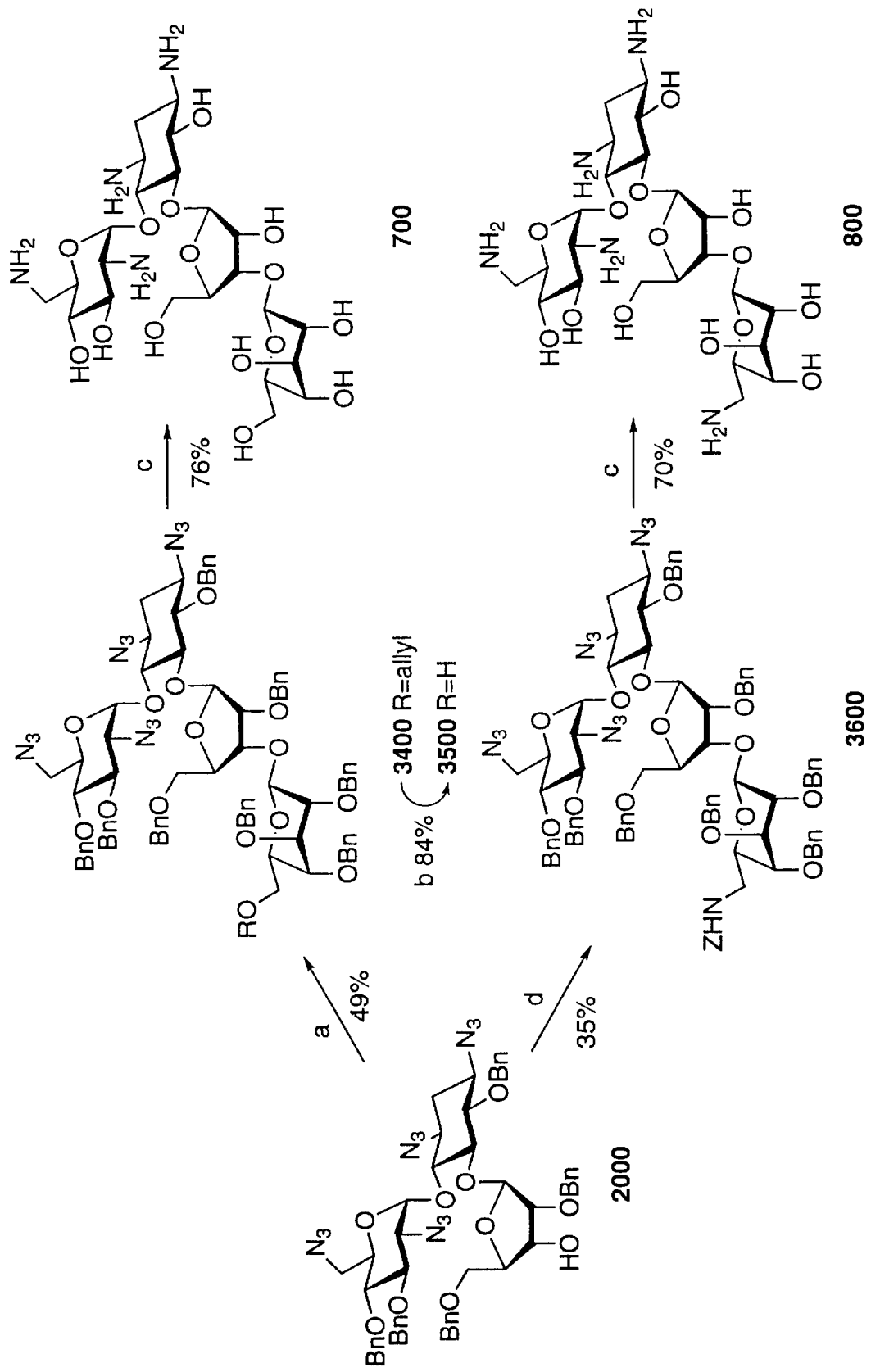
FIG. 31 illustrates the synthesis of compounds 700 and 800 with the following conditions:(a) 3100, NIS, AgOTf, 3 Å MS, CH2Cl2; (b) i. bis(methyl diphenylphosphino)COD Ir(I) PF6 activated by hydrogen, THF, ii. OsO4, Me4NO.2H2O, CH2Cl2; (c) i. PMe3, THF, H2O, 1N NaOH, ii. Na, NH$_3$, THF, EtOH, iii. Amberlite CG-50 anion exchange chromatography; (d) 3300, NIS, AgOTf, 3 A MS, CH2Cl2.

The tetrasaccharide core was assembled by glycosidation of 2000 with the glycosyl donors 3100 and 3300 to yield the protected pseudotetrasaccharides 3400 and 3600 respectively (FIG. 31). Both reactions proceeded with complete selectivity for the desired β anomer, presumably due to the triaxial confomation of the donor in solution (evident by the small coupling constants of the ring protons) and in the transition state. This conformation would lead to a severe (1,3) diaxial interaction if the product was formed in the a configuration. Compound 3400 was deallylated to afford 3500 and then subjected to our standard two-step deprotection protocol to afford 2''', 6'''-desamino-2'''-6'''-hydroxy neomycin B (700). Analogous deprotection of 3600 yielded 2'''-desamino-2'''-hydroxy neomycin B (800).

Figure 36:
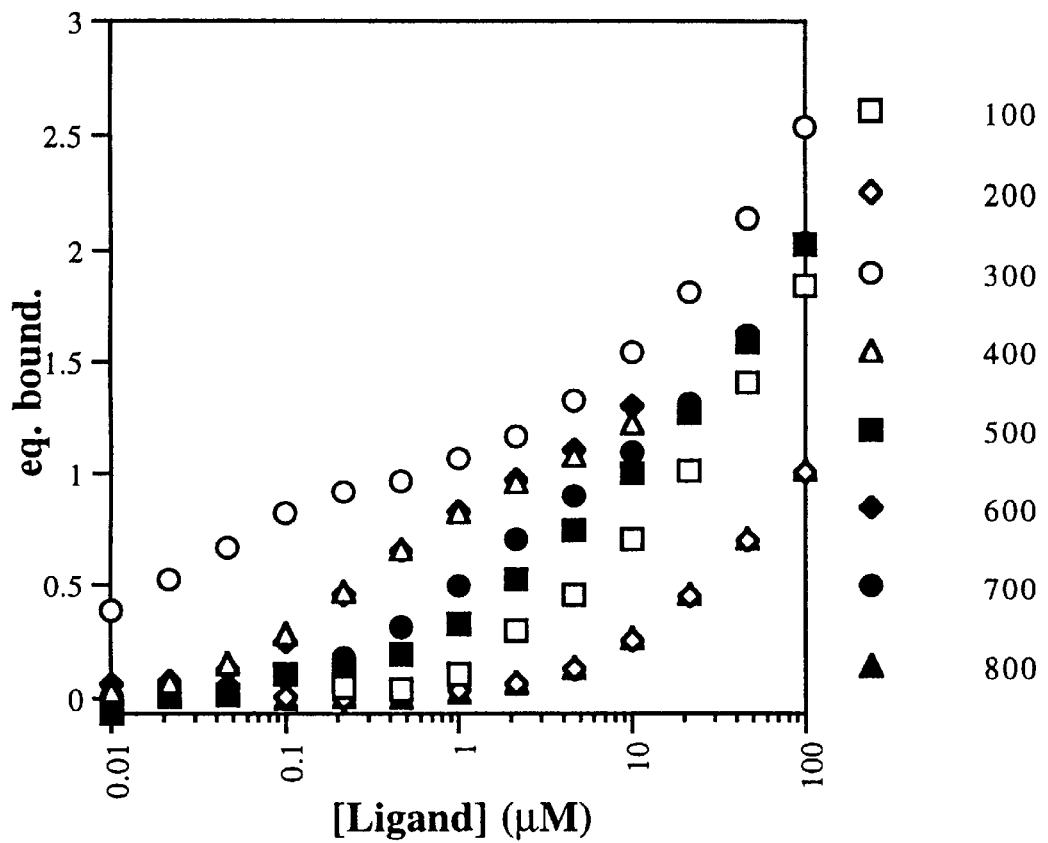
FIG. 36 shows titration curves for compounds 100–800 binding to AS-wt.

The RNA binding properties of 100–800 were analyzed using a surface plasmon resonance based assay that was recently developed in these laboratories. This assay allows the determination of both affinity and specificity of small molecule-RNA interactions. For the analysis, the compounds were injected over a matrix containing RNA that was immobilized through a biotin tag and the equilibrium binding values were recorded at various concentrations. A sample of binding curves is shown in FIG. 36.

Non-linear curve fitting was then used to determine the values of the dissociation constants (KD). The specificity of binding, i.e. the ability to discriminate between different RNA sequences was evaluated by comparing the binding to the target sequence (AS-wt) and the negative control (AS-U1495A). The ratio of KD(AS-U1495A) to KD(AS-wt) was taken to be a representation of the specificity of the binding event. The data are summarized in FIG. 38.

The compounds were assayed for biological activity against three bacterial reference strains, *Escherischia coli*

Figure 37A:
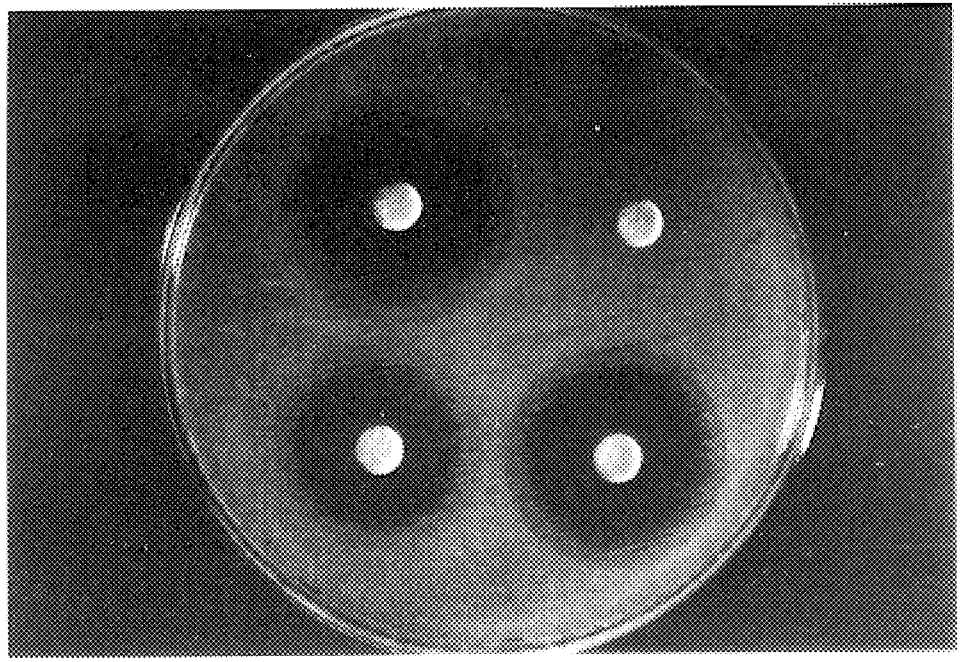
FIGS. 37A and 37B illustrate a representative Kirby-Bauer disc assay (Top) The compounds on the plate are (in clockwise order): Neomycin (33 nmol); negative control; compound 600 (33 nmol); Neamine (200 nmol); (Bottom), Clockwise from top left: compound 500 (33 nmol); compound 800 (33 nmol); compound 700 (33 nmol); and compound 600 (33 nmol).
Figure 37B:
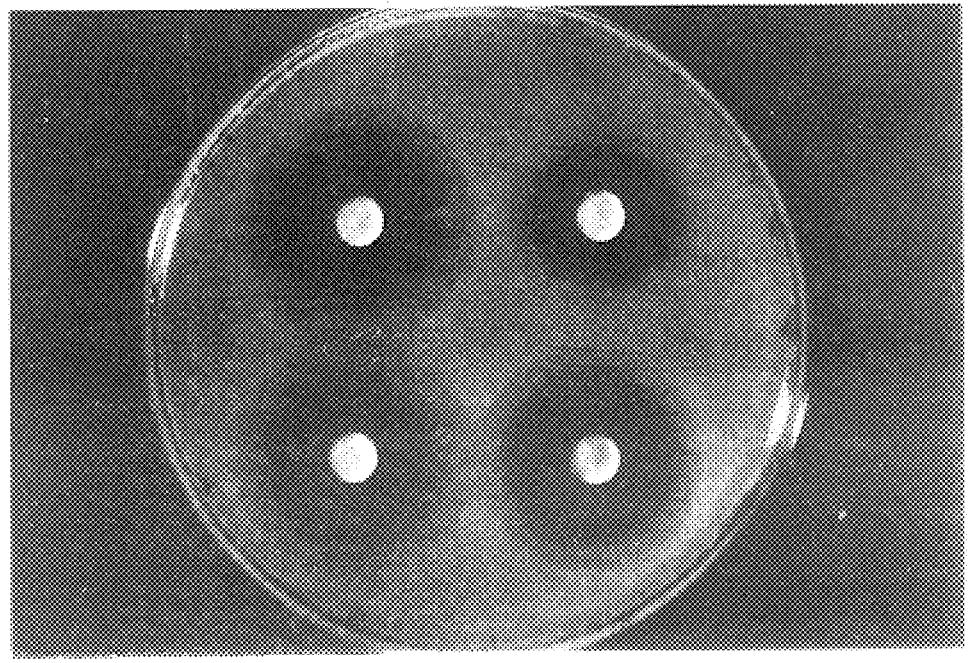

(ATCC 25922), Pseudomonas aeruginosa (ATCC 27853), and Staphylococcus aureus (ATCC 25923), using the Kirby-Bauer disc method in which paper discs containing known amounts of antibiotic are placed on plates inoculated with bacterial cultures, and the diameters of the zones of inhibition (DZI), apparent as clear regions around the discs, are measured after overnight growth. FIG. 37 shows a representative disc assay.

FIG. 39A gives the zone diameters measured for the three bacterial strains. The zone diameters measured for the strains with known antibiotics are well within the accepted limits. The minimum inhibitory concentrations were determined via the broth dilution technique, and the results are shown in FIG. 39b. The results for neomycin are within accepted ranges for sensitive E. coli strains. It is worth noting that some testing protocols recommend overnight growth of the cultures, rather than the minimum time required to obtain good growth of the control. MIC values were tested for several of the control antibiotics using overnight growth, and the MIC values observed were 2–4× greater than those observed for 4–6 hour growth.

The available NMR structure of the paromomycin-AS-wt complex suggested that the pseudodisaccharide portion of the molecule was mainly responsible for recognition. However, the Biacore data on neamine (100), ribostamycin (200) and neomycin B (300) suggested that the idose ring was responsible for a large portion of both affinity and specificity. This observation made a good case for studying the role of this ring in the binding event.

To probe this role, the neomycin B analogs synthesized (using the single key intermediate 1300 and tested in this study have the idose ring replaced with a flexible monoamine tail (500), or a diamine tail (600) or with idose analogs containing only hydroxy groups (700) or one amine group (800). In contrast to previous observations, all of the aminoglycosides tested here using surface plasmon resonance show some degree of specificity in the recognition of AS-wt. As expected, the overall affinity correlates with the net charge of the molecule, neomycin B being the tightest binder.

The binding data for compounds 100–800 can be compared by starting with neamine (100) and observing the changes in binding that occur as functionality is added on to the molecule. Neamine (100) binds the AS-wt sequence with a dissociation constant of 7.8 mM and approximately 4-fold specificity relative to the AS-U1495A sequence. Ribostamycin (200) adds a ribose ring to this core at the 500 position of 2-deoxystreptamine and has 3-fold lower affinity and similar specificity to neamine while retaining the same overall charge. Addition of an uncharged idose platform to ribostamycin (200) to generate 700 results in a molecule which has virtually the same RNA binding profile. This result implies that the idose ring by itself (without amines) does not contribute to the affinity or specificity of binding.

Addition of an amine at a defined position on the idose platform to give compound 800 improves affinity by 40 fold in relation to (700) and makes the interaction relatively specific. Addition of a second amine to this platform to generate the parent agent neomycin B (300) results in further improvement of the overall affinity, without affecting specificity. When a single positive charge on a flexible ethyl tether rather than a saccharide platform is attached to ribostamycin (200) to give 500, the binding affinity goes up by an order of magnitude but specificity is unaffected. The addition of another positive charge on an even more flexible linker (600) gives diminishing returns on the affinity without affecting the specificity. These results indicate that within the scope of this model, the rigid scaffold of the idose ring is necessary in order to preserve the specificity exhibited by neomycin B.

Paromomycin (400) which differs from neomycin B (300) only in position 6', can best be compared to 800, which has the same number of charges. Compared to 800, paromomycin (400) shows somewhat higher affinity but lower specificity. The control antibiotic streptomycin was used to demonstrate that unrelated aminoglycoside antibiotics which are not known to bind to this sequence exhibit a much reduced binding affinity and no specificity for the native sequence over the AS U1495A mutant.

The MIC data for these compounds in E. coli (FIG. 39b) indicate that the in vivo activity does not always correlate well with the in vitro binding data. Compounds 500 and 600 both have significantly lower binding affinities toward the AS wt RNA than neomycin and show considerably higher non-specific binding to the AS U1495A species (FIG. 38), yet have very nearly the same anti microbial activity as neomycin B (300) itself. Neamine, which appears to bind better to AS wt than ribostamycin, shows inferior anti microbial activity. These discrepancies may reflect different uptake dynamics of the different compounds, or perhaps a slightly different conformation of the ribosome in vivo.

The presumption that the binding mode is similar for the two molecules can be justified by the near identity of rings I, II and III and the comparison between neomycin B and the synthetic analogs regarding their $^{13}$C-NMR shifts and coupling constants (FIG. 40). The 5' phosphate of A1493 makes a fairly long range contact with the 6' OH of paromomycin but since neomycin-like structures feature a 1,3-hydroxyamine motif between the 4 and 6 positions, this interaction may well be closer for this class of molecules. The structure shows that the diamine tail is in an area rich in potential phosphate contacts with the 5' phosphates of U1406, C1407, A1408, G1488 and G1489 all being candidates. This may mean that the interaction of a simple doubly positively charged appendage with a highly electronegative major groove of RNA is enough to orient rings I, II and III into their binding pocket.

The anti microbial activity of compounds 500 and 600 holds promise for the design of novel antibiotics. It is apparent that gross changes are tolerated in the structure of aminoglycoside antibiotics without significant effect on biological activity. This observation should allow design of structurally simpler molecules which could have activity and could possibly address issues of drug resistance.

EXAMPLE 5

Probing the Specificity of RNA Recognition by Aminoglycosides

Due to their multiple positive charge, aminoglycosides have a general affinity for all RNAs. More important from a medicinal perspective, however, is the binding specificity, i.e. the ability to discriminate between different RNA structures. The challenge of sequence and structure specific recognition of a particular target site against the backdrop of a very homogeneous biopolymer is also of fundamental importance to the field of molecular recognition. Even proteins often show only moderate specificity ($\leq 100$ fold) in the recognition of RNA, underscoring the difficulties that are likely to be encountered in the design of specific small molecules.

In addition to the interaction with their natural targets on the prokaryotic ribosome, aminoglycosides have been shown to bind a number of different RNA sequences as described in the examples above. These include two mRNA sequences from HIV, the Rev-Responsive Element (RRE) and TAR. They also inhibit catalytically active RNAs such as the self splicing group I introns and hammerhead ribozyme. Other aminoglycoside-binding RNA sequences have been derived by in vitro selection, striving to understand the "rules", if any, that govern aminoglycoside-RNA recognition. Some authors have also put forward the hypothesis that antibiotics may have played a role in the evolution of an RNA world as so-called low-molecular-weight effectors. However, in most of these cases the specificity of the interactions remains unproven. This is primarily due to the scarcity of methods available to address this issue. We have developed a new method for the direct observation of aminoglycoside-RNA interactions based on surface plasmon resonance (SPR) as described in example 3 above. Using this method, we have investigated the recognition of the ribosomal decoding region A-site by aminoglycoside antibiotics.

Aminoglycoside target sites on the bacterial ribosome

The natural targets of aminoglycosides are the prokaryotic ribosomes. A number of antibiotics binding to the ribosomes has been measured directly using equilibrium dialysis, with the dissociation constants being in the low micromolar range. Different lines of evidence point to the direct involvement of ribosomal RNA in this recognition process. First, aminoglycoside producing organisms carry specific methyl transferases that methylate certain nucleotides of their ribosomes, thereby protecting themselves from the antibiotic action of their own metabolites. Furthermore, point mutations in ribosomal RNA have been discovered that confer aminoglycoside resistance. Finally, footprinting studies on either the complete ribosome or isolated subunits have shown specific footprints (protections or enhancements) at ribosomal RNA bases. In many cases, footprints of the aminoglycosides are found directly adjacent to sites that are implicated in resistance or self-protection. Although none of these observations represent a definitive proof, taken together they point to the direct involvement of ribosomal RNA in aminoglycoside binding.

Figure 41A:
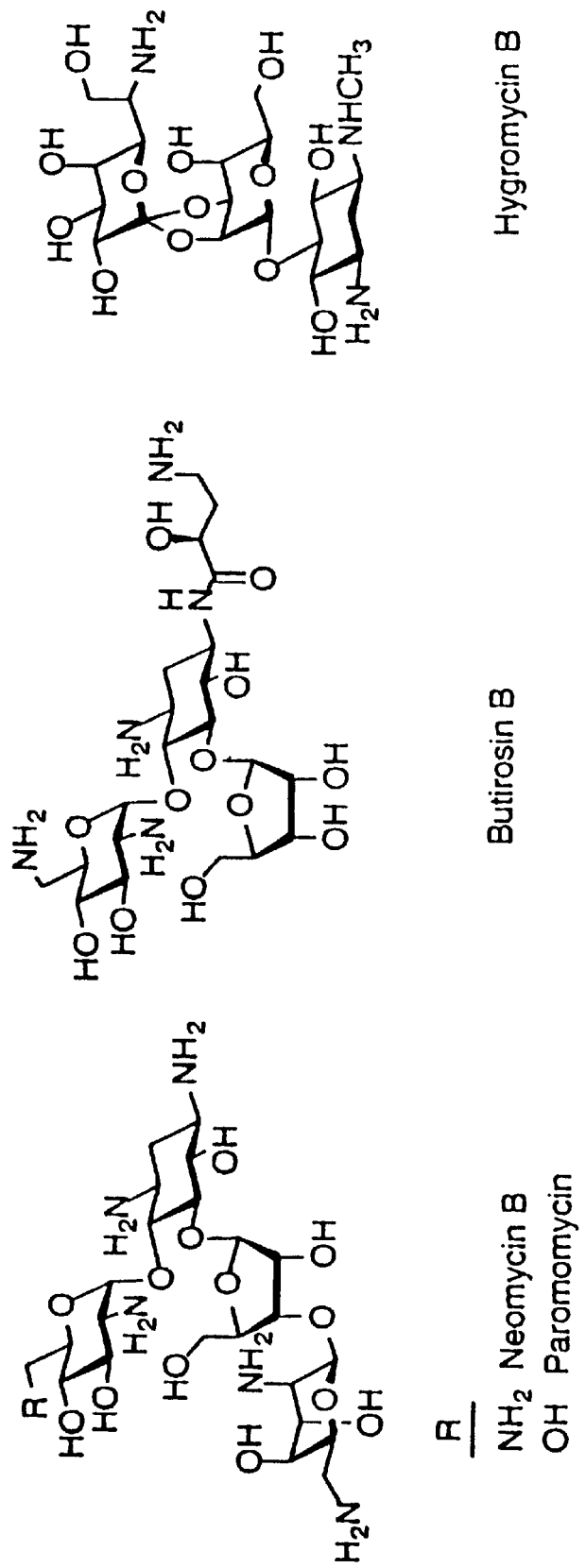
FIGS. 41A–41C illustrate structures of aminoglycoside antibiotics binding to the A-site.
Figure 41B:
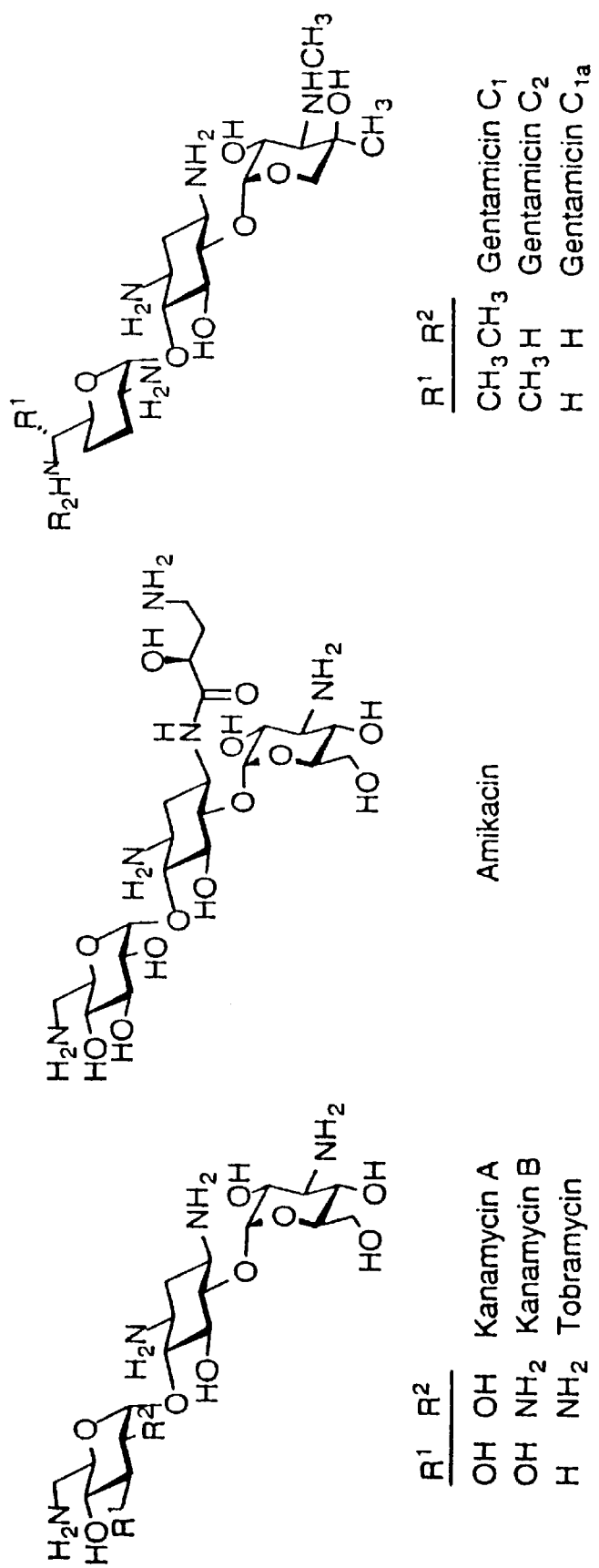
Figure 41C:
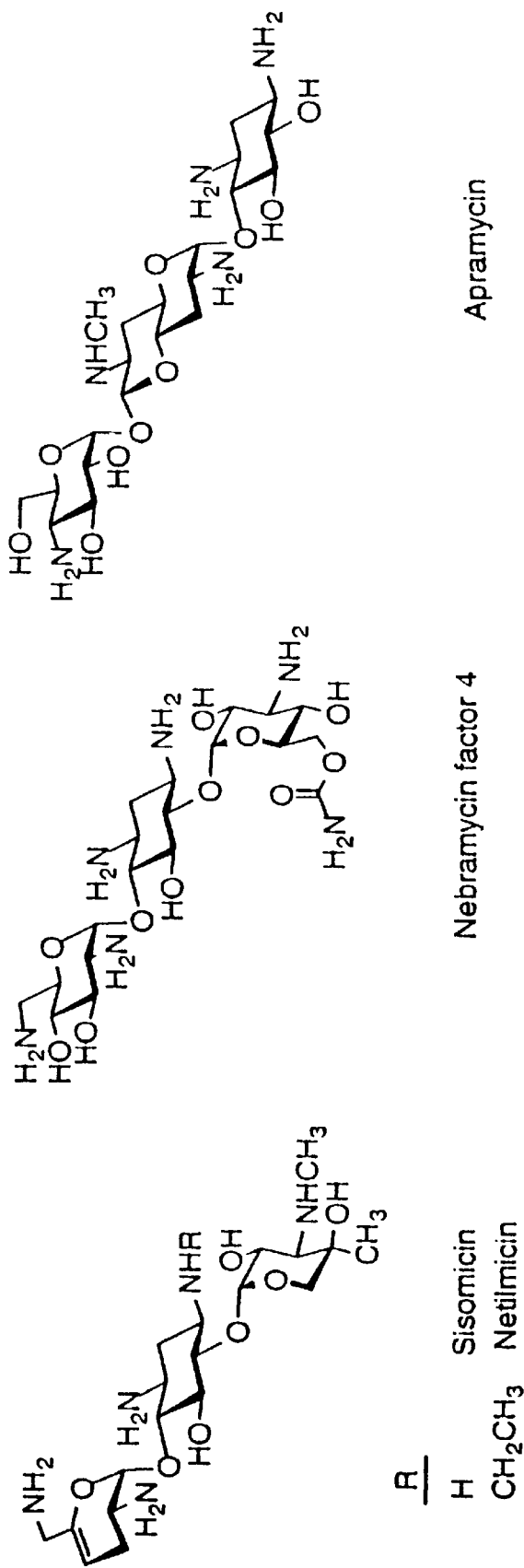

By far the largest number of aminoglycosides falls in the class that binds to the A-site of the ribosomal decoding region (FIG. 41). The function of the A-site during protein synthesis is to bind the charged aminoacyl tRNA corresponding to the next mRNA codon in a transcript. In a mechanism that is yet to be clarified, the decoding region ensures the selection of the cognate tRNA, which is chosen with higher specificity than the three base pair codon-anticodon interaction can account for. Aminoglycosides that bind to the decoding region interfere with this ribosomal "proofreading" mechanism. The resulting miscoding and/or premature termination is believed to be the cause of the bactericidal action of these antibiotics.

The A-site binding aminoglycosides include the 4,5-linked 2-deoxystreptamine derivatives neomycin B, paromomycin and ribostamycin as well as the 4,6-linked kanamycins and gentamycins. The structurally dissimilar antibiotics hygromycin B and apramycin also belong in this group. Characteristic of all these A-site binders is the strong protection of N7 of G1494 of the 16S ribosomal RNA. Otherwise, there are notable differences with respect to other footprints as well as the observed patterns of resistance (FIG. 42). For example, methylation of N7 of G1405 which is found in the gentamicin producer strain *Micromonospora purpurea*, confers resistance to the 4,6-linked 2-deoxystreptamine derivatives gentamicin and kanamycin but not to neomycin B which falls into the 4,5-linked class.

RNA models for studying aminoglycoside binding to the decoding region A-site

Figure 43:
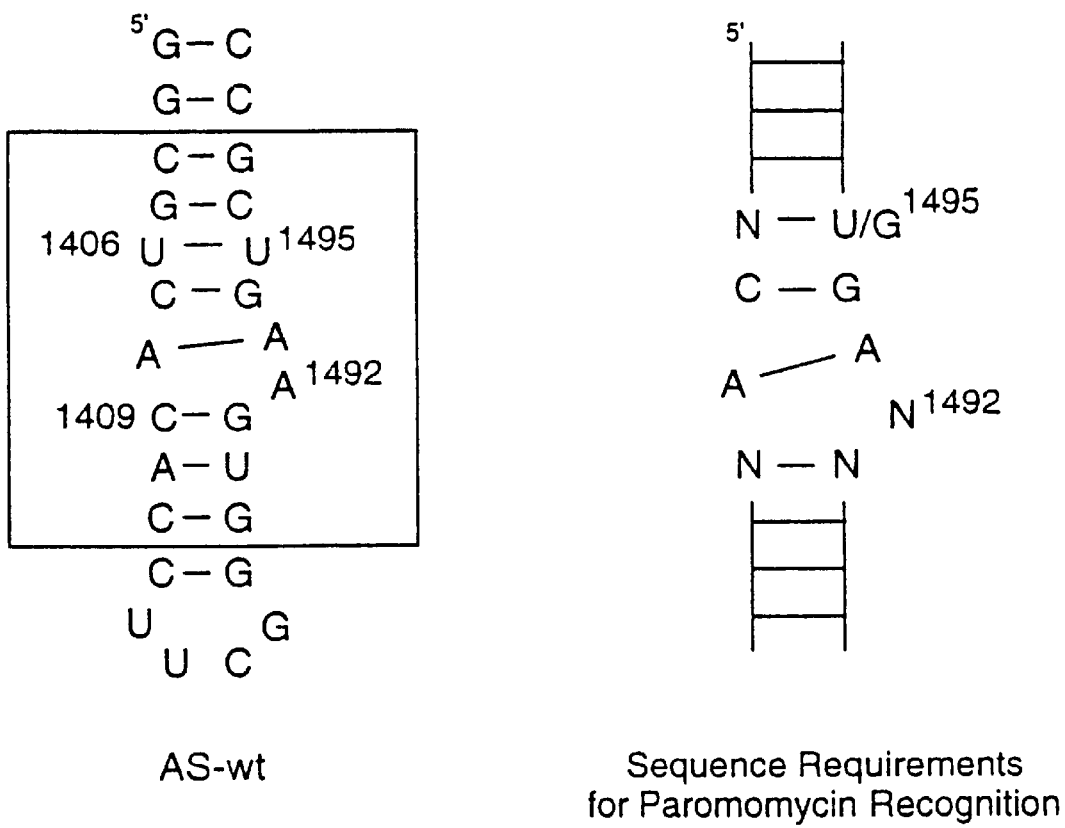
FIG. 43 shows short models of ribosomal decoding region RNA that still contain the paromomomycin/neomycin binding site (SEQ ID NO 12).

The presence of ribosomal proteins is not necessary for aminoglycoside binding to the decoding region. This was first demonstrated by Purohit and Stern, who showed that a 50 nucleotide stemloop containing nucleotides corresponding to both the A- and P-site of the decoding region binds neomycin B and paromomycin with high affinity, giving rise to a protection pattern similar to that observed for 16S ribosomal RNA in the context of the full ribosome. Later it was shown that an even shorter RNA hairpin (AS-wt) corresponding only to bases of the A-site still contains the intact binding site. Extensive mutational analysis has defined the nucleotides required for specific recognition (FIG. 43). These include a looped out nucleotide adjacent to a G:C base pair. In the position corresponding to base 1492 in *E. coli* 16S rRNA numbering either a uridine or a guanosine is required. A base pair needs to close up the other side of the bulge.

Figure 34:
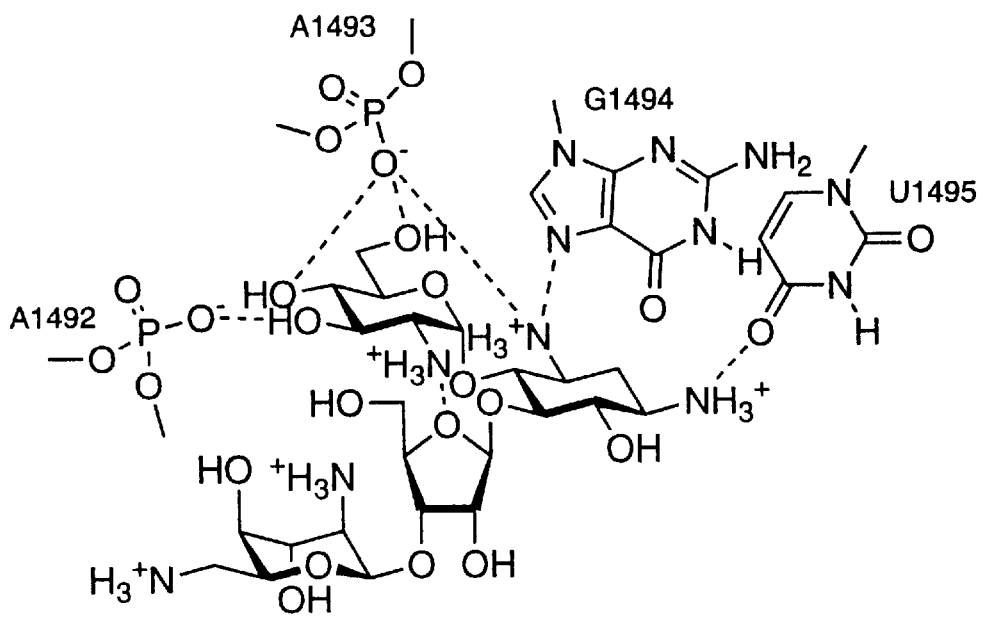
FIG. 34 illustrates schematic representation of the binding of paromomycin to the target fragment of 16S Ribosomal RNA based on the study reported by Puglisi et al.

The structure of the complex of paromomycin with the A-site model AS-wt has recently been determined by NMR (FIG. 34). Paromomycin sits in a pocket created by a bulged residue (A1493) and a non-canonical A1408:A1492 base pair. The 2,6-diaminoglucose ring stacks against the underside of the C1409:G1491 base pair which forms the floor of the bulge created by the looped out adenosine residue and the non-canonical A1408:1493 base pair. The 2-deoxystreptamine ring spans across two base pairs in the major groove and its two amino groups make specific hydrogen bond contacts to N7 of G1494 and O6 of U1495. In addition, the N3 of the cyclitol ring and the hydroxy groups of the glucosamine residue are involved in ionic and/or hydrogen bond interactions with the phosphates of A1493 and A1492. The other two rings of the bound aminoglycoside, the ribo- and ido-ring, are dynamic in structure and do not appear to be involved in any particular hydrogen bonds.

Figure 44:
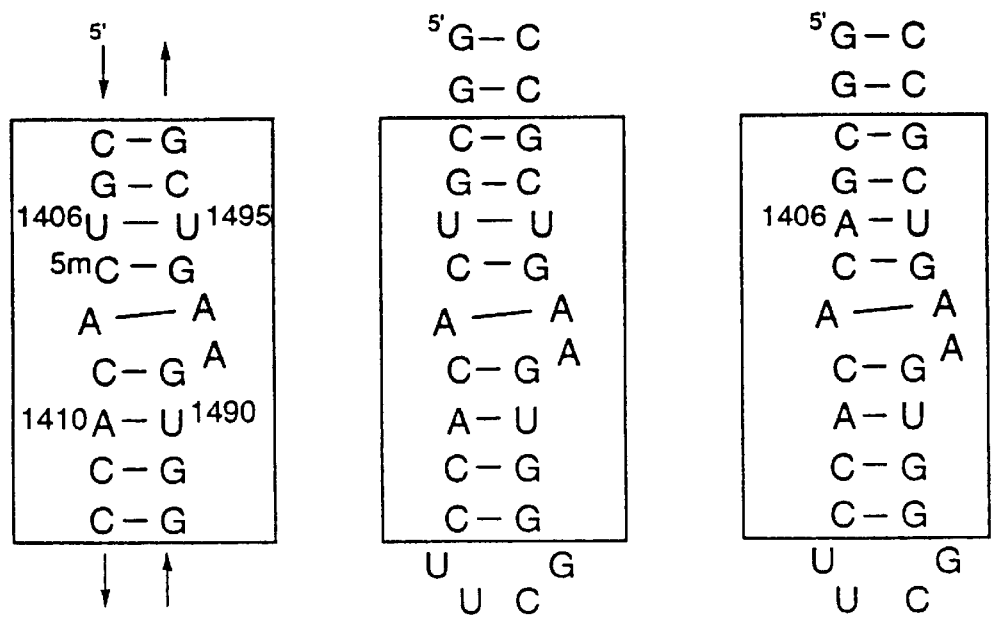
FIG. 44 shows RNA sequences related to the ribosomal decoding region A-site.
Figure 44:
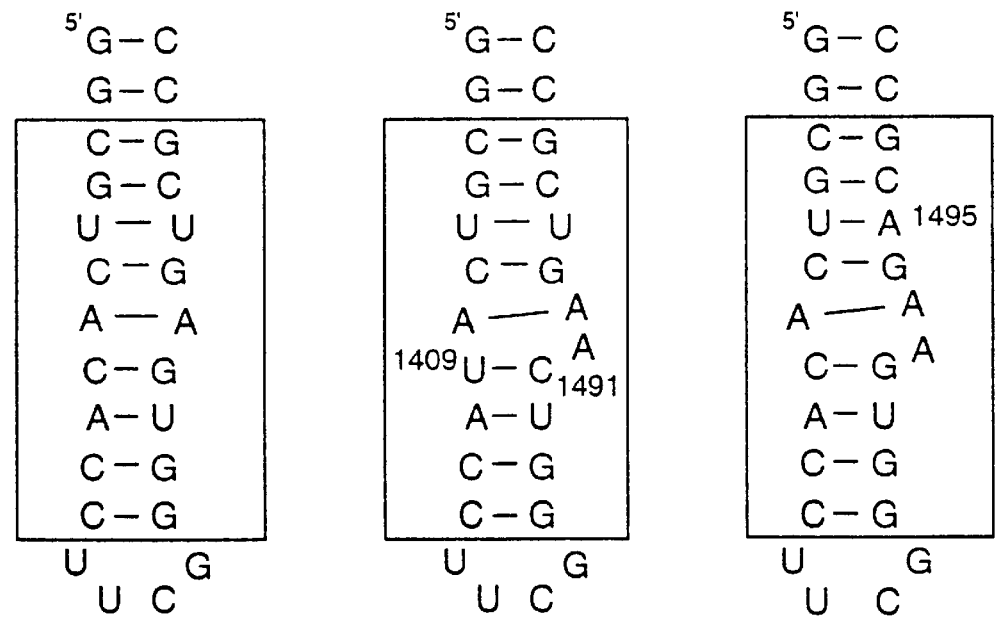

Specificity of aminoglycoside binding to the decoding region A-site model AS-wt analyzed by SPR To understand the specificity of ribosomal RNA recognition by the various aminoglycosides, we decided to investigate their binding to AS-wt and compare the results to a series of control mutants which have likewise been characterized by footprinting (FIG. 44). These include the negative controls AS-U1495A, AS-DA1492 and AS-res. The mutations found in these RNAs have been shown to abrogate specific binding to paromomycin. In AS-U1495A a critical hydrogen bond acceptor which interacts with N1 of the 2-deoxystreptamine ring has been removed. The mutation DA1492 destroys the bulged pocket in which paromomycin ring II (the glucose ring) is positioned. Finally, in the AS-res mutant the G1491:C1409 base pair which creates the floor of the binding pocket is disrupted by replacing it with a C1491:U1409 mismatch. Breaking up this critical base pair in the *E. coli* 16S ribosomal RNA causes resistance to a broad range of aminoglycosides. In contrast to these negative controls, the mutant hairpin AS-U1406A still contains all necessary elements for specific aminoglycoside recognition and binds paromomycin with wild type specificity.

For the quantitative measurement of aminoglycoside binding to these sequences, we utilized our recently developed SPR-based assay. Biotinylated derivatives of all sequences were prepared by in vitro transcription in the presence of guanosine 5'-monophosphorothioate followed by alkylation with a biotin iodoacetamide derivative. The RNA conjugates were then immobilized onto streptavidin coated SPR-sensorchips for analysis.

Figure 45:
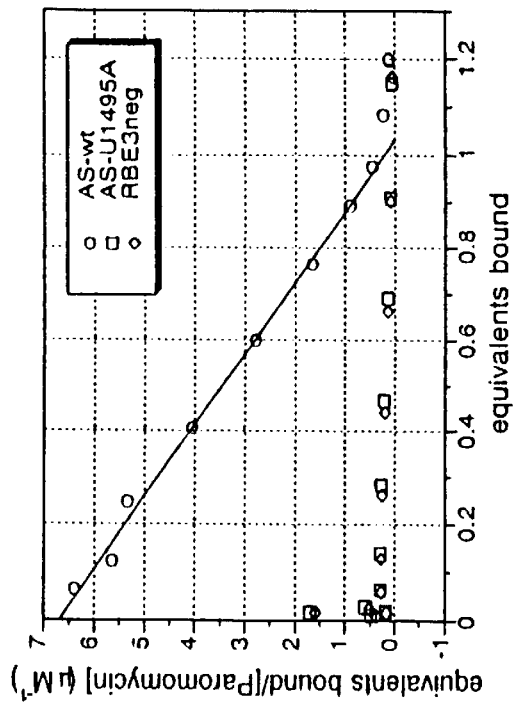
FIG. 45 shows binding of paromomycin to AS-wt compared with negative control RNAs. U1495A is a point mutant known to abolish specific binding and RBE3-neg is a completely unrelated RNA hairpin.
Figure 45:
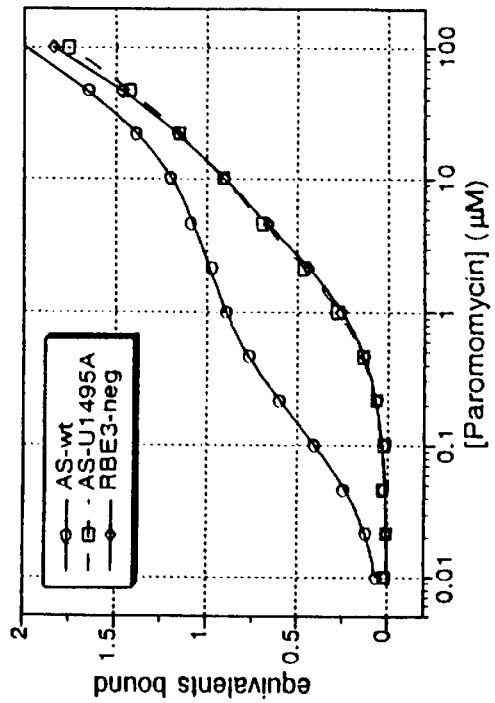

FIG. 45 shows the results for paromomycin binding to AS-wt. A clear 1:1 binding isotherm is visible at low concentrations which is overlayed by nonspecific binding to additional equivalents at higher concentrations. This binding curve contrasts with the result obtained for the negative control mutant AS-U1495A which binds paromomycin 20-fold more weakly without the appearance of any discernible initial 1:1 complex.

Figure 47:
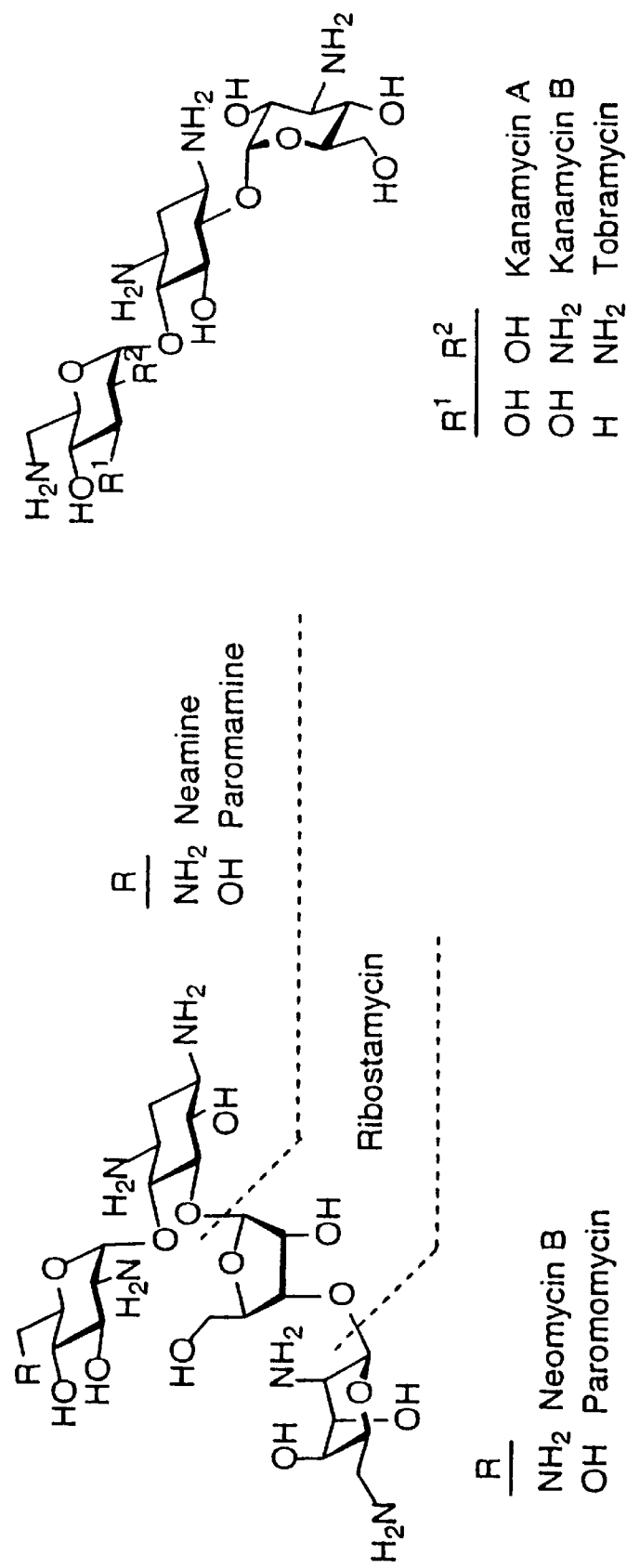
FIG. 47 shows binding of aminoglycosides to variants of the decoding region A-site as found in the table of FIG. 46.

In the same manner as illustrated for paromomycin, a panel of aminoglycosides was screened and the results are compiled in the table of FIGS. 46 and 47. In addition to the naturally occuring aminoglycoside antibiotics, some of the compounds in FIG. 46 are synthetically derived, unnatural aminoglycosides. The number of independent determinations for each dissociation constant ranged from 1–3. In general, we have found that the SPR-assay results have good reproducibility and based on the observed variation in multiple determinations, we assume that all Kd values are accurate within a factor of 2. All data were recorded under near physiological salt conditions (HBS-buffer: 150 mM NaCl, 10 mM HEPES, pH7.4, 3.4 mM EDTA) unless noted otherwise. Data points were taken at concentrations ranging from 0.01–100 mM. Below this concentration range, surface transport limitations prevent the attainment of equilibrium.

Figure 48:
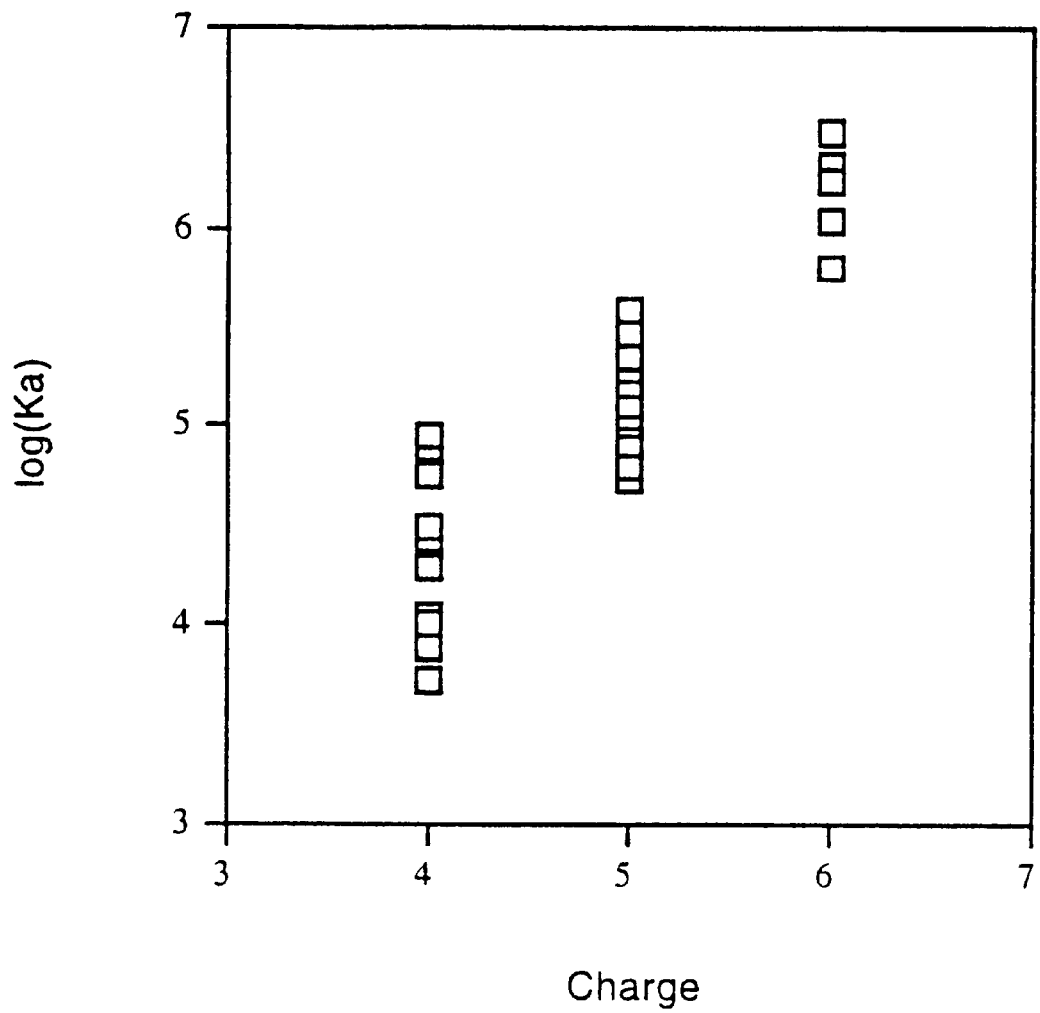
FIG. 48 shows the relationship between charge and log (Ka) for nonspecific RNA binding. The number given for charge refers to the fully protonated state. With every added charge, the nonspecific affinity increases circa 10-fold.

Except for the very weakest binders, all aminoglycosides have dissociation constants of less than 100 mM for all RNAS, including the negative controls. The compounds in Table 46 are grouped according to the number of positive charges at full protonation. Due to the low pKa of some amino groups within the aminoglycosides (e.g. N3 of neomycin B has a pKa<6) the actual protonation state at pH 7.4 will be lower. Nonetheless a clear trend can be seen when examining the charge dependence of binding to the negative control mutants AS-U1495A, AS-res and AS-DA1492 (FIG. 48). Depending on the number of amines, nonspecific binding is in the 1, 10 or 100 mM range for compounds with six, five or four aminogroups, respectively. This general trend of an increase in binding affinity by a factor of 10 for every added charge also applies when comparing compounds that bind specifically (e.g., paromomycin and neomycin B).

For any given compound, the affinities for the three different negative controls show very little variation. Comparison of the binding data for AS-wt with these values reveals the specificity of recognition of this sequence. The 4,5-linked compounds with a 2-deoxystreptamine core (neomycin B, paromomycin, ribostamycin and derivatives thereof) are all specific for AS-wt over the negative control RNAs. Within this group, compounds with four rings show the tightest affinities and highest specificities. Binding is yet enhanced to the positive control AS-U1406A. By contrast, the specificity for ribostamycin is low and binding is only weakly enhanced in the AS-U1406A mutant. Butirosin which is a trisaccharide carrying a 4-amino-2-hydroxy-butyric acid substituent on N1 likewise shows only moderate specificity for AS-wt, but unlike ribostamycin, binding is significantly enhanced for the AS-U1406A mutant. The aminogroups in the L-ido ring of neomycin are important for high affinity binding as can be seen from the comparison of neomycin B to its 2'''-hydroxy- and 2''',6'''-dihydroxy derivative.

The 4,6-linked 2-deoxystreptamine derivatives (kanamycin A, kanamycin B, tobramycin and gentamycin) have only very moderate specificity for AS-wt. Furthermore, their binding affinity is not increased in the U1406A mutant relative to AS-wt but rather decreased. Compounds from both groups, the 4,5- and the 4,6-limked 2-deoxystreptamine derivatives, share a common disaccharide motif. The core structure for most of the aminoglycosides considered here is neamine. This aminoglycoside has increased general nonspecific binding affinity compared to other compounds with four amines. Like ribostamycin, neamine still retains moderate specificity for AS-wt over AS-U1495A. Removing the 6'-amino group of neamine (paromamine) leads to a substantial decrease in binding to AS-wt and a loss of most specificity.

Apramycin shows only marginal if any specificity for AS-wt and hygromycin B shows none. Both compounds are known to be A-site binders but they are structurally dissimilar to the group of the neamine containing antibiotics. Structurally, it is clear that neither compound can occupy the same binding site that was seen for paromomycin in its AS-wt complex. It is therefore likely, that AS-wt is not an appropriate model for examining binding of these two compounds to ribosomal RNA. Finally, streptomycin which binds a different region of the ribosome not involving the A-site does not show any specificity for AS-wt as expected.

Both ionic strength and pH influence aminoglycoside binding as shown in the table found in FIG. 49. Raising the pH from 7.4 to 7.8 has a modest effect of decreasing binding but, as judged from the ratio of Kd(AS-U1495A) to Kd(AS-wt), the specificity remains unchanged. Increasing the amount of competing ions by adding ammonium chloride likewise decreases both the specific (AS-wt) and the nonspecific (AS-U1495A) binding to paromomycin or neomycin B. However, the effect is greater on the nonspecific binding thus increasing the specificity of either compound for AS-wt at higher salt concentrations. This observation agrees well with the general notion that charge-charge interactions are the main—if not only—driving force for nonspecific RNA binding but that specific recognition involves additional, nonionic contributions.

FIG. 50 shows a table which indicates comparison of the binding specificities in the 4,5- and the 4,6-linked series. The average Kd for nonspecific binding was calculated from the binding constants to the negative controls AS-U1495A, AS-res and AS-DA1492. The Kd(nonspecific) was then compared to both Kd(AS-wt) and Kd(AS-U1406A) to derive the specificity values given in the table. The results provide a clear picture of the structure activity relationships in the neomycin B series. The amino groups in ring IV (the L-ido ring) as well as the ring itself make contributions to specific binding as can be seen from comparison of the series neomycin B, 2'''-hydroxy-neomycin B, 2''',6'''-dihydroxy-neomycin B, and ribostamycin. Displaying the amino groups of ring IV attached through a flexible linker does not fully restore the lost specificity (see ribostamycin-3''-(CH2) 2NH2 and ribostamycin-3''-(CH2)2NH(CH2)3NH2).

For the neomycin series (i.e. the 4,5-linked 2-deoxystreptamine derivatives) the same order of specificities as seen for AS-wt is seen for the AS-U1406A mutant but the magnitude of the specificity is increased. An entirely different situation is encountered with the 4,6-linked series (kanamycins, tobramycin, gentamycin) where the observed specificities with the exception of gentamycin are very moderate and practically no specificity is seen for the binding of these compounds to the AS-U1406A mutant.

We believe that these results reflect the fact that AS-wt is a model system which is taken out of its ribosomal context. As such it has certain strengths and weaknesses which reflect the choice of the model. These include the lack of geometric constraints imposed by the ribosomal surroundings and the absence of the naturally occuring posttranscriptional methylation of the 5-position of C1407. Clearly, AS-wt is a good model system to study the interaction of the ribosomal A-Site with the 4,5-linked aminoglycosides. In this regard it is likely that the positive control mutant AS-U1406A approximates the conformation of the bound ribosomal complex even better than AS-wt and is thus the preferred model for developing structure-activity relationships in this series.

On the other hand, AS-wt appears to be a poor model for the binding behavior of the other major class of clinically important aminoglycosides, namely the 4,6-linked trisaccharides kanamycin A, kanamycin B, tobramycin and gentamycin. This may be due to the fact that this class recognizes a different conformation of the same RNA sequence which is not well represented in AS-wt or because tertiary interactions with other parts of the ribosome are important for this class of antibiotics.

Although the footprints on the intact ribosome for the 4,6-linked compounds overlap the footprints for neomycin B and paromomycin, the binding orientation of the molecule may well be different as indicated by the adverse effects of the AS-U1406A mutant. An intriguing possibility is that the naturally occuring methylation on C1405 might be required for recognition by these compounds and experiments to address this question are currently ongoing in our group. Comparison of the specificity of aminoglycoside binding to different natural and artifical receptors A number of RNAs of widely differing structures have been shown to bind to aminoglycosides. These RNA sequences include the catalytic group I introns and hammerhead ribozyme. as well as the HIV regulatory elements RRE and TAR. In each of these cases the binding has been claimed to be specific for neomycin B. This assertion is usually based on the fact that when examining a series of aminoglycosides, binding or inhibition by neomycin B is strongest. However, given our understanding of strength and behavior of nonspecific binding, the same result would be expected if the binding event in question was entirely nonspecific, as neomycin B is the most highly charged of the commonly available aminoglycosides and thus has the highest degree of nonspecific binding.

We have investigated the specificity of aminoglycoside-RNA recognition in one such system, the Rev Responsive Element. RRE is a regulatory element in HIV mRNA which controls the nuclear export of unspliced or partially spliced HIV mRNA transcripts. Neomycin B can inhibit the interaction of RRE with its cognate protein Rev and it has been suggested that this is due to specific binding of neomycin B to the binding site for Rev which is located at the bubble region. We have probed the specificity of HIV-RRE recognition with three different RNA constructs: the wild type RRE domain II (wt-RRE-II), a shorter hairpin still containing a functional Rev binding site (RBE3) and a negative control that is deficient in Rev binding (RBE3-neg).

To further improve our understanding of specific aminoglycoside recognition, we have also included an artificial aminoglycoside receptor that was evolved in vitro to recognize an aminoglycoside. A number of RNA aptamers for small molecules have been reported in recent years. Among them are aptamers that recognize the aminoglycosides tobramycin, lividomycin and kanamycin. These RNAs typically show very tight binding to their targets and are able to discriminate between closely related aminoglycosides. The RNA hairpin Neo16bd contains the binding region of an aptamer selected to recognize neomycin B. This aptamer has been reported to discriminate between paromomycin and neomycin B.

Figure 51B:
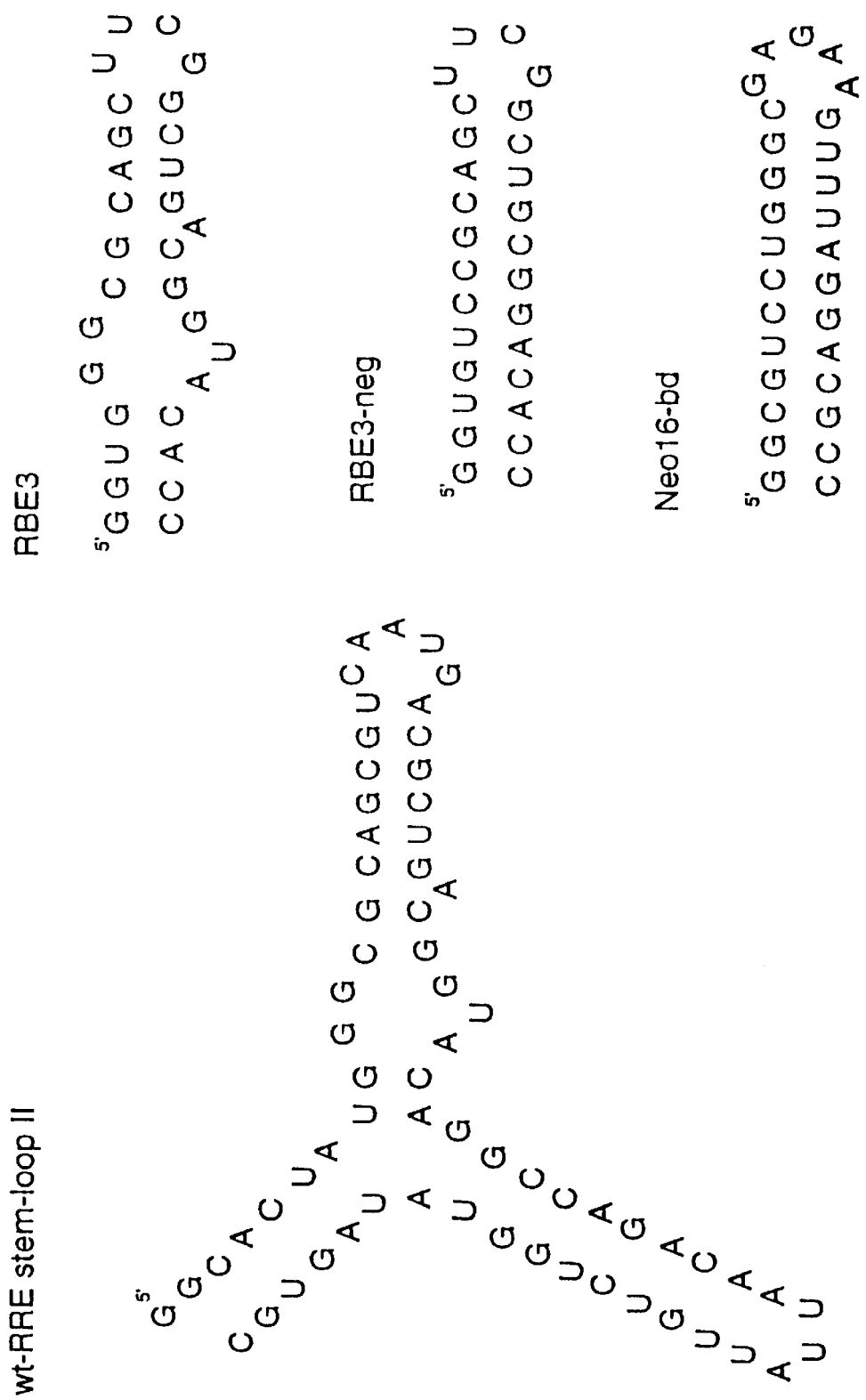

The binding results for a panel of aminoglycosides to the RRE related sequences and the neomycin aptamer are compiled in FIG. 51. For comparison, the corresponding values for AS-wt are also included. From the data it is clear that the aptamer Neo16bd is indeed highly specific for neomycin and neomycin derivatives which are modified distal to the neamine recognition motif (ribostamycin-3"-(CH2)2NH$_2$ and ribostamycin-3"-(CH2)2NH(CH2)3NH2, 2'''-hydroxy-neomycin B). In fact, binding to these derivatives is so tight, that the Kd-values are outside the accessible range (<10 nM) due to surface transport limitations. Furthermore, the discrimination between paromomycin and neomycin derivatives having the same charge as paromomycin is greater than 20 fold. Even ribostamycin, which has fewer charges than paromomycin but contains the same 2,6-diaminoglucose ring as neomycin, is bound more tightly to the aptamer than paromomycin. It is this type of discrimination between closely related compounds with the same or more charges which is the hallmark of truly specific binding.

By contrast, binding of neomycin B to RBE3, RBE3-neg and wt-RRE-II lacks specificity. There is no discrimination for neomycin B binding between the three RRE related sequences. As expected, neomycin B has the tightest non-specific binding to all three sequences. Comparison of the neomycin binding of the RRE related RNAs with AS-wt and Neo16bd clearly illustrates the order of selectivities. The aptamer, which was selected in vitro to bind neomycin B, does so with very high affinity. AS-wt, which is a model for the natural target site of neomycin B, despite its likely shortcomings (vide supra) still has good affinity for neomycin B, albeit weaker than the aptamer. The binding of neomycin B to the three RRE related RNAs is 12-fold weaker than to AS-wt. Only a lower limit can be given for the difference compared to Neo16bd.

An interesting result from the study of the RRE related RNAs is that the 4,6-linked trisaccharides seem to recognize all three sequences better than AS-wt or any of the negative controls used for the A-Site. As this "selectivity" also includes the negative control hairpin RBE3-neg, it has no implications for Rev-like RRE recognition, but rather points to the fact that affinity variations of under 10-fold can occur quite easily.

Some insight into the energetic nature of specific vs. nonspecific binding can be gained from examining the temperature dependence of the dissociation constants. As shown in FIG. 52, binding of paromomycin to Neo16bd, AS-wt and RBE3 is tighter at lower temperature, implying an entropically disfavored process (DS<0) in all three cases. This is a priori expected for the association of two molecules to form a complex as individual degrees of freedom are restricted and a more ordered entity is created. Interestingly, however, the specific binding event between paromomycin and AS-wt is entropically more costly than the nonspecific binding of paromomycin to RBE3. This observation likely reflects the fact that short RNA haipins like AS-wt are quite unstructured in solution and have to significantly restrict their conformational freedom in a tight, specific complex.

Figure 53:
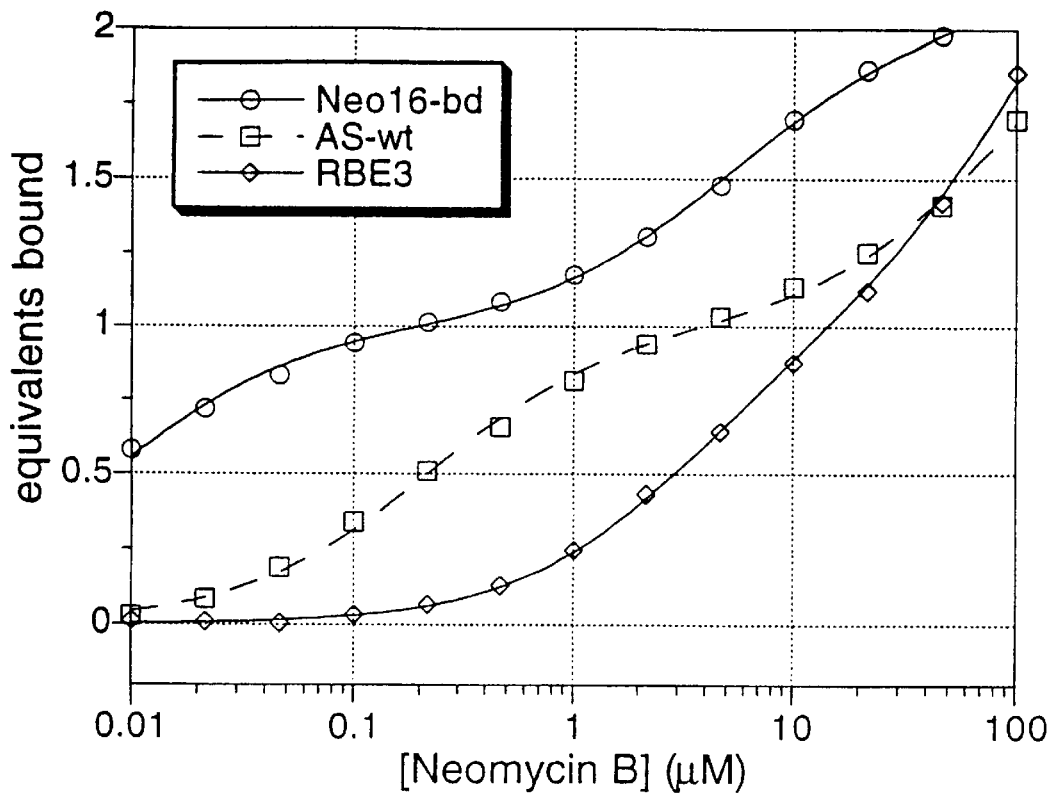
FIG. 53 shows a comparison of the binding of neomycin B to the aptamer Neo16bd, the decoding region model AS-wt and the Rev-binding sequence RBE3. Solution conditions: HBS buffer+150 mM NH$_4$Cl.
Figure 54:
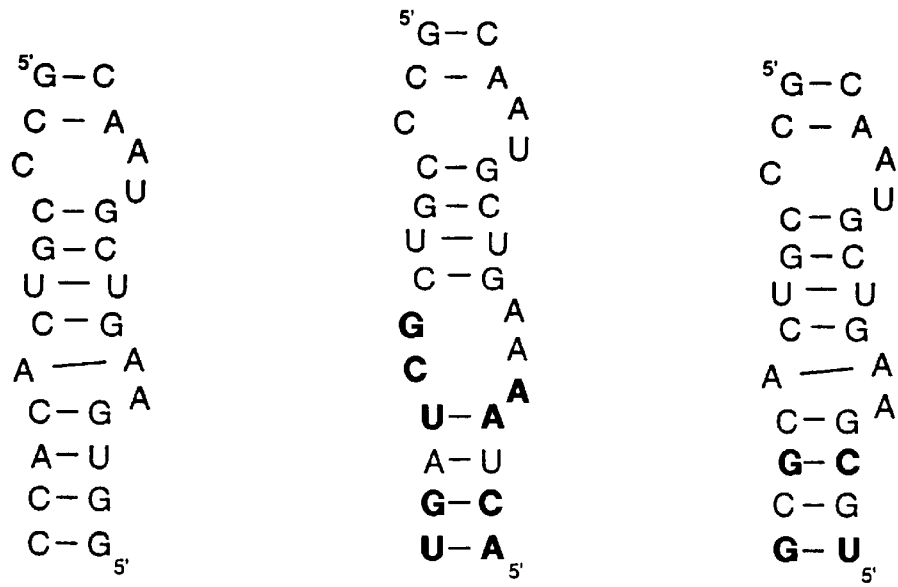
FIG. 54 shows decoding region RNA from different species.
Figure 54:
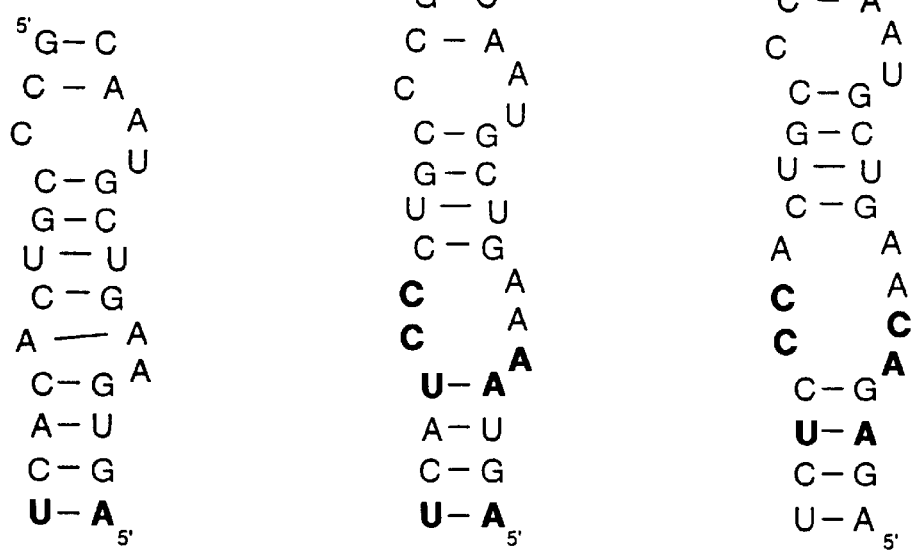

A similar trend is observed for the binding of neomyin B, although the temperature dependence is less pronounced and no quantitative analysis is feasible given the limits of the accuracy of Kd determinations. The latter binding curves were recorded under conditions of high salt which probably influences binding entropy. It is remarkable that even under these highly stringent conditions neomycin is still bound by Neo16bd with a Kd lower than 10 nM. This means that the specificity (relative to RBE3) of Neo16bd for neomycin is greater than 300-fold. The result is graphically illustrated in FIG. 53.

Implications for the design of small molecules to selectively target chosen RNA sequences From our studies, several conclusions can be reached about small molecules designed to recognize RNA following the aminoglycoside paradigm. Successful target sites will have to have a well defined structure, involving unusual secondary structure such as bulges or loops. The main challenge will be to achieve specificity particularly when trying to target structures other than the ribosome which has micromolar (!) concentration in cells. In this regard the high specificity of the neomycin aptamer is comforting, as it provides hope that the basic molecular interactions can provide this specificity when arranged in an optimal pattern.

Care must be taken in the selection of the proper in vitro RNA model system as seen from the results for the A-Site models. The available structural evidence from NMR suggests that short RNA hairpins are quite disordered in the absence of a bound ligand. This dynamic behavior will impose energetic penalties that may obscure binding events of moderate specificity. As the case of RRE illustrates, it is imperative to always check aminoglycoside binding to any RNA sequence with properly chosen control RNAs.

With regard to the rational design of new antibiotics based on aminoglycoside lead structures, a number of caveats exist. Binding of aminoglycosides to their ribosomal target sites will likely not follow a simple "competitive inhibition" paradigm. Rather, a bound aminoglycoside molecule allosterically interferes with protein synthesis by lowering the selectivity of cognate vs non-cognate aminoacyl-tRNA selection. Conceptually, this is more akin to a receptor signalling event, where a bound ligand irrespective of its affinity may either behave as an agonist or an antagonist. It is not at all clear whether increased affinity of a ligand for the ribosomal A-site would translate into better potency as an antibacterial drug.

A chemical challenge that may be more straightforward to address, however, is that of selectivity of a compound for the bacterial A-Site versus ribosomal RNA in other organisms, including humans. FIG. 48 shows the decoding region A-Site from different ribosomes. Presumably, lack of discrimination of a compound between the different RNA sequences would mean higher toxicity. The structural variations of human ribosomal RNA to its bacterial counterpart is significant and would suggest likely selectivity based on the disrupted 1409:1491 base pair but this supposition remains to be verified.

EXAMPLE 5

Figure 55:
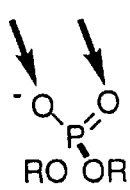
FIG. 55 illustrates the hydroxyamine motif.
Figure 55:
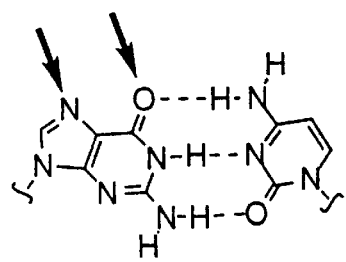
Figure 55:
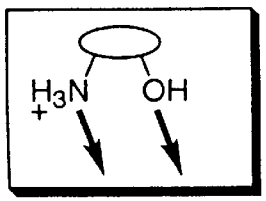
Figure 55:
Figure 55:

A Combinatorial Approach for the Discovery of Small Molecules that Recognize RNA Design of a library with the hydroxyamine core motif:

We have used the structure of aminoglycosides as an inspiration in a search for general motifs that may be suitable for RNA recognition. In this regard we have identified 1,2- and 1,3-hydroxyamines as an interesting binding motif. Hydroxyamines are bidentate hydrogen bond donors that can interact with a variety of bidentate hydrogen bond acceptors on the RNA. These include the backbone phosphodiesters and the Hoogsteen face of guanosine. Using model systems we have shown that in particular 1,3-hydroxyamines with a gluco-configuration are strong binders for phosphodiesters (FIG. 55).

Figure 56A:
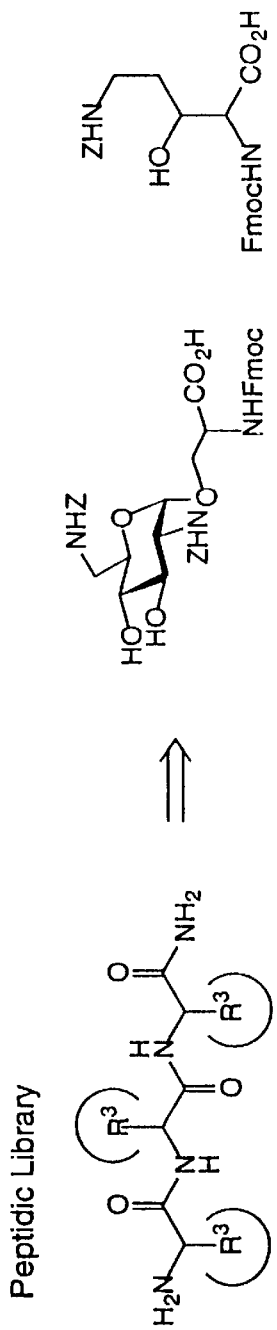
FIGS. 56A and 56B illustrate possible library concepts using hydroxyamine building blocks.
Figure 56B:
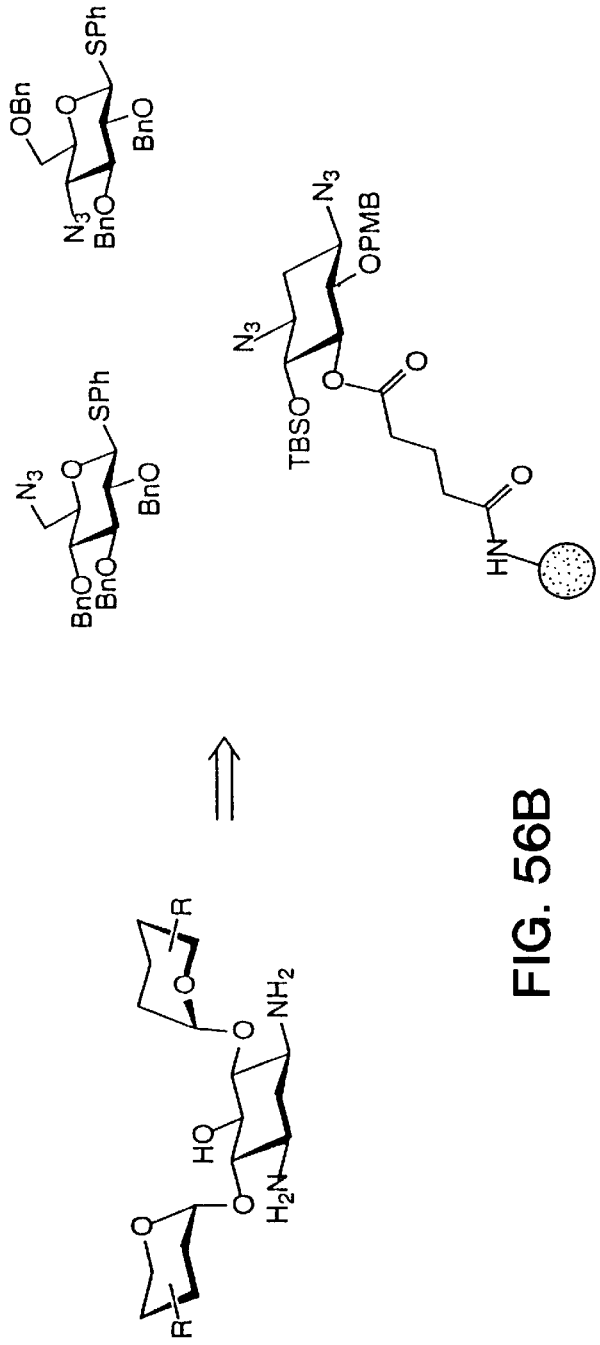

Constructing combinatorial libraries incorporating the hydroxyamine motif may therefore lead to the discovery of compounds that bind to RNA. Two potential approaches are illustrated in FIG. 56. As there are no natural amino acids incorporating hydroxyamines one possibility is to synthesize a variety of unnatural hydroxyamine containing amino acid building blocks and incorporate them into a peptide library. For example, the building blocks may include glycosyl amino acids. The advantage of such an approach would be that combinatorial chemistry involving amide bond formation is very well worked out. However, to produce a variety of hydroxyamine building blocks, considerable synthetic investment is required. Furthermore, it may be difficult to develop peptide lead structures into non-peptide ligands which are ultimately more desirable.

Another approach is to build a carbohydrate library wherein hydroxyamines are contained as part of the monosaccharides involved. This approach would give rise to unnatural aminoglycoside structures. The challenge of such an undertaking is the unresolved problem of reliable glycosidic coupling chemistry. While a number of combinatorial approaches involving the formation of a glycosidic bond have been reported, a true oligosaccharide library covering a wide array of structural diversity is yet to be produced.

Figure 57:
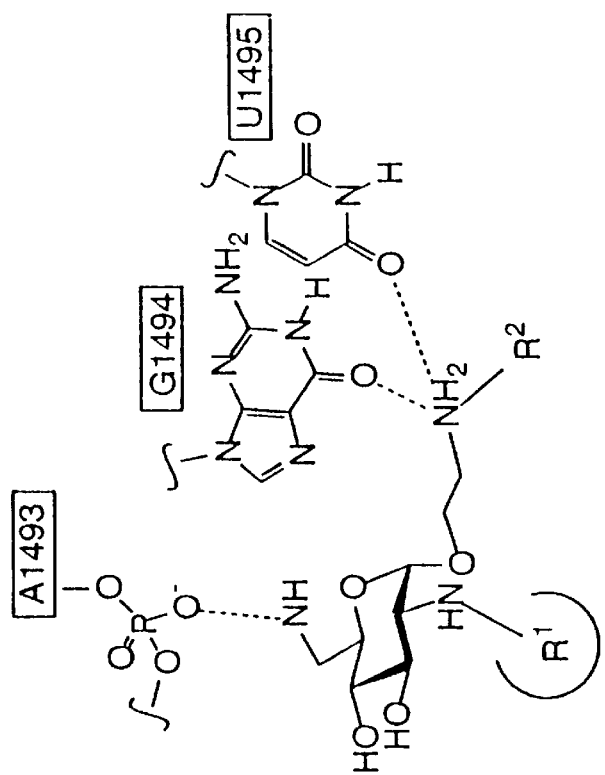
FIG. 57 shows the design of library compounds and a model showing possible contacts with the ribosomal decoding region RNA.
Figure 57:
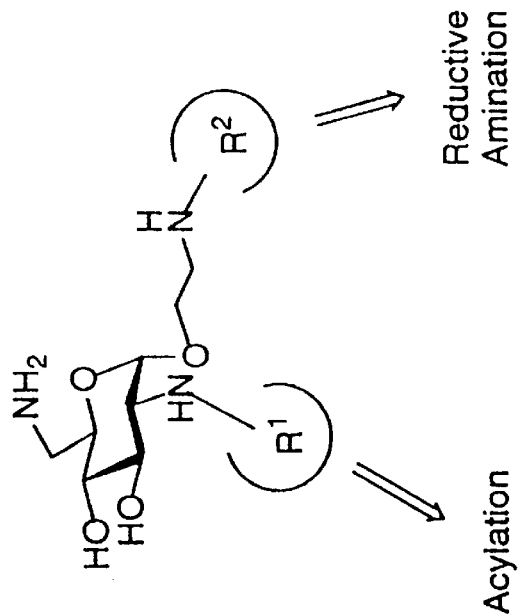

Given the above mentioned considerations we designed an approach that would take advantage of the hydroxyamine motif as the central core and would otherwise utilize readily available building blocks and rely on straightforward coupling chemistry. As shown in FIG. 57 the gluco-configured 1,3-hydroxyamine builds the core structure of our library. Two points of variation are introduced at the anomeric position and at position 2 of the glucose ring through reductive amination and acylation, respectively.

Although this approach is very general, the particular design chosen here included a structural bias for recognition of the ribosomal decoding region A-site. Based on the available NMR structure of the aminoglycoside paromomycin complexed with a model of the *E. coli* decoding region A-site, the core of the library could be aligned with the 2-deoxy-2-aminoglucose ring of paromomycin. Assuming this possible alignment, the α-anomeric substituent would be poised to make hydrogen bonding contacts to acceptors on the bases in the major groove of the RNA, especially G1494 and U1495. The acyl substituent in the 2-position could make contacts with the phosphate backbone.

Synthesis of the library

To construct the library, we desired a suitably protected building block (17, FIG. 19) which would incorporate a free amine for the introduction of the acyl residue and a masked aldehyde for the subsequent reductive amination. The latter is provided in the form of an allyl group which can be cleaved by ozonolysis to reveal the aldehyde.

A convenient starting material for the synthesis of 2-aminosugars is N-acetylglucosamine. This was converted to the allyl glycoside by Fischer glycosidation. An anomeric mixture (7:1=a:b) is obtained, from which pure 14 can be isolated by peracetylation, chromatographic separation and subsequent deacetylation. Selective tosylation of the primary alcohol and displacement with sodium azide lead to the 6-azido glucoside 16. The N-acetyl group of 16 was cleaved under basic conditions by refluxing with concentrated barium hydroxide to provide the desired building block 17. For the large scale synthesis of this building block, formation of the allyl glycoside, tosylation and azide displacement were carried out without the purification of any intermediates. At the stage of azide 16, chromatography then afforded a clean, anomerically pure compound.

Several approaches exist for the construction of libraries. A strategic choice must be made between the synthesis of individual compounds or compound mixtures. We expected that specific recognition of RNA would be difficult to achieve and were aware that even the selectivity of the naturally occuring aminoglycosides for their decoding region target site is only 5- to 20-fold. This kind of moderate specificity would likely be obscured by overwhelming non-specific binding when screening mixtures of compounds. We therefore decided to synthesize all library members individually using a parallel solution phase approach.

Figure 58A:
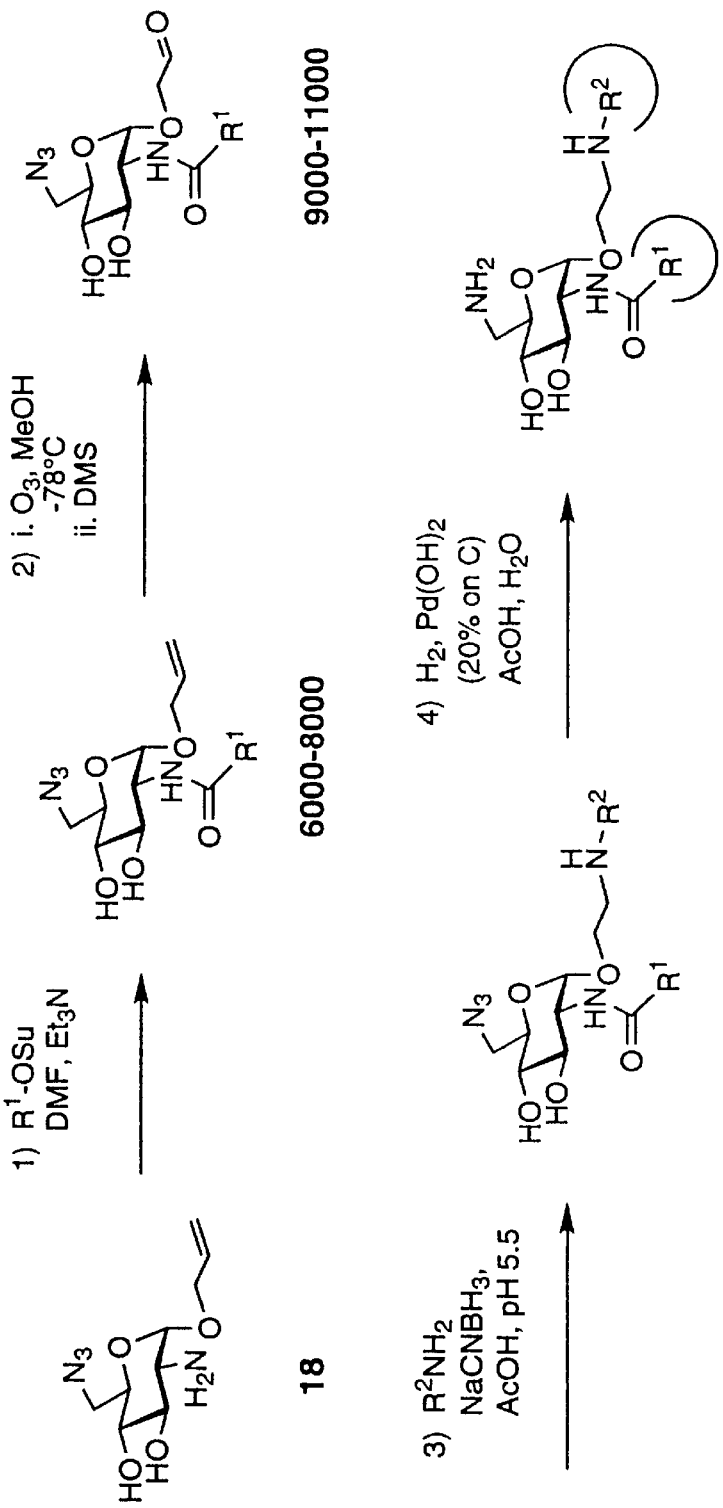
FIGS. 58A and 58B illustrate parallel solution phase synthesis of aminoglycoside mimetics based on the 1,3-hydroxyamine motif as a core structure.
Figure 58B:
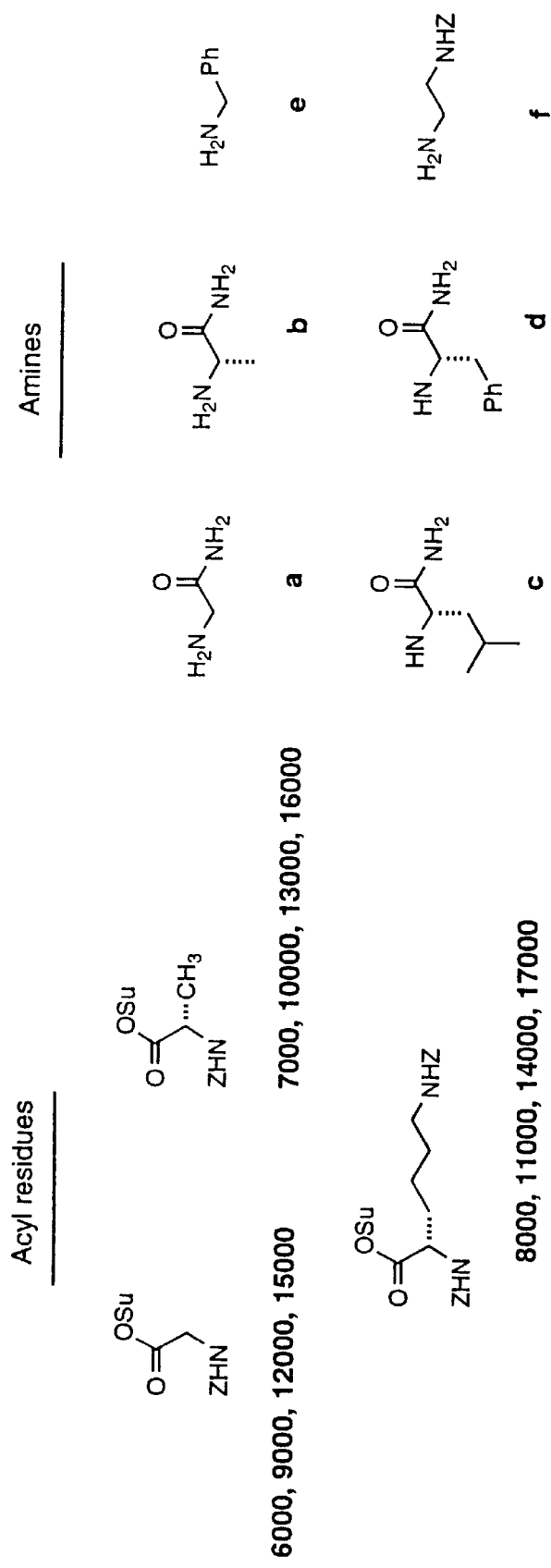

FIG. 58 (see also FIG. 20) shows the series of four combinatorial steps leading from the key intermediate to the final library compounds. For the initial acylation, four Cbz-protected amino acid N-hydroxysuccinimide esters were used to provide amino acyl derivatives 6000–8000. These compounds were individually purified and then subjected to the remaining three combinatorial steps. Treatment with ozone and subsequent quenching with dimethylsulfide lead to the clean production of the aldehydes 9000–11000 which were reacted with any of six different amines (a–f). These included four amino acid amides (a–d) as well as benzylamine and mono-Cbz-protected ethylene diamine. The reductive amination products 12000–14000 a–f were then deprotected by hydrogenation in aqueous acetic acid using palladium hydroxide as a catalyst to form compounds 15000–17000.

The three step sequence was carried out without purification of any intermediates. Instead, the final compounds were purified by ion exchange chromatography using Amberlite CG-50 resin (a carboxylic acid containing resin) eluting with aqueous ammonia. This procedure achieved excellent purification and led to very clean final compounds as judged by 1H-NMR and 13C-NMR. All library members were also characterized by electrospray mass spectrometry, which provided further evidence of the purity.

Figure 59:
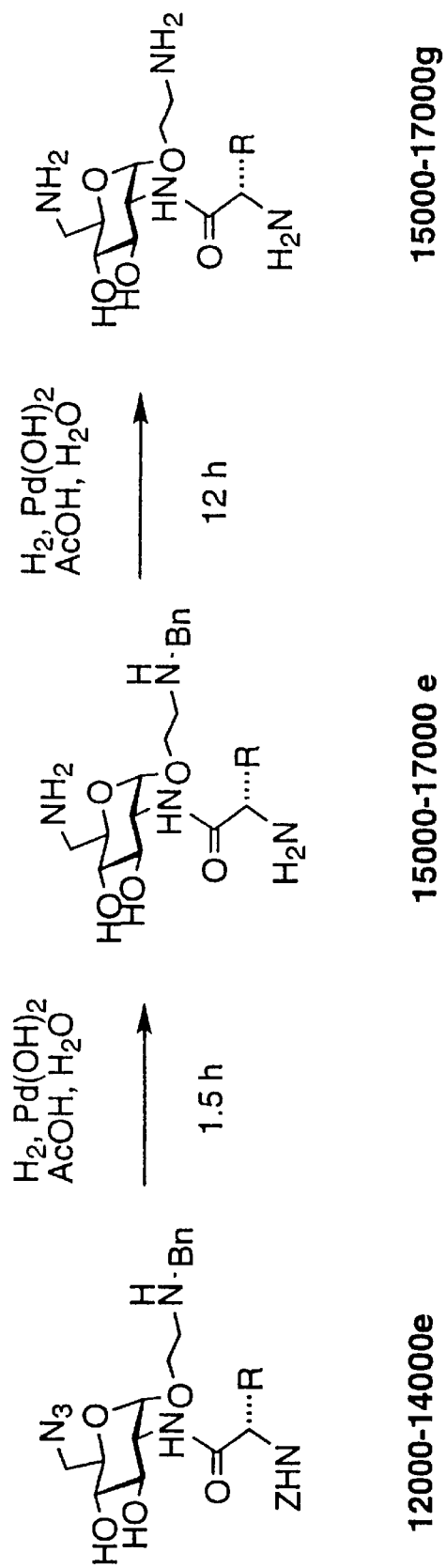
FIG. 59 illustrates selective reduction giving rise to otherwise deprotected N-benzyl derivatives.

An interesting observation was made during the reduction of N-benzyl containing compounds 12000–14000 e (FIG. 59). Limited hydrogenation selectively produced intermediates (15000–17000 e) in which both the azide and the Cbz groups had been reduced but in which the N-benzyl group was still present. These intermediates could be isolated and when resubjected to the same hydrogenation conditions, they were reduced to the primary amines 15000–17000 g overnight.

Screening of the library

Figure 60:
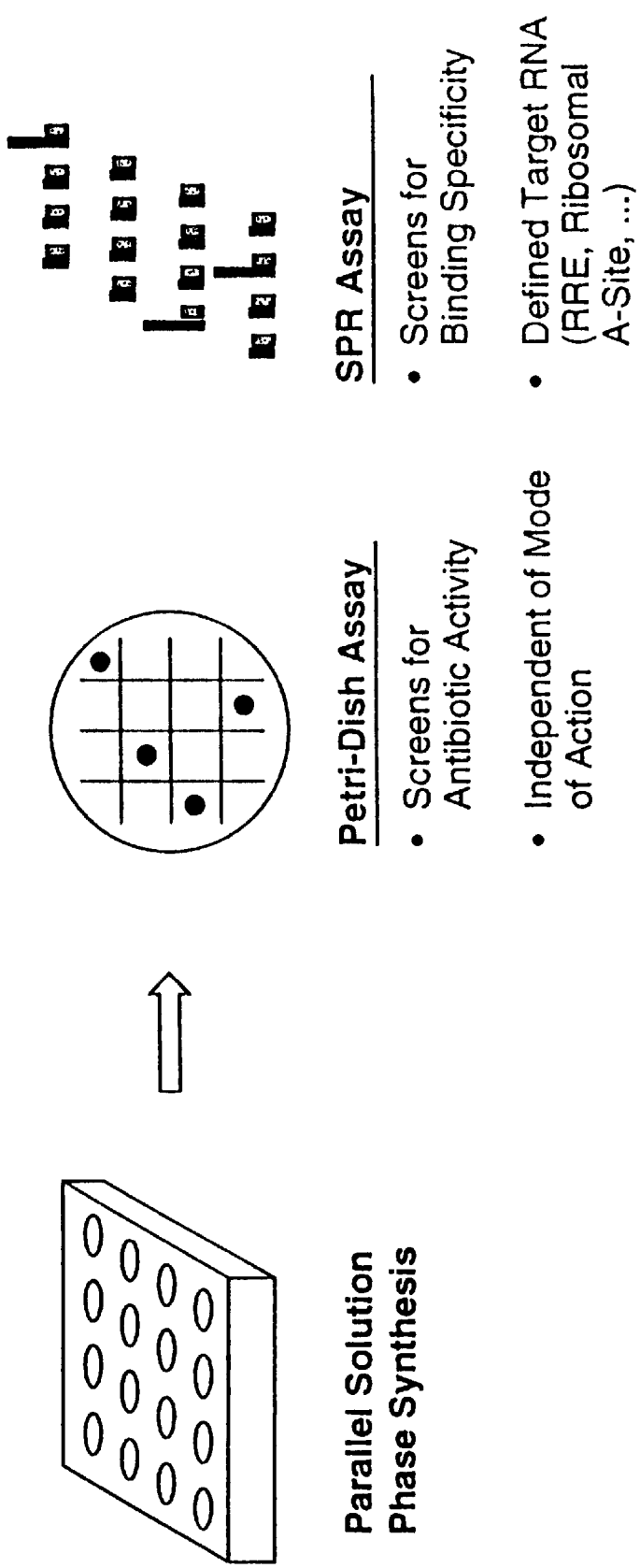
FIG. 60 illustrates screening of the hydroxyamine library.

We envision two possible ways in which to evaluate the library compounds: A direct testing of their RNA binding affinities to various selected target RNAs using our surface plasmon resonance (SPR) assay11 and the screen for biological function, in this case an antibiotic assay (FIG. 60). Initially, the former test is our preferred method of screening, as it can provide a straightforward assessment of the desired RNA binding properties whithout being obscured by other issues such as metabolic stability or cellular uptake.

The library compounds were tested for RNA binding with a set of A-Site related RNAs described earlier. Briefly, AS-wt and AS-U1406A are model systems of the aminoglycoside binding site found in *E. coli* ribosomes. They form specific complexes with a number of aminoglycosides, particularly the 4,5-linked 2-deoxystreptamine derivatives of the neomycin class. The mutants AS-U1495A, AS-res and AS-DA1492 no longer possess this specificity and serve as negative controls for aminoglycoside binding.

The binding measurements were performed using the surface plasmon resonance assay introduced earlier. The library compounds were tested at a range of concentrations between 3 and 100 mM. Assuming a 1:1 binding stoichiometry, Kd values were then derived. This procedure neglects the contribution of additional equivalents binding simultaneously, and thus overestimates the actual binding constants (i.e. the calculated Kd values are lower than the true value). However, the error should be relatively small, and since all data are treated in the same manner, they can be compared.

Figure 61:
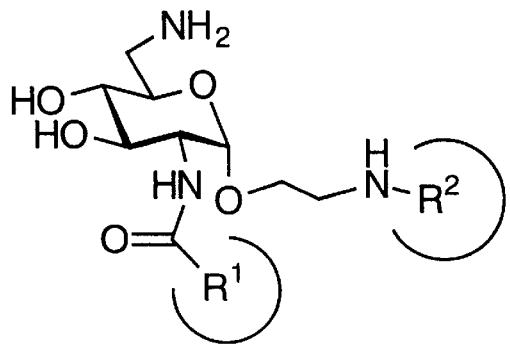
FIG. 61 shows the screening of the library against A-Site related RNAS.

FIG. 61 shows the SPR-assay results obtained with library compounds 15000–17000. There is considerable variation in the affinity of individual library members for the A-Site related RNAs. Within a series having the same acyl residue, all compounds have the same numer of amines, exept for the last entry (the condensation product with ethylene diamine) thus enabling comparison between compounds of the same charge. In general, compounds 15000–17000 *a* and *g* with NHCH2CONH$_2$ and NH2 in the anomeric position have the highest RNA binding afiinity. Compounds with aliphatic hyprophobic residues (alaninamide, valine amide) show much weakerbinding. Interestingly, phenylalanine amide is noticably better in affinty than valine in the first two series in FIG. 61 (i.e. those with glycine or alanine as the acyl residue), but noticably worse in in the third series.

The variation observed for the affinities of the RNAs for closely related library members is quite stunning in some cases. Thus, introduction of a single methyl group into compound 16000*a* to form 16000*b* lead to a 15-fold drop in affinity and the difference to valine is even larger. Thus, small R2 substituents seem important for high RNA binding affinity in this class of compounds. Introduction of an additional amine into the R2 substituent increases binding by a factor of two in the 15000 and 16000 series, but has no substantial effect in the 17000 series, where the lysine residue already provides an extra charge. Presumably, the pKa of the added amine is quite low in this case and the added amine can not be significantly protonated at pH 7.4, where the assay is conducted.

Thus the A-Site related RNA sequences can discriminate very well between individual library members. The observed affinities are quite high, particularly when considering that most library compounds only possess three amino groups. This can be taken as an indication that the hydroxyamine structure chosen in the scaffold design is an effective core structure to achieve high affinity RNA binding. However, there is little specificity of any library compounds with regard to discriminating between different RNA sequences. This is perhaps not surprising, considering the very minor variations between the individual mutants.

In conclusion, we have demonstrated that a library of small molecule RNA binders can be assembled rapidly in a parallel solution phase approach. An intersting range of RNA binding affinities is obtained with the library compounds, spanning about two orders of magnitude. The hydroxyamine core structure is effective for the design of high affinity RNA binders, providing hope that with the right choice of substituents specificity can be attained as well.

Synthetic Protocals:

General.

Methylene chloride and methanol were dried over CaH$_2$ and powdered magnesium respectively. Polyethylene glycol monomethyl ether (MeO-PEG, MW.=5000) was purchased from Aldrich and was dried over P$_2$O$_5$ under vacuum before use. All other solvents and chemicals were obtained from commercial sources, and were used without further purification, unless otherwise stated. NMR spectra were obtained on a Bruker AM-300 spectrometer. Surface Plasmon Resonance measurements were performed using a BIAcore 2000 system from Pharmacia Biosensor AB. Circular dichroism spectra were measured on an AVIV Model 62DS spectropolarimeter. UV-spectra were taken on a Beckman DU650 spectrophotometer.

Synthesis of Biotinylated RNA.

In vitro transcription reactions were performed according to the general procedure reported by Uhlenbeck and coworkers (Milligan et al. *Nucleic Acids Res.* 1987, 15, 8783; Milligan et al. *Methods in Enzymol.* 1989, 180, 51).

The DNA templates (for wt-RRE-II: 5'-GCA CTA TAC CAG ACA ATA ATT GTC TGG CCT GTA CCG TCA GCG TCA TTG ACG CTG CGC CCA TAG TGC CTA TAG TGA GTC GTA TTA-3', for RBE3: 5'-GGT GTA CCG TCA GCC GAA GCT GCG CCC ACC TAT AGT GAG TCG TAT TA, for RBE3-neg: GGT GTC CGC AGC CGA AGC TGC GGA CAC CTA TAG TGA GTC GTA TTA, for Neo16-bd: GGC GTC CTA AAC TTC TCG CCC AGG ACG CCT ATA GTG AGT CGT ATT A) were annealed to a 2-fold excess of 18-mer T7 promoter (TAA TAC GAC TCA CTA TAG) in H$_2$O by heating to 65° C and slow cooling to below 37° C. The 5'-phosphorothioate transcripts were generated by incubating the annealed templates (0.2 μM) in 50 mM Tris (pH 7.5), 15 mM MgCl$_2$, 2 mM spermidine, 5 mM DTT, 2 mM ATP, 2 mM CTP, 2 mM UTP, 0.2 mM GTP, 4 mM Guanosine-5'-monophosphorothioate (5'-GMPS) with 5 U/μL T7 RNA polymerase and 0.001 U/μL inorganic pyrophosphatase for 2 h at 37° C in a total volume of 100 μL. Additional 1 μL aliquots of 20 mM GTP were added at 20 min intervals and 500 U of T7 RNA polymerase were added after one hour. Reactions were quenched by addition of EDTA, extracted with phenol and precipitated with ethanol. Electrophoresis was carried out on 20% denaturing polyacrylamide gels. Full-length transcripts were excised from the gel and eluted into 200 mM NaCl, 10 mM Tris (pH 7.5), 0.5 mM EDTA and desalted on a Nensorb column (DuPont/NEN). Typically, a 100 μL transcription reaction produced 150–500 pmol of RNA-5'-phosphorothioate. The purified RNA transcripts were resuspended in 18 μL of 100 mM NaH$_2$PO$_4$ (pH 8.0) containing 1 mM EDTA and were treated with 2 μL of 20 mM biotin-iodoacetamide in DMF (USB). After 2 h at RT, an additional 2 μL of the biotinylation reagent was added and incubation was continued for 1 h. The RNA was ethanol precipitated in the presence of glycogen, gel purified and desalted as described above. The RNA oligonucleotides for the gel in FIG. 2A were body labeled by incorporation of [-$^{32}$P]-ATP (0.4 μCi/μL) in the transcription reactions containing either 5'-GMP or 5'-GMPS.

Immobilization of Biotinylated RNAs on the Sensorchip.

Streptavidin functionalized BIAcore sensorchips were either obtained directly from Pharmacia Biosensor AB (sensorchip SA5) or were prepared from carboxymethylated sensorchips (CM5) by EDC activation followed by injection of streptavidin (Pierce, immunopure grade) in acetate buffer (10 mM, pH 5) over all four flowcells according to the manufacturers recommendations. Prior to immobilization, frozen solutions of biotinylated RNA (1–10 pmol) in 80 μL buffer (10 mM HEPES, 0.1 mM EDTA, 100 mM NaCl, pH 6.8) were renatured by heating to 80° C for 2 min followed by slow cooling to RT. Typically, individual flowcells were functionalized by injecting 60 μL of RNA buffer using the QUICKINJECT command at a flowrate of 2 μL/min, followed by injection of running buffer. Three flowcells were used to immobilize RNA while the fourth remained unmodified to serve as a blank control for matrix affects. Levels of RNA capture and ligand binding were calculated by subtracting response units of the blank flowcell from response units in the RNA functionalized flowcells.

General Procedures for SPR Binding Studies.

Samples were prepared by serial dilutions from stock solutions in RNase free microfuge tubes (Ambion) and were centrifuged at 14000 rpm for degassing. Buffers were filtered through sterile 0.2 μm nylon membranes (Nalgene) under vacuum, except for BIA certified HBS buffer (Pharmacia Biosensor AB) which was used as obtained. All procedures for binding studies were automated as methods using repetitive cycles of sample injection and regeneration. Typically, buffer was injected in the first two cycles to establish a stable baseline value. Samples were injected at a flowrate of 5–10 μL/min using either the KINJECT or the COINJECT command. All aminoglycoside and Rev27 samples were injected from autoclaved 7 mm plastic vials that were capped with pierceable plastic crimp caps. To minimize carry over, samples were injected in order of increasing concentration. The running buffer was identical to the injection buffer, except for the salt dependence study where a single running buffer was used for all injections. Expected values for the equilibrium response of one equivalent of analyte were calculated from the relative molecular weight of the analyte and the immobilized RNA ligand in each flowcells. These values were adjusted by multiplying with a factor of 0.8 or 0.57 for Rev27 or aminoglycosides respectively. These factors arise from the different molar refractive indices of RNA and the analyte and were determined from the Scatchard plot x-axis intercepts of the 1:1 binding isotherms for Rev27 and neomycin B.

Binding Studies with Rev27.

Rev27 was obtained from QCB Inc. (Hopkinton, Mass.). Analytical data (HPLC, capillary electrophoresis, Miss.) were in agreement with the structure and indicated a purity of >95%. Aliquots of a stock solution of Rev27 (100 μM) in injection buffer (10 mM HEPES, pH 7.4, 150 mM NaCl, 3.4 mM EDTA, 5 mM DTT) were stored frozen (−30° C.) until used and samples were made up freshly by serial dilution in injection buffer. Data points were taken after an association phase of 20 min. A 3 min regeneration pulse of 300 mM Na$_2$SO$_4$ in injection buffer was used between injections. Binding constants for RBE3 and wt-RRE-II were from nonlinear curve fitting to the equation:

$$Resp = Resp_{max} \cdot [Rev27]/([Rev27] + K_d)$$

wherein Resp is the observed response and Resp$_{max}$ is the response of one equivalent Rev27 bound.

CD Spectra of Rev27.

Samples were made up freshly from stock solutions of Rev27 (0.1 mM) in CD buffer (10 mM potassium phosphate, pH 7.5, 100 mM KF) using a 1 cm path-length quartz cuvette. The signal was averaged over 30s and 5 scans of the full spectrum were averaged. The concentration of Rev27 was determined from its UV spectrum using the absorption at 279.8 nm due to the single tryptophan residue. The helical content was calculated from the mean residue ellipticity at 222 nm relative to the expected value at full-helicity (35740 deg·cm$^2$/dmol for a 27-mer).

Binding Studies with Aminoglycosides.

Neomycin B sulfate (Fluka) was converted to the free base by passing it through Amberlite IRA 400 (OH— form) and purified by ion exchange chromatography on Dowex 1-X2 100 to remove neomycin C; the purity of neomycin B was verified by NMR in D$_2$O. Paromomycin sulfate was obtained from Sigma and used as received. Samples were prepared by dilution from 10 mM stock solutions in injection buffer (10 mM HEPES, pH 7.4, 150 mM NaCl, 3.4 mM EDTA). Data points were taken after an association phase of 30 min. A 2 min regeneration pulse of 150 mM Na$_2$SO$_4$ in injection buffer was used between injections. Binding constants for RBE3 and RBE3-neg were obtained by fitting the linear part of the Scatchard plot to a straight line (slope=−1/K$_d$).

Figure 19:
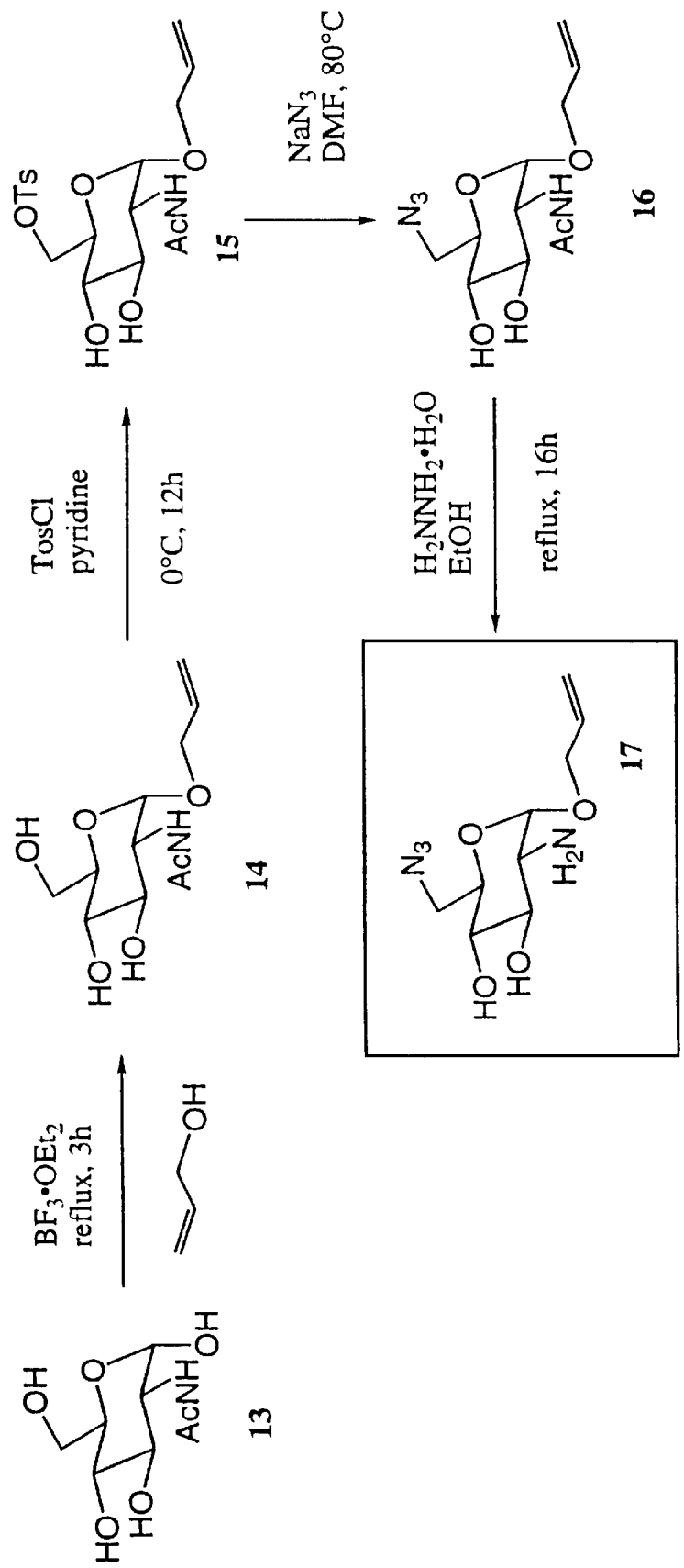
FIG. 19 illustrates the synthesis of compound 17.

Synthesis of compound 14 as illustrated in FIG. 19:

N-acetylglucosamine (13, available from Aldrich) is dissolved in allylalcohol to a concentration of 0.1 M and 0.2 equivalents of borontrifluoride diethyl etherate is added and the reaction heated to reflux for 4h. The product is precipitated by the addition of ether and recrystallized from ethanol.

Synthesis of compound 15 as illustrated in FIG. 19:

Compound 14 is dissolved in pyridine to a concentration of 0.1 M and 1.1 equivalents of tosylchloride is added at 0% C. The reaction is stirred at 0% C for 12h and quenched by the addition of water. The reaction mixture is evaporated and the product is purified by column chromatography in chloroform/methanol.

Synthesis of compound 16 as illustrated in FIG. 19:

Compound 15 is dissolved in pyridine to a concentration of 0.1 M and 3 equivalents of sodium azide is added. The reaction is stirred at 80% C. Upon completion, the reaction mixture is evaporated and the product is purified by column chromatography in chloroform/methanol.

Synthesis of compound 17 as illustrated in FIG. 19:

Compound 16 is dissolved in a mixture of hydrazine monohydrate and ethanol to a concentration of 0.1 M and the reaction is stirred at reflux. Upon completion, the reaction mixture is evaporated and the product is purified by column chromatography in chloroform/methanol.

Figure 20A:
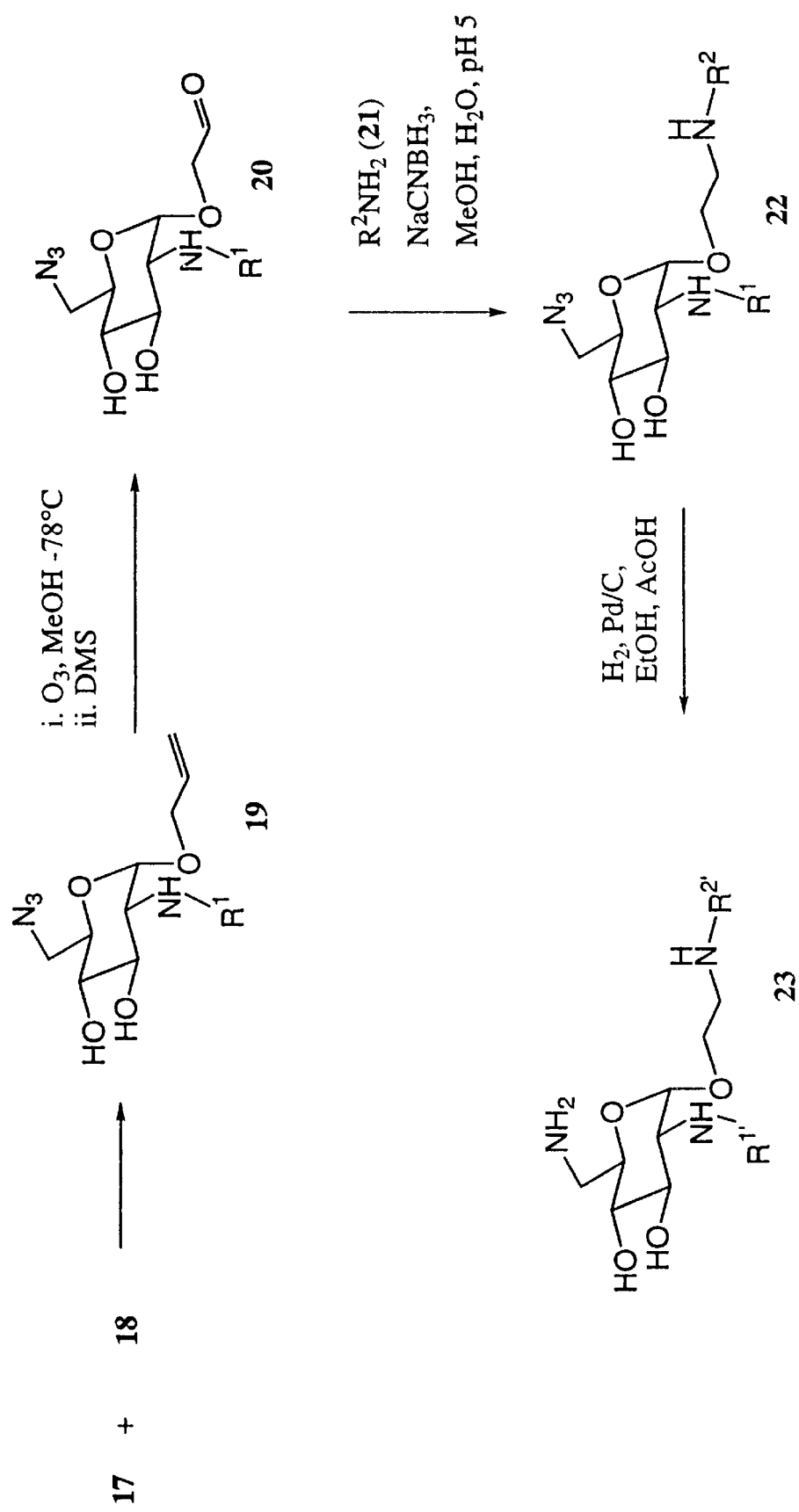

Synthesis of compound 18 as illustrated in FIG. 20 is selected from the group consisting of Cbz-Ala-OSu, Cbz-Arg(di-Cbz)-OSu, Cbz-Asn-ONp, Cbz-Gln-ONp, Cbz-Gly-OSu, Cbz-Ile-OSu, Cbz-Leu-OSu, Cbz-Lys(Cbz)-OSu, Cbz-Phe-OSu, Cbz-Pro-OSu, Cbz-Thr-OSu, Z-Val-OSu, Cbz-OSu available from Novabiochem.

Synthesis of compound 19 as illustrated in FIG. 20:

Compound 17 is dissolved in a mixture of dioxane and water to a concentration of 0.1 M and 1.1 equivalents of succinimides 18 is added. The reaction is stirred at reflux. Upon completion, the reaction mixture is evaporated and the product is purified by column chromatography in chloroform/methanol.

Synthesis of compound 20 as illustrated in FIG. 20:

Compound 19 is dissolved in a mixture of methanol and methylene chloride to a concsentration of 0.05 M and treated with ozone at −78% C. Upon completion, the reaction is quenched with dimethylsulfide and and evaporated. The product is purified by column chromatography in chloroform/methanol.

Synthesis of compound 21 as illustrated in FIG. 20:

is selected from the group consisting of benzylamine, propylamine, isopropylamine, ethylenediamine, 1,3-diaminopropane, 1,2-diaminopropane, 1,4-diaminobutane, 1,6-hexanediamine, N-ethylethylenediamine, Diethylenetriamine, 3,3'-iminobispropylamine, spermine, spermidine, triethylenetetramine, tris(2-aminoethyl)amine, ethanolamine, 3-aminopropanol, serinol or their hydrochloride salts available from Aldrich.

Synthesis of compound 22 as illustrated in FIG. 20:

Compound 20 is dissolved in a mixture of methanol and water to a concsentration of 0.1 M and treated with 1 to 10 equivalents of amine 21 and the pH is adjusted to pH 5 by addition of acetic acid. Sodium cyanoborohydride (1–4 equivalents) is added. Upon completion, the reaction is quenched with dimethylsulfide and the mixture evaporated. The product is purified by column chromatography in chloroform/methanol.

Synthesis of compound 23 as illustrated in FIG. 20:

Compound 22 is dissolved in a mixture of methanol and acetic acid to a concsentration of 0.1 M and treated 0.3 equivalents 10% palladium on activated charcoal. Upon completion, the reaction is quenched with dimethylsulfide and and evaporated. The product is purified by ion exchange chromatography on Amberlite CG50 (ammonium form).

Figure 21A:
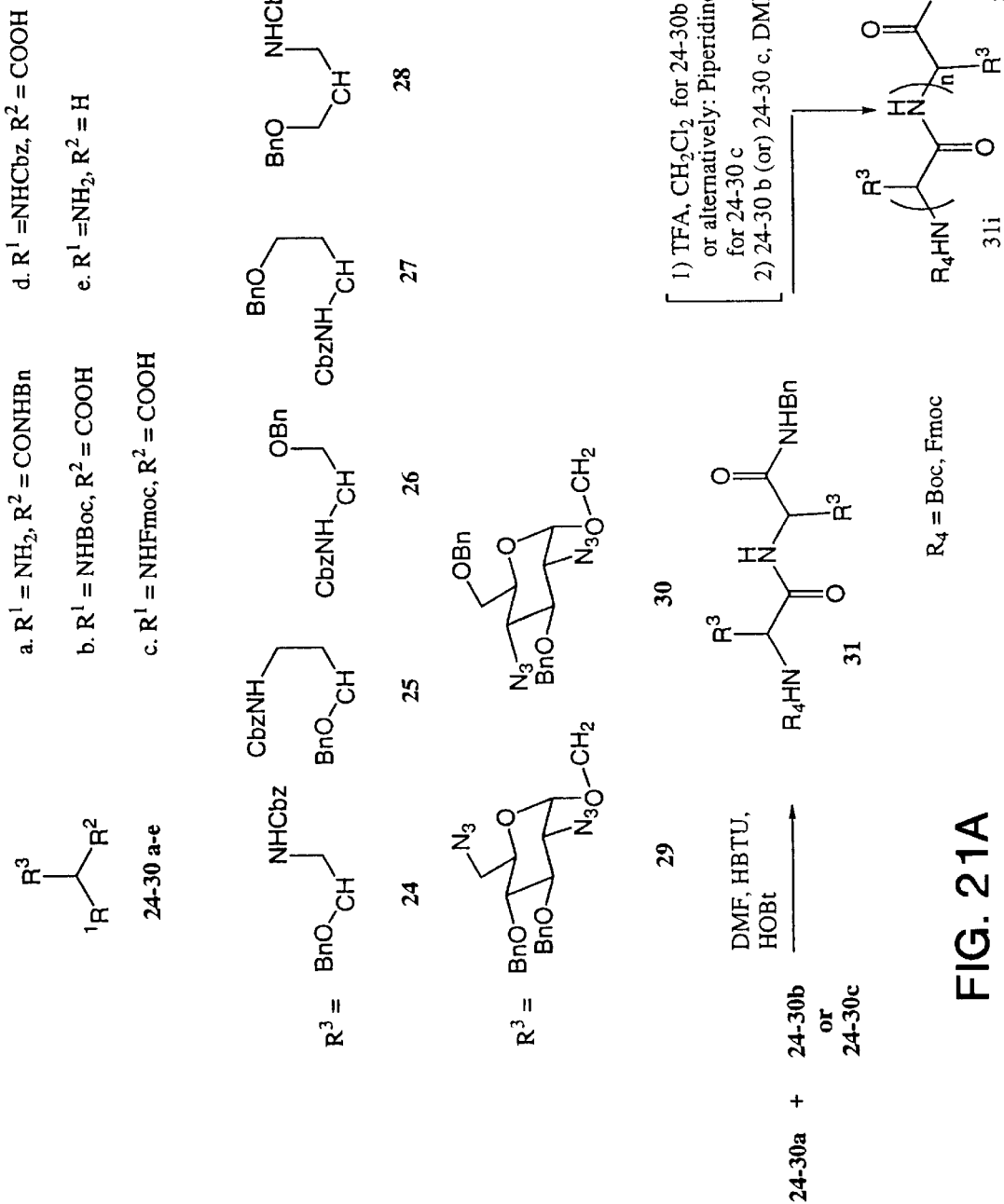
FIGS. 21A and 21B illustrate the synthesis of library 33 starting from the protected scaffolds 24–30a and 24–30b, wherein $R^{3'}$ represents the various combinations of the indicated hydroxyl amine containing functionalities.
Figure 21B:
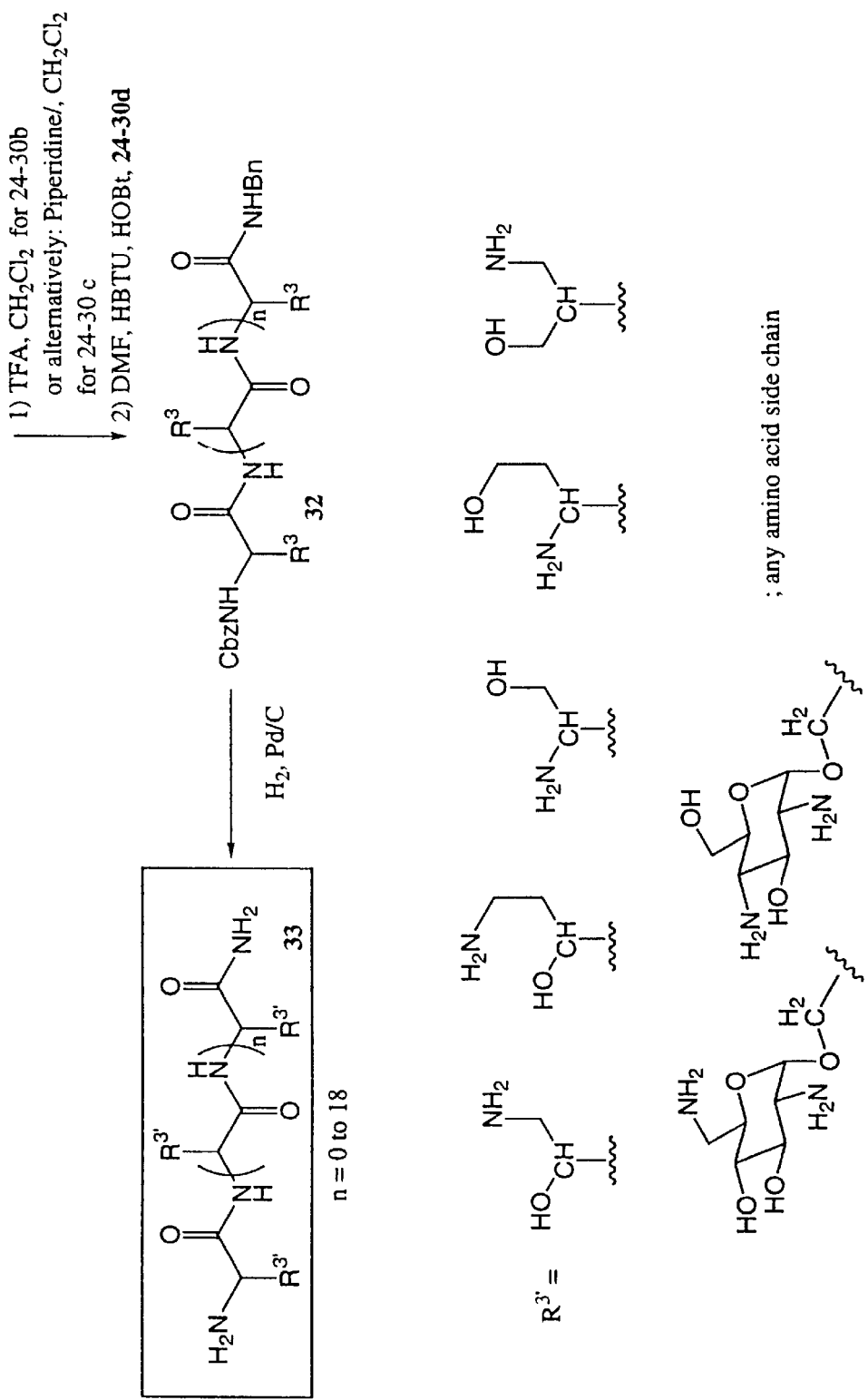

Synthesis of compound 24b as illustrated in FIG. 21:

Ethyl (2S,3R)-2-azido-4-bezyloxy-3-hydroxybutanoate (Woltering, T. J.; Weitz-Schmidt, G.; Wong, C.-H., *Tetrahedron Lett.*, in press) is dissolved to a 0.1 M concentration in a solvent chosen from the group consisting of ethyl acetate, methanol and THF and treated with 0.05 equivalents of Pd/C and hydrogenated under 40 psi of hydrogen until the starting material is consumed. The reaction is then filtered through a pad of celite and the solvent is removed. The resulting residue is dissolved to a 0.1 N concentration in a solvent chosen from the group consisting of methylene chloride and DMF and cooled using an ice bath. The reaction is then treated with DIEA (1.2 eq) and $Boc_2O$ (1.05 eq). Upon completion, the solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product. The product from the last reaction is dissolved to a 0.1 M concentration in a solvent chosen from the group consisting of pyridine and 2,4,6-lutidine. The reaction is cooled to ice bath temperatures and treated with p-toluenesulfonyl chloride (0.95 eq) as a 0.5 M solution in the same solvent. The reaction is allowed to proceed at ice bath temperature until completion. The solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product. The product from the last reaction is dissolved to a 0.1 M concentration in acetone and treated with sodium iodide (1.1 eq.) The reaction is then refluxed until complete and then filtered. The solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product. The product from the last reaction is dissolved to a 0.1 M concentration in a solvent chosen from the group consisting of DMF, acetone and a mixture of either of the above with water. The reaction is then treated with sodium azide (2 eq.) and warmed to 70% C. until the reaction is complete. Upon completion, the solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product. The product from the last reaction is dissolved to a 0.1 M concentration in a solvent chosen from the group consisting of a mixture of cyclohexane and methylene chloride, DMF, acetonitrile and toluene and cooled to ice bath temperature. The reaction is then treated with activated molecular sieves and benzyl 2,2,2-trichloroacetimidate (2 eq.) TfOH (0.005 eq.) is then added and the reaction is allowed to go to completion. Upon completion, the solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product. The product from the last reaction is dissolved in a solvent chosen from the group consisting of THF, dioxane and DMF to a concentration of 0.2 M and 10 eq. of water are added. The reaction is treated with triphenylphosphine (2 eq) and allowed to stir until completion. The solvent is removed in vacuo and the product is obtained by silica gel chromatography using a solvent system chosen from the group of ethyl acetate/hexane, toluene/acetone and chloroform/methanol. The product from the last reaction is dissolved in a solvent chosen from the group consisting of methylene chloride and DMF and cooled using an ice bath. The reaction is then treated with DIEA (1.2 eq) and benzyl chloroformate (1.05 eq.). Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in an ice cold solution of LiOH (0.25 M in MeOH/water 3:1) to a concentration of 0.05 M. Stirring is continued at 4% C. until the reaction is complete. The reaction is acidified with cold 1 N HCl and extracted with a solvent chosen from the group consisting of ethyl acetate, chloroform and toluene and dried with MgSO$_4$. Removal of solvent affords the title compound.

Synthesis of compound 24c as illustrated in FIG. 21: Compound 24b is dissolved in a solution of TFA in methylene chloride (20% by volume) to a concentration of 0.2 M. Upon completion of the deprotection, the solvent is removed and the reaction is co-rotary evaporated with methylene chloride three times to afford the product. The resulting residue is dissolved to a 0.1 N concentration in a solvent chosen from the group consisting of methylene chloride and DMF and cooled using an ice bath. The reaction is then treated with DIEA (1.2 eq) and Fmoc-Cl (1.05 eq). Upon completion, the solvent is removed and the reaction is picked up in ethyl acetate and extracted twice with 1 N HCl. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 24d as illustrated in FIG. 21: Compound 24b is dissolved in a solution of TFA in methylene chloride (20% by volume) to a concentration of 0.2 M. Upon completion of the deprotection, the solvent is removed and the reaction is co-rotary evaporated with methylene chloride three times to afford the product. The resulting residue is dissolved to a 0.1 N concentration in a solvent chosen from the group consisting of methylene chloride and DMF and cooled using an ice bath. The reaction is then treated with DIEA (1.2 eq) and benzyl chloroformate (1.05 eq). Upon completion, the solvent is removed and the reaction is picked up in ethyl acetate and extracted twice with 1 N HCl. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 24a as illustrated in FIG. 21 Compound 24c is dissolved in a solvent chosen from the group consisting of methylene chloride, DMF and THF to a concentration of 0.1 M and cooled in an ice bath. The reaction is then treated with HOBt (1.1 eq.), benzylamine (1.05 eq.) and DIEA (1.1 eq) and finally, EDC (1.05 eq.) is added in one portion. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in a 20% solution of piperidine in DMF to a concentration of 0.1 M. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 25a as illustrated in FIG. 21: The same procedure is used for the synthesis of this compound as that of compound 24a except that compound 13c is used as starting material.

Synthesis of compound 25b as illustrated in FIG. 21: The same procedure is used for the synthesis of this compound as that of compound 24b except that Ethyl (2S,3R)-2-azido-4-bezyloxy-3-hydroxypentanoate (Woltering, T. J.; Weitz-Schmidt, G.; Wong, C.-H., *Tetrahedron Lett.*, in press) is used as starting material.

Synthesis of compound 25c as illustrated in FIG. 21: The same procedure is used for the synthesis of this compound as that of compound 24c except that Ethyl (2S,3R)-2-azido-4-bezyloxy-3-hydroxypentanoate (Woltering, T. J.; Weitz-Schmidt, G.; Wong, C.-H., *Tetrahedron Lett.*, in press) is used as starting material.

Synthesis of compound 25d as illustrated in FIG. 21: The same procedure is used for the synthesis of this compound as that of compound 24d except that Ethyl (2S,3R)-2-azido-4-bezyloxy-3-hydroxypentanoate (Woltering, T. J.; Weitz-Schmidt, G.; Wong, C.-H., *Tetrahedron Lett.*, in press) is used as starting material.

Synthesis of compound 25e as illustrated in FIG. 21: The same procedure is used for the synthesis of this compound as that of compound 24e except that compound 25c is used as starting material.

Synthesis of compound 26b as illustrated in FIG. 21: Ethyl (2S,3R)-2-azido-4-bezyloxy-3-hydroxybutanoate (Woltering, T. J.; Weitz-Schmidt, G.; Wong, C.-H., *Tetrahedron Lett.*, in press) is dissolved to a 0.1 M concentration in a solvent chosen from the group consisting of ethyl acetate, methanol and THF and treated with 0.05 equivalents of Rh/C and hydrogenated under an atmospheric pressure of hydrogen until the starting material is consumed. The reaction is then filtered through a pad of celite and the solvent is removed. The resulting residue is dissolved to a 0.1 N concentration in a solvent chosen from the group consisting of methylene chloride and DMF and cooled using an ice bath. The reaction is then treated with DIEA (1.2 eq) and Boc$_2$O (1.05 eq). Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. Triphenylphosphine (1 eq.) is dissolved in a solvent chosen from the group consisting of THF, dioxane and methylene chloride to a concentration of 0.1 M. The solution is cooled using an ice bath and treated with DEAD (1 eq.). After 30 min of stirring, the product from the last reaction (1 eq.) is introduced as a 1 M solution in the same solvent. After an additional 30 min of stirring, the triphenylphosphoryl azide (1 eq) is introduced and the reaction is allowed to slowly warm to room temperature. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in a solvent chosen from the group consisting of THF, dioxane and DMF to a concentration of 0.2 M and 10 eq. of water are added. The reaction is treated with triphenylphosphine (2 eq) and allowed to stir until completion. The solvent is removed in vacuo and the product is obtained by silica gel chromatography using a solvent system chosen from the group of ethyl acetate/hexane, toluene/acetone and chloroform/methanol. The product from the last reaction is dissolved in a solvent chosen from the group consisting of methylene chloride and DMF and cooled using an ice bath. The reaction is then treated with DIEA (1.2 eq) and benzyl chloroformate (1.05 eq.). Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in an ice cold solution of LiOH (0.25 M in MeOH/water 3:1) to a concentration of 0.05 M. Stirring is continued at 4% C. until the reaction is complete. The reaction is acidified with cold 1 N HCl and extracted with a solvent chosen from the group consisting of ethyl acetate, chloroform and toluene and dried with MgSO$_4$. Removal of solvent affords the title compound.

Synthesis of compound 26c as illustrated in FIG. 21: Compound 26b is dissolved in a solution of TFA in methylene chloride (20% by volume) to a concentration of 0.2 M. Upon completion of the deprotection, the solvent is removed and the reaction is co-rotary evaporated with methylene chloride three times to afford the product. The resulting residue is dissolved to a 0.1 N concentration in a solvent chosen from the group consisting of methylene chloride and DMF and cooled using an ice bath. The reaction is then treated with DIEA (1.2 eq) and Fmoc-Cl (1.05 eq). Upon completion, the solvent is removed and the reaction is picked up in ethyl acetate and extracted twice with 1 N HCl. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 26d as illustrated in FIG. 21: Compound 24b is dissolved in a solution of TFA in methylene chloride (20% by volume) to a concentration of 0.2 M. Upon completion of the deprotection, the solvent is removed and the reaction is co-rotary evaporated with methylene chloride three times to afford the product. The resulting residue is dissolved to a 0.1 N concentration in a solvent chosen from the group consisting of methylene chloride and DMF and cooled using an ice bath. The reaction is then treated with DIEA (1.2 eq) and benzyl chloroformate (1.05 eq). Upon completion, the solvent is removed and the reaction is picked up in ethyl acetate and extracted twice with 1 N HCl. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 26a as illustrated in FIG. 21: Compound 26c is dissolved in a solvent chosen from the group consisting of methylene chloride, DMF and THF to a concentration of 0.1 M and cooled in an ice bath. The reaction is then treated with HOBt (1.1 eq.), benzylamine (1.05 eq.) and DIEA (1.1 eq) and finally, EDC (1.05 eq.) is added in one portion. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in a 20% solution of piperidine in DMF to a concentration of 0.1 M. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product.

Synthesis of compound 26a as illustrated in FIG. 21: Compound 26c is dissolved in a solvent chosen from the group consisting of methylene chloride, DMF and THF to a concentration of 0.1 M and cooled in an ice bath. The reaction is then treated with 4-methyl morpholine (1.2 eq) and isobutyl chloroformate (1.1 eq). The reaction is allowed to stir for 30 min. at ice bath temperatures before the addition of sodium 2-mercaptopyridine N-oxide (1.1 eq.) The reaction is allowed to warm up to room temperature and upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in a solvent chosen from the group consisting of toluene, benzene and 1,4 dioxane to a concentration of 1 M and degassed with a stream of argon. The solution is brought to reflux and a degassed solution of tri-n-butyl tin hydride (1.05 eq) and AIBN (0.05 eq) (1 M in the same solvent) is added slowly. The reaction is allowed to stir an additional hour at reflux and then cooled to room temperature. The solvent is then removed and the reaction is chromatographed over silica gel using a solvent system chosen from the group of ethyl acetate/hexane, toluene/acetone and chloroform/methanol to afford the product. The product from the last reaction is dissolved in a 20 % solution of piperidine in DMF to a concentration of 0.1 M. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 27a as illustrated in FIG. 21: The same procedure is used for the synthesis of this compound as that of compound 26a except that compound 27c is used as starting material.

Synthesis of compound 27b as illustrated in FIG. 21: The same procedure is used for the synthesis of this compound as that of compound 26b except that Ethyl (2S,3R)-2-azido-4-bezyloxy-3-hydroxypentanoate (Woltering, T. J.; Weitz-Schmidt, G.; Wong, C.-H., *Tetrahedron Lett.*, in press) is used as starting material.

Synthesis of compound 27c as illustrated in FIG. 21: The same procedure is used for the synthesis of this compound as that of compound 26c except that Ethyl (2S,3R)-2-azido-4-bezyloxy-3-hydroxypentanoate (Woltering, T. J.; Weitz-Schmidt, G.; Wong, C.-H., *Tetrahedron Lett.*, in press) is used as starting material.

Synthesis of compound 27d as illustrated in FIG. 21: The same procedure is used for the synthesis of this compound as that of compound 14d except that Ethyl (2S,3R)-2-azido-4-bezyloxy-3-hydroxypentanoate (Woltering, T. J.; Weitz-Schmidt, G.; Wong, C.-H., *Tetrahedron Lett.*, in press) is used as starting material.

Synthesis of compound 27e as illustrated in FIG. 21: The same procedure is used for the synthesis of this compound as that of compound 26e except that compound 27c is used as starting material.

Synthesis of compound 28b as illustrated in FIG. 21: Ethyl (2S,3R)-2-azido-4-bezyloxy-3-hydroxybutanoate (Woltering, T. J.; Weitz-Schmidt, G.; Wong, C.-H., *Tetrahedron Lett.*, in press) is dissolved to a 0.1 M concentration in a solvent chosen from the group consisting of ethyl acetate, methanol and THF and treated with 0.05 equivalents of Rh/C and hydrogenated under an atmospheric pressure of hydrogen until the starting material is consumed. The reaction is then filtered through a pad of celite and the solvent is removed. The resulting residue is dissolved to a 0.1 N concentration in a solvent chosen from the group consisting of methylene chloride and DMF and cooled using an ice bath. The reaction is then treated with DIEA (1.2 eq) and $Boc_2O$ (1.05 eq). Upon completion, the solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product.

The product from the last reaction is dissolved in pyridine to a concentration of 0.2 M and cooled to ice bath temperature. The reaction is then treated with p-toluenesulfonyl chloride and allowed to warm to room temperature slowly. Upon completion, the solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product. Vinyl bromide (1.2 eq) is condensed into a cooled flask and dissolved in diethyl ether to a concentration of 0.5 M. The reaction is then treated with an excess of magnesium turnings and a crystal of iodine. The reaction is refluxed gently until the formation of the reagent is complete. The reaction is cooled to ice bath temperature and transferred via wide bore canula into another cooled flask (ice) containing HMPA (1.2 eq), trethyl phosphite (1.2 eq) and $CuBr.SMe_2$ (1.2 eq). as a solution (0.5 M) in diethyl ether. The reaction temperature is then dropped to −60% C. and the product from the last reaction is added slowly as a 1 M solution in diethyl ether. The reaction is allowed to go to completion and then quenched at low temperature by the introduction of alkaline hydrogen peroxide. The reaction is diluted with water and extracted twice with ethyl acetate. The organic layer is dried over $MgSO_4$ and chromatographed over silica gel using a solvent system chosen from the group of ethyl acetate/hexane, toluene/acetone and chloroform/methanol to afford the product. The product from the last reaction is dissolved to a 0.1 M concentration in a solvent chosen from the group consisting of methylene chloride and methanol and cooled to −78% C. The reaction is then treated with a stream of ozone until the blue color persists. The reaction is then purged with a stream of argon and treated with dimethyl sulfide (10 eq.) After warming up overnight, the sovent is removed and the residue is chromatographed over silica gel using a solvent system chosen from the group of ethyl acetate/hexane, toluene/acetone and chloroform/methanol to afford the product. The product from the last reaction is dissolved to a 0.1 M concentration in methanol and treated with ammonium acetate (5 eq.) The reaction is then treated with sodium cyanoborohydride (0.5 eq.) After completion of the reaction, the solvent is removed and the reaction is picked up in ethyl acetate and extracted twice with 1 N NaOH. The organic layer is then dried over $MgSO_4$ and chromatographed over silica gel using a solvent system chosen from the group of ethyl acetate/hexane, toluene/acetone and chloroform/methanol to afford the product. The product from the last reaction is dissolved to a 0.1 N concentration in a solvent chosen from the group consisting of methylene chloride and DMF and cooled using an ice bath. The reaction is then treated with DIEA (1.2 eq) and $Boc_2O$ (1.05 eq). Upon completion, the solvent is removed and the reaction is picked up in ethyl acetate and extracted twice with 1 N $NaHCO_3$. The organic layer is then dried over $MgSO_4$ and chromatographed over silica gel using a solvent system chosen from the group of ethyl acetate/hexane, toluene/acetone and chloroform/methanol to afford the product. The product from the last reaction is dissolved in an ice cold solution of LiOH (0.25 M in MeOH/water 3:1) to a concentration of 0.05 M. Stirring is continued at 4% C. until the reaction is complete. The reaction is acidified with cold 1 N HCl and extracted with a solvent chosen from the group consisting of ethyl acetate, chloroform and toluene and dried with $MgSO_4$. Removal of solvent affords the title compound.

Synthesis of compound 28c as illustrated in FIG. 21: Compound 28b is dissolved in a solution of TFA in methylene chloride (20% by volume) to a concentration of 0.2 M. Upon completion of the deprotection, the solvent is removed and the reaction is co-rotary evaporated with methylene chloride three times to afford the product. The resulting residue is dissolved to a 0.1 N concentration in a solvent chosen from the group consisting of methylene chloride and DMF and cooled using an ice bath. The reaction is then treated with DIEA (1.2 eq) and Fmoc-Cl (1.05 eq). Upon completion, the solvent is removed and the reaction is picked up in ethyl acetate and extracted twice with 1 N HCl. The organic layer is then dried over $MgSO_4$ and chromatographed over silica gel using a solvent system chosen from the group of ethyl acetate/hexane, toluene/acetone and chloroform/methanol to afford the title compound.

Synthesis of compound 28d as illustrated in FIG. 21: Compound 28b is dissolved in a solution of TFA in methylene chloride (20% by volume) to a concentration of 0.2 M. Upon completion of the deprotection, the solvent is removed and the reaction is co-rotary evaporated with methylene chloride three times to afford the product. The resulting residue is dissolved to a 0.1 N concentration in a solvent chosen from the group consisting of methylene chloride and DMF and cooled using an ice bath. The reaction is then treated with DIEA (1.2 eq) and benzyl chloroformate (1.05 eq). Upon completion, the solvent is removed and the reaction is picked up in ethyl acetate and extracted twice with 1 N HCl. The organic layer is then dried over $MgSO_4$ and chromatographed over silica gel using a solvent system chosen from the group of ethyl acetate/hexane, toluene/acetone and chloroform/methanol to afford the title compound.

Synthesis of compound 28a as illustrated in FIG. 21: Compound 28c is dissolved in a solvent chosen from the group consisting of methylene chloride, DMF and THF to a concentration of 0.1 M and cooled in an ice bath. The reaction is then treated with HOBt (1.1 eq.), benzylamine (1.05 eq.) and DIEA (1.1 eq) and finally, EDC (1.05 eq.) is added in one portion. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in a 20% solution of piperidine in DMF to a concentration of 0.1 M. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product.

Synthesis of compound 28e as illustrated in FIG. 21: Compound 28c is dissolved in a solvent chosen from the group consisting of methylene chloride, DMF and THF to a concentration of 0.1 M and cooled in an ice bath. The reaction is then treated with 4-methyl morpholine (1.2 eq) and isobutyl chloroformate (1.1 eq). The reaction is allowed to stir for 30 min. at ice bath temperatures before the addition of sodium 2-mercaptopyridine N-oxide (1.1 eq.) The reaction is allowed to warm up to room temperature and upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the product. The product from the last reaction is dissolved in a solvent chosen from the group consisting of toluene, benzene and 1,4 dioxane to a concentration of 1 M and degassed with a stream of argon. The solution is brought to reflux and a degassed solution of tri-n-butyl tin hydride (1.05 eq) and AIBN (0.05 eq) (1 M in the same solvent) is added slowly. The reaction is allowed to stir an additional hour at reflux and then cooled to room temperature. The solvent is then removed and the reaction is chromatographed over silica gel using a solvent system chosen from the group of ethyl acetate/hexane, toluene/acetone and chloroform/methanol to afford the product. The product from the last reaction is dissolved in a 20 % solution of piperidine in DMF to a concentration of 0.1 M. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 29 as illustrated in FIG. 21: Compound 38 is dissolved in diethylether to a concentration of 0.1 M and treated with 1 equivalent of N-Cbz-L-serine and then with 1.1 equivalents N-iodosuccinimide and 0.05 equivalents triflic acid. Upon completion, the reaction mixture is quenched by addition of saturated sodiumbicarbonate solution, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 29.

Synthesis of compound 30 as illustrated in FIG. 21: Compound 39 is dissolved in diethylether to a concentration of 0.1 M and treated with 1 equivalent of N-Cbz-L-serine and then with 1.1 equivalents N-iodosuccinimide and 0.05 equivalents triflic acid. Upon completion, the reaction mixture is quenched by addition of saturated sodiumbicarbonate solution, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 30.

Synthesis of compound 31 as illustrated in FIG. 21: The appropriate amine 24a–30a (1 eq.) and the appropriate acid 24b–30b (1 eq.) are dissolved together to a concentration of 0.2 M in DMF and treated with HOBt (2eq.) and DIEA (1.1 eq). Then, HBTU (1.05 eq) is added in one portion. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 31 LIBRARY as illustrated in FIG. 21:

STEP 1) Compound 31 is dissolved in a solution of TFA in methylene chloride (20% by volume) to a concentration of 0.2 M. Upon completion of the deprotection, the solvent is removed and the reaction is co-rotary evaporated with methylene chloride three times to afford the product. The product from the last reaction and the appropriate acid 12d–18d (1 eq.) are dissolved together to a concentration of 0.2 M in DMF and treated with HOBt (2eq.) and DIEA (1.1 eq). Then, HBTU (1.05 eq) is added in one portion. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the title compound.

STEP 2) Compound 31 (1 eq.) and the appropriate acid 24b–30b or 24c–30c (1 eq.) are dissolved together to a concentration of 0.2 M in DMF and treated with HOBt (2 eq.) and DIEA (1.1 eq). Then, HBTU (1.05 eq) is added in one portion. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the title compound.

Steps 1 and 2 are repeated up to 18 times to afford a library of compounds ranging from diners (wherein the compound 31i has n=1; here no extra cycles are performed) to 19mer compounds (wherein the compound 31i has n=18; here 18 extra cycles of steps 1 and 2 are repeated vida supra). The final product is carried onto the next step after purification.

Synthesis of compound 32 as illustrated in FIG. 21: Compound 31i (wherein n=1 to 18) is dissolved in a solution of TFA in methylene chloride (20% by volume) to a concentration of 0.2. M. Upon completion of the deprotection, the solvent is removed and the reaction is co-rotary evaporated with methylene chloride three times to afford the product. The product from the last reaction and the appropriate acid 12d–18d (1 eq.) are dissolved together to a concentration of 0.2 M in DMF and treated with HOBt (2eq.) and DIEA (1.1 eq). Then, HBTU (1.05 eq) is added in one portion. Upon completion, the solvent is removed and the reaction is picked up in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol to afford the title compound.

Synthesis of compound 33 as illustrated in FIG. 21: Compound 32 is dissolved in MeOH/H$_2$O/AcOH (1:1:1) to a concentration of 0.1 M and treated with Pd/C 10% (1 wt. equivalent). The reaction is then hydrogenated over 40 psi of hydrogen until completion. The solvent is then removed and the residue is applied to a column of Amberlite CG-50 resin (NH$_4$ form) of the appropriate size and eluted with a linear gradient of ammonia (0–5% conc. NH$_3$ in H$_2$O). Lyophilization of the appropriate fractions yields the title compound.

Synthesis of compounds 34–38 as illustrated in FIG. 22: Compounds 34, 35, 36, 37 and 38 are synthesized by an identical protocol, beginning with 6-azido-6-deoxy-2,3,4-tris-O-phenylmethyl-alpha-D-glucopyrano syl chloride (Kavadias, G., et al. *Can. J. Chem.* 1978, 56, 2086–2092), 4-azido-4-deoxy-2,3,6-tris-O-phenylmethyl-alpha-D-glucopyranosyl chloride (Takagi, Y., et al. *Bull. Chem. Soc. Jpn.* 1973, 46, 1261–1262), 3-azido-3-deoxy-2,4,6-tris-o-phenylmethyl-alpha-D-glucopyrano syl chloride (Tang, J.-Y.; Anderson, L. *Carbohydr. Res.* 1977, 59, 319–331), 2-azido-2-deoxy-3,4,6-tris-O-phenylmethyl-alpha-D-glucopyranosyl bromide (Plourde, R., et al. *J. Org. Chem.* 1992, 57, 2606–2610), and 2,6-diazido-2, 6-dideoxy-3,4-bis-O-phenylmethyl-alpha-D-glucopyranosyl chloride (Paulsen, H., et al. *Carbohydr. Res.* 1979, 68, 239–255), respectively. The appropriate glycosyl halide is dissolved in a solvent selected from the group consisting of THF, acetonitrile, and DMF to a concentration of 0.1 M and 1 molar equivalent of sodium thiophenoxide dissolved in the same solvent is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give either compound 34, 35, 36, 37 or 38.

Synthesis of compound 39 as illustrated in FIG. 22: 6-O-acetyl-2,4-diazido-2,4-dideoxy-3-O-phenylmethyl-b-D-glucopyra nosyl chloride (Paulsen, H., et al. *Tetrahedron Letters* 1976, 2301–2304) is dissolved in a solvent selected from the group consisting of THF, acetonitrile, and DMF to a concentration of 0.1 M and 1 molar equivalent of sodium thiophenoxide dissolved in the same solvent is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved to a concentration of 0.1 M in methanol containing 0.05 molar equivalents of sodium methoxide. Upon completion, the reaction is neutralized with acetic acid, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in DMF to a concentration of 0.1 M under an argon atmosphere and 2 molar equivalents of benzyl bromide is added, followed by 1.5 molar equivalents of sodium hydride. Upon completion, the reaction is quenched with methanol, neutralized with acetic acid, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform, to give compound 39.

Synthesis of compound 40 as illustrated in FIG. 23: N-alpha- Cbz-L-aspartic acid-alpha-benzyl ester (Novabiochem) is dissolved in methanol to a concentration of 0.1 M and 3 to 6 molar equivalents of NaBH3CN is added. Upon completion, the reaction is quenched by addition of excess acetone, concentrated, and purified by ion exchange chromatography. The product is dissolved in dimethylformamide to a concentration of 0.1 M and treated with 1.1 molar equivalents of Cs2CO3, followed by 1 equivalent of methyl iodide. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 40.

Synthesis of compound 41 as illustrated in FIG. 23: Methyl 3-butenoate (Aldrich) is added to 1 molar equivalent of AD-mix-a (Aldrich) in 1:1 t-butyl alcohol/water. Upon completion, the reaction is quenched by addition of sodium sulfite and the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in pyridine to a concentration of 0.1 M under an argon atmosphere and 1.2 molar equivalents of p-toluenesulphonyl chloride is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. This product is dissolved in DMF to a concentration of 0.1 M and 5 molar equivalents of sodium azide is added. The reaction is heated to 50% C. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in ethanol to a concentration of 0.1M and a catalytic amount of 10% palladium on carbon is added, followed by hydrogen gas (1 atm). Upon completion, the reaction is filtered, and the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. This product is dissolved in DMF to a concentration of 0.1M and 3 molar equivalents of triethylamine are added, followed by 1.1 molar equivalents of benzyl chloroformate. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 41.

Synthesis of compound 42 as illustrated in FIG. 23: N-alpha- Cbz-D-serine (Novabiochem) is dissolved in dimethylformamide to a concentration of 0.1 M and treated with 1.1 molar equivalents of Cs2CO3, followed by 1 equivalent of methyl iodide. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 42.

Synthesis of compound 43 as illustrated in FIG. 23: Racemic 3-amino-2-hydroxypropionic acid (Aldrich) is dissolved in a solvent from the group consisting of THF, DMF, and DMSO to a concentration of 0.1M. 3 equivalents of triethylamine are added, followed by 1.1 equivalents of benzyl chloroformate. Upon completion, the reaction is concentrated and purified by ion exchange chromatography. The product is dissolved in dimethylformamide to a concentration of 0.1 M and treated with 1.1 molar equivalents of Cs2CO3, followed by 1 equivalent of methyl iodide. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. This product is dissolved in pyridine to a concentration of 0.1 M. Two equivalents of acetic anhydride are added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in a solvent chosen from the group of THF, DMF, ethanol, methanol, water, and DMF/water, and treated with 0.1 molar equivalents of an enzyme from the group consisting of subtilisin, acetylcholine esterase, pig liver esterase, porcine pancreatic lipase, and Pseudomonas sp. lipase. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 43.

Synthesis of compounds 44, 45, and 46 as illustrated in FIG. 23 are commercially available from Aldrich as methyl salicylate, methyl 3-hydroxybenzoate, and methyl 4-hydroxybenzoate, respectively.

Synthesis of compound 47 as illustrated in FIG. 23: L-asparagine (Novabiochem) is dissolved in a solvent from the group consisting of diethyl ether, dioxane, and THF to a concentration of 0.1M. 4 molar equivalents of lithium aluminum hydride is added. Upon completion, the reaction is quenched by addition of acetone, concentrated, and purified by ion exchange chromatography. The product is dissolved in DMF to a concentration of 0.1M and 3 molar equivalents of Na2CO3 is added, followed by 1 molar equivalent of 9-fluorenylmethyl chloroformate. Upon completion of this reaction, 1.5 molar equivalents of benzyl chloroformate is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 47.

Synthesis of compound 48 as illustrated in FIG. 23: 3-butenal diethyl acetal (Aldrich) is added to 1 molar equivalent of AD-mix-a (Aldrich) in 1:1 t-butyl alcohol/water. Upon completion, the reaction is quenched by addition of sodium sulfite and the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in pyridine to a concentration of 0.1 M under an argon atmosphere and 1.2 molar equivalents of p-toluenesulphonyl chloride is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/ chloroform. This product is dissolved in DMF to a concentration of 0.1 M and 5 molar equivalents of sodium azide is added. The reaction is heated to 50% C. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/ chloroform. The product is dissolved to a concentration of 0.1M in 1:1 THF/water, and 0.05 molar equivalents of acetic acid is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. This product is dissolved in methanol to a concentration of 0.1M and 1.1 molar equivalents of allyl amine is added, followed by 3 molar equivalents of NaBH3CN. Upon completion, the reaction is quenched with acetone, and the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. This product is dissolved in dichloromethane to a concentration of 0.1M and 1 molar equivalent of triphenylphosphine is added. After 1 hour, the reaction is concentrated, and dissolved to a concentration of 0.1M in a 1:1 mixture of THF/water. Upon completion, the product is purified by ion exchange chromatography. The product is dissolved in DMF to a concentration of 0.1M and 2 molar equivalents of triethylamine are added, followed by 1.1 molar equivalents of benzyl chloroformate. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. This product is dissolved in dichloromethane to a concentration of 0.1M and 1 molar equivalent of Rh(Ph3P)3Cl is added. Upon completion, the product is purified by ion exchange chromatography. The product is dissolved in DMF to a concentration of 0.1M and 3 molar equivalents of Na2CO3 is added, followed by 1.2 molar equivalent of 9-fluorenylmethyl chloroformate. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/ chloroform to give compound 48.

Synthesis of compound 49 as illustrated in FIG. 23: Allyl amine (Aldrich) is added to 1 molar equivalent of AD-mix-a (Aldrich) in 1:1 t-butyl alcohol/water. Upon completion, the reaction is quenched by addition of sodium sulfite and the product purified by ion exchange chromatography. The product is dissolved in DMF to a concentration of 0.1M and 3 molar equivalents of Na2CO3 is added, followed by 1.2 molar equivalent of 9-fluorenylmethyl chloroformate. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. This product is dissolved in DMF to a concentration of 0.1 M under an argon atmosphere and 1.5 molar equivalents of imidazole is added, followed by 1.2 molar equivalents of t-butyldimethylsilyl chloride. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in pyridine to a concentration of 0.1 M under an argon atmosphere and 1.2 molar equivalents of p-toluenesulphonyl chloride is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. This product is dissolved in DMF to a concentration of 0.1 M and 5 molar equivalents of sodium azide is added. The reaction is heated to 50% C. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. The product is dissolved in dichloromethane to a concentration of 0.1M and 1 molar equivalent of triphenylphosphine is added. After 1 hour, the reaction is concentrated, and dissolved to a concentration of 0.1M in a 1:1 mixture of THF/water. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in DMF to a concentration of 0.1M and 2 molar equivalents of triethylamine are added, followed by 1.1 molar equivalents of benzyl chloroformate. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. This product is dissolved in dichloromethane to a concentration of 0.1M and 1 molar equivalent of HF.pyridine is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 49.

Synthesis of compound 50 as illustrated in FIG. 23: Allyl amine (Aldrich) is added to 1 molar equivalent of AD-mix-a (Aldrich) in 1:1 t-butyl alcohol/water. Upon completion, the reaction is quenched by addition of sodium sulfite and the product purified by ion exchange chromatography. The product is dissolved in DMF to a concentration of 0.1M and 3 molar equivalents of Na2CO3 is added, followed by 1.2 molar equivalent of 9-fluorenylmethyl chloroformate. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. This product is dissolved in pyridine to a concentration of 0.1 M under an argon atmosphere and 1.2 molar equivalents of p-toluenesulphonyl chloride is added. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in DMF to a concentration of 0.1 M and 5 molar equivalents of sodium azide is added. The reaction is heated to 50% C. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. This product is dissolved in dichloromethane to a concentration of 0.1M and 1 molar equivalent of triphenylphosphine is added. After 1 hour, the reaction is concentrated, and dissolved to a concentration of 0.1M in a 1:1 mixture of THF/water. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform. The product is dissolved in DMF to a concentration of 0.1M and 2 molar equivalents of triethylamine are added, followed by 1.1 molar equivalents of benzyl chloroformate. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 50.

Synthesis of compound 51 as illustrated in FIG. 23: 2-aminophenol (Aldrich) is dissolved in DMF to a concentration of 0.1 M. 1.5 molar equivalents of Na2CO3 are added, followed by 1.1 equivalents of FmocCl. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 51.

Synthesis of compound 52 as illustrated in FIG. 23: 3-aminophenol (Aldrich) is dissolved in DMF to a concentration of 0.1 M. 1.5 molar equivalents of Na2CO3 are added, followed by 1.1 equivalents of FmocCl. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 52.

Synthesis of compound 53 as illustrated in FIG. 23: 4-aminophenol (Aldrich) is dissolved in DMF to a concentration of 0.1 M. 1.5 molar equivalents of Na2CO3 are added, followed by 1.1 equivalents of FmocCl. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform to give compound 53.

Synthesis of compound 54 as illustrated in FIG. 23: N3-Alloc-2-deoxystreptamine (Orsat, B., et al. *J. Am. Chem. Soc.* 1996, 118, 712–713.) is dissolved in 9:1 methanol/water (v/v) to a concentration of 0.1 M. 0.05 molar equivalents of CuSO4 is added, followed by 4 molar equivalents of CF3SO2N3. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. The product is dissolved in a solvent from the group consisting of DMF and DMSO at a concentration of 0.1 M and treated with 2 molar equivalents of sodium hydride. Upon completion, the reaction is cooled to 0% C. and neutralized by addition of acetic acid. The reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. This product is dissolved in DMF to a concentration of 0.1M under an argon atmosphere and treated with 3 molar equivalents of benzyl bromide, followed by 2.2 molar equivalents of sodium hydride. Upon completion, the reaction is quenched by addition of methanol, and the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. The product is dissolved in a solvent from the group consisting of DMF and DMSO at a concentration of 0.1 M and treated with 3 molar equivalents of benzyl alcohol, followed by 3 molar equivalents of sodium hydride. Upon completion, the reaction is cooled to 0% C., neutralized with acetic acid, and the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/ chloroform. The product is dissolved in CH2Cl2 to a concentration of 0.1M and 1 molar equivalent of triphenylphosphine is added. Upon completion, the reaction is concentrated and the residue treated with a 1:1 mixture of THF/water. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. This product is dissolved in DMF to a concentration of 0.1 M. 1.5 molar equivalents of Na2CO3 are added, followed by 1.1 equivalents of FmocCl. Upon completion, the reaction mixture is concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform to give compound 54.

Synthesis of compound 55 as illustrated in FIG. 24. The alcohol component, selected from the group consisting of 40–46 (1 eq.), and the glycosyldonor, selected from the group consisting of 34–39 (1.1 eq.) are dissolved in ether to a concentration of 0.1 M and treated at −30% C. with N-iodosuccinimide (1.1 eq.) and 0.05 equivalents triflic acid. The reaction is then allowed to warm to ambient temperature. Upon completion, the reaction mixture is quenched by addition of saturated sodiumbicarbonate solution, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform. This product is dissolved in MeOH to a concentration of 0.1 M and treated with lithium hydroxide (3 eq.) Upon completion of ester cleavage, the reaction mixture is quenched by addition of saturated ammonium chloride solution, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/ hexanes, acetone/toluene, and methanol/chloroform.

A solution of this carboxylic acid at a concentration 0.2 M in DMF is treated with 1.1 eq. of an amine component, selected from the group consisting of 24–28e, HOBt (2eq.) and DIEA (1.1 eq). Then, HBTU (1.05 eq) is added in one portion. Upon completion, the solvent is removed and the reaction mixture is taken up in ethyl acetate and extracted twice with 1 N NaHCO$_3$. The organic layer is then dried over MgSO4 and chromatographed over silica gel using a solvent system chosen from the group of ethyl acetate/ hexane, toluene/acetone and chloroform/methanol.

This coupling product is dissolved in MeOH/H$_2$O/AcOH (1:1:1) to a concentration of 0.1 M and treated with Pd/C 10% (1 wt. equivalent). The reaction is then hydrogenated over 40 psi of hydrogen until completion. The solvent is then removed and the residue is applied to a column of Amberlite CG-50 resin (NH$_4$ form) and eluted with a linear gradient of ammonia (0–5% conc. NH$_3$ in H$_2$O). Lyophilization of the appropriate fractions yields compound 55.

Synthesis of compound 56 as illustrated in FIG. 25. The alcohol component, selected from the group consisting of 47–54 (1 eq.), and the glycosyldonor, selected from the group consisting of 34–39 (1.1 eq.) are dissolved in ether to a concentration of 0.1 M and treated at −30% C. with N-iodosuccinimide (1.1 eq.) and 0.05 equivalents triflic acid. The reaction is then allowed to warm to ambient temperature. Upon completion, the reaction mixture is quenched by addition of saturated sodiumbicarbonate solution, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform.

This product is dissolved in DMF to a concentration of 0.2 M and treated with an equal volume of piperidine. Upon completion of Fmoc-cleavage, the reaction mixture is quenched by addition of saturated ammonium chloride solution, concentrated, dissolved in one of the group consisting of ether, ethyl acetate, chloroform, or methylene chloride, and extracted with saturated aqueous sodium bicarbonate solution, then with brine. The organic layer is dried over either Na2SO4 or MgSO4, filtered, and concentrated. The residue is purified by chromatography on silica gel with a solvent system from the group consisting of ethyl acetate/hexanes, acetone/toluene, and methanol/chloroform.

A solution of this amine at a concentration 0.2 M in DMF is treated with 1.1 eq. of a carboxylic acid component, selected fro the group consisting of 24–28d, HOBt (2 eq.) and DIEA (1.1 eq). Then, HBTU (1.05 eq) is added in one portion. Upon completion, the solvent is removed and the mixture is dissolved in ethyl acetate and extracted twice with 1 N NaHCO$_3$. The organic layer is then dried over MgSO$_4$ and chromatographed over silica gel using a solvent system chosen from the group of ethyl acetate/hexane, toluene/acetone and chloroform/methanol.

This coupling product is dissolved in a mixture of MeOH/H$_2$O/AcOH (1:1:1) to a concentration of 0.1 M and treated with Pd/C 10% (1 wt. equivalent). The reaction is then hydrogenated over 40 psi of hydrogen until completion. The solvent is then removed and the residue is applied to a column of Amberlite CG-50 resin (NH$_4$ form) and eluted with a linear gradient of ammonia (0–5% conc. NH$_3$ in H$_2$O) Lyophilization of the appropriate fractions yields compound 56.

Plasmon resonance and antimicrobial testing for Example 4. Synthesis of the biotinylated RNA and surface plasmon resonance detected binding experiments were performed as described vida supra. Solution conditions: 150 mM NaCl, 10 mM HEPES (pH 7.4), 3.4 mM EDTA. KD determination from the binding curves.

The fitting routine of the program kaleidagraph was used for all calculations. The starting values for a and b were set to 1 and 0 respectively. The number of KD values used in the fitting was adjusted depending on the observed range of equivalents bound but generally varied from 3 to 4.

Anti microbial testing: Kirby-Bauer disc test. These tests were performed exactly as described. Reference strains *E. coli* ATCC 25922, *S. aureus* ATCC 25923, and Ps. aeruginosa ATCC 27853 were obtained as packs of lyophilized pellets (Difco), which were freshly reconstituted every few days. To make the antibiotic discs, paper discs (6 mm diameter, BBL Microbiology Systems) were wetted through with 20 mL of solution containing an appropriate amount (usually 33 nmol) of antibiotic. The wet discs were placed in a dessicator overnight, and used the next day.

Minimal Inhibitory Concentration (MIC) testing. *E. coli* ATCC 25922 was grown in Mueller-Hinton broth (cation-adjusted, BBL Microbiology Systems) to an optical density of approx. 0.5 (absorbance read at 600 nm), then diluted to an OD600 of 0.1. Samples of antibiotic were prepared in Mueller-Hinton broth, typically a series of 2-fold dilutions from 0.1 mM to <1 mM. 50 mL of the diluted culture was added to 1 mL of each of the antibiotic samples, and the cultures were allowed to grow at 37° C. for 4–6 hours, at which point the negative control sample (no antibiotic) typically had an absorbance of 1.2–1.5. The absorbance of each sample was read (1=600 nm), and MIC was considered to be the lowest antibiotic concentration at which the absorbance was less than 1% of the no-antibiotic control.

Synthesis of 5-O-benzyl-1,2-O-isopropylidene-α-D-xylofuranose (1300) as illustrated in FIG. 27. 1,2-O-isopropylidene-a-D-xylofuranose (1200) (4.2 g, 22.08 mmol; Aldrich/common acetonide) was dissolved in toluene (120 mL) and treated with Bu$_2$SnO (5.76 g, 23.19 mmol). The reaction was then refluxed overnight with azeotropic removal of water. The Dean-Stark trap was then removed and replaced with a standard reflux condenser. The reaction was treated with BnBr (5.66 g, 33.12 mmol) and kept at 110° C. for 7 h. Upon addition of EtOAc and water, a solid formed which was filtered. The organic phase was washed with saturated sodium bicarbonate solution and brine and dried over Na2SO4. Chromatography of the resulting oil using a gradient of 25% to 30% to 35% EtOAc in hexane afforded 4.01 g, 65% of the title compound as an oil which solidified after standing under vacuum. H1 NMR (CDCl3, 500 MHz) :d1.31(s, 3H, acetonide methyl), d1.48 (s, 3H, acetonide methyl), d3.68 (s,1H, OH), d3.90 (dd, 2H, J1=11 Hz, J2=4 Hz, H5a), d3.93 (dd, 2H, J1=11 Hz, J2=4 Hz, H5b), d4.25 (dd, 1H, J1=7 Hz, J2=4 Hz, H4), d4.27 (m, 1H, H3), d4.50 (d, 1H, J=4 Hz, H2), d4.60 (ABq, 2H, J=12 Hz, Dn=29.7 Hz, PhCH2O), d5.97, (d, 1H, J=4 Hz, H1), d7.25–7.4 (m, 5H, C6H5); 13C NMR (CDCl3, 125 MHz): d 26.1, 26.7, 68.1, 74.0, 76.3, 78.0, 85.2, 104.8, 111.5, 127.8, 128.0, 128.5, 137.0; HRMS for C15H20O5 (M+Na): calcd. 303.1208; found 303.1201.

Synthesis of 5-O-benzyl-3-keto-1,2-O-isopropylidene-a-D-xylofuranose (1400) as illustrated in FIG. 27. Methylene chloride (100 mL) was cooled to −78° C. and DMSO (2.79 g, 35.76 mmol) was added, followed by oxalyl chloride (2.18 g, 17.16 mmol). The reaction was allowed to stir for 20 min at this temperature and then treated with a solution of 1300 (4.01 g, 14.3 mmol) in 30 mL of CH2Cl2. The reaction was allowed to slowly warm to −35° C. and was kept at that temperature for 15 min before the addition of triethyl amine (7.24 g, 71.5 mmol). The reaction was allowed to warm to room temperature and extracted with saturated sodium bicarbonate solution and saturated NaCl solution and dried over Na2SO4. Flash chromatography on 200 ml of silica gel using a gradient of 0 to 0.5 to 1 to 1.5% MeOH in CHCl3 afforded 3.2 g, 80.4% of the title compound. H1 NMR (CDCl3, 500 MHz): d1.43 (s, 3H, acetonide methyl), d1.46 (s, 3H, acetonide methyl), d3.72–3.75 (m, 2H, H5a and H5b), d4.35 (dd, J1=4 Hz, J2=1 Hz, 1H, H2), d4.45 (m; 1H, H4), d4.51 (ABq, J=12 Hz, Dn=15.75 Hz, PhCH2O), d6.13 (d, J=4 Hz, H1), d7.2–7.4 (m, 5H, C6H5); 13C NMR (125 MHz): d 27.2, 27.6, 70.0, 73.6, 76.7, 79.8, 103.5, 114.1, 127.4, 127.8, 128.4, 128.5, 137.3; HRMS for C15H18O5 (M+Na): calcd. 301.1052; found 303.1043.

Synthesis of 5-O-benzyl-1,2-O-isopropylidene-a-D-ribofuranose (1500) as illustrated in FIG. 27. Compound 1400 (3.2 g, 11.5 mmol) was dissolved in 50 ml of anhydrous methanol and treated with NaBH4 (218 mg, 5.75 mmol). The reaction was allowed to stir for one hour and then quenched with water. The solvent was removed and the reaction was partitioned between EtOAc and saturated sodium bicarbonate solution. The organic phase was dried with brine and Na2SO4. Flash chromatography on 120 ml of silica gel using a gradient of 25% to 3050 to 35% to 40% EtOAc in hexane afforded 2.53 g, 79% of the title compound. H1 NMR (CDCl3, 500 MHz): d1.37 (s, 3H, acetonide methyl) , d1.56 (s, 3H, acetonide methyl), d2.42 (d, 1H, J=10 Hz, OH), d3.64 (dd, 1H, J1=11 Hz, J2=4.5 Hz, H5a), d3.79 (dd, 1H, J1=11 Hz, J2=2.5 Hz, H5b), d3.92 (m, 1H, H4), d3.3.97 (m, 1H, H3), d4.56 (dd, 1H, J1=4.5 Hz, J2=3.5 Hz, 1H, H2), d4.60 (s, 2H, PhCH2O), d5.84 (d, 1H, J=3.5 Hz, H1), d7.27–7.37 (m, 4H, C6H5); 13C NMR (CDCl3, 125 MHz): d 26.4, 26.5, 68.5, 71.7, 73.5, 78.3, 79.7, 104.1, 112.6, 127.6, 127.7, 128.4, 137.8; HRMS for C15H20O5 (M+Na): calcd. 303.1208; found 303.1200.

Synthesis of 3-O-allyl-5-O-benzyl-1,2-O-isopropylidine-a-D-ribofuranose (1600) as illustrated in FIG. 27. Compound 1500 (500 mg, 1.784 mmol) was dissolved in 10 ml of DMF and cooled to ice bath temperature. The reaction was treated with sodium hydride (47 mg, 1.963 mmol) followed by allyl bromide (647 mg, 5.352 mmol). After 20 min, another 20 mg of NaH was added. After all starting material was consumed, the reaction was quenched with AcOH and the solvent was removed. The residue was taken up in EtOAc and washed with water, saturated sodium bicarbonate solution, brine and dried over Na2SO4. Flash chromatography on 70 ml of silica gel using a gradient of 12% to 15% to 18% to 20% EtOAc in hexane afforded 555 mg, 97% of the title compound. H1 NMR (CDCl3, 500 MHz): d1.36 (s, 3H, acetonide methyl) , d1.58 (s, 3H, acetonide methyl), d3.61 (dd, 1H, J1=11 Hz, J2=4 Hz, H5a), d3.79 (dd, 1H, J1=11 Hz, J2=2 Hz, H5b), d3.85 (dd, 1H, J1=9 Hz, J2=4.5 Hz, H3), d4.07 (dddd, 1H, J1=12.5 Hz, J2=6 Hz, J3=J4=1.5 Hz, 1H, H4), d4.12–4.17 (m, 2H, CH2CHCH2O), d4.60 (ABq, 2H, J=12 Hz, Dn=45 Hz, PhCH2O), d4.60 (dd, 1H, J1=J2=4 Hz, H2), d5.21 (ddd, 1H, J1=11.5 Hz, J2=J3=1.5 Hz, CH2CHCH2O), d5.28 (ddd, 1H, J1=17.5 Hz, J2=J3=1.5 Hz, CH2CHCH2O), d5.78 (d, 1H, J=4 Hz, H1), d5.36–5.46 (m, 1H, CH2CHCH2O), d5.27–7.36 (m, 5H, C6H5); 13C NMR (CDCl3, 125 MHz): d 26.4, 26.7, 67.8, 71.6, 73.5, 77.3, 77.4, 77.8, 103.9, 112.8, 118.0, 127.6, 127.7, 128.3, 134.4, 138.0; HRMS for C18H24O5 (M+Na): calcd. 343.1521; found 343.1513.

Synthesis of 1,2-O-(4-nitrobenzoyl)-3-O-allyl-5-O-benzyl-a/b-D-ribofuranose (1100) as illustrated in FIG. 27. Compound 1600 (757 mg, 2.36 mmol) was dissolved in 15 ml of dioxane and treated with 5 mL of 1N HCl solution. The reaction was then warmed to 80° C. for 1.5 h and cooled back to RT. The acid was quenched by addition of solid sodium bicarbonate and the solvent was removed. The residue was partitioned between water and EtOAc. The water layer was further extracted twice with EtOAc and the combined organic extracts were dried over MgSO4. The solvent was removed and the residue was treated with pyridine (15 mL), 4-nitrobenzoyl chloride (1.04 g, 5.60) and a few crystals of DMAP. The reaction was stirred overnight and the solvent was removed. The residue was taken up in EtOAc and washed with water, saturated CuSO4 solution followed by saturated ammonium chloride solution and brine. The combined organic phases were dried over MgSO4 and the solvent was removed. The residue was chromatographed over 50 mL of silica gel using 10% to 12% to 15% EtOAc in hexane to afford 910 mg, 68% (over 2 steps) of the product as a chromatographically separable mixture (approx. 4:1) of anomers. β anomer:H1 NMR (CDCl3, 500 MHz): d3.73 (dd, 1H, J1=11 Hz, J2=3 Hz, H5a), d3.86 (dd, 1H, J1=11 Hz, J2=2.5 Hz, H5b), d4.05–4.18 (m, 2H, CH2CHCH2O), d4.40 (ddd, 1H, J1=8 Hz, J2=J3=3 Hz, H4), d4.53 (s, 2H, PhCH2O), d4.63 (dd, 1H, J1=8 Hz, J2=4.5 Hz, H3), d5.15–5.28 (m, 2H, CH2CHCH2O), d5.70 (d, 1H, J=4.5 Hz, H2), d5.75–5.86 (m, 1H, CH2CHCH2O), d6.56 (s, 1H, H1), d7.20–7.30 (m, 5H, C6H5), d8.00–8.35 (m, 8H, C6H4NO2); 13C NMR (CDCl3, 125 MHz): d 68.5, 72.3, 73.5, 75.0, 75.8, 82.1, 99.4, 118.1, 123.5, 123.7, 127.6, 127.8, 128.4, 130.9, 131.0, 133.6, 134.5, 137.7, 150.6, 150.8, 163.0 163.5; HRMS for C29H26N2O11 (M+Na): calcd. 601.1434; found 601.1447; a anomer: H1 NMR (CDCl3, 500 MHz): d3.70 (dd, 2H, J1=3.5 Hz, J2=3 Hz, 2H, H5a&b), d4.05–4.10 (m, 2H, CH2CHCH2O), d3.70 (dd, J1=6.5 Hz, J2=3 Hz, 1H, H3), d4.55–4.60 (m, 3H, H4 and PhCH2O), d5.22–5.37 (m, 2H, CH2CHCH2O), d5.47 (dd, J1=6 Hz, J2=4 Hz, 1H, H2), d5.77–5.86 (m, 1H, CH2CHCH2O), d6.81 (d, J=4 Hz), d7.35–7.42 (m, 5H, C6H5), d8.08–8.30 (m, 8H, C6H4NO2); 13C NMR (CDCl3, 125 MHz): d 69,3, 72.1, 73.3, 73.7, 75.6, 84.9, 95.9, 117.3, 123.6, 127.7, 127.9, 128.5, 130.7, 131.0, 134.0, 134.4, 135.1, 137.5, 150.7, 163.5, 163.6; MS for C29H26N2O11 (M+Na): calcd. 601; found 601, for C29H26N2O11 (M+Cl−) calcd. 613; found 613.

Synthesis of 6,3',4'-tri-O-acetyl-3"-O-allyl, 5"-O-benzyl-1,3,2',6'-tetraazido ribostamycin (1800) as illustrated in FIG. 28. Compound 1100 (3.5 g, 6.18 mmol) and compound 1000 (1.34 g, 2.43 mmol) were dissolved in 15 mL of CH2Cl2 and cooled in an ice bath. Then, BF3.OEt2 (922 mg, 6.5 mmol) was added via syringe and the reaction was allowed to stir for 4.5 h. By this time a large amount of precipitate had formed. The reaction was quenched by addition of triethylamine until the solution became homogenous. Chloroform was added and the reaction was extracted with saturated NaHCO3 solution and brine and dried over Na2SO4. Chromatography over 200 mL of silica gel using a gradient of 5% to 10% to 15% to 20% to 25% to 30 % EtOAc in Hexane yielded 2.02 g of the donor, 1.47 g of the β anomer (63%) and 0.43 g of the α anomer (18%). b anomer: H1 NMR (CDCl3, 500 MHz): d1.61 (ddd, 1H, J1=J2=J3=13 Hz, H2 eq), d2.05 (s, 3H, COCH3), d2.08 (s, 3H, COCH3), d2.14 (s, 3H, COCH3), d2.37 (ddd, 1H, J1=13 Hz, J2=J3=4.5 Hz, H2 ax), d3.10 (dd, 1H, J1=11 Hz, J2=3.5 Hz, H2'), d3.22 (dd, 1H, J1=13.5 Hz, J2=5.5 Hz, H6'a),d3.32 (dd, 1H, J1=13.5 Hz, J2=3 Hz, H6'b), d3.42 (ddd, 1H, J1=13 Hz, J2=10 Hz, J3=4.5 Hz, H1) , d3.49 (ddd, 1H, J1=13 Hz, J2=10 Hz, J3=4.5 Hz, H3), d3.58 (dd, 1H, J1=10.5 Hz, J2=4.5 Hz, H5"a), d3.68 (dd, 1H, J1=J2=10 Hz, H4), d3.82 (dd, 1H, J1=10.5 Hz, J2=2.5 Hz, H5"b), d3.85 (dd, 1H, J1=J2=10 Hz, H5), d3.90 (dd, 1H, J1=12.5 Hz, J2=6 Hz, CH2CHCH2O), d4.00 (dd, 1H, J1=12.5 Hz, J2=5.5 Hz, 1H, CH2CHCH2O), d4.16–4.22 (m, 2H, H3" and H4"), d4.38–4.42 (m, 1H, H5'), d4.58 (ABq, 2H, J=11.5 Hz, Dn=51.2 Hz, PhCH2O), d4.86 (dd, 1H, J1=J2=10 Hz, H4'), d4.96 (dd, 1H, J1=J2=10 Hz, H6), d5.09 (dd, 1H, J1=10 Hz, J2=1.5 Hz, CH2CHCH2O), d5.16 (dd, J1=17 Hz, J2=115 Hz, 1H, CH2CHCH2O), d5.29 (d, 1H, J=3 Hz, H2"), d5.38 (dd, 1H, J1=11 Hz, J2=9.5 Hz, H3'), d5.40 (s, 1H, H1"), d5.63–5.74 (m, 1H, CH2CHCH2O), d6.07 (d, 1H, J=3.5 Hz, H1'), d7.2–7.35 (m, 5H, C6H5), d8.15–8.35 (m, C6H4NO2); 13C NMR (CDCl3, 125 MHz): d 20.7, 20.9, 31.3, 50.9, 58.1, 58.9, 61.0, 69.0, 69.2, 69.4, 70.2, 73.5, 75.1, 75.9, 76.2, 76.6, 80.4, 82.6, 96.1, 107.8, 118.1, 123.7, 127.8, 127.9, 128.6, 130.9, 133.5, 134.7, 137.7, 150.8, 163.5, 169.7, 170.0; HRMS for C40H45N13O16 (M+Na): calcd. 986.3005; found 986.3035. a anomer: H1 NMR (CDCl3, 500 MHz): d1.58 (ddd, 1H, J1=J2=J3=13 Hz, H2 eq), d2.04 (s, 3H, COCH3), d2.10 (s, 3H, COCH3), d2.14 (s, 3H, COCH3), d2.38 (ddd, 1H, J1=13 Hz, J2=J3=4.5 Hz, H2 ax), d3.18 (dd, 1H, J1=13.5 Hz, J2=4.5 Hz, H6'a), d3.30–3.37 (m, 2H, H6'b, H2'), d3.43 (ddd, 1H, J1=12 Hz, J2=10 Hz, J3=4.5 Hz, H3), d3.50 (ddd, 1H, J1=12.5 Hz, J2=10 Hz, J3=4.5 Hz, H1), d3.57 (dd, 1H, J1=J2=9.5 Hz, H4), d3.58 (dd, 1H, J1=11 Hz, J2=4 Hz, H5'a), d3.71 (dd, 1H, J1=11 Hz, J2=2.5 Hz, H5'b), d3.80 (dd, 1H, J1=J2=9.5 Hz, H5), d3.88–4.02 (m, 2H, CH2CHCH2O), d4.08 (dd, J1=7.5 Hz, J2=5 Hz, 1H, H3"), d4.22–4.26 (m, 1H, H4"), d4.42–4.47 (m, 1H, H5'), d4.58 (ABq, 2H, J=12 Hz, Dn=43.5 Hz, PhCH2O), d4.92–4.99 (m, 2H, H6, H4'), d5.08–5.19 (m, 2H, CH2CHCH2O), d5.47–5.44 (m, 2H, H1', H3'), d5.58 (d, 1H, J=4 Hz, H1"), d5.67 (dd, 1H, J1=J2=5 Hz, H2"), d5.67–5.76 (m, 1H, CH2CHCH2O), d7.28–7.42 (m, 5H, C6H5), d8.23–8.35 (m, 2H, C6H4NO2); 13C NMR (CDCl3, 125 MHz): d 20.57, 20.63, 21.1, 31.5, 50.5, 58.1, 58.6, 61.0, 68.7, 69.0, 69.4, 70.3, 71.5, 72.0, 73.5, 73.6, 75.8, 79.4, 80.0, 82.5, 97.4, 103.0, 118.1, 123.7, 127.8, 128.4, 130.4, 131.1, 133.6, 134.7, 137.6, 150.8, 164.2, 169.6, 169.9, 170.0; HRMS for C40H45N13O16 (M+Cs): calcd. 1096.2162; found 1096.2119.

Synthesis of 3"-O-allyl-5"-O-benzyl-1,3,2',6'-tetraazido ribostamycin (1900) as illustrated in FIG. 28. Compound 1800 (1.47 g, 1.525 mmol) was dissolved in a mixture of MeOH and dioxane 1:1 (30 mL). The reaction was then treated with a solution of LiOH (384 mg, 9.151 mmol) in 10 mL of H2O. The mixture was allowed to stir overnight at room temperature and the solvent was removed. The reaction was partitioned between EtOAc and saturated NaHCO3 and extracted 3 times with EtOAc. The combined organic phases were dried over MgSO4 and purified on 100 mL of silica gel using 50% to 55% to 60% EtOAc in hexane to afford 947 mg, 93% of product as a white foam. 1H NMR (CD3OD, Bruker AMX-500): d1.35 (ddd, 1H, J1=J2=J3=12.5 Hz, H2 eq), d2.19 (ddd, J1=12.5 Hz, 1H, J2=J3=4.5 Hz, H2 ax), d3.02 (dd, 1H, J1=10.5 Hz, J2=4 Hz, H2'), d3.27 (dd, 1H, J1=10 Hz, J2=9 Hz, H4'), d3.34–3.45 (m, 3H, H1, H3, H6'a), d3.46–3.54 (m, 1H, H5),d3.50 (dd, 1H, J1=13 Hz, J2=2.5 Hz, H6'b), d3.58 (dd, 1H, J1=11 Hz, J2=5.5 Hz, H5"a), d3.61–3.65 (m, 2H, H4, H6), d3.72 (dd, 1H, J1=11 Hz, J2=3 Hz, H5"b), d3.84 (dd, 1H, J1=10.5 Hz, J2=9 Hz, H3'), d3.98 (dddd, 1H, J1=12.5 Hz, J2=6 Hz, J3=J3=1.5 Hz, CH2CHCH2O), d4.01 (dd, 1H, J1=7 Hz, J2=4.5 Hz, H3"), d4.06–4.15 (m, 3H, H5', H4", CH2CHCH2O), d4.31 (dd, 1H, J1=4.5 Hz, J2=1 Hz, H2"), d4.57 (ABq, 2H, J=12 Hz, Dn=25.3 Hz, PhCH2O), d5.15 (ddd, J1=10.5 Hz, J2=J3=1.5 Hz, 1H, CH2CHCH2O), d5.27 (ddd, 1H, J1=17 Hz, J2=J3=1.5 Hz, CH2CHCH2O), d5.33 (d, 1H, J=1 Hz, H1"), d5.86–5.94 (m, 1H, CH2CHCH2O), d5.91 (d, 1H, J=4 Hz, H1'), d7.25–7.40 (m, 5H, C6H5); 13C NMR (CD3OD, 125 MHz): d 33.1, 52.6, 61.3, 61.8, 64.8, 71.6, 72.3, 72.4, 72.6, 73.1, 74.3, 74.5, 77.2, 77.4, 79.1, 81.4, 85.4, 97.9, 110.6, 117.8, 128.7, 129.0, 129.4, 135.9, 139.4; HRMS for C27H36N12O10 (M+Cs): calcd. 821.1732; found 821.1726.

Synthesis of 3"-O-allyl-6,3',4',3",5"-penta-O-benzyl-1,3,2',6'-tetraazido ribostamycin (900) as illustrated in FIG. 28. Compound 1900 (974 mg, 1.414 mmol) was dissolved in 20 mL of DMF and treated with 8 mL of BnBr. The solution was cooled using an ice bath and treated with sodium hydride (204 mg, 8.484 mmol) in one portion. The cooling bath was then removed and the reaction was stirred for one hour. AcOH was added to quench the NaH and the solvent was removed. The reaction was picked up in EtOAc and washed with water twice. The organic phases were combined and dried over MgSO4 and purified on 100 mL of silica gel using 10% to 12.5% to 15% EA/H to afford 1.24 g, 84% of product. 1H NMR (CDCl3, 500 MHz): d1.43 (ddd, 1H, J1=J2=J3=12.5 Hz, H2 eq), d2.26 (ddd, 1H, J1=12.5 Hz, J2=J3=4.5 Hz, H2 ax), d3.20–3.27 (m, 2H, H5, H2'), d3.30 (dd, 1H, J1=13.5 Hz, J2=5 Hz, H6'a), d3.35–3.45 (m, 3H, H1, H3, H4'), d3.30 (dd, 1H, J1=13.5 Hz, J2=2.5 Hz, H6'b), d3.58 (dd, 1H, J1=10.5 Hz, J2=4.5 Hz, H5"a), d3.60–3.72 (m, 3H, H4, H6, H5"b), d3.72–3.82 (m, 2H, CH2CHCH2O), d3.84 (dd, 1H, J1=J2=5.5 Hz, H3"), d3.92 (dd, 1H, J1=5 Hz, J2=3.5 Hz, H2"), d3.98 (dd, 1H, J1=10 Hz, J2=9 Hz, H3'), d4.15–4.22 (m, 2H, H4", H5'), d4.42–4.90 (m, 10 H, PhCH2O), d5.12 (ddd, J1=10.5 Hz, J2=J3=1.5 Hz, 1H, CH2CHCH2O), d5.12 (ddd, J1=17 Hz, J2=J3=1.5 Hz, 1H, CH2CHCH2O), d5.12 (d, 1H, J=3 Hz, H1"), d5.75–5.84 (m, 1H, CH2CHCH2O), d5.96 (d, 1H, J=3.5 Hz, H1'), d7.2–7.4 (m, 25 H, C6H5); 13C NMR (CDCl3, 125 MHz): d 32.2, 51.1, 59.6, 60.4, 63.5, 70.2, 70.9, 71.0, 72.3, 73.3, 74.9, 75.1, 75.5, 76.1, 78.5, 80.1, 80.5, 80.8, 81.2, 83.3, 96.0, 107.3, 116.8, 127.5, 127.8, 127.9, 128.1, 128.3, 128.4, 134.5, 137.4, 137.8, 138.0, 138.2; HRMS for C55H60N12O10 (M+Cs): calcd. 1181.3610; found 1181.3641.

Synthesis of 6,3',4',3",5"-penta-O-benzyl-1,3,2',6'-tetraazido ribostamycin (2000) as illustrated in FIG. 28. Bis(methyldiphenylphoshino)cyclooctadienyl IrI hexafluorophosphate (40 mg, 0.05 mmol) was suspended in THF (5 mL) and H2 was bubbled through this suspension for 20 minutes. The resulting clear solution was transferred via syringe into a solution of compound 9 (1.24 g., 1.18 mmol) in THF (15 mL). After 1 h., a quantitative conversion to a slightly less polar material was observed by TLC (25% EtOAc in hexane). The solvent was removed and the residue was co-rotary evaporated with CH2Cl2 several times. The reaction was then taken up in CH2Cl2 (30 mL) and treated with trimethylamine N-oxide dihydrate (197 mg, 1.77 mmol), and a solution of OsO4 in tBuOH (enough solution to deliver 3 mg of OsO4, 0.012 mmol). After the reaction was complete (overnight) the solvent was removed and the residue was purified over 100 mL of silica gel using 20% to 25% to 30% EtOAc in hexane to obtain 1.11 g, 93.3% of the title compound as a colorless oil. 1H NMR (CDCl3, 500 MHz): d1.45 (ddd, 1H, J1=J2=J3=12.5 Hz, H2 eq), d2.28 (ddd, J1=12.5 Hz, 1H, J2=J3=4.5 Hz, H2 ax), d2.35 (d, 1H, J=4 Hz, OH), d3.21 (dd, 1H, J1=10.5 Hz, J2=4 Hz, H2'), d3.25 (dd, 1H, J1=J2=9 Hz, H5), d3.21 (dd, 1H, J1=13 Hz, J2=5 Hz, H6'a), d3.35–3.44 (m, 3H, H1, H3, H4'), d3.47 (dd, 1H, J1=13 Hz, J2=2.5 Hz, H6'b), d3.57 (dd, 1H, J1=10.5 Hz, J2=4 Hz, H5"a), d3.61 (dd, 1H, J1=J2=9 Hz, H4 or H6), d3.65 (dd, 1H, J1=J2=9 Hz, H4 or H6), d3.72 (dd, 1H, J1=10.5 Hz, J2=3 Hz, H5'b), d3.92 (dd, 1H, J1=4 Hz, J2=3 Hz, H2"), d3.97 (dd, 1H, J1=10.5 Hz, J2=4 Hz, H3'), d4.00–4.06 (m, 2H, H3", H4"), d4.15–4.20 (m, 1H, H5'), d4.39 (ABq 2H, J=11.5, Dn=23.6 Hz, PhCH2O), d4.52 (d, 1H, J=12.5 Hz, PhCH2O), d4.60 (dd, 2H, J1=J2=11 Hz, PhCH2O), d4.76 (d, 1H, J=11 Hz, PhCH2O), d4.80–4.90 (m, 4H PhCH2O), d5.45 (d, 1H, J=3 Hz, H1'), d5.98 (d, 1H, J=4 Hz, H1'), d7.13–7.40 (m, 25H, C6H5); 13C NMR (CDCl3, 125 Mz): d 32.3, 51.1, 59.6, 60.6, 63.5, 70.5, 70.6, 70.9, 72.9, 73.3, 74.9, 75.37, 75.41, 76.0, 78.5, 80.1, 81.6, 82.2, 83.0, 83.5, 127.5, 127.6, 127.8, 128.0, 128.1, 128.4, 128.5, 137.1, 137.4, 137.76, 137.78, 138.1; HRMS for C52H56N12O10 (M+Cs): calcd. 1141.3297; found 1141.3267.

Figure 29:
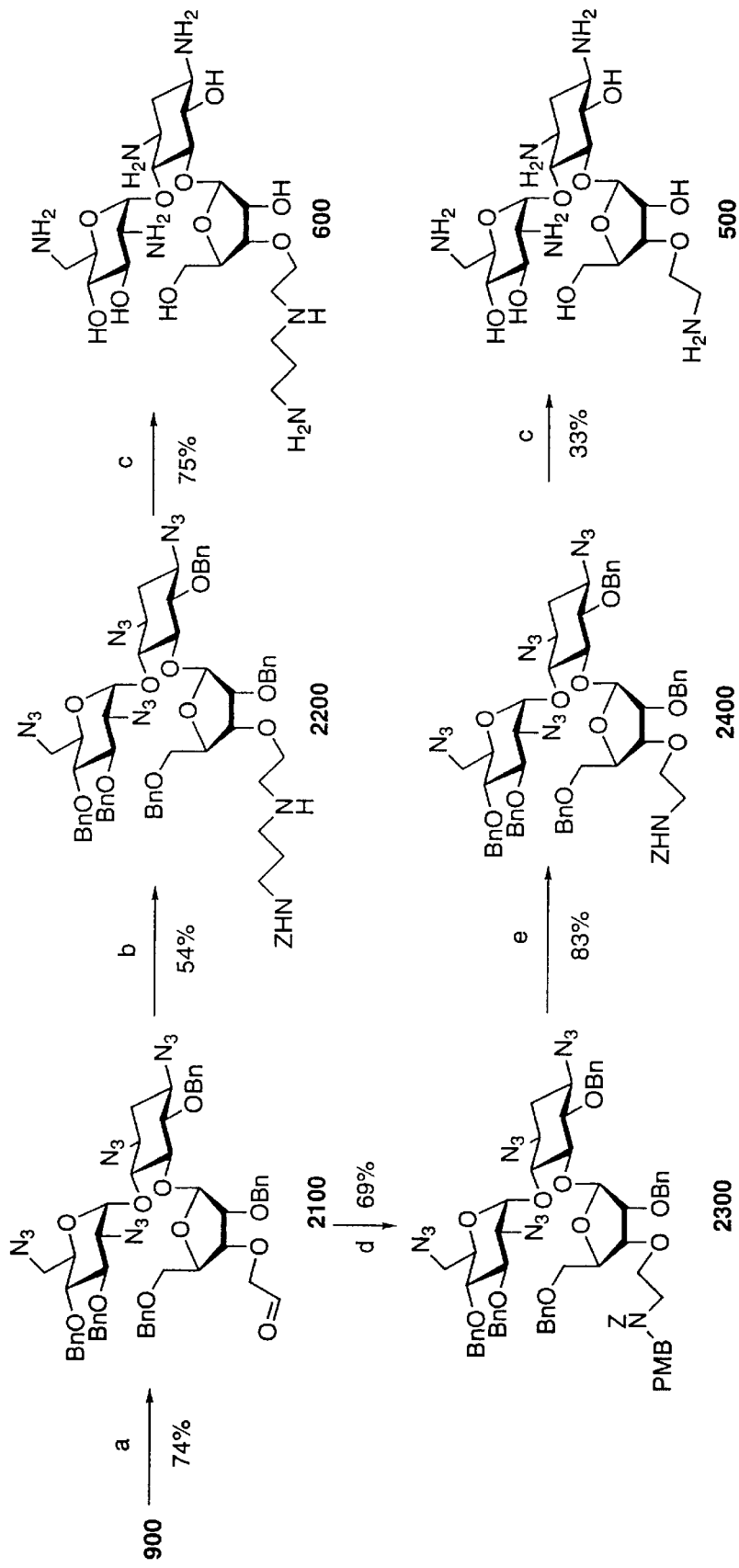
FIG. 29 illustrates the synthesis of compounds 500 with the following conditions:onditions: (a) i. O3, CH2Cl2, ii. DMS; (b) Mono Cbz propylene diamine, AcOH, pH 6, MeOH, NaBH3CN; (c) i. PMe3, THF, H2O, 1N NaOH, ii. Na, NH$_3$, THF, iii. Amberlite CG-50 cation exchange chromatography; (d) i. PMB-NH$_2$, AcOH, pH 6, MeOH, NaBH3CN, ii. ZOSu, CH2Cl2; (e) Acetonitrile:H2O (9:1), CAN.

Synthesis of 3"-O-(ethan-2-alo)-6,3',4',3",5"-penta-O-benzyl-1,3,2',6'-tetraazido ribostamycin (2100) as illustrated in FIG. 29. Compound 900 (112 mg, 107 mmol) was dissolved in CH2Cl2 (5 mL) and cooled to −78° C. Ozone was passed through the solution until the blue color persisted. Then DMS (66 mL, 1.07 mmol) was added to the reaction and the mixture was stirred at ambient temperature for 2 days. The solvent was removed and the residue was chromatographed over 50 mL of silica gel using a 25% to 30% to 35% to 40% gradient of EtOAc in hexane to afford 83 mg, 74% of the title compound as an oil. 1H NMR (CDCl3, 500 MHz): d1.44 (ddd, 1H, J1=J2=J3=12.5 Hz, H2 eq), d2.17 (ddd, 1H, J1=12.5 Hz, J2=J3=4.5 Hz, H2 ax), d3.19–3.25 (m, 2H, H5, H2'), d3.30 (dd, 1H, J1=11 Hz, J2=5 Hz, H6'a), d3 36–3.45 (m, 3H, H4', H1, H3), d3.48 (dd, 1H, J1=11 Hz, J2=2 Hz, H6'b), d3.59 (dd, 1H, J1=10 Hz, J2=4

Hz, H5" a), d3.62–3.78 (m, 5H, H4,H6, H5"b, OCH2CHO), d3.80 (dd, 1H, J1=J2=4.5 Hz, H3"), d3.92 (dd, 1H, J1=4.5 Hz, J2=3.5 Hz, H2"), d3.99 (dd, 1H, J1=9.5 Hz, J2=9 Hz, H3'), d4.15–4.22 (m, 2H, H4", H5'), d4.46–4.90 (m, 10H, PhCH2O), d5.58 (d, 1H, J1=3.5 Hz, H1"), d5.93 (d, 1H, J1=3.5 Hz, H1'), d7.23–7.37 (m, 25H, C6H5); 13C NMR (CDCl3, 125 MHz): d 32.3, 51.1, 59.6, 60.4, 63.5, 69.9, 71.0, 72.7, 73.4, 74.9, 75.0, 75.2, 75.5, 76.0, 78.5, 78.9, 80.0, 80.7, 80.8, 81.0, 83.4, 96.0, 106.7, 127.4, 127.6, 127.7, 127.8, 127.9, 128.1, 128.4, 137.5, 137.6, 137.7, 138.0, 200.4; MS: for C54H58N12O11 (M+Cs) : calcd. 1183; found 1183 (the peak was too weak for an exact match).

Synthesis of 3"-O-2-N-(3-N-Cbz-propylamino)-ethylamino-6,3',4',3",5"-penta-O-benzyl-1,3,2',6'-tetraazido ribostamycin (2200) as illustrated in FIG. 29. Compound 2100 (50 mg, 48 mmol) was suspended in MeOH (2 mL). A solution of mono-CBZ propylene diamine (81 mg, 389 mmol) was made up in MeOH (2 mL) and acidified with glacial acetic acid until pH 6 (pH paper). This solution was then added to the aldehyde mixture and to this was added THF until homogeneity was achieved. The reaction was treated with an excess of solid NaCNBH3 and the amination was complete in minutes. The reaction was diluted with ethyl acetate and extracted with 1 N NaOH twice. The organic phases were dried over MgSO4 and the solvent was removed. The residue was purified on 50 mL of silica gel using a gradient of 2% to 3% to 4% to 5% MeOH in CHCL3 to afford 32 mg, 54% of the title compound. 1H NMR (CDCl3, 500 MHz): d1.42 (ddd, 1H, J1=J2=J3=12.5 Hz, H2 eq), d1.45–1.53 (m, 2H, NHZCH2CH2CH2NH—), d2.24 (ddd, 1H, J1=12.5 Hz, J2=J3=4.5 Hz, H2 ax), d2. 50–2.58 (m, 2H, NHZCH2CH2CH2NH—), d2.55–2.66 (m, 2H, N—CH2CH2—O), d3.09–3.22 (m, 2H, NHZCH2CH2CH2NH—), d3.18–3.31 (m, 4H, H5, H2', N—CH2CH2—O), d3.30 (dd, 1H, J1=13.5 Hz, J2=5.5 Hz, H6'a), d3.34–3.42 (m, 2H, H1, H3), d3.41 (dd, 1H, J1=J2= 9.5 Hz, H4'), d3.48 (dd, 1H, J1=13.5 Hz, J2=2.5 Hz, H6'b), d3.56 (dd, 1H, J1=10.5 Hz, J2=4 Hz, H5"a), d3.59–3.69 (m, 3H, H4, H6, H5"b), d3.78 (dd, 1H, J1=J2=5 Hz, H3"), d3.93 (dd, 1H, J1=5 Hz, J2=3.5 Hz, H2"), d3.98 (dd, 1H, J1=J2= 9.5 Hz, H3'), d4.12–4.21 (m, 2H, H5', H4"), d4.42–4.55 (m, 3H, PhCH2O), d4.56–4.63 (m, 2H, PhCH2O), d4.73–4.90 (m, 5H, PhCH2O), d5.05–5.10 (m, 2H, PhCH2O), d5.45–5.50 (m, 1H, NHZCH2CH2CH2NH—), d5.55 (d, 1H, J=3.5 Hz, H1"), d5.95 (d, 1H, J=3.5 Hz, H1'), d7.23–7.37 (m, 30 H, C6H5); 13C NMR (CDCl3, 125 MHz): d 29.1, 29.7, 32.2, 39.9, 47.5, 49.1, 51.1, 59.6, 60.4, 63.5, 6.4, 69.1, 70.3, 70.9, 72.3, 73.3, 74.9, 75.0, 75.4, 76.2, 78.1, 78.5, 80.1, 80.4, 80.8, 81.1, 83.3, 96.0, 107.1, 127.5, 127.6, 127.7, 127.9, 128.1, 128.3, 128.4, 128.5, 136.8, 137.6, 137.60, 137.83, 138.1, 156.4; HRMS: for C65H74N14O12 (M+Cs): calcd. 1375.4665; found 1375.4709.

Synthesis of 3"-O-2-N-(3-propylamino)-ethylamino ribostamycin (600)as illustrated in FIG. 29. Compound 2200 (45 mg, 36 mmol) was dissolved in THF (5 mL) and treated with H2O (500 mL) and 1 N NaOH (50 mL). A solution of PMe3 in THF (159 mL of a 1 N solution) was added and the reaction was allowed to stir for 10 h. The reaction mixture was then loaded onto a 50 mL column of silica gel and eluted with a gradient of 0% to 2.5% to 5% to 10% conc. NH3 in MeOH. The product fractions were pooled and coevaporated with THF (3 times). THF (7 mL) was added via syring to a dry 3 neck flask equipped with a Dewar condenser. Then ammonia (~20 mL) was condensed into the reaction vessel. A chunk of Na (93 mg, 4 mmol) was then allowed to dissolve in the ammonia for 15 min. Then a solution of the polyamine in a mixture of EtOH and THF (500 mL each) was added in one portion and washed down with THF. The reaction was stirred until the blue color was discharged. Then an aqueous solution of ammonium fomate (235 mg, 3.7 mmol) was added and the ammonia was allowed to evaporate overnight. The remaining solvent was removed in vacuo and the residue was loaded onto a column of Amberlite CG-50 cation exchange resin (0.5 cm×7 cm) in its NH4+ form and eluted with a linear gradient of 0% to 7.5 % NH3 in H2O (100 mL of each in a gradient maker). After lyophilization, neutralization and relyophilization, 21.5 mg, 75% of 6◇6 HCl salt was obtained. 1H NMR (D2O, pD 2 with Cl— as counterinon, 500 MHz): d1.95 (ddd, 1H, J1=J2=J3=12.6 Hz, H2 eq), d2.09–2.17 (m, 2H, NH2CH2CH2CH2NH—), d2.53 (ddd, 1H, J1=12.6 Hz, J2=J3=4.1 Hz, H2 ax), d3.13 (dd, 2H, J1=J2=7.9 Hz, NH2CH2CH2CH2NH—), d3.23 (dd, 2H, J1=J2=8.0 Hz, NH2CH2CH2CH2NH—), d3.33 (dd, 1H, J1=13.2 Hz, J2=6.4 Hz, H6'a), d3.32–3.39 (m, 2H, N—CH2CH2—O), d3.40 (ddd, 1H, J1=12.6 Hz, J2=10.6 Hz, J3=4.1 Hz, H1), d3.44–3.52 (m, 2H, H2', H6'b), d3.52 (dd, 1H, J1=J2=9.5 Hz, H4'), d3.60 (ddd, 1H, J1=12.6 Hz, J2=10.4 Hz, J3=4.1 Hz, H3), d3.72–3.78(m, 2H, H6, H5"a), d3.88–4.01 (m, 5H, N—CH2CH2—O, H5"b, H5', H5), d4.04 (dd, 1H, J1=10.9 Hz, J2=9.5 Hz, H3'), d4.11 (dd, 1H, J1=7.2 Hz, J2=4.6 Hz, H3"), d4.18 (dd, 1H, J1=10.4 Hz, J2=9.9 Hz, H4), d4.18–4.21 (m, 1H, H4"), d4.48 (dd, 1H, J1=4.6 Hz, J2=1.7 Hz, H2"), d5.45 (d, 1H, J=1.6 Hz, H1"), d6.06 (d, 1H, J=3.9 Hz, H1'); 13C NMR (CDCl3, 500 MHz): d 25.1 (NH2CH2CH2CH2NH—), 29.5 (C2), 38.0 (NH2CH2CH2CH2NH—), 41.5 (C6'), 46.0 (NH2CH2CH2CH2NH—), 48.8 (N—CH2CH2—O), 49.9 (C3), 51.3 (C1), 55.0 (C2'), 62.3 (C5"), 66.5 (N—CH2CH2—O), 69.5 (C3'), 70.9 (C5'), 72.0 (C4'), 74.0 (C6), 76.9 (C4), 78.4 (C3"), 82.6 (C4"), 86.2 (C5), 97.1 (C1'), 112.0 (C1"); MS: for C22H46N6O10 (M+H): calcd. 555; found 555, for C23H45N5O14 (M-H): calcd. 553; found 553.

Synthesis of 3"-O-2-N-(paramethoxybenzyl, Cbz)-ethylamino-6,3',4',3",5"-penta-O-benzyl-1,3,2',6'-tetraazido ribostamycin (2300)as illustrated in FIG. 29. Compound 2100 (76 mg, 72 mmol) was suspended in MeOH (2 mL). A solution of para-methoxybenzylamine (99 mg, 720 mmol) was made up in MeOH (2 mL) and acidified with glacial acetic acid until pH 6 (pH paper). This solution was then added to the aldehyde mixture and to this was added THF until homogeneity was achieved. The reaction was treated with an excess of solid NaCNBH3 and the amination was over in a matter of minutes. The reaction was diluted with ethyl acetate and extracted with 1 N NaOH twice. The organic phases were dried over MgSO4 and the solvent was removed. The residue was purified on 50 mL of silica gel using a gradient of 2% to 3% to 4% to 5% MeOH in CHCL3. The resulting amine was then dissolved in CH2Cl2 and treated with ZOSu (22 mg, 86 mmol). The reaction mixture was then directly chromatographed on 50 mL of silica gel using a gradient of 5% to 10% to 15% Ethyl Acetate in Hexane to afford 65 mg, 69% of the title compound. 1H NMR (CDCl3, 500 MHz): d1.43 (ddd, 1H, J1=J2=J3=12.5 Hz, H2 eq), d2.25 (ddd, 1H, J1=12.5 Hz, J2=J3=4.5 Hz, H2 ax), d3.22 (dd, 1H, J1=10.5 Hz, J2=4 Hz, H2'), d3.16–3.35 (m, 4H, N—CH2CH2—O), d3.30 (dd, 1H, J1=13.5 Hz, J2=5.5 Hz, H6'a), d3.30–3.44 (m, 3 H, H1, H3, H4'), d3.47 (dd, 1H, J1=13.5 Hz, J2=2.5 Hz, H6'b), d3.45–3.55 (m, 1H, H5"a), d3.58–3.61 (m, 3H, H4, H6, H5"b), d3.62–3.71 (m, 4H, OMe, H3"), d3.83–3.93 (m, 1H, H2"), d3.97 (dd, 1H, J1=10.5 Hz, J2=9 Hz, H3'), d4.03–4.15 (m, 1H, H4"), d4.15–4.21 (m, 1H, H5'), d4.32–4.52 (m, 5H, PhCH2O), d4.59 (d, J=12 Hz, 2H, PhCH2O), d4.71–4.89 (m, 5H, PhCH2O), d5.14 (s, 2H, PhCH2O), d5. 48–5.52 (m, 1H, H1"), d5. 92–5.98 (m, 1H, H1'), d6.76 (dd, J1=17.5 Hz, J2=8 Hz, C6H4OMe), d7.04 (dd, J1=61 Hz, J2=8 Hz, 2H, C6H4OMe), d7.14–7.37 (m, 30 H, C6H5); 13C NMR (CDCl3, Bruker 125 MHz): d 32.2, 45.6, 46.5, 50.78, 50.82, 51.1, 55.2, 59.6, 60.5, 63.5, 67.2, 68.8, 70.2, 70.3, 70.9, 72.36, 72.39, 73.3, 74.9, 75.06, 75.10, 75.4, 76.11, 76.15, 78.3, 78.5, 80.1, 80.6, 80.78, 80.84, 81.2, 81.4, 83.3, 96.0, 107.4, 107.5, 113.8, 127.5, 127.6, 127.7, 127.8, 127.9, 128.0, 128.3, 128.4, 128.7, 129.4, 129.8, 137.5, 137.8, 138.1; HRMS: for C70H75N13O13 (M+Cs): calcd. 1438.4662; found 1438.4597.

Synthesis of 3"-O-2-N-Cbz-ethylamino-6,3',4',3',5"-penta-O-benzyl-1,3,2',6'-tetraazido ribostamycin (2400) as illustrated in FIG. 29. Compound 2300 (65 mg, 50 mmol) was dissolved in a mixture of acetonitrile and water (9:1, 4 mL) and treated with CAN (136 mg, 249 mmol). After 4.5 h., the reaction was quenched by addition of a 1 N solution of Na2S2O4. The aqueous layer was extracted twice with ethyl acetate and the pooled organic phases were dried over MgSO4. Chromatography of the residue over 40 mL of silica gel using a gradient of 15% to 20% to 25% to 30% ethyl acetate in hexane afforded 49 mg, 83% of product. 1H NMR (CDCl3, 500 MHz): d1.42 (ddd, 1H, J1=J2=J3=12.5 Hz, H2 eq), d2.26 (ddd, 1H, J1=12.5 Hz, J2=J3=4.5 Hz, H2 ax), d3.05–3.27 (m, 6H, H5, H2', NHZCH2CH2—O), d3.31 (dd, 1H, J1=13.5 Hz, J2=5 Hz, H6'a), d3.34–3.43 (m, 2H, H1, H3), d3.42 (dd, 1H, J1=J2=9.5 Hz, H4'), d3.48 (dd, 1H, J1=13.5 Hz, J2=2.5 Hz, H6'b), d3.54 (dd, 1H, J1=10.5 Hz, J2=4 Hz, H5"a), d3.56–3.66 (m, 3H, H4, H6, H5"b), d3.71 (dd, 1H, J1=J2=5 Hz, H3"), d3.89 (dd, 1H, J1=5 Hz, J2=3 Hz, H2"), d3.97 (dd, J1=10 Hz, J2=9.5 Hz, 1H, H3'), d4.07–4.12 (m, 1H, H4"), d4.17–4.22 (m, 1H, H5'), d4.42–4.53 (m, 3H, PhCH2O), d4.59 (d, J=12 Hz, 2H, PhCH2O), d4.73–4.89 (m, 5H, PhCH2O), d5.06 (s, 2H, PhCH2O), d5.13–5.18 (m, 1H, NHZCH2CH2—O), d5.52 (d, 1H, J=3 Hz, H1"), d5.91 (d, 1H, J=3.5 Hz, H1'), d7.10–7.7.45 (m, 30H, C6H5); 13C NMR (CDCl3, 125 MHz): d 29.7, 32.3, 40.9, 51.1, 59.5, 60.4, 63.5, 66.6, 68.9, 70.2, 70.9, 72.4, 73.3, 74.9, 75.0, 75.5, 76.2, 78.3, 78.5, 80.1, 80.2, 80.7, 81.0, 83.3, 96.0, 107.1, 127.3, 127.6, 127.7, 127.8, 127.9, 128.0, 128.1, 128.3, 128.4, 136.5, 137.5, 137.6, 137.7, 138.0, 156.3; HRMS: for C62H67N13O12 (M+Cs): calcd. 1318.4086; found 1318.4032.

Synthesis of 3"-O-Ethyl-2-amino ribostamycin (500) as illustrated in FIG. 29. The deprotection was carried out starting with compound 2400 in the exact manner as the preparation of compound 600 to afford the title substance in 33% yield. It should be noted that this is a result from a single experiment where there was a problem with the reduction of the azides and a better yield can probably be obtained. 1H NMR (D2O, pD 2 adjusted with DCl, 500 MHz): d1.41 (ddd, 1H, J1=J2=J3=12.6 Hz, H2 eq), d2.24 (ddd, 1H, J1=12.6 Hz, J2=J3=4.1 Hz, H2 ax), d3.26 (dd, 2H, J1=J2=4.9 Hz, NH2CH2CH2—O), d3.32 (dd, 1H, J1=13.6 Hz, J2=6.4 Hz, H6'a), d3.41 (ddd, 1H, J1=12.6 Hz, J2=10.7 Hz, J3=4.1 Hz, H1), d3.44–3.52 (m, 2H, H2', H6'b), d3.51 (dd, 1H, J1=J2=9.3 Hz, H4'), d3.60 (ddd, 1H, J1=12.6 Hz, J2=10.5 Hz, J3=4.1 Hz, H3), d3.71–3.78 (m, 2H, H5"a, H6), d3.83–3.92 (m, 2H, NH2CH2CH2—O), d3.93 (dd, 1H, J1=12.6 Hz, J2=2.8 Hz, H5"b), d3.93–4.00 (m, 1H, H5'), d3.98 (dd, 1H, J1=J2=10.1 Hz, H5), d4.03 (dd, 1H, J1=10.8 Hz, J2=9.3 Hz, H3'), d4.10 (dd, 1H, J1=7.2 Hz, J2=4.5 Hz, H3"), d4.13–4.20 (m, 2H, H4, H4"), d4.46 (dd, 1H, J1=4.5 Hz, J2=1.4 Hz Hz, H2"), d5.44 (dd, 1H, J1=1.4 Hz, H1"), d6.05 (dd, 1H, J1=4 Hz, H1'); 13C NMR (CDCl3, 125 MHz): d 29.5 (C2), 40.8 (NH2CH2CH2—O), 41.5 (C6'), 49.9 (C3), 51.3 (C1), 55.0 (C2'), 62.2 (C5"), 67.5 (NH2CH2CH2—O), 69.5 (C3'), 70.9 (C5'), 72.0 (C4'), 74.0 (C6), 74.9 (C2"), 76.8 (C4), 78.3 (C3"), 82.7 (C4"), 86.2 (C5), 97.1 (C1'), 112.0 (C1"); MS: for C19H39N5O10 (M+H): calcd. 498; found 498, for C19H39N5O10 (M—H): calcd. 496; found 496.

Synthesis of 1,6-Anhydro-2,3,4-Tri-O-benzyl idopyranoside (2800) as illustrated in FIG. 30. α-O-Methyl-2,3,4-O-benzyl, 5,6-anhydro glucopyranoside (2500) (5.62 g, 12.098 mmol) was dissolved in THF (20 mL) and cooled in an ice/water bath. The reaction was then treated with a 1M solution of BH3.THF in THF (50.9 mL, 50.9 mmol). The hydroboration was complete after an hour and the reaction mixture was then slowly dripped into a cooled flask containing concentrated HOOH (18.1 mL) in 1 N NaOH (181 mL). The aqueous layer was extracted 3 times with EtOAc and the organic phases were back extracted with water. The EtOAc solution was dried over MgSO4 and the solvent was removed. The residue was dissolved in 50 mL of AcOH and treated with 10 drops of 12 N HCl. The reaction was warmed to 70° C. and allowed to proceed for 1 hr, after which time the solvent was removed and the residue was purified by column chromatography over 200 mL of silica gel using 10% to 12.5% to 15% EtOAc in hexane to obtain 2.74 g, 51% or 80% per step of the product as an oil which solidifies upon standing under vacuum. 2,3,4-Tri-O-benzyl-a-methyl glucopyranoside (2800). H1 NMR (CDCl3, 500 MHz): d1.63 (dd, 1H, J1=7.5 Hz, J2=5.5 Hz, OH), d3.36 (s, 3H, OCH3), d3.50 (dd, 1H, J1=9.5 Hz, J2=3.5 Hz, H2), d3.52 (dd, 1H, J1=J2=9.5 Hz, H4), d3.62–3.67, (m, 1H, H6a), d3.67–3.72, (m, 1H, H5), d3.74–3.79, (m, 1H, H6b), d4.01 (dd, 1H, J1=J2=9.5 Hz, H3), d4.56 (d, 1H, J=3.5 Hz, H1), d4.65 (dd, 1H, J1=J2=12 Hz, PhCH2O), d4.85 (dd, 1H, J1=J2=11.5 Hz, PhCH2O), d4.92 (ABq, 2H, J=11 Hz, Dn=49.3 Hz, PhCH2O), d7.25–7.40, (m, 15H, C6H5); 13C NMR (CDCl3, 125 MHz): d 55.2, 61.8, 70.6, 73.4, 75.0, 75.8, 79.9, 81.9, 98.1, 127.6, 127.9, 128.0, 128.1, 128.4, 128.5, 138.1, 138.7; HRMS for C28H32O6 (M+Cs): calcd. 597.1253; found 597.1265. 2,3,4-Tri-O-benzyl-b-methyl idopyranioside (27). H1 NMR (CDCl3, 500 MHz): d2.74 (dd, 1H, J1=9 Hz, J2=5 Hz, OH), d3.48 (dd, 1H, J1=8 Hz, J2=3 Hz, H2), d3.48 (s, 3H, OCH3), d3.64 (dd, 1H, J1=8 Hz, J2=5.5 Hz, H4), d3.80–3.87, (m, 1H, H6a), d3.88–3.94, (m, 1H, H6b), d3.97 (ddd, 1H, J1=J2=J3=5.5 Hz, H5), d4.05 (dd, 1H, J1=J2=8 Hz, H3), d4.53 (d, 1H, J=3 Hz, H1), d4.54–4.83, (m, 6H, PhCH2O), d7.25–7.40, (m, 15H, C6H5); 13C NMR (CDCl3, 125 MHz): d 56.9, 63.1, 73.7, 73.8, 74.9, 75.0, 76.9, 77.8, 78.2, 99.9, 127.8, 127.9, 128.0, 128.1, 128.4, 128.5, 137.7, 138.2, 138.3; HRMS for C28H32O6 (M+Na): calcd. 465.2277; found 487.2108. 1,6-Anhydro-2,3,4-Tri-O-benzyl idopyranoside (28) H1 NMR (CDCl3, 500 MHz): d3.48 (dd, 1H, J1=8 Hz, J2=1.5 Hz, H2), d3.66–3.75, (m, 2H, H4, H6a), d3.78 (dd, 1H, J1=J2=8 Hz, H3), d4.13 (d, 1H, J=8 Hz, H6b), d4.39 (dd, 1H, J1=J2=4.5 Hz, H5), d4.60–4.88, (m, 6H, PhCH2O), d5.30 (d, 1H, J=1.5 Hz, H1), d7.25–7.40, (m, 15H, C6H5); 13C NMR (CDCl3, 125 MHz): d 65.5, 73.0, 73.1, 73.2, 75.5, 79.3, 81.8, 82.4, 99.6, 127.6, 127.7, 127.9, 128.0, 128.3, 128.4, 128.5, 137.9, 138.0, 138.6; HRMS for C27H28O5 (M+Cs): calcd. 565.0991; found 565.1015.

Synthesis of 2,3,4-Tri-O-benzyl-1-deoxy-1-b-thiomethyl idopyranoside (3000) as illustrated in FIG. 30. Compound 2800 (1.31 g, 2,820 mmol) was dissolved in 15 mL of CH2Cl2 and treated with (methylthio)trimethylsilane (1.07 g, 8.460 mmol) and trimethylsilyl trifluoromethanesulfonate (1.25 g, 5.640 mmol) and stirred for 40 h. The reaction was then quenched by addition of an excess of triethylamine and was subsequently treated with a 1M solution of TBAF in THF (15 mL). After the desilylation was complete, the reaction was diluted with EtOAc and extracted 3 times with 1 N NaOH and once with water. The EtOAc solution was dried over MgSO4 and the solvent was removed. The residue was purified by column chromatography over 100 mL of silica gel using 30% to 35% to 40% to 45% EtOAc in hexane to obtain the α anomer first (70 mg, 5%) and then the β anomer (1.20 g, 88.5%). 2,3,4-Tri-O-benzyl-1-deoxy-1-a-thiomethyl idopyranioside (2900) H1 NMR (CDCl3, 500 MHz): d2.17 (s, 3H, SCH3), d3.51 (dd, 1H, J1=J2=4.5 Hz, H2), d3.55 (dd, 1H, J1=J2=4.5 Hz, H3), d3.71 (dd, 1H, J1=12 Hz, J2=4.5 Hz, H6a), d3.76 (dd, 1H, J1=J2=4.5 Hz, H3), d3.94 (dd, 1H, J1=12 Hz, J2=7 Hz, H6b), d4.30–4.35, (m, 1H, H5), d4.40–4.78, (m, 6H, PhCH2O), d5.13 (d, 1HJ=4 Hz, H1), d7.20–7.40, (m, 15H, C6H5); 13C NMR (CDCl3, 125 MHz): d 14.3, 62.0, 69.6, 72.6, 73.2, 75.4, 75.7, 77.1, 83.6, 127.8, 127.9, 128.1, 128.2, 128.4, 128.5, 137.6, 137.7, 137.8. 2,3,4-Tri-O-benzyl-1-deoxy-1-b-thiomethyl idopyranioside (30) H1 NMR (CDCl3, 500 MHz): d1.89 (dd, 1H, J1=9.5 Hz, J2=3.5 Hz, OH), d2.24 (s, 3H, SCH3), d3.25–3.27 (m, 1H, H4), d3.51–3.57 (m, 2H, H2, H6a), d3.66 (dd, 1H, J1=J2=3 Hz, H3), d3.83 (ddd, 1H, J1=8 Hz, J2=4 Hz, J3=2 Hz, H6b), d4.00 (ddd, 1H, J1=11.5 Hz, J2=8 Hz, J3=3.5 Hz, H5), d4.22–4.39 (m, 3H, PhCH2O), d4.55–4.64 (m, 3H, PhCH2O), d4.79 (d, 1H, J=1.5 Hz, H1), d7.14–7.38, (m, 15H, C6H5); 13C NMR (CDCl3, 125 MHz): d 14.7, 62.7, 70.7, 71.7, 71.8, 72.1, 73.2, 75.3, 77.2, 85.1, 127.8, 127.9, 128.0, 128.1, 128.3, 128.4, 128.5, 137.4, 137.6, 137.7; HRMS for C28H32O5S (M+Cs): calcd. 613.1025; found 613.1051.

2,3,4-Tri-O-benzyl-1-deoxy-1-b-thiomethyl-6-deoxy-6-allyloxy idopyranoside (3100) as illustrated in FIG. 30. Compound 3000 (245 mg, 510 mmol) was dissolved in 3 mL of DMF and treated with NaH (24 mg, 1.02 mmol) followed by allyl bromide (185 mg, 1.53 mmol). After stirring overnight, the reaction was quenced by addition of MeOH and the solvent was removed in vacuo. The resulting residue was partitioned between EtOAc and H2O. The organic phases were then dried over MgSO4 and the solvent was removed. Chromatography over 50 mL of silica gel using a gradient of 15% to 20% to 25% EtOAc in hexane afforded 160 mg, 60% of the title compound. H1 NMR (CDCl3, 500 MHz): d 2.22 (s, 3H, SCH3), d3.34–3.47 (m, 1H, H4), d3.45–3.48 (m, 1H, H2), d3.60–3.65 (m, 2H, H3, H6a), d3.71 (dd, 1H, J1=10 Hz, J2=6 Hz, H6b), d3.92–3.97 (m, 2H, H3, CH2CHCH2O), d3.99–4.05 (m, 1H, CH2CHCH2O), d4.28 (s, 2H, PhCH2O), d4.31 (ABq, 2H, J=12 Hz, Dn=49.7 Hz, PhCH2O), d4.51–4.58 (m, 2H, PhCH2O), d4.77 (d, 1H, J=1.5 Hz, H1), d5.12–5.28 (m, 2H CH2CHCH2O), d5.82–5.92 (m, 1H, CH2CHCH2O), d7.05–7.38 (m, 15H, C6H5); 13C NMR (CDCl3, Bruker AMX-500): d 14.5, 69.5, 71.0, 71.8, 71.9, 72.1, 72.3, 73.0, 75.1, 76.2, 84.9, 116.8, 127.7, 127.8, 127.9, 128.2, 128.4, 128.5, 134.8, 137.8, 138.0, 138.1; HRMS for C31H36O5S (M+Cs): calcd. 653.1338; found 653.1366.

Synthesis of 2,3,4-Tri-O-benzyl-1-deoxy-1-b-thiomethyl-6-deoxy-6-allylamino idopyranoside (3200) as illustrated in FIG. 30. DMSO (1.3 g, 3.39 mmol) was dissolved in CH2Cl2 (20 mL) and cooled to −78° C. The reaction was treated with 2 M oxalyl chloride in CH2Cl2 (2.21 mL, 4.42 mmol) and the reaction was allowed to stir for 15 min. Then, a solution of compound 3000 (1.63 g, 3.39 mmol) in CH2Cl2 (10 mL) was added dropwise via syringe. The reaction was allowed to proceed at −78° C. for 45 min. then triethylamine (1.72 g, 16.96 mmol) was added and the reaction was allowed to warm up to room temperature. The reaction was diluted with EtOAc and extracted twice with water. The organic phases were dried over MgSO4 and the solvent was removed. The residue was dissolved in methanol (15 mL). A solution of allylamine (1.94 g, 33.9 mmol) was neutralized to pH 6 (pH paper) using glacial acetic acid and this solution was added to the solution of the aldehyde. The reaction was then treated with NaCNBH3 (213 mg, 3.4 mmol). The transformation was complete within 15 minutes. The solvent was removed and the reaction was taken up in EtOAc. The organic phases were dried over MgSO4 and the solvent was removed. The residue was purified by column chromatography over 100 mL of silica gel using 5% to 6% to 7% MeOH in CHCL3 to obtain 1.20 g, 68%. of the title compound as an oil. H1 NMR (CDCl3, 500 MHz): d 2.23 (s, 3H, SCH3), d2.53 (dd, 1H, J1=12.5 Hz, J2=3.5 Hz, H6a), d3.16 (dd, 1H, J1=12.5 Hz, J2=9 Hz, H6b), d3.18–3.26 (m, 3H, H4 and CH2CHCH2O), d3.49–3.51 (m, 1H, H2), d3.66 (dd, 1H, J1=J2=3 Hz, H3), d3.87–3.92 (m, 1H, H5), d4.26–4.61 (m, 6H, PhCH2O), d4.78 (d, 1H, J=1.5 Hz, H1), d5.03–5.17 (m, 2H, CH2CHCH2O), d5.78–5.88 (m, 1H, CH2CHCH2O), d7.14–7.38, (m, 15H, C6H5); 13C NMR (CDCl3, 125 MHz): d 14.7, 49.6, 52.2, 70.8, 71.8, 72.0, 72.6, 73.2, 75.3, 75.9, 85.2, 116.2, 127.7, 127.8, 128.0, 128.3, 128.4, 128.5, 136.5, 137.5, 137.9; HRMS for C31H37NO4S (M+Na): calcd. 542.2341; found 542.2353.

Synthesis of 2,3,4-Tri-O-benzyl-1-deoxy-1-b-thiomethyl-6-deoxy-6-carbobenzyloxyamido idopyranoside (3300). Compound 3200 (894 mg, 1.72 mmol) was dissolved in a mixture of acetonitrile and water (84/16) and brought to reflux. A system was set up such that the solvent in the pot was continuously being distilled off while fresh acetonitrile/water mixture was added to replace the distillate. A suspension of Wilkinson's catalyst (300 mg, 1.720 mmol) in the acetonitrile/water mixture was added and the reaction was allowed to reflux vigorously. The reaction was complete in 2 h and the solvent was removed. The residue was dissolved in CH2Cl2 and cooled with an ice bath. The reaction was then treated with a solution of N-benzyloxycarbonyloxy succinimide (536 mg, 2.15 mmol) in CH2Cl2 (5 mL). The reaction was complete within 15 minutes. The solvent was removed and the residue was chromatographed over 100 mL of silica gel using 17.5% to 20% to 22.5% to 25% EtOAc in hexane to afford 706 mg, 67% of the title compound as a colorless oil. H1 NMR (CDCl3, 500 MHz): d 2.20 (s, 3H, SCH3), d3.20–3.23 (m, 1H, H4), d3.34–3.41 (m, 1H, H6a), d3.44–3.52 (m, 2H, H6b, H2), d3.64 (dd, 1H, J1=J2=2.5 Hz, H3), d3.79–3.84 (m, 1H, H5), d4.20–4.36 (m, 3H, benzillic protons), d4.52–4.61 (m, 3H, PhCH2O), d4.74 (s, 1H, H1), d4.86–4.91 (m, 1H, CH2—NHZ), d5.02–5.1 (m, 2H, PhCH2O), d7.13–7.20 (m, 4H, C6H5), d7.26–7.37, (m, 16H, C6H5); 13C NMR (CDCl3, 125 MHz): d 14.6, 41.8, 66.6, 70.4, 71.7, 71.8, 72.0, 73.2, 75.1, 75.3, 85.0, 127.9, 128.0, 128.3, 128.4, 128.5, 136.6, 137.3, 137.5, 137.8, 156.4; HRMS for C36H39NO6S (M+Cs): calcd. 746.1552; found 746.1568.

Synthesis of Compound 34 as illustrated in FIG. 31. Compound 2000 (69.4 mg, 69 mmol) and 31 (97 mg, 186 mmol) were mixed and dried overnight over P2O5. Then CH2Cl2 (5mL) was added via syringe. The reaction was cooled to −10° C. using an ice/salt bath and NIS (46 mg, 20 mmol) was added. The reaction was allowed to stir for 15 min. and then a catalytic amount of AgOTf (∼2 mg) was added. The reaction assumed a purple color and was allowed to proceed for 45 min before quenching with triethylamine. The reaction was then filtered through a pad of celite and the solvent was removed. Chromatography of the residue over 50 mL of silica gel using a gradient of 10% to 15% to 20 % to 25% ethyl acetate in hexane afforded 50 mg, 49% of the desired product. 1H NMR (CDCl3, 500 MHz): d1.42 (ddd, 1H, J1=J2=J3=12.5 Hz, H2 eq), d2.24 (ddd, 1H, J1=12.5 Hz, J2=J3=4.5 Hz, H2 ax), d3.10 (dd, 1H, J1=10.5 Hz, J2=4 Hz), d3.22–3.32 (m, 4H), d3.36–3.48 (m, 4H), d3.10 (dd, 1H, J1=10 Hz, J2=5.5 Hz), d3.59 (dd, 1H, J1=J2=3.5 Hz), d3.61–3.67 (m, 2H), d3.83 (dd, 1H, J1=10.5 Hz, J2=2 Hz), d3.84–3.97 (m, 5H), d4.00 (dd, 1H, J1=J2=9.5 Hz), d4.10–4.25 (m, 4 H), d4.34–4.61 (m, 10H), d4.67–4.75 (m, 3H), d4.76–4.89 (m, 3H), d4.93 (d, 1H, J=11 Hz), d5.11–5.16 (m, 1H), d5.19–5.27 (m, 1H), d5.55 (d, J=4.5 Hz, 1H, H1"), d5.79–5.89 (m, 1H), d6.14 (d, 1H, J=4 Hz, H1'), d7.02–7.37 (m, 40H); 13C NMR (CDCl3, 125 MHz): d 32.4, 51.2, 59.8, 60.4, 63.2, 69.4, 70.2, 70.8, 71.9, 72.1, 72.2, 72.4, 72.6, 73.2, 73.9, 74.0, 74.1, 74.8, 75.2, 75.3, 75.4, 76.5, 78.5, 80.1, 81.8, 82.0, 82.3, 83.9, 95.6, 100.5, 107.0, 116.9, 127.3, 127.4, 127.5, 127.6, 127.7, 127.8, 128.0, 128.1, 128.2, 128.4, 128.5, 134.8, 137.6, 137.7, 137.82, 137.84, 138.0, 138.4, 138.8; HRMS: for C82H89N12O15 (M+Cs): calcd. 1614.5625; found 1614.5539.

Synthesis of compound 3500 as illustrated in FIG. 31. Bis(methyldiphenylphoshino)cyclooctadienyl IrI hexafluorophosphate (5 mg, 6 mmol) was suspended in THF (5 mL) and H2 was bubbled through this suspension for 20 minutes. The resulting crear solution was transferred via syringe into a solution of compound 3400 (50 mg., 34 mmol) in THF (15 mL). After 1 hr, a quantitative conversion to a slightly less polar material was observed. The solvent was removed and the residue was co-evaporated with CH2Cl2 several times. The reaction was then taken up in CH2Cl2 (30 mL) and treated with trimethylamine N-oxide dihydrate (19 mg, 0.17 mmol), and a solution of OsO4 in tBuOH (20 mL of the 2.5 wt. % commercial preparation). After the reaction was over (overnight) the solvent was removed and the residue was purified over 50 mL of silica gel using 15% to 20% to 25% to 30% EtOAc in hexane to obtain 41 mg, 84% of the title compound. 1H NMR (CDCl3, 500 MHz): d1.41 (ddd, 1H, J1=J2=J3=16 Hz, H2 eq), d2.24 (ddd, 1H, J1=16 Hz, J2=J3= 5.5 Hz, H2 ax), d2.70–2.82 (m, 1H, OH), d3.15–3.23 m, 2H), d3.25–3.43 (m, 6H), d3.47 (dd, 1H, J1=16.5 Hz, J2=2.5 Hz), d3.47–3.57 (m, 1H), d3.59 (dd, J1=J2=11.5 Hz, 1H), d3.63–3.77 (m, 4H), d3.78–3.84 (m, 1H), d3.89–4.03 (m, 3H), d4.15–4.21 (m, 1H), d4.23–4.49 (m, 8H), d4.52–4.72 (m, 7H), d4.78–4.90 (m, 4H), d5.52 (d, 1H, J=4.5 Hz, H1"), d5.98 (d, 1H, J=4.5 Hz), d7.06–7.37 (m, 40H); 13C NMR (CDCl3, 125 MHz): d 32.3, 51.1, 59.6, 60.4, 62.6, 63.3, 69.3, 70.9, 72.1, 15 72.3, 73.0, 73.6, 74.0, 74.7, 74.9, 75.1, 75.4, 75.8, 76.0, 78.4, 80.0, 81.3, 81.5, 81.9, 83.4, 95.9, 99.9, 107.4, 127.3, 127.5, 127.6, 127.7, 127.8, 127.9, 128.0, 128.1, 128.2, 128.3, 128.4, 137.65, 137.69, 137.8, 137.9, 138.0, 138.6; HRMS: for C79H85N12O15 (M+Cs): calcd. 1574.5312; found 1574.5397.

Synthesis of 2''',6'''-desamino-2'''-6'''-hydroxy neomycin B (700) as illustrated in FIG. 31. The deprotection of 3500 (31 mg, 2.15 mmol) was carried out in the exact manner as the preparation of compound 6 to afford 12.4 mg, 76% of 7◊4 HCl. 1H NMR (D2O, adjusted with DCl, 600 MHz): d1.85 (ddd, 1H, J1=J2=J3=12.6 Hz, H2 eq), d2.24 (ddd, 1H, J1=12.6 Hz, J2=J3=4.1 Hz, H2 ax), d3.24 (dd, 1H, J1=13.7 Hz, J2=6.3 Hz, H6'a), d3.32 (ddd, 1H, J1=12.6 Hz, J2=10.6 Hz, J3=4.1 Hz, H1), d3.37–3.43 (m, 2H, H2', H6'b), d3.43 (dd, 1H, J1=J2=9.4 Hz, H4'), d3.51 (ddd, 1H, J1=12.6 Hz, J2=10.3 Hz, J3=4.1 Hz, H3), d3.57–3.60 (m, 1H, H4'''), d3.65 (dd, 1H, J1=10.6 Hz, J2=9.2 Hz, H6), d3.72–3.82 (m, 4H, H6'''a, H6'''b, H5''a, H2''), d3.85–3.97 (m, 5H, H5''b, H5', H5, H3', H5'''), d3.99 (dd, 1H, J1=J2=3.7 Hz, H3'''), d4.06 (dd, 1H, J1=10.3 Hz, J2=9.2 Hz, H4), d4.14–4.18 (m, 1H, H4''), d4.35 (dd, 1H, J1=4.7 Hz, J2=1.7 Hz, H2''), d4.42 (dd, 1H, J1=7.2 Hz, J2=4.7 Hz, H3''), d4.89 (d, 1H, J=1.3 Hz, H1'''), d5.35 (d, 1H, J=1.7 Hz, H1''), d5.98 (d, 1H, J=4 Hz, H1'); 13C NMR (CDCl3, 125 MHz): d 29.5 (C2), 41.5 (C6'), 49.9 (C3), 51.3 (C1), 55.0 (C2'), 62.8 (C5'' and (C2''' or C2'')), 69.46 (C4''), 69.52 (C3'), 70.7 (C2''' or C6'''), 70.9 (C5'), 71.1 (C3'''), 72.0 (C4'), 74.0 (C6), 75.3 (C2''), 76.8, 76.9 (C3'', C4, C5'''), 83.0 (C4''), 86.1 (C5), 97.1 (C1'), 100.3 (C1'''), 111.6 (C1''); MS: for C23H44N4O15 (M+H): calcd. 617; found 617, for C23H45N5O14 (M–H): calcd. 615; found 615.

Synthesis of compound 3600 as illustrated in FIG. 31. Compound 2000 (321 mg, 0.32 mmol) and compound 3300 (312 mg, 0.510 mmol) were dried together with 3 Å MS (250 mg) overnight. Then CH2Cl2 (5 mL) was added and the reaction was cooled to –10° C. using an ice/salt bath. After stirring for 30 min, NIS (125 mg, 0.56 mmol) was added and the reaction was allowed to stir for 15 min Then, a catalytic amount of AgOTf was added and the reaction was allowed to stir for 30 min. prior to quenching with triethylamine. The reaction was then filtered through a pad of celite and the solvent was removed. Chromatography of the residue over 50 mL of silica gel using a gradient of 10% to 15% to 20% to 25% ethyl acetate in hexane afforded 175 mg, 35%. of the desired product. 1H NMR (CDCl3, 500 MHz): d1.35 (ddd, 1H, J1=J2=J3=12.5 Hz, H2 eq), d2.17 (ddd, 1H, J1=12.5 Hz, J2=J3=4.5 Hz, H2 ax), d3.12 (dd, J1=10 Hz, J2=3.5 Hz, 1H, H2'), d3.15 (dd, J1=J2=9 Hz, 1H, H3'''), d3.21–3.33 (m, 3H, H1, H3, H4''') d3.29 (dd, 1H, J1=13.5 Hz, J2=4.5 Hz, H6'a), d3.34–3.49 (m, 4H, H5, H4', H6'''a, H6''b), d3.47 (dd, 1H, J1=13.5 Hz, J2=2.5 Hz, H6'b), 63.55–3.72 (m, 5H, H4, H6, H5''a, H5''b, H2'''), d3.77–3.83 (m, 1H, H5'''), d3.95 (dd, 1H, J1=4.5 Hz, J2=4 Hz, H2''), d4.00 (dd, 1H, J1=10 Hz, J2=9.5 Hz, H3'), d4.13–4.19 (m, 1H, H5'), d4.19–4.24 (m, 2H, H3'', PhCH2O), d4.29–4.34 (m, 2H, H4'', PhCH2O), d4.38–5.12 (m, 17H, PhCH20 and H1'''), d5.47–5.53 (m, 1H, CbzNH), d5.54 (d, 1H, J1=4 Hz, H1''), d5.99 (d, 1H, J1=3.5 Hz, H1'), d7.02–7.37 (m, 40 H, C6H5); 13C NMR (CDCl3, 125 MHz): d 32.2, 41.6, 51.2, 59.6, 60.3, 63.2, 66.5, 69.4, 70.9, 71.7, 72.4, 72.6, 73.3, 73.89, 73.93, 74.2, 74.3, 74.9, 75.1, 75.3, 75.8, 76.6, 78.5, 79.9, 81.3, 81.5, 82.1, 83.4, 95.9, 100.1, 107.2, 127.2, 127.5, 127.6, 127.7, 127.8, 127.9, 128.0, 128.2, 128.3, 128.4, 128.5, 136.6, 137.56, 137.60, 137.80, 137.81, 138.1, 138.6, 156.5; HRMS for C87H91N13O16 (M+Cs): calcd, 1706.5761; found, 1706.5849.

Synthesis of 2'''-desamino-2'''-hydroxy neomycin B (800) as illustrated in FIG. 31. The deprotection of compound 3600 (60.7 mg, 39 mmol) was carried out in the exact manner as the preparation of compound 6 to afford 21.6 mg, 70% of 8◊5 HCl. 1H NMR (D2O, pD 2 adjusted with DCl, Bruker AMX-500): d1.95 (ddd, 1H, J1=J2=J3=12.6 Hz, H2 eq), d2.24 (ddd, 1H, J1=12.6 Hz, J2=J3=4.1 Hz, H2 ax), d3.33 (dd, 1H, J1=13.7 Hz, J2=6.4 Hz, H6'a), d3.35–3.44 (m, 3H, H6'''a, H1, H6'''b), d3.46–3.51 (m, 2H, H2', H6'b), d3.52 (dd, 1H, J1=J2=9.3 Hz, H4'), d3.60 (ddd, 1H, J1=12.8 Hz, J2=10.2 Hz, J3=4.1 Hz, H3), d3.71–3.74 (m, H4'''), d3.77 (dd, 1H, J1=10.4 Hz, J2=9.3 Hz, H6), d3.80 (dd, 1H, J1=12.4 Hz, J2=5.1 Hz, H5''a), d3.85–3.88 (m, 1H, H2'''), d3.95 (dd, 1H, J1=12.4 Hz, J2=3.0 Hz, H5''b), d3.94–3.99 (m, 1H, H5'), d3.99 (dd, 1H, J1=10.2 Hz, J2=9.3 Hz, H5), d4.04 (dd, 1H, J1=10.9 Hz, J2=9.3 Hz, H3'), d4.11 (dd, 1H, J1=J2=3.5 Hz, H3'''), d4.18 (dd, 1H, J1=J2=10.2 Hz, H4), d4.23–4.28 (m, 2H, H4'', H5'''), d4.44 (dd, 1H, J1=4.8 Hz, J2=2.4 Hz, H2''), d4.52 (dd, 1H, J1=6.5 Hz, J2=4.8 Hz, H3"), d5.03 (d, 1H, J=1.2 Hz, H1'''), d5.46 (d, 1H, J=2.4 Hz, H1"), d6.09 (d, 1H, J=4 Hz, H1'); 13C NMR (CDCl3, 125 MHz): d 29.5 (C2), 41.6 (C6'), 42.0 (C6'''), 49.9 (C3), 51.3 (C1), 54.9 (C2'), 61.8 (C5"), 69.5 (C3'), 70.0 (C4"), 70.2 (C2'''), 70.9 (C5'), 71.0 (C3'''), 72.01 (C4'), 72.04 (C5'''), 73.9 (C6), 75.2 (C2"), 76.7 (C4), 76.9 (C3"), 83.1 (C4''), 86.3 (C5), 97.0 (C1'), 100.1 (C'''), 111.7 (C1"); MS: for C23H45N5O14 (M+H): calcd. 616; found 616, for C23H45N5O14 (M−H): calcd. 614; found 614.

General Procedures for SPR Binding Studies done in Example 5. Samples were prepared by serial dilutions from stock solutions in RNase free microfuge tubes (Ambion) and were centrifuged at 14000 rpm for degassing. Unless otherwise noted, all binding studies were carried out using HBS buffer (Pharmacia Biosensor AB) which was used as obtained. All procedures for binding studies were automated as methods using repetitive cycles of sample injection and regeneration. Typically, buffer was injected in the first two cycles to establish a stable baseline value. Samples were injected at a flowrate of 5–10 mL/min using either the KINJECT command. All aminoglycoside samples were injected from autoclaved 7 mm plastic vials that were capped with pierceable plastic crimp caps. To minimize carry over, samples were injected in order of increasing concentration. The running buffer was identical to the injection buffer. Expected values for the equilibrium response of one equivalent of analyte were calculated from the relative molecular weight of the analyte and the immobilized RNA ligand in each flowcells and adjusted with a correction factor of 0.76 which arises from the different molar refractive indices of RNA and the analyte. Binding constants were calculated by fitting the recorded binding isotherm (equivalents bound vs, concentration) to a model with n independent binding constants using the fitting program provided in the program Kaleidagraph (Macintosh).

Neomycin B sulfate (Fluka) was converted to the free base by passing it through Amberlite IRA 400 (OH— form) and purified by ion exchange chromatography on Dowex 1-X2 100 to remove neomycin C;23 the purity of neomycin B was verified by NMR in D2O. Neamine was obtained by acid catalyzed cleavage of neomycin B and purified by ion exchange chromatography on Amberlite CG-50. Paromamine was obtained by acid catalyzed cleavage of paromomycin and purified in the same manner. Paromomycin sulfate, kanamycin A, kanamycin B and streptomycin were obtained from Sigma and used as received. Tobramycin, gentamicin, apramycin, ribostamycin, butirosin and hygromycin B were obtained from Fluka and used as received. 2'''-hydroxy-neomycin B, 2''',6'''-dihydroxy-neomycin B and derivatives of ribostamycin were obtained via total synthesis.

General Procedure for Ozonolysis of Compounds 6000–8000 as shown in FIG. 58: (For each library compound to be produced, 0.15 mmol of the 2-acylamido-glucosamine derivative was used.) A solution of compounds 6000–9000 in a total of 7 mL of a MeOH:CH2Cl2 mixture (containing only as much CH2Cl2 as needed for solubility) was cooled to −78° C. and treated successively with oxygen, then ozone (until the faint blue color was visible) and then oxygen again. After all remaining ozone had been purged, dimethylsulfide was added (200 uL, 3 mmol) and the solution allowed to warm to ambient temperature (circa 1 h). The solvent was evaporated and the product dried for 1 h under high vacuum. The crude aldehydes 9000–11000 were then used in the reductive amination.

General Procedure for Reductive Amination of Compounds 9000–11000 as shown in FIG. 58: The aldehydes 9000–11000 (0.15 mmol) were dissolved in 1 mL MeOH and treated first with 0.45 mL of a 1 M solution of the amine in MeOH, then with 0.5 mL of a 1 M solution of acetic acid in MeOH, and finally with 0.22 mL of a freshly prepared 0.3 M solution of NaCNBH3 in MeOH. (If an amine hydrochloride salt was used instead of a free amine, water was added to the amine solution as needed for solubility, the amount of ACOH solution was reduced to 0.05 mL and the amount of NaCNBH3 solution was increased to 0.25 mL.) After 2 h, water was added (0.5 mL) and stirring was continued for 20 min, after which time the mixture was evaporated. The crude products 12000–14000 were used without further purification in the hydrogenation step.

General Procedure for Hydrogenation of Compounds 12000–14000 a–f as shown in FIG. 58: A solution of compounds 12000–14000 (0.15 mmol) in 3 mL AcOH and 2 mL water was degassed by evacuating and refilling with argon several times. Hydrogenation catalyst (20% Pd(OH)2 on carbon, wet Degussa type, circa 20 mg) was added, the flask carefully evacuated and then refilled with hydrogen from a balloon. The needle connected to the balloon was inserted into the solution and hydrogen was allowed to bubble though the solution for circa 3 min by piercing the septum with another needle. Then the flask was kept under positive hydrogen pressure and stirred for 3–12 h until reduction was complete (TLC of the products in MeOH:conc. NH3=9:1 to 3:1, staining with ninhydrin). The balloon was removed and the solution purged with argon. Water was added (5 mL) and the reaction mixture filtered through a celite pad which was washed with 5 mL water. The combined filtrates were evaporated, dissolved in 2 mL water and applied onto an Amberlite CG-50 column (NH4+ form, 16×1.5 cm) and eluted with a gradient made from 250 mL water (solution A) and 250 mL water containing 1–30% concentrated aqueous ammonia. Fractions containing 5 mL were collected with an automatic fraction collector and the product-containing fractions were pooled and lyophilized. Hydrochloride salts of the final products were prepared by adding excess 1 M HCl and lyophilizing again. All compounds were characterized by 1H-NMR, 13C-NMR and Electrospray-MS.

Selective Hydrogenation of Compounds 12000–14000 e as shown in FIG. 58: Following the hydrogenation procedure as outline above, the reaction was stopped and filtered after 2–3 h (TLC control) and the product isolated by ion exchange chromatography as described above to form compounds 15000–17000 a–g.

Screening/Surface Plasmon Resonance Binding Assays of Library Compounds as diagramed in FIG. 60. Following the general protocols outlined previously, biotinylated RNA sequences were prepared and immobilized on SA5 sensor-chips. Binding to three sequences was assayed at once in three parallel flowcells, with the fourth flowcell containing no immobilized RNA serving as a control. Compounds were assayed at four concentrations (100, 31.6, 10, 3.16 mM). Using the known molecular weight of the compounds, the SPR responses for each ligand were normalized and expressed as fraction of equivalents bound to the RNA at each concentration. From this titration curve, the Kd for each compound was estimated from a single appropriate datapoint which represented just under 0.5 bound equivalents assuming a 1:1 binding isotherm.

Automated Method for Library Analysis. The samples were screened at four concentrations with injection times 4 min 30 s each. After recording three different series,. a control sample of paromomycin is tested to ensure reproducibility. With the available autosampler racks, up to 12 compounds can be screened at once over a period of 24 h.

What is claimed is:

1. A library of compounds having nucleic acid binding hydroxyamine substructures comprising a plurality of compounds represented by the following structure:

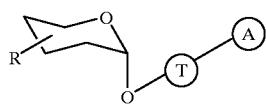

wherein

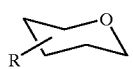

is selected from a group consisting of radicals represented by the following structures:

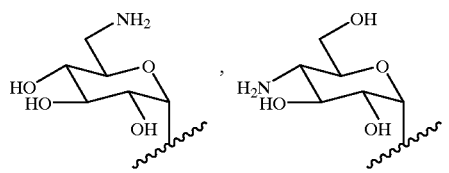

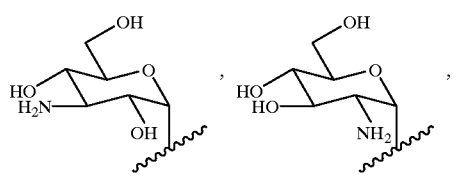

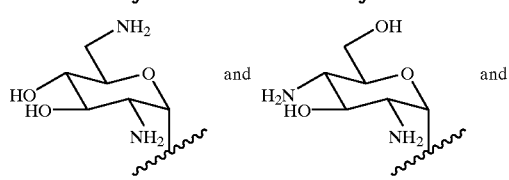

wherein Ⓣ is selected from a group consisting of diradicals represented by the following structures:

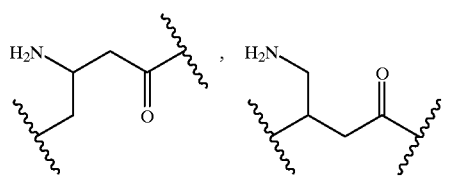

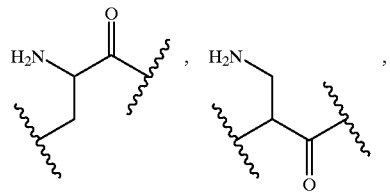

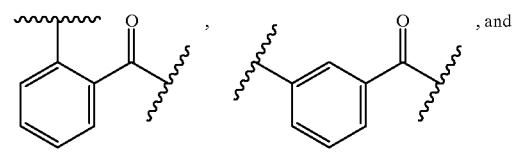

wherein Ⓐ is selected from a group consisting of radicals represented by the following structures:

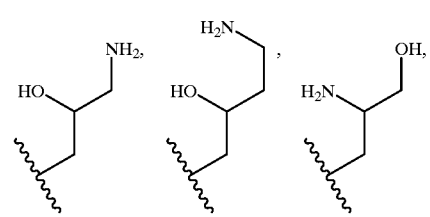

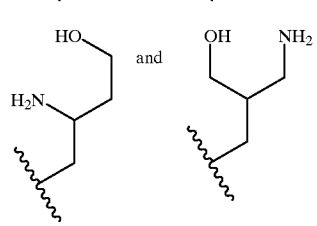

wherein the carbonyl of Ⓣ is linked to Ⓐ.

* * * * *